US011292837B2

United States Patent
Morrison et al.

(10) Patent No.: US 11,292,837 B2
(45) Date of Patent: Apr. 5, 2022

(54) NECTIN-4 BINDING PROTEINS AND METHODS OF USE THEREOF

(71) Applicant: AGENSYS, INC., Santa Monica, CA (US)

(72) Inventors: Karen Jane Meyrick Morrison, Santa Monica, CA (US); Fernando Donate, Santa Monica, CA (US); Peng Yang, Santa Monica, CA (US)

(73) Assignee: AGENSYS, INC., Northbrook, IL (US)

( * ) Notice: Subject to any disclaimer, the term of this patent is extended or adjusted under 35 U.S.C. 154(b) by 104 days.

(21) Appl. No.: 16/619,439

(22) PCT Filed: Jun. 4, 2018

(86) PCT No.: PCT/US2018/035840
§ 371 (c)(1),
(2) Date: Dec. 4, 2019

(87) PCT Pub. No.: WO2018/226578
PCT Pub. Date: Dec. 13, 2018

(65) Prior Publication Data
US 2020/0231670 A1  Jul. 23, 2020

Related U.S. Application Data

(60) Provisional application No. 62/515,454, filed on Jun. 5, 2017.

(51) Int. Cl.
*C07K 16/28* (2006.01)
*G01N 33/574* (2006.01)

(52) U.S. Cl.
CPC ... *C07K 16/2803* (2013.01); *G01N 33/57492* (2013.01); *C07K 2317/21* (2013.01); *C07K 2317/24* (2013.01); *C07K 2317/565* (2013.01)

(58) Field of Classification Search
None
See application file for complete search history.

(56) References Cited

U.S. PATENT DOCUMENTS

2008/0268476 A1  10/2008  Lopez
2011/0150886 A1  6/2011  Caswell et al.

FOREIGN PATENT DOCUMENTS

| WO | WO 2010067487 A1 | 6/2010 |
|----|------------------|--------|
| WO | WO 2016203053 A2 | 12/2016 |
| WO | WO 2016203053 A3 | 12/2016 |
| WO | WO 2017042210 A1 | 3/2017 |

OTHER PUBLICATIONS

Challita-Eid et al., 2016, "Enfortumab Vedotin Antibody-Drug Conjugate Targeting Nectin-4 Is a Highly Potent Therapeutic Agent in Multiple Preclinical Cancer Models," Cancer Res., 76(10):3003-3013.

(Continued)

*Primary Examiner* — Aurora M Fontainhas
(74) *Attorney, Agent, or Firm* — Jones Day

(57) ABSTRACT

Provided herein are compositions, methods and uses involving antibodies that specifically bind to Nectin-4. Also provided herein are methods for assessing Nectin-4 expression in a sample or a patient and methods for assessing responsiveness of a cancer patient to an anti-cancer therapeutic agent.

17 Claims, 13 Drawing Sheets

Specification includes a Sequence Listing.

(56) References Cited

OTHER PUBLICATIONS

Fabre-Lafay et al., 2007, "Nectin-4 is a new histological and serological tumor associated marker for breast cancer," BMC Cancer, 7:73 (16 pages).
International Search Report and Written Opinion dated Sep. 10, 2018 of International Patent Application No. PCT/US2018/035840 (published as WO 2018226578), 8 pages.
Campbell et al., 2016, "Preclinical Evaluation of an Anti-Nectin-4 ImmunoPET Reagent in Tumor-Bearing Mice and Biodistribution Studies in Cynomolgus Monkeys," Mol. Imaging. Biol., 18(5):768-775.
M-Rabet et al., 2017, "Nectin-4: a new prognostic biomarker for efficient therapeutic targeting of primary and metastatic triple-negative breast cancer," Ann. Oncol., 28(4):769-776.
Nishiwada et al., 2015, "Nectin-4 expression contributes to tumor proliferation, angiogenesis and patient prognosis in human pancreatic cancer," J. Exp. Clin. Cancer Res., 34(1):30 (9 pages).
Perez De La Lastra et al., 1999, "Epitope mapping of 10 monoclonal antibodies against the pig analogue of human membrane cofactor protein (MCP)," Immunology, 96(4):663-670.

SEQUENCE LISTING

```
<160> NUMBER OF SEQ ID NOS: 46

<210> SEQ ID NO 1
<211> LENGTH: 510
<212> TYPE: PRT
<213> ORGANISM: Homo sapiens
<220> FEATURE:
<223> OTHER INFORMATION: GenBank accession number NP_112178

<400> SEQUENCE: 1

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
                20                  25                  30

Glu Leu Glu Thr Ser Asp Val Val Thr Val Val Leu Gly Gln Asp Ala
            35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
                100                 105                 110

Leu Leu Arg Asn Ala Val Gln Ala Asp Glu Gly Glu Tyr Glu Cys Arg
            115                 120                 125

Val Ser Thr Phe Pro Ala Gly Ser Phe Gln Ala Arg Leu Arg Leu Arg
    130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
```

```
            180                 185                 190
Ser Arg Ser Phe Lys His Ser Arg Ser Ala Ala Val Thr Ser Glu Phe
            195                 200                 205

His Leu Val Pro Ser Arg Ser Met Asn Gly Gln Pro Leu Thr Cys Val
            210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Ile Gly Arg Glu Gly Ala Met Leu Lys Cys Leu Ser
            260                 265                 270

Glu Gly Gln Pro Pro Ser Tyr Asn Trp Thr Arg Leu Asp Gly Pro
            275                 280                 285

Leu Pro Ser Gly Val Arg Val Asp Gly Asp Thr Leu Gly Phe Pro Pro
            290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Asp Pro Gln
                325                 330                 335

Glu Asp Ser Gly Lys Gln Val Asp Leu Val Ser Ala Ser Val Val Val
                340                 345                 350

Val Gly Val Ile Ala Ala Leu Leu Phe Cys Leu Leu Val Val Val Val
                355                 360                 365

Val Leu Met Ser Arg Tyr His Arg Arg Lys Ala Gln Gln Met Thr Gln
            370                 375                 380

Lys Tyr Glu Glu Glu Leu Thr Leu Thr Arg Glu Asn Ser Ile Arg Arg
385                 390                 395                 400

Leu His Ser His His Thr Asp Pro Arg Ser Gln Pro Glu Glu Ser Val
                405                 410                 415

Gly Leu Arg Ala Glu Gly His Pro Asp Ser Leu Lys Asp Asn Ser Ser
                420                 425                 430

Cys Ser Val Met Ser Glu Glu Pro Glu Gly Arg Ser Tyr Ser Thr Leu
            435                 440                 445

Thr Thr Val Arg Glu Ile Glu Thr Gln Thr Glu Leu Leu Ser Pro Gly
            450                 455                 460

Ser Gly Arg Ala Glu Glu Glu Asp Gln Asp Glu Gly Ile Lys Gln
465                 470                 475                 480

Ala Met Asn His Phe Val Gln Glu Asn Gly Thr Leu Arg Ala Lys Pro
                485                 490                 495

Thr Gly Asn Gly Ile Tyr Ile Asn Gly Arg Gly His Leu Val
            500                 505                 510

<210> SEQ ID NO 2
<211> LENGTH: 316
<212> TYPE: PRT
<213> ORGANISM: Artificial Sequence
<220> FEATURE:
<223> OTHER INFORMATION: Synthetic polypeptide

<400> SEQUENCE: 2

Ala Gly Glu Leu Glu Thr Ser Asp Val Val Thr Val Val Leu Gly Gln
1               5                   10                  15

Asp Ala Lys Leu Pro Cys Phe Tyr Arg Gly Asp Ser Gly Glu Gln Val
                20                  25                  30

Gly Gln Val Ala Trp Ala Arg Val Asp Ala Gly Glu Gly Ala Gln Glu
```

```
              35                  40                  45
Leu Ala Leu Leu His Ser Lys Tyr Gly Leu His Val Ser Pro Ala Tyr
 50                  55                  60

Glu Gly Arg Val Glu Gln Pro Pro Pro Arg Asn Pro Leu Asp Gly
 65                  70                  75                  80

Ser Val Leu Leu Arg Asn Ala Val Gln Ala Asp Glu Gly Glu Tyr Glu
                 85                  90                  95

Cys Arg Val Ser Thr Phe Pro Ala Gly Ser Phe Gln Ala Arg Leu Arg
                100                 105                 110

Leu Arg Val Leu Val Pro Pro Leu Pro Ser Leu Asn Pro Gly Pro Ala
                115                 120                 125

Leu Glu Glu Gly Gln Gly Leu Thr Leu Ala Ala Ser Cys Thr Ala Glu
130                 135                 140

Gly Ser Pro Ala Pro Ser Val Thr Trp Asp Thr Glu Val Lys Gly Thr
145                 150                 155                 160

Thr Ser Ser Arg Ser Phe Lys His Ser Arg Ser Ala Ala Val Thr Ser
                165                 170                 175

Glu Phe His Leu Val Pro Ser Arg Ser Met Asn Gly Gln Pro Leu Thr
                180                 185                 190

Cys Val Val Ser His Pro Gly Leu Leu Gln Asp Gln Arg Ile Thr His
                195                 200                 205

Ile Leu His Val Ser Phe Leu Ala Glu Ala Ser Val Arg Gly Leu Glu
210                 215                 220

Asp Gln Asn Leu Trp His Ile Gly Arg Glu Gly Ala Met Leu Lys Cys
225                 230                 235                 240

Leu Ser Glu Gly Gln Pro Pro Ser Tyr Asn Trp Thr Arg Leu Asp
                245                 250                 255

Gly Pro Leu Pro Ser Gly Val Arg Val Asp Gly Asp Thr Leu Gly Phe
                260                 265                 270

Pro Pro Leu Thr Thr Glu His Ser Gly Ile Tyr Val Cys His Val Ser
                275                 280                 285

Asn Glu Phe Ser Ser Arg Asp Ser Gln Val Thr Val Asp Val Leu Asp
                290                 295                 300

Pro Gln Glu Asp Ser Gly Lys Gln Val Asp Leu Val
305                 310                 315

<210> SEQ ID NO 3
<211> LENGTH: 133
<212> TYPE: PRT
<213> ORGANISM: Artificial Sequence
<220> FEATURE:
<223> OTHER INFORMATION: Synthetic polypeptide

<400> SEQUENCE: 3

Asp Ile Val Met Thr Gln Ala Ala Phe Ser Asn Pro Val Thr Leu Gly
 1                   5                  10                  15

Thr Ser Ala Ser Ile Ser Cys Arg Ser Ser Lys Ser Leu Leu His Ser
                 20                  25                  30

Asn Gly Ile Thr Tyr Leu Tyr Trp Tyr Leu Gln Lys Pro Gly Gln Ser
                 35                  40                  45

Pro Gln Leu Leu Ile Tyr His Met Ser Asn Leu Ala Ser Gly Val Pro
                 50                  55                  60

Asp Arg Phe Thr Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
```

```
                    85                  90                  95

Leu Glu Leu Pro Phe Thr Phe Gly Gly Gly Thr Lys Leu Glu Thr Lys
                100                 105                 110

Arg Ala Asp Ala Ala Pro Thr Val Ser Ile Phe Pro Pro Ser Ser Glu
            115                 120                 125

Gln Leu Thr Ser Gly
        130

<210> SEQ ID NO 4
<211> LENGTH: 136
<212> TYPE: PRT
<213> ORGANISM: Artificial Sequence
<220> FEATURE:
<223> OTHER INFORMATION: Synthetic polypeptide

<400> SEQUENCE: 4

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Thr Tyr
            20                  25                  30

Trp Met Gln Trp Val Lys Gln Arg Pro Gly Gln Gly Leu Glu Trp Ile
        35                  40                  45

Gly Ser Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Ile Gln Leu Ser Thr Leu Ala Ser Glu Asp Ser Ala Val Tyr Tyr Cys
                85                  90                  95

Ala Arg Glu Tyr Tyr Gly Leu Asp Tyr Trp Gly Gln Gly Thr Thr Leu
                100                 105                 110

Thr Val Ser Ser Ala Lys Thr Thr Ala Pro Ser Val Tyr Pro Leu Ala
            115                 120                 125

Pro Val Cys Gly Asp Thr Thr Gly
        130                 135

<210> SEQ ID NO 5
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 5

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr His Met Ser Asn Leu Ala Ser Gly Val Pro
    50                  55                  60

Asp Arg Phe Thr Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Phe Thr Phe Gly Gly Gly Thr Lys Leu Glu Thr Lys
                100                 105                 110
```

```
Arg Ala Asp Ala Ala Pro Thr Val Ser Ile Phe Pro Ser Ser Glu
            115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
            165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
            195                 200                 205

Pro Ile Val Lys Thr Phe Asn Arg Asn Glu Cys
    210                 215
```

<210> SEQ ID NO 6
<211> LENGTH: 446
<212> TYPE: PRT
<213> ORGANISM: Artificial Sequence
<220> FEATURE:
<223> OTHER INFORMATION: Synthetic polypeptide

<400> SEQUENCE: 6

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Thr Tyr
            20                  25                  30

Trp Met Gln Trp Val Lys Gln Arg Pro Gly Gln Gly Leu Glu Trp Ile
        35                  40                  45

Gly Ser Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Ile Gln Leu Ser Thr Leu Ala Ser Glu Asp Ser Ala Val Tyr Tyr Cys
            85                  90                  95

Ala Arg Glu Tyr Tyr Gly Leu Asp Tyr Trp Gly Gln Gly Thr Thr Leu
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
            165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
    210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
            245                 250                 255
```

Ile Val Thr Cys Val Val Asp Val Ser Glu Asp Asp Pro Asp Val
              260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
    370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
        435                 440                 445

<210> SEQ ID NO 7
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 7

Arg Ser Ser Lys Ser Leu Leu His Ser Asn Gly Ile Thr Tyr Leu Tyr
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 8

Ile Thr Tyr Leu Tyr Trp Tyr
1               5

<210> SEQ ID NO 9
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 9

Leu Leu Ile Tyr His Met Ser Asn Leu Ala Ser
1               5                   10

<210> SEQ ID NO 10
<211> LENGTH: 7
<212> TYPE: PRT

```
<213> ORGANISM: Artificial Sequence
<220> FEATURE:
<223> OTHER INFORMATION: Synthetic polypeptide

<400> SEQUENCE: 10

His Met Ser Asn Leu Ala Ser
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 11

Leu Leu Ile Tyr His Met Ser Asn Leu Ala
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 12

Ala Gln Asn Leu Glu Leu Pro Phe Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 13

Ala Gln Asn Leu Glu Leu Pro Phe
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 14

Gly Tyr Thr Phe Thr Thr Tyr Trp Met Gln
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 15

Thr Tyr Trp Met Gln
1               5

<210> SEQ ID NO 16
<211> LENGTH: 7
<212> TYPE: PRT
<213> ORGANISM: Artificial Sequence
```

```
<220> FEATURE:
<223> OTHER INFORMATION: Synthetic polypeptide

<400> SEQUENCE: 16

Gly Tyr Thr Phe Thr Thr Tyr
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 17

Thr Thr Tyr Trp Met Gln
1               5

<210> SEQ ID NO 18
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 18

Trp Ile Gly Ser Ile Tyr Pro Gly Asp Gly Asp Thr Arg Tyr Thr Gln
1               5                   10                  15

Lys Phe Lys Gly
            20

<210> SEQ ID NO 19
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 19

Ser Ile Tyr Pro Gly Asp Gly Asp Thr Arg Tyr Thr Gln Lys Phe Lys
1               5                   10                  15

Gly

<210> SEQ ID NO 20
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 20

Tyr Pro Gly Asp Gly Asp
1               5

<210> SEQ ID NO 21
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 21

Trp Ile Gly Ser Ile Tyr Pro Gly Asp Gly Asp Thr Arg
1               5                   10
```

```
<210> SEQ ID NO 22
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 22

Ala Arg Glu Tyr Tyr Gly Leu Asp Tyr
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 23

Glu Tyr Tyr Gly Leu Asp Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 24

Ala Arg Glu Tyr Tyr Gly Leu Asp
1               5

<210> SEQ ID NO 25
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 25

Asp Ile Val Met Thr Gln Ala Ala Phe Ser Asn Pro Val Thr Leu Gly
1               5                   10                  15

Thr Ser Ala Ser Ile Ser Cys
            20

<210> SEQ ID NO 26
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 26

Trp Tyr Leu Gln Lys Pro Gly Gln Ser Pro Gln Leu Leu Ile Tyr
1               5                   10                  15

<210> SEQ ID NO 27
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 27

Gly Val Pro Asp Arg Phe Thr Ser Ser Gly Ser Gly Thr Asp Phe Thr
1               5                   10                  15
```

```
Leu Arg Ile Ser Arg Val Glu Ala Glu Asp Val Gly Val Tyr Tyr Cys
            20                  25                  30
```

```
<210> SEQ ID NO 28
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 28

Phe Gly Gly Gly Thr Lys Leu Glu Thr Lys Arg
1               5                   10
```

```
<210> SEQ ID NO 29
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 29

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr
            20                  25                  30
```

```
<210> SEQ ID NO 30
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 30

Trp Val Lys Gln Arg Pro Gly Gln Gly Leu Glu Trp Ile Gly
1               5                   10
```

```
<210> SEQ ID NO 31
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 31

Lys Ala Thr Leu Thr Ala Asp Lys Ser Ser Ser Thr Ala Tyr Ile Gln
1               5                   10                  15

Leu Ser Thr Leu Ala Ser Glu Asp Ser Ala Val Tyr Tyr Cys Ala Arg
            20                  25                  30
```

```
<210> SEQ ID NO 32
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 32

Trp Gly Gln Gly Thr Thr Leu Thr Val Ser Ser
1               5                   10
```

```
<210> SEQ ID NO 33
<211> LENGTH: 86
<212> TYPE: PRT
```

<213> ORGANISM: Artificial Sequence
<220> FEATURE:
<223> OTHER INFORMATION: Synthetic polypeptide

<400> SEQUENCE: 33

```
Gly Ala Ser Val Val Cys Phe Leu Asn Asn Phe Tyr Pro Lys Asp Ile
1               5                   10                  15

Asn Val Lys Trp Lys Ile Asp Gly Ser Glu Arg Gln Asn Gly Val Leu
            20                  25                  30

Asn Ser Trp Thr Asp Gln Asp Ser Lys Asp Ser Thr Tyr Ser Met Ser
        35                  40                  45

Ser Thr Leu Thr Leu Thr Lys Asp Glu Tyr Glu Arg His Asn Ser Tyr
50                  55                  60

Thr Cys Glu Ala Thr His Lys Thr Ser Thr Ser Pro Ile Val Lys Thr
65                  70                  75                  80

Phe Asn Arg Asn Glu Cys
                85
```

<210> SEQ ID NO 34
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 34

```
Ser Ser Val Thr Leu Gly Cys Leu Val Lys Gly Tyr Phe Pro Glu Pro
1               5                   10                  15

Val Thr Leu Thr Trp Asn Ser Gly Ser Leu Ser Ser Gly Val His Thr
            20                  25                  30

Phe Pro Ala Val Leu Gln Ser Asp Leu Tyr Thr Leu Ser Ser Ser Val
        35                  40                  45

Thr Val Thr Ser Ser Thr Trp Pro Ser Gln Ser Ile Thr Cys Asn Val
50                  55                  60

Ala His Pro Ala Ser Ser Thr Lys Val Asp Lys Lys Ile Glu Pro Arg
65                  70                  75                  80

Gly Pro Thr Ile Lys Pro Cys Pro Pro Cys Lys Cys Pro Ala Pro Asn
            85                  90                  95

Leu Leu Gly Gly Pro Ser Val Phe Ile Phe Pro Pro Lys Ile Lys Asp
                100                 105                 110

Val Leu Met Ile Ser Leu Ser Pro Ile Val Thr Cys Val Val Val Asp
            115                 120                 125

Val Ser Glu Asp Asp Pro Asp Val Gln Ile Ser Trp Phe Val Asn Asn
130                 135                 140

Val Glu Val His Thr Ala Gln Thr Gln Thr His Arg Glu Asp Tyr Asn
145                 150                 155                 160

Ser Thr Leu Arg Val Val Ser Ala Leu Pro Ile Gln His Gln Asp Trp
                165                 170                 175

Met Ser Gly Lys Glu Phe Lys Cys Lys Val Asn Asn Lys Asp Leu Pro
            180                 185                 190

Ala Pro Ile Glu Arg Thr Ile Ser Lys Pro Lys Gly Ser Val Arg Ala
        195                 200                 205

Pro Gln Val Tyr Val Leu Pro Pro Glu Glu Glu Met Thr Lys Lys
    210                 215                 220

Gln Val Thr Leu Thr Cys Met Val Thr Asp Phe Met Pro Glu Asp Ile
225                 230                 235                 240
```

Tyr Val Glu Trp Thr Asn Asn Gly Lys Thr Glu Leu Asn Tyr Lys Asn
                245                 250                 255

Thr Glu Pro Val Leu Asp Ser Asp Gly Ser Tyr Phe Met Tyr Ser Lys
            260                 265                 270

Leu Arg Val Glu Lys Lys Asn Trp Val Glu Arg Asn Ser Tyr Ser Cys
        275                 280                 285

Ser Val Val His Glu Gly Leu His Asn His Thr Thr Lys Ser Phe
290                 295                 300

Ser Arg Thr Pro Gly Lys
305                 310

<210> SEQ ID NO 35
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 35

Pro Arg Gly Pro Thr Ile Lys Pro Cys Pro Pro Cys Lys Cys Pro Ala
1               5                   10                  15

Pro Asn Leu Leu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
        35                  40                  45

Val Asp Val Ser Glu Asp Asp Pro Asp Val Gln Ile Ser Trp Phe Val
    50                  55                  60

Asn Asn Val Glu Val His Thr Ala Gln Thr Gln Thr His Arg Glu Asp
65                  70                  75                  80

Tyr Asn Ser Thr Leu Arg Val Val Ser Ala Leu Pro Ile Gln His Gln
                85                  90                  95

Asp Trp Met Ser Gly Lys Glu Phe Lys Cys Lys Val Asn Asn Lys Asp
            100                 105                 110

Leu Pro Ala Pro Ile Glu Arg Thr Ile Ser Lys Pro Lys Gly Ser Val
        115                 120                 125

Arg Ala Pro Gln Val Tyr Val Leu Pro Pro Pro Glu Glu Glu Met Thr
    130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
        195                 200                 205

Ser Cys Ser Val Val His Glu Gly Leu His Asn His Thr Thr Lys
    210                 215                 220

Ser Phe Ser Arg Thr Pro Gly Lys
225                 230

<210> SEQ ID NO 36
<211> LENGTH: 1533
<212> TYPE: DNA
<213> ORGANISM: Homo sapiens
<220> FEATURE:
<223> OTHER INFORMATION: GenBank accession number NM_030916

<400> SEQUENCE: 36

```
atgcccctgt ccctgggagc cgagatgtgg gggcctgagg cctggctgct gctgctgcta      60
ctgctggcat catttacagg ccggtgcccc gcgggtgagc tggagacctc agacgtggta     120
actgtggtgc tgggccagga cgcaaaactg ccctgcttct accgagggga ctccggcgag     180
caagtggggc aagtggcatg ggctcgggtg gacgcgggcg aaggcgccca ggaactagcg     240
ctactgcact ccaaatacgg gcttcatgtg agcccggctt acgagggccg cgtggagcag     300
ccgccgcccc cacgcaaccc cctggacggc tcagtgctcc tgcgcaacgc agtgcaggcg     360
gatgagggcg agtacgagtg ccgggtcagc accttccccg ccggcagctt ccaggcgcgg     420
ctgcggctcc gagtgctggt gcctcccctg ccctcactga atcctggtcc agcactagaa     480
gagggccagg gcctgaccct ggcagcctcc tgcacagctg agggcagccc agcccccagc     540
gtgacctggg acacggaggt caaaggcaca acgtccagcc gttccttcaa gcactcccgc     600
tctgctgccg tcacctcaga gttccacttg gtgcctagcc gcagcatgaa tgggcagcca     660
ctgacttgtg tggtgtccca tcctggcctg ctccaggacc aaaggatcac ccacatcctc     720
cacgtgtcct tccttgctga ggcctctgtg aggggccttg aagaccaaaa tctgtggcac     780
attggcagag aaggagctat gctcaagtgc ctgagtgaag gcagcccccc tcccctcatac    840
aactggacac ggctggatgg ggcctctgccc agtggggtac gagtggatgg ggacactttg     900
ggctttcccc cactgaccac tgagcacagc ggcatctacg tctgccatgt cagcaatgag     960
ttctcctcaa gggattctca ggtcactgtg gatgttcttg accccaggga agactctggg    1020
aagcaggtgg acctagtgtc agcctcggtg gtggtggtgg gtgtgatcgc cgcactcttg    1080
ttctgccttc tggtggtggt ggtggtgctc atgtcccgat accatcggcg caaggcccag    1140
cagatgaccc agaaatatga ggaggagctg acccctgacca gggagaactc catccggagg    1200
ctgcattccc atcacacgga ccccaggagc cagccggagg agagtgtagg gctgagagcc    1260
gagggccacc ctgatagtct caaggacaac agtagctgct ctgtgatgag tgaagagccc    1320
gagggccgca gttactccac gctgaccacg gtgagggaga tagaaacaca gactgaactg    1380
ctgtctccag gctctgggcg ggccgaggag gaggaagatc aggatgaagg catcaaacag    1440
gccatgaacc attttgttca ggagaatggg accctacggg ccaagcccac gggcaatggc    1500
atctacatca atgggcgggg acacctggtc tga                                 1533
```

<210> SEQ ID NO 37
<211> LENGTH: 399
<212> TYPE: DNA
<213> ORGANISM: Artificial Sequence
<220> FEATURE:
<223> OTHER INFORMATION: Synthetic polynucleotide

<400> SEQUENCE: 37

```
gatattgtga tgacgcaggc tgcattctcc aatccagtca ctcttggaac atcagcttcc      60
atctcctgca ggtctagtaa gagtctccta catagtaatg gcatcactta tttgtattgg     120
tatctgcaga agccaggcca gtctcctcag ctcctgattt atcatatgtc caaccttgcc     180
tcaggagtcc cagacaggtt cactagcagt gggtcaggaa ctgatttcac actgagaatc     240
agcagagtgg aggctgagga tgtggtgttt tattactgcg ctcaaaatct agaacttccg     300
ttcacgttcg gaggggggac caagctggaa acaaaacggg ctgatgctgc accaactgta     360
tccatcttcc caccatccag tgagcagtta acatctgga                            399
```

<210> SEQ ID NO 38

<211> LENGTH: 408
<212> TYPE: DNA
<213> ORGANISM: Artificial Sequence
<220> FEATURE:
<223> OTHER INFORMATION: Synthetic polynucleotide

<400> SEQUENCE: 38

| caggttcagc tccagcagtc tggggctgag ctggcaagac ctggggcttc agtgaaattg | 60 |
| tcctgcaagg cttctggcta tacctttact acctactgga tgcagtgggt aaaacagagg | 120 |
| cctggacagg gtctggaatg gattgggtct atttatcctg agatggtga tactaggtac | 180 |
| actcagaagt tcaagggcaa ggccacattg actgcagata atcctccag cacagcctac | 240 |
| attcaactca gcaccttggc atctgaggac tctgcggtct attactgtgc aagagaatac | 300 |
| tacggtcttg actactgggg ccaaggcacc actctcacag tctcctcagc caaaacaaca | 360 |
| gccccatcgg tctatccact ggcccctgtg tgtggagata caactggc | 408 |

<210> SEQ ID NO 39
<211> LENGTH: 657
<212> TYPE: DNA
<213> ORGANISM: Artificial Sequence
<220> FEATURE:
<223> OTHER INFORMATION: Synthetic polynucleotide

<400> SEQUENCE: 39

| gatattgtga tgacgcaggc tgcattctcc aatccagtca ctcttggaac atcagcttcc | 60 |
| atctcctgca ggtctagtaa gagtctccta catagtaatg gcatcactta tttgtattgg | 120 |
| tatctgcaga agccaggcca gtctcctcag ctcctgattt atcatatgtc caaccttgcc | 180 |
| tcaggagtcc cagacaggtt cactagcagt gggtcaggaa ctgatttcac actgagaatc | 240 |
| agcagagtgg aggctgagga tgtgggtgtt tattactgcg ctcaaaatct agaacttccg | 300 |
| ttcacgttcg gaggggggac caagctggaa acaaaacggg ctgatgctgc accaactgta | 360 |
| tccatcttcc caccatccag tgagcagtta acatctggag tgcctcagt cgtgtgcttc | 420 |
| ttgaacaact tctaccccaa agacatcaat gtcaagtgga gattgatgg cagtgaacga | 480 |
| caaaatggcg tcctgaacag ttggactgat caggacagca agacagcac ctacagcatg | 540 |
| agcagcaccc tcacgttgac caaggacgag tatgaacgac ataacagcta tacctgtgag | 600 |
| gccactcaca agacatcaac ttcacccatt gtcaagacct caacaggaa tgagtgt | 657 |

<210> SEQ ID NO 40
<211> LENGTH: 1338
<212> TYPE: DNA
<213> ORGANISM: Artificial Sequence
<220> FEATURE:
<223> OTHER INFORMATION: Synthetic polynucleotide

<400> SEQUENCE: 40

| caggttcagc tccagcagtc tggggctgag ctggcaagac ctggggcttc agtgaaattg | 60 |
| tcctgcaagg cttctggcta tacctttact acctactgga tgcagtgggt aaaacagagg | 120 |
| cctggacagg gtctggaatg gattgggtct atttatcctg agatggtga tactaggtac | 180 |
| actcagaagt tcaagggcaa ggccacattg actgcagata atcctccag cacagcctac | 240 |
| attcaactca gcaccttggc atctgaggac tctgcggtct attactgtgc aagagaatac | 300 |
| tacggtcttg actactgggg ccaaggcacc actctcacag tctcctcagc caaaacaaca | 360 |
| gccccatcgg tctatccact ggcccctgtg tgtggagata caactggctc ctcggtgact | 420 |
| ctaggatgcc tggtcaaggg ttatttccct gagccagtga ccttgacctg gaactctgga | 480 |

```
tccctgtcca gtggtgtgca caccttccca gctgtcctgc agtctgacct ctacaccctc    540
agcagctcag tgactgtaac ctcgagcacc tggcccagcc agtccatcac ctgcaatgtg    600
gcccacccgg caagcagcac caaggtggac aagaaaattg agcccagagg gcccacaatc    660
aagccctgtc ctccatgcaa atgcccagca cctaacctct ggggtggacc atccgtcttc    720
atcttccctc caaagatcaa ggatgtactc atgatctccc tgagccccat agtcacatgt    780
gtggtggtgg atgtgagcga ggatgaccca gatgtccaga tcagctggtt tgtgaacaac    840
gtggaagtac acacagctca gacacaaacc catagagagg attacaacag tactctccgg    900
gtggtcagtg ccctccccat ccagcaccag gactggatga gtggcaagga gttcaaatgc    960
aaggtcaaca acaaagacct cccagcgccc atcgagagaa ccatctcaaa acccaaaggg    1020
tcagtaagag ctccacaggt atatgtcttg cctccaccag aagaagagat gactaagaaa    1080
caggtcactc tgacctgcat ggtcacagac ttcatgcctg aagacattta cgtggagtgg    1140
accaacaacg ggaaaacaga gctaaactac aagaacactg aaccagtcct ggactctgat    1200
ggttcttact tcatgtacag caagctgaga gtggaaaaga gaactgggt ggaaagaaat     1260 agctactcct gttcagtggt ccacgagggt ctgcacaatc accacacgac taagagcttc    1320
tcccggactc cgggtaaa                                                  1338

<210> SEQ ID NO 41
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 41
ggctggagtt caatgaggtt tattt                                           25

<210> SEQ ID NO 42
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 42
tccagcagat ttcagactaa gaaga                                           25

<210> SEQ ID NO 43
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 43
agaacatcat ccctgcctct actg                                            24

<210> SEQ ID NO 44
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 44
aaatgagctt gacaaagtgg tcgt                                            24
```

```
<210> SEQ ID NO 45
<211> LENGTH: 150
<212> TYPE: PRT
<213> ORGANISM: Homo sapiens

<400> SEQUENCE: 45

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
                20                  25                  30

Glu Leu Glu Thr Ser Asp Val Val Thr Val Val Leu Gly Gln Asp Ala
            35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
            115                 120                 125

Val Ser Thr Phe Pro Ala Gly Ser Phe Gln Ala Arg Leu Arg Leu Arg
            130                 135                 140

Val Leu Val Pro Pro Leu
145                 150

<210> SEQ ID NO 46
<211> LENGTH: 120
<212> TYPE: PRT
<213> ORGANISM: Homo sapiens

<400> SEQUENCE: 46

Ala Gly Glu Leu Glu Thr Ser Asp Val Val Thr Val Val Leu Gly Gln
1               5                   10                  15

Asp Ala Lys Leu Pro Cys Phe Tyr Arg Gly Asp Ser Gly Glu Gln Val
                20                  25                  30

Gly Gln Val Ala Trp Ala Arg Val Asp Ala Gly Glu Gly Ala Gln Glu
            35                  40                  45

Leu Ala Leu Leu His Ser Lys Tyr Gly Leu His Val Ser Pro Ala Tyr
    50                  55                  60

Glu Gly Arg Val Glu Gln Pro Pro Pro Arg Asn Pro Leu Asp Gly
65                  70                  75                  80

Ser Val Leu Leu Arg Asn Ala Val Gln Ala Asp Glu Gly Glu Tyr Glu
                85                  90                  95

Cys Arg Val Ser Thr Phe Pro Ala Gly Ser Phe Gln Ala Arg Leu Arg
            100                 105                 110

Leu Arg Val Leu Val Pro Pro Leu
            115                 120
```

NECTIN-4 BINDING PROTEINS AND METHODS OF USE THEREOF

1. CROSS REFERENCE TO RELATED APPLICATIONS

This application is a U.S. National Stage Application of International Patent Application No. PCT/US2018/035840, filed Jun. 4, 2018, which claims the benefit of U.S. Provisional Application No. 62/515,454, filed Jun. 5, 2017, the disclosure of each of which is incorporated by reference herein in its entirety.

2. FIELD

Provided herein are compositions, methods, and uses involving antibodies that specifically bind to human Nectin-4 and detect the expression level of Nectin-4.

3. REFERENCE TO SEQUENCE LISTING SUBMITTED ELECTRONICALLY

This application incorporates by reference a Computer Readable Form (CRF) of a Sequence Listing in ASCII text format submitted with this application, entitled 14369-208-228_SEQ_LISTING.txt, was created on May 31, 2018, and is 37,280 bytes in size.

4. BACKGROUND

Nectin-4, also known as poliovirus receptor-related protein 4 (PVRL4), is a single pass type I transmembrane protein of about 52 kDa in size that belongs to the Nectin family of cellular adhesion molecules. Nectins mediate Ca2+-independent cell-cell adhesion at adherens junctions via both homophilic interaction where one Nectin-4 interacts with another Nectin-4, and heterophilic interactions where Nectin-4 interacts with another Nectin family protein such as Nectin-1, Nectin-2, or Nectin-3. (Miyoshi J et al., 2007, *Am J Nephrol* 27:590-604; Takai et al., 2003, *Cancer Sci* 94:655-667; Reymond N. et al., 2001, *Journal of Biological Chemistry*, 276:43205-15). The extracellular domain of Nectin-4 has three Ig-like subdomains designated as V, C1 and C2. It has been shown that the C1 domain in Nectin-2 is responsible for homophilic interactions, while V domains of most Nectin molecules contribute to heterophilic interactions and cell-cell adhesion. (Miyoshi J et al., 2007, *Am J Nephrol* 27:590-604; Takai et al., 2003, *Cancer Sci* 94:655-667; Reymond N. et al., 2001, *Journal of Biological Chemistry*, 276:43205-15)

Nectins are expressed in various tissues, including, for example, hematopoietic, neuronal, endothelial, and epithelial cells. (Mendelsohn C et al., 1989, *Cell* 56:855-865; Lopez M et al., 1995, *Gene* (Amst.) 155:261-265; Lopez M et al., 1998, *Blood* 92:4602-4611; Reymond N et al., 2000, *Gene* (Amst.) 255:347-355; Cocchi F. et al., 1998, *Journal of Virology*. 72:9992-10002; Takahashi K. et al., 1999, *Journal of Cell Biology* 145:539-549; Miyoshi J et al., 2007, *Am J Nephrol* 27:590-604; Takai et al., 2003, *Cancer Sci* 94:655-667).

Besides mediating cell-cell adhesions by homophilic interactions or heterophilic interactions with other Nectin family proteins, Nectins can recruit other cell adhesion molecules such as cadherins, or other cell surface receptors such as the prolactin receptor. By recruiting other cell surface receptors, Nectins can also serve as a stimulatory co-receptor and thus have a signaling function. For example, in the mouse mammary gland, Nectin-4 interacts with the prolactin receptor through its extracellular and transmembrane domain and binds to and sequesters suppressor-of-cytokinesignaling-1 (SOCS-1), which normally inhibits the kinase activity of the Janus Kinase-2 (JAK2), thereby enhancing prolactin induced JAK2 activation and signaling. (Maruoka et al., 2017, *Journal of Biological Chemistry*, doi: 10.1074/jbc.M116.769091, jbc.M116.769091, Epub Ahead of Print; Kitayama et al., 2016, *Journal of Biological Chemistry* 291:5817-5831). Nectins can also cooperate with cadherins to induce and then rapidly suppress Rac1 activity during initial cell-cell adhesion. (Khameeka et al., 2011, *PLoS ONE* 6: e17841).

There has been a lack of success in anti-Nectin-4 antibodies developed so far for specifically detecting and assessing Nectin-4 expression in various biological samples. Thus there is need to identify an anti-Nectin-4 antibody that can specifically detect and assess Nectin-4 expression in biological samples.

5. SUMMARY

The present disclosure provides proteins that bind to Nectin-4 (e.g., human Nectin-4, SEQ ID NO:43), including binding proteins such as antibodies that bind to Nectin-4. Such binding proteins, including antibodies, may bind to a Nectin-4 polypeptide, a Nectin-4 fragment, and/or a Nectin-4 epitope.

The present disclosure also provides, in certain embodiments, binding proteins, including antibodies or fragments thereof, that binds specifically to a cell expressing Nectin-4.

Also provided herein are polynucleotides and vectors comprising sequences encoding such antibodies, cells (e.g., host cells) comprising such polynucleotides or vectors, and compositions, reagents, and kits comprising such antibodies. In another aspect, provided herein are methods for modulating Nectin-4 activity (e.g., activating Nectin-4 signaling) or Nectin-4 expression levels, diagnostic methods and uses of such anti-Nectin-4 antibodies.

In some embodiments, a binding protein (e.g., an anti-Nectin-4 antibody) comprises six complementarity determining regions (CDRs) or fewer than six CDRs. In other embodiments, a binding protein (e.g., an anti-Nectin-4 antibody) comprises one, two, three, four, five, or six CDRs selected from heavy chain variable region (VH) CDR1, VH CDR2, VH CDR3, light chain variable region (VL) CDR1, VL CDR2, and/or VL CDR3. In certain embodiments, a binding protein (e.g., an anti-Nectin-4 antibody) comprises one, two, three, four, five, or six CDRs selected from VH CDR1, VH CDR2, VH CDR3, VL CDR1, VL CDR2, and/or VL CDR3 of a monoclonal antibody designated as M22-321b41.1 as described herein, or a humanized variant thereof. In some embodiments, a binding protein (e.g., an anti-Nectin-4 antibody) further comprises a scaffold region or framework region (FR), including a VH FR1, VH FR2, VH FR3, VH FR4, VL FR1, VL FR2, VL FR3, and/or VL FR4 of a human immunoglobulin amino acid sequence or a variant thereof.

In some embodiments, the antibody or antigen-binding fragment thereof comprises a VL comprising VL CDR1, VL CDR2, and VL CDR3 of the antibody M22-321b41.1 as set forth in Table 1.

In other embodiments, the antibody or antigen-binding fragment thereof comprises a VH comprising VH CDR1, VH CDR2, and VH CDR3 of the antibody M22-321b41.1 as set forth in Table 1.

In other embodiments, the antibody or antigen-binding fragment thereof comprises:
(a) a VL comprising VL FR1, VL FR2, VL FR3, and VL FR4 of the antibody M22-321b41.1 as set forth in Table 2; and
(b) a VH comprising VH FR1, VH FR2, VH FR3, and VH FR4 of the antibody M22-321b41.1 as set forth in Table 2.

In certain embodiments, the VL CDR1, VL CDR2, and VL CDR3 of the antibody or antigen-binding fragment thereof comprise amino acid sequences of SEQ ID NOS:7, 10, and 12, respectively, and the VH CDR1, VH CDR2, and VH CDR3 of the antibody or antigen-binding fragment thereof comprise amino acid sequences of SEQ ID NOS:15, 19, and 23, respectively.

In another embodiment, the antibody or antigen-binding fragment thereof comprises a VL comprising an amino acid sequence of SEQ ID NO:3. In some embodiments, the amino acid sequence comprises one or more conservative modifications thereof.

In certain embodiments, the antibody or antigen-binding fragment thereof comprises a VH comprising an amino acid sequence of SEQ ID NO:4. In some embodiments, the amino acid sequence comprises one or more conservative modifications thereof.

In certain embodiments, the antibody or antigen-binding fragment thereof comprises: (a) a VL comprising an amino acid sequence of SEQ ID NO:3; and (b) a VH comprising an amino acid sequence of SEQ ID NO:4.

In some embodiments, the antibody comprises a human IgG1 Fc region. In other embodiments, the antibody comprises a mutant human IgG1 Fc region.

In some embodiments, the antibody or antigen-binding fragment thereof further comprises a light chain constant region comprising an amino acid sequence of SEQ ID NO:33.

In other embodiments, the antibody or antigen-binding fragment thereof further comprises a heavy chain Fc region comprising an amino acid sequence of SEQ ID NO:35.

In yet another embodiment, the antibody or antigen-binding fragment thereof further comprises a light chain constant region comprising an amino acid sequence of SEQ ID NO:33; and a heavy chain Fc region comprising an amino acid sequence of SEQ ID NO:35.

In some embodiments, the antibody or antigen-binding fragment thereof comprises a light chain comprising an amino acid sequence of SEQ ID NO:5.

In certain embodiments, the antibody or antigen-binding fragment thereof, when bound to Nectin-4, binds to at least one of residues 31-346 within an amino acid sequence of SEQ ID NO:1. In some embodiments, the antibody or antigen-binding fragment thereof, when bound to Nectin-4, binds to at least one of residues 31-150 within an amino acid sequence of SEQ ID NO:1. In certain embodiments, the antibody or antigen-binding fragment thereof, when bound to Nectin-4, binds to at least one of residues 1-150 within an amino acid sequence of SEQ ID NO:1.

In one embodiment, the epitope of human Nectin-4 is distinct from the Nectin-4 ligand binding site.

In one aspect, provided herein is an antibody or antigen-binding fragment thereof that binds to an epitope of human Nectin-4, wherein the antibody or antigen-binding fragment thereof binds specifically to a cell expressing Nectin-4.

In one embodiment, the antibody or the antibody or antigen-binding fragment thereof that binds to an epitope of human Nectin-4 is used to assess Nectin-4 expression in a tissue sample from a subject suspected of having cancer, comprising: (a) contacting said tissue sample with the antibody or antigen binding fragment thereof; (b) detecting the binding of said antibody or antigen binding fragment thereof to said tissue sample; and (c) determining the expression of Nectin-4 in the tissue sample, wherein the expression level of Nectin-4 in the tissue sample is compared with a reference expression level of Nectin-4.

In certain embodiments, the antibody is a monoclonal antibody. In some embodiments, the antibody is a humanized, human, or chimeric antibody. In another embodiment, the humanized antibody is a deimmunized antibody or a composite human antibody. In certain embodiments, the antibody is a humanized antibody. In specific embodiments, the antibody is a humanized antibody that specifically binds human Nectin-4.

In certain embodiments, the antibody or antigen-binding fragment thereof is a Fab, a Fab', a F(ab')2, a Fv, a scFv, a dsFv, a diabody, a triabody, or a tetrabody. In some embodiments, the antibody or antigen-binding fragment thereof is a multispecific antibody formed from antibody fragments.

In some embodiments, the antibody or antigen-binding fragment thereof is conjugated to an agent. In one embodiment, the agent is a radioisotope, a metal chelator, an enzyme, a fluorescent compound, a bioluminescent compound, or a chemiluminescent compound.

Also provided herein is a composition comprising an antibody or antigen-binding fragment thereof provided herein. In certain embodiments, the composition further comprises a pharmaceutically acceptable carrier.

Also provided herein is a polynucleotide comprising nucleotide sequences encoding a VH, a VL, or both a VH and a VL of an antibody provided herein.

The present disclosure also provides, in certain embodiments, a polynucleotide comprising nucleotide sequences encoding a heavy chain, a light chain, or both a heavy chain and a light chain of an antibody provided herein.

In certain embodiments, the polynucleotide is operably linked to a promoter.

Also provided herein is a population of polynucleotides comprising: (a) a first polynucleotide comprising nucleotide sequences encoding a VH or a heavy chain of an antibody provided herein, and (b) a second polynucleotide comprising nucleotide sequences encoding a VL or a light chain of an antibody provided herein. In certain embodiments, the first polynucleotide is operably linked to a first promoter, and the second polynucleotide is operably linked to a second promoter.

Also provided herein is a vector comprising a polynucleotide provided herein.

The present disclosure also provides, in certain embodiments, a population of vectors comprising: (a) a first vector comprising nucleotide sequences encoding a VH or a heavy chain of an antibody provided herein, and (b) a second vector comprising nucleotide sequences encoding a VL or a light chain of an antibody provided herein.

The present disclosure further provides, in certain embodiments, a population of vectors comprising: (a) a first vector comprising nucleotide sequences encoding a VH or a heavy chain of an antibody provided herein operably linked to a first promoter, and (b) a second vector comprising nucleotide sequences encoding a VL or a light chain of an antibody provided herein operably linked to a second promoter.

The present disclosure provides, in certain embodiments, a cell comprising a polynucleotide or a population of polynucleotides provided herein.

The present disclosure also provides, in certain embodiments, a cell comprising a vector or a population of vectors provided herein.

The present disclosure further provides, in certain embodiments, an isolated cell producing an antibody or antigen-binding fragment thereof provided herein.

Also provided herein is a population of cells comprising: (a) a first host cell comprising a polynucleotide comprising nucleotide sequences encoding a VH or a heavy chain of an antibody provided herein, and (b) a second host cell comprising a polynucleotide comprising nucleotide sequences encoding a VL or a light chain of an antibody provided herein.

Further provided herein is a population of cells comprising: (a) a first host cell comprising a polynucleotide comprising nucleotide sequences encoding a VH or a heavy chain of an antibody provided herein operably linked to a first promoter, and (b) a second host cell comprising a polynucleotide comprising nucleotide sequences encoding a VL or a light chain of an antibody provided herein operably linked to a second promoter.

Also provided herein is a kit comprising an antibody or antigen-binding fragment thereof provided herein.

Also provided herein is a method of making an antibody or antigen-binding fragment thereof that specifically binds to an epitope of human Nectin-4. In certain embodiments, the method comprises culturing a cell provided herein to express the antibody or antigen-binding fragment thereof. In other embodiments, the method comprises expressing a polynucleotide provided herein. In one embodiment, the epitope of human Nectin-4 is distinct from the Nectin-4 ligand binding site.

6. BRIEF DESCRIPTION OF THE FIGURES

Figure 13:
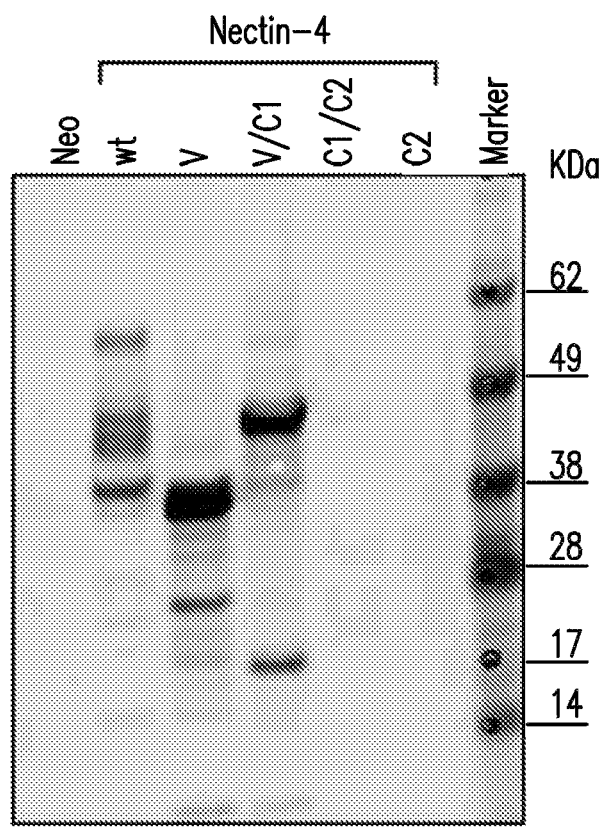
Figure 13:
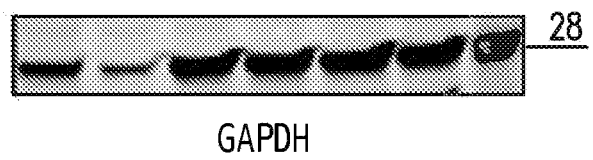

FIG. 13 depicts the results of a Western blotting experiment showing that M22-321b41.1 antibody recognized a protein band containing the V fragment/domain (amino acid residues 1-150) of Nectin-4. In the upper panel, M22-321b41.1 antibody was tested in a Western blot assay against cell lysates expressing wild type full length (wt), V fragment/domain (V), V and C1 fragment/domain (V/C1), C1 and C2 fragment/domain, C2 fragment/domain, and negative control (neo). In the lower panel, blotting of GAPDH was used as a loading control.

7. DETAILED DESCRIPTION

Binding proteins, such as antibodies that bind to Nectin-4, including human Nectin-4, are provided herein. In one embodiment, the Nectin-4 antibodies bind to human Nectin-4. In some embodiments, the binding of Nectin-4 antibodies to Nectin-4 is assayed in vitro. In other embodiments, the binding of Nectin-4 antibodies to Nectin-4 is assayed ex vivo. In certain embodiments, assays include immunohistochemistry (IHC) assays, fluorescence activated cell sorting (FACS) assays, ELISA, immunoblotting (e.g. western blotting, dot blotting, or in-cell western blotting), and other immunoassays.

In specific embodiments, the binding proteins, such as antibodies that bind to Nectin-4, provided herein share the common feature of competing with each other for the binding of Nectin-4. This competitive inhibition can indicate that each antibody binds to the same region of Nectin-4 (e.g., the same epitope), thereby asserting similar effects. In certain embodiments, anti-Nectin-4 antibodies provided herein include humanized anti-Nectin-4 antibodies, such as those derived from or based on antibody M22-321b41.1. In other embodiments, anti-Nectin-4 antibodies provided herein compete for binding with an antibody derived from or based on M22-321b41.1. In some embodiments, the anti-Nectin-4 antibodies have CDR sequences as described in Table 1. In certain embodiments, the anti-Nectin-4 antibodies bind to a specific domain of human Nectin-4 (e.g., residues 31-346, 1-150, or 31-150 within an amino acid sequence of SEQ ID NO:1). Moreover, such binding can be largely attributed to particular amino acid residues within the region, which comprise the epitope recognized by the anti-Nectin-4 antibodies described herein. Taken together, the results described herein demonstrate that the effects observed for an anti-Nectin-4 antibody that is derived from or based on M22-321b41.1, including an antibody having one or more CDRs described in Table 1, can be extrapolated to other anti-Nectin-4 antibodies described herein having the same or similar epitope specificity (e.g., the same or similar CDRs).

In some embodiments of the present disclosure, the binding proteins such as anti-Nectin-4 antibodies may comprise immunoglobulin variable regions which comprise one or more CDRs as described in Table 1. In such binding proteins (e.g., anti-Nectin-4 antibodies), the CDRs may be joined with one or more scaffold regions or framework regions (FRs) such as those described in Table 2, which orient(s) the CDR(s) such that the proper antigen binding properties of the CDR(s) is achieved. Such binding proteins, including anti-Nectin-4 antibodies as described herein, can bind to Nectin-4 in various assays.

7.1 General Techniques

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual (3d ed. 2001); Current Protocols in Molecular Biology (Ausubel et al. eds., 2003); Therapeutic Monoclonal Antibodies: From Bench to Clinic (An ed. 2009); Monoclonal Antibodies: *Methods and Protocols* (Albitar ed. 2010); and *Antibody Engineering* Vols 1 and 2 (Kontermann and Dithel eds., 2d ed. 2010).

7.2 Terminology

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications, and other publications are incorporated by reference in their entirety. In the event that any description of terms set forth conflicts with any document incorporated herein by reference, the description of term set forth below shall control.

The terms "Nectin-4," "Nectin-4 polypeptide," or "Nectin-4 protein" encompasses a polypeptide ("polypeptide" and "protein" are used interchangeably herein), including any native polypeptide, from any vertebrate source, including mammals such as primates (e.g., humans and cynomolgus monkeys (cynos)), dogs, and rodents (e.g., mice and rats), unless otherwise indicated. In certain embodiments, the terms include "related Nectin-4 polypeptides," including SNP variants thereof. The term "Nectin-4" also encompasses "full-length," unprocessed Nectin-4 as well as any form of Nectin-4 that results from processing in the cell. In some embodiments, the Nectin-4 has an amino acid sequence of SEQ ID NO:1. GenBank™ accession number NM_030916 (mRNA), NG_028109 (genomic DNA), Gene ID 81607 (gene), NP_112178 (pre-cursor amino acid sequences) provides other exemplary human Nectin-4 nucleic acid or amino acid sequences. An exemplary human Nectin-4 amino acid sequence is provided below:

(SEQ ID NO: 1)
MPLSLGAEMWGPEAWLLLLLLLASFTGRCPAGELETSDVVTVVLGQD

AKLPCFYRGDSGEQVGQVAWARVDAGEGAQELALLHSKYGLHVSPAY

EGRVEQPPPPRNPLDGSVLLRNAVQADEGEYECRVSTFPAGSFQARL

RLRVLVPPLPSLNPGPALEEGQGLTLAASCTAEGSPAPSVTWDTEVK

-continued
GTTSSRSFKHSRSAAVTSEFHLVPSRSMNGQPLTCVVSHPGLLQDQR

ITHILHVSFLAEASVRGLEDQNLWHIGREGAMLKCLSEGQPPPSYNW

TRLDGPLPSGVRVDGDTLGFPPLTTEHSGIYVCHVSNEFSSRDSQVT

VDVLDPQEDSGKQVDLVSASVVVVGVIAALLFCLLVVVVVLMSRYHR

RKAQQMTQKYEEELTLTRENSIRRLHSHHTDPRSQPEESVGLRAEGH

PDSLKDNSSCSVMSEEPEGRSYSTLTTVREIETQTELLSPGSGRAEE

EEDQDEGIKQAMNHFVQENGTLRAKPTGNGIYINGRGHLV

GenBank™ accession number NM_030916 provides one exemplary human Nectin-4 nucleic acid sequence:

(SEQ ID NO: 36)
atgcccctgtccctgggagccgagatgtgggggcctgaggcctggct gctgctgctgctactgctggcatcatttacaggccggtgccccgcgg gtgagctggagacctcagacgtggtaactgtggtgctgggccaggac gcaaaactgccctgcttctaccgaggggactccggcgagcaagtggg gcaagtggcatgggctcgggtggacgcgggcgaaggcgcccaggaac tagcgctactgcactccaaatacgggcttcatgtgagcccggcttac gagggccgcgtggagcagccgccgcccccacgcaacccctggacgg ctcagtgctcctgcgcaacgcagtgcaggcggatgagggcgagtacg agtgccgggtcagcaccttccccgccggcagcttccaggcgcggctg cggctccgagtgctggtgcctccctgccctcactgaatcctggtcc agcactagaagagggccagggcctgaccctggcagcctcctgcacag ctgagggcagcccagccccagcgtgacctgggacacggaggtcaaa ggcacaacgtccagccgttccttcaagcactcccgctctgctgccgt cacctcagagttccacttggtgcctagccgcagcatgaatgggcagc cactgacttgtgtggtgtcccatcctggcctgctccaggaccaaagg atcacccacatcctccacgtgtccttccttgctgaggcctctgtgag gggcctgaagaccaaaatctgtggcacattggcagagaaggagcta tgctcaagtgcctgagtgaagggcagcccctccctcatacaactgg acacggctggatgggcctctgcccagtggggtacgagtggatgggga cactttgggctttcccccactgaccactgagcacagcggcatctacg tctgccatgtcagcaatgagttctcctcaagggattctcaggtcact gtggatgttcttgaccccccaggaagactctgggaagcaggtggacct agtgtcagcctcggtggtggtggtgggtgtgatcgccgcactcttgt tctgccttctggtggtggtggtggtgctcatgtcccgataccatcgg cgcaaggcccagcagatgacccagaaatatgaggaggagctgaccct gaccagggagaactccatccggaggctgcattcccatcacacggacc ccaggagccagccggaggagagtgtagggctgagagccgagggccac cctgatagtctcaaggacaacagtagctgctctgtgatgagtgaaga gcccgagggccgcagttactccacgctgaccacggtgagggagatag aaacacagactgaactgctgtctccaggctctgggcgggccgaggag -continued

```
gaggaagatcaggatgaaggcatcaaacaggccatgaaccattttgt tcaggagaatgggaccctacgggccaagcccacgggcaatggcatct acatcaatgggcggggacacctggtctga
```

GenBank™ accession number AF472510, NM_027893, XM_203738, NM_001122680 provides exemplary mouse Nectin-4 nucleic acid and an amino acid sequences; GenBank™ accession number XM_005541220 and XM_005541223 provides exemplary monkey Nectin-4 nucleic acid and an amino acid sequences "Related Nectin-4 polypeptides" include allelic variants (e.g., SNP variants); splice variants; fragments; derivatives; substitution, deletion, and insertion variants; fusion polypeptides; and interspecies homologs, which can retain Nectin-4 activity. As those skilled in the art will appreciate, an anti-Nectin-4 antibody provided herein can bind to a Nectin-4 polypeptide, a Nectin-4 polypeptide fragment, a Nectin-4 antigen, and/or a Nectin-4 epitope. An "epitope" may be part of a larger Nectin-4 antigen, which may be part of a larger Nectin-4 polypeptide fragment, which, in turn, may be part of a larger Nectin-4 polypeptide. Nectin-4 may exist in a native or denatured form. Nectin-4 polypeptides described herein may be isolated from a variety of sources, such as from human tissue types or from another source, or prepared by recombinant or synthetic methods. Orthologs to the Nectin-4 polypeptide are also well known in the art.

A "Nectin-4 ligand" refers to a molecule which binds or otherwise interacts with Nectin-4. Nectin-4 can have homophilic interactions with another Nectin-4 molecule and heterophilic interactions with other Nectin family proteins, such as Nectin-1, Nectin-2, and Nectin-3. Nectin-4 can also interaction with other surface adhesion molecules such as cadherins and other cell surface receptors, such as prolactin receptors. Nectin-4 can further interact with virus particles and viral proteins on viral particles, for example measles viruses and polioviruses. Therefore, Nectin-4 ligands can include Nectin-1, Nectin-2, Nectin-3, or Nectin-4 or the fragments of any of the Nectin family proteins. Nectin-4 ligands can also include domains or the full-length molecule of the other cell surface receptors such as cadherins or fragments thereof, or prolactin receptors or fragments thereof. Nectin-4 ligands can further include viral particles, viral capside proteins, viral surface proteins, and fragments of any of the viral proteins that can bind to Nectin-4. Non-limiting examples of Nectin-4 ligand besides the naturally occurring ligands described herein or known to a person skilled in the art include artificially generated ligands, for example ligands identified by screening a library of peptides for ones that can bind to Nectin-4.

The terms "Nectin-4 activity," and "Nectin signaling" means a biological effect or biological response induced by the binding of Nectin-4 ligand to Nectin-4, e.g., in vivo or in vitro. The terms also refers to similar effect or response induced by molecules that can mimic the function of a Nectin-4 ligand. Such Nectin-4 ligand mimetics induces a biological response or biological effects otherwise would result from Nectin-4 ligand binding.

The term "binding protein" refers to a protein comprising a portion (e.g., one or more binding regions such as CDRs) that binds to Nectin-4 and, optionally, a scaffold or framework portion (e.g., one or more scaffold or framework regions) that allows the binding portion to adopt a conformation that promotes binding of the binding protein to a Nectin-4 polypeptide, fragment, or epitope. Examples of such binding proteins include antibodies, such as a human antibody, a humanized antibody, a chimeric antibody, a recombinant antibody, a single chain antibody, a diabody, a triabody, a tetrabody, a Fab fragment, a F(ab')2 fragment, an IgD antibody, an IgE antibody, an IgM antibody, an IgG1 antibody, an IgG2 antibody, an IgG3 antibody, or an IgG4 antibody, and fragments thereof. The binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the binding protein as well as wholly synthetic scaffolds comprising, for example, a biocompatible polymer. See, e.g., Korndorfer et al., 2003, Proteins: Structure, Function, and Bioinformatics 53(1):121-29; and Roque et al., 2004, Biotechnol. Prog. 20:639-54. In addition, peptide antibody mimetics ("PAMs") can be used, as well as scaffolds based on antibody mimetics utilizing fibronectin components as a scaffold. In the context of the present disclosure, a binding protein is said to specifically bind or selectively bind to Nectin-4.

The term "antibody," "immunoglobulin," or "Ig" is used interchangeably herein, and is used in the broadest sense and specifically covers, for example, individual anti-Nectin-4 monoclonal antibodies (including full length or intact monoclonal antibodies), anti-Nectin-4 antibody compositions with polyepitopic or monoepitopic specificity, polyclonal or monovalent antibodies, multivalent antibodies, formed from at least two intact antibodies, single chain anti-Nectin-4 antibodies, and fragments of anti-Nectin-4 antibodies, as described below. An antibody can be human, humanized, chimeric and/or affinity matured, as well as an antibody from other species, for example, mouse and rabbit, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., *Antibody Engineering* (Borrebaeck ed., 2d ed. 1995); and Kuby, *Immunology* (3d ed. 1997). In specific embodiments, the specific molecular antigen can be bound by an antibody provided herein, including a Nectin-4 polypeptide, a Nectin-4 fragment, or a Nectin-4 epitope. Antibodies also include, but are not limited to, synthetic antibodies, recombinantly produced antibodies, camelized antibodies, intrabodies, anti-idiotypic (anti-Id) antibodies, and functional fragments (e.g., antigen-binding fragments such as Nectin-4-binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments such as Nectin-4-binding fragments) include single-chain Fvs (scFv), Fab fragments, F(ab') fragments, F(ab)$_2$ fragments, F(ab')$_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to a Nectin-4 antigen (e.g., one or more CDRs of an anti-Nectin-4 antibody). Such antibody fragments can be found in, for example, Harlow and Lane, *Antibodies: A Laboratory Manual* (1989); *Mol. Biology and Biotechnology: A Comprehensive Desk Reference* (Myers ed., 1995); Huston et al., 1993, Cell Biophysics 22:189-224; Plückthun and Skerra, 1989, Meth. Enzymol. 178:497-515; and Day, *Advanced Immunochemistry* (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule.

An "antigen" is a predetermined antigen to which an antibody can selectively bind. A target antigen may be a polypeptide, carbohydrate, nucleic acid, lipid, hapten, or other naturally occurring or synthetic compound. In some embodiments, the target antigen is a polypeptide.

The terms "antigen-binding fragment," "antigen-binding domain," "antigen-binding region," and similar terms refer to that portion of an antibody, which comprises the amino acid residues that interact with an antigen and confer on the binding agent its specificity and affinity for the antigen (e.g., the CDRs).

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as Nectin-4, is the affinity of the antibody or functional fragment for that epitope. The ratio of dissociation rate ($k_{off}$) to association rate ($k_{on}$) of an antibody to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent Nectin-4, come in contact with antibodies containing multiple binding sites, the interaction of antibody with antigen at one site will increase the probability of a reaction at a second site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The terms "antibodies that specifically bind to Nectin-4," "antibodies that specifically bind to a Nectin-4 epitope," and analogous terms are also used interchangeably herein and refer to antibodies that specifically bind to a Nectin-4 polypeptide, such as a Nectin-4 antigen, or fragment, or epitope (e.g., human Nectin-4 such as a human Nectin-4 polypeptide, antigen, or epitope). An antibody that specifically binds to Nectin-4 (e.g., human Nectin-4) may bind to the extracellular domain or peptide derived from the extracellular domain of Nectin-4. An antibody that specifically binds to a Nectin-4 antigen (e.g., human Nectin-4) may be cross-reactive with related antigens (e.g., cyno Nectin-4). In certain embodiments, an antibody that specifically binds to a Nectin-4 antigen does not cross-react with other antigens such as but not limited to Nectin-1, Nectin-2, and/or Nectin-3. An antibody that specifically binds to a Nectin-4 antigen can be identified, for example, by immunoassays, Biacore, or other techniques known to those of skill in the art.

An antibody which "binds an antigen of interest" (e.g., a target antigen such as Nectin-4) is one that binds the antigen with sufficient affinity such that the antibody is useful as a agent in targeting or detecting a cell or tissue expressing the antigen, and does not significantly cross-react with other proteins. In such embodiments, the extent of binding of the antibody to a "non-target" protein will be less than about 10% of the binding of the antibody to its particular target protein, for example, as determined by fluorescence activated cell sorting (FACS) analysis or RIA. With regard to the binding of an antibody to a target molecule, the term "specific binding," "specifically binds to," or "is specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "anti-Nectin-4 antibody" or "an antibody that binds to Nectin-4" includes an antibody that is capable of binding Nectin-4 with sufficient affinity such that the antibody is useful, for example, as a diagnostic agent in targeting Nectin-4. The term "specific binding," "specifically binds to," or "is specific for" a particular polypeptide or an epitope on a particular polypeptide target as used herein refers to binding where a molecule binds to a particular polypeptide or epitope on a particular polypeptide without substantially binding to any other polypeptide or polypeptide epitope. Provided here in is an anti-Nectin-4 antibody that specifically binds to Nectin-4. Also provided here in is an anti-Nectin-4 antibody that specifically binds to Nectin-4 over Nectin-1, Nectin-2, and/or Nectin-3.

An antibody binds specifically to a Nectin-4 antigen when it binds to a Nectin-4 antigen with higher affinity than to any cross-reactive antigen as determined using experimental techniques, such as radioimmunoassays (RIA) and enzyme linked immunosorbent assays (ELISAs). Typically a specific or selective reaction will be at least twice background signal or noise and may be more than 10 times background. See, e.g., *Fundamental Immunology* 332-36 (Paul ed., 2d ed. 1989) for a discussion regarding antibody specificity. Alternatively, specificity of an antibody can be determined qualitatively, for example in an IHC assay. In such an IHC assay, an antibody binds specifically to a Nectin-4 antigen or has specificity for a Nectin 4 antigen when the antibody binds to, e.g. immunohistochemically stains, cells expressing Nectin-4 but does not substantially bind to, e.g. does not substantially stain cells expressing no Nectin-4. As an example, an antibody does not substantially bind to, e.g. does not substantially stain, a cell in IHC when the antibody binds to, e.g. immunohistochemically stains, a cell at a level substantially similar to the level of binding seen with an immunoglobulin isotype control.

The terms "fully human antibody" or "human antibody" are used interchangeably herein and refer to an antibody that comprises a human variable region and, for example, a human constant region. In specific embodiments, the terms refer to an antibody that comprises a variable region and constant region of human origin. "Fully human" anti-Nectin-4 antibodies, in certain embodiments, can also encompass antibodies which bind Nectin-4 polypeptides and are encoded by nucleic acid sequences which are naturally occurring somatic variants of human germline immunoglobulin nucleic acid sequence. In a specific embodiment, the anti-Nectin-4 antibodies provided herein are fully human antibodies. The term "fully human antibody" includes antibodies having variable and constant regions corresponding to human germline immunoglobulin sequences as described by Kabat et al. (See Kabat et al. (1991) *Sequences of Proteins of Immunological Interest*, Fifth Edition, U.S. Department of Health and Human Services, NIH Publication No. 91-3242). Exemplary methods of producing fully human antibodies are provided, e.g., in the Examples herein, but any method known in the art may be used.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see e.g., Taylor, L. D. et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) *Sequences of Proteins of Immunological Interest*, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "compete" when used in the context of anti-Nectin-4 antibodies (e.g., antibodies and binding proteins that bind to Nectin-4 and compete for the same epitope or binding site on a target) means competition as determined by an assay in which the antibody (or binding fragment) thereof under study prevents or inhibits the specific binding of a reference molecule (e.g., a reference ligand or reference antigen-binding protein, such as a reference antibody) to a common antigen (e.g., Nectin-4 or a fragment thereof). Numerous types of competitive binding assays can be used to determine if a test antibody competes with a reference antibody for binding to Nectin-4 (e.g., human Nectin-4). Examples of assays that can be employed include solid phase direct or indirect RIA, solid phase direct or indirect enzyme immunoassay (EIA), sandwich competition assay (see, e.g., Stahli et al., 1983, Methods in Enzymology 9:242-53), solid phase direct biotin-avidin EIA (see, e.g., Kirkland et al., 1986, J. Immunol. 137:3614-19), solid phase direct labeled assay, solid phase direct labeled sandwich assay (see, e.g., Harlow and Lane, *Antibodies, A Laboratory Manual* (1988)), solid phase direct label RIA using 1-125 label (see, e.g., Morel et al., 1988, Mol. Immunol. 25:7-15), and direct labeled RIA (Moldenhauer et al., 1990, Scand. J. Immunol. 32:77-82). Typically, such an assay involves the use of a purified antigen (e.g., Nectin-4 such as human Nectin-4) bound to a solid surface, or cells bearing either of an unlabelled test antigen-binding protein (e.g., test anti-Nectin-4 antibody) or a labeled reference antigen-binding protein (e.g., reference anti-Nectin-4 antibody). Other exemplary competitive binding assays that can be used include ELISA, FACS, cell adhesion assays (for example as described in Humphries et al. Methods Mol Biol. 2009; 522:203-10), surface plasmon resonance (SPR), or other competitive binding assays known to a person skilled in the art. Competitive inhibition may be measured by determining the amount of label bound to the solid surface or cells in the presence of the test antigen-binding protein. Usually the test antigen-binding protein is present in excess. Antibodies identified by competition assay (competing antibodies) include antibodies binding to the same epitope as the reference antibody and/or antibodies binding to an adjacent epitope sufficiently proximal to the epitope bound by the reference for antibodies steric hindrance to occur. Additional details regarding methods for determining competitive binding are described herein. Usually, when a competing antibody protein is present in excess, it will inhibit specific binding of a reference antibody to a common antigen by at least 30%, for example 40%, 45%, 50%, 55%, 60%, 65%, 70%, or 75%. In some instance, binding is inhibited by at least 80%, 85%, 90%, 95%, 96%, 97%, 98%, 99%, or more.

As used herein, the term "in combination" in the context of the administration of other therapies refers to the use of more than one therapy. The use of the term "in combination" does not restrict the order in which therapies are administered to a subject with an infection. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a Nectin-4-mediated disease. Any additional therapy can be administered in any order with the other additional therapies. In certain embodiments, the antibodies provided herein can be administered in combination with one or more therapies (e.g., therapies that are not the antibodies provided herein that are currently administered to prevent, treat, manage, and/or ameliorate a Nectin-4-mediated disease. Non-limiting examples of therapies that can be administered in combination with an antibody provided herein include analgesic agents, anesthetic agents, antibiotics, or immunomodulatory agents or any other agent listed in the *U.S. Pharmacopoeia* and/or *Physician's Desk Reference*.

An "isolated" antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 25%, 20%, 15%, 10%, 5%, or 1% (by dry weight) of heterologous protein (also referred to herein as a "contaminating protein"). In certain embodiments, when the antibody is recombinantly produced, it is substantially free of culture medium, e.g., culture medium represents less than about 20%, 15%, 10%, 5%, or 1% of the volume of the protein preparation. In certain embodiments, when the antibody is produced by chemical synthesis, it is substantially free of chemical precursors or other chemicals, for example, it is separated from chemical precursors or other chemicals that are involved in the synthesis of the protein. Accordingly such preparations of the antibody have less than about 30%, 25%, 20%, 15%, 10%, 5%, or 1% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al., 1951, J. Bio. Chem. 193: 265-75), such as 96%, 97%, 98%, or 99%, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step. In specific embodiments, antibodies provided herein are isolated.

A 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, *Basic and Clinical Immunology* 71 (Stites et al. eds., 8th ed. 1994).

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see, e.g., Kabat et al., *Sequences of Proteins of Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering as in Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHon and are well understood by a person of ordinary skill in the art.

An "intact" antibody is one comprising an antigen-binding site as well as a CL and at least heavy chain constant regions, CH1, CH2 and CH3. The constant regions may include human constant regions or amino acid sequence variants thereof. In certain embodiments, an intact antibody has one or more effector functions.

"Antibody fragments" comprise a portion of an intact antibody, such as the antigen-binding or variable region of the intact antibody. Examples of antibody fragments include, without limitation, Fab, Fab', F(ab')$_2$, and Fv fragments; diabodies and di-diabodies (see, e.g., Holliger et al., 1993, Proc. Natl. Acad. Sci. 90:6444-48; Lu et al., 2005, J. Biol. Chem. 280:19665-72; Hudson et al., 2003, Nat. Med. 9:129-34; WO 93/11161; and U.S. Pat. Nos. 5,837,242 and 6,492, 123); single-chain antibody molecules (see, e.g., U.S. Pat.

Nos. 4,946,778; 5,260,203; 5,482,858; and 5,476,786); dual variable domain antibodies (see, e.g., U.S. Pat. No. 7,612,181); single variable domain antibodies (sdAbs) (see, e.g., Woolven et al., 1999, Immunogenetics 50: 98-101; and Streltsov et al., 2004, Proc Natl Acad Sci USA. 101:12444-49); and multispecific antibodies formed from antibody fragments.

A "functional fragment," "binding fragment," or "antigen-binding fragment" of a therapeutic antibody will exhibit at least one if not some or all of the biological functions attributed to the intact antibody, the function comprising at least binding to the target antigen (e.g., a Nectin-4 binding fragment or fragment that binds to Nectin-4).

The term "fusion protein" as used herein refers to a polypeptide that comprises an amino acid sequence of an antibody and an amino acid sequence of a heterologous polypeptide or protein (e.g., a polypeptide or protein not normally a part of the antibody (e.g., a non-anti-Nectin-4 antigen-binding antibody). The term "fusion" when used in relation to Nectin-4 or to an anti-Nectin-4 antibody refers to the joining of a peptide or polypeptide, or fragment, variant, and/or derivative thereof, with a heterologous peptide or polypeptide. In certain embodiments, the fusion protein retains the biological activity of the Nectin-4 or anti-Nectin-4 antibody. In certain embodiments, the fusion protein comprises a Nectin-4 antibody VH region, VL region, VH CDR (one, two, or three VH CDRs), and/or VL CDR (one, two, or three VL CDRs), wherein the fusion protein binds to a Nectin-4 epitope, a Nectin-4 fragment, and/or a Nectin-4 polypeptide.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and ε contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains. Light chain amino acid sequences are well known in the art. A light chain can be a human light chain.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "monoclonal antibody" as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell, wherein the antibody binds to only a Nectin-4 epitope as determined, for example, by ELISA or other antigen-binding or competitive binding assay known in the art. The term "monoclonal" is not limited to any particular method for making the antibody. For example, the monoclonal antibodies useful in the present disclosure may be prepared by the hybridoma methodology first described by Kohler et al., 1975, Nature 256:495, or may be made using recombinant DNA methods in bacterial or eukaryotic animal or plant cells (see, e.g., U.S. Pat. No. 4,816,567). The "monoclonal antibodies" may also be isolated from phage antibody libraries using the techniques described in Clackson et al., 1991, Nature 352:624-28 and Marks et al., 1991, J. Mol. Biol. 222:581-97, for example. Other methods for the preparation of clonal cell lines and of monoclonal antibodies expressed thereby are well known in the art. See, e.g., *Short Protocols in Molecular Biology* (Ausubel et al. eds., 5th ed. 2002). Exemplary methods of producing monoclonal antibodies are provided in the Examples herein.

The term "native" when used in connection with biological materials such as nucleic acid molecules, polypeptides, host cells, and the like, refers to those which are found in nature and not manipulated, modified, and/or changed (e.g., isolated, purified, selected) by a human being.

The antibodies provided herein can include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55).

"Humanized" forms of nonhuman (e.g., murine) antibodies are chimeric antibodies that include human immunoglobulins (e.g., recipient antibody) in which the native CDR residues are replaced by residues from the corresponding CDR of a nonhuman species (e.g., donor antibody) such as mouse, rat, rabbit, or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., 1986, Nature 321:522-25; Riechmann et al., 1988, Nature 332:323-29; Presta, 1992, Curr. Op. Struct. Biol. 2:593-96; Carter et al., 1992, Proc. Natl. Acad. Sci. USA 89:4285-89; U.S. Pat. Nos. 6,800,738; 6,719,971; 6,639,055; 6,407,213; and 6,054,297.

A "human antibody" is one that possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries (Hoogenboom and Winter, 1991, J. Mol. Biol. 227:381; Marks et al., 1991, J. Mol. Biol. 222:581) and yeast display libraries (Chao et al., 2006, Nature Protocols 1: 755-68). Also available for the preparation of human monoclonal antibodies are methods described in Cole et al., *Monoclonal Antibodies and Cancer Therapy* 77 (1985); Boerner et al., 1991, J. Immunol. 147(1):86-95; and van Dijk and van de Winkel, 2001, Curr. Opin. Pharmacol. 5: 368-74. Human antibodies can be prepared by administering the antigen to a transgenic animal that has been modified to produce such antibodies in response to antigenic challenge, but whose endogenous loci have been disabled, e.g., mice (see, e.g., Jakobovits, 1995, Curr. Opin. Biotechnol. 6(5): 561-66; Bruggemann and Taussing, 1997, Curr. Opin. Biotechnol. 8(4):455-58; and U.S. Pat. Nos. 6,075,181 and 6,150,584 regarding XENOMOUSE' technology). See also, for example, Li et al., 2006, Proc. Natl. Acad. Sci. USA 103:3557-62 regarding human antibodies generated via a human B-cell hybridoma technology.

A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., 1997, J. Biol. Chem. 252:6609-16; Kabat, 1978, Adv. Prot. Chem. 32:1-75). CDR region sequences also have been defined structurally by Chothia as those residues that are not part of the conserved β-sheet framework, and thus are able to adapt different conformations (Chothia and Lesk, 1987, J. Mol. Biol. 196:901-17). Both terminologies are well recognized in the art. CDR region sequences have also been defined by AbM, Contact, and IMGT. The positions of CDRs within a canonical antibody variable region have been determined by comparison of numerous structures (Al-Lazikani et al., 1997, J. Mol. Biol. 273:927-48; Morea et al., 2000, Methods 20:267-79). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra). Such nomenclature is similarly well known to those skilled in the art.

The term "hypervariable region," "HVR," or "HV," when used herein refers to the regions of an antibody variable region that are hypervariable in sequence and/or form structurally defined loops. Generally, antibodies comprise six hypervariable regions, three in the VH (H1, H2 and H3) and three in the VL (L1, L2, L3). A number of hypervariable region delineations are in use and are encompassed herein. The Kabat Complementarity Determining Regions (CDRs) are based on sequence variability and are the most commonly used (see, e.g., Kabat et al., supra). Chothia refers instead to the location of the structural loops (see, e.g., Chothia and Lesk, 1987, J. Mol. Biol. 196:901-17). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., *Antibody Engineering Vol.* 2 (Kontermann and Dithel eds., 2d ed. 2010)). The "contact" hypervariable regions are based on an analysis of the available complex crystal structures. The residues from each of these hypervariable regions or CDRs are noted below.

Recently, a universal numbering system has been developed and widely adopted, ImMunoGeneTics (IMGT) Information System® (Lafranc et al., 2003, Dev. Comp. Immunol. 27(1):55-77). IMGT is an integrated information system specializing in immunoglobulins (IG), T-cell receptors (TCR), and major histocompatibility complex (MEW) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Plückthun, 2001, J. Mol. Biol. 309: 657-70. Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra).

|  | IMGT | Kabat | AbM | Chothia | Contact |
| --- | --- | --- | --- | --- | --- |
| $V_H$ CDR1 | 27-38 | 31-35 | 26-35 | 26-32 | 30-35 |
| $V_H$ CDR2 | 56-65 | 50-65 | 50-58 | 53-55 | 47-58 |
| $V_H$ CDR3 | 105-117 | 95-102 | 95-102 | 96-101 | 93-101 |
| $V_L$ CDR1 | 27-38 | 24-34 | 24-34 | 26-32 | 30-36 |
| $V_L$ CDR2 | 56-65 | 50-56 | 50-56 | 50-52 | 46-55 |
| $V_L$ CDR3 | 105-117 | 89-97 | 89-97 | 91-96 | 89-96 |

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35A (H1), 50-65 or 49-65 (H2), and 93-102, 94-102, or 95-102 (H3) in the VH. As used herein, the terms "HVR" and "CDR" are used interchangeably.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

An "affinity matured" antibody is one with one or more alterations (e.g., amino acid sequence variations, including changes, additions, and/or deletions) in one or more HVRs thereof which result in an improvement in the affinity of the antibody for antigen, compared to a parent antibody which does not possess those alteration(s). Affinity matured antibodies can have nanomolar or even picomolar affinities for the target antigen. Affinity matured antibodies are produced by procedures known in the art. For review, see Hudson and Souriau, 2003, Nature Medicine 9:129-34; Hoogenboom, 2005, Nature Biotechnol. 23:1105-16; Quiroz and Sinclair, 2010, Revista Ingeneria Biomedia 4:39-51.

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a RIA, for example, performed with the Fab version of an antibody of interest and its antigen (Chen et al., 1999, J. Mol Biol 293:865-81). The $K_D$ or $K_D$ value may also be measured by using surface plasmon resonance assays by Biacore®, using, for example, a Biacore®TM-2000 or a Biacore®TM-3000, or by biolayer interferometry using, for example, the Octet®QK384 system. An "on-rate" or "rate of association" or "association rate" or "$k_{on}$" may also be determined with the same surface plasmon resonance or biolayer interferometry techniques described above using, for example, a Biacore®TM-2000 or a Biacore®TM-3000, or the Octet®QK384 system.

The phrase "substantially similar" or "substantially the same" denotes a sufficiently high degree of similarity between two numeric values or signals (e.g. IHC staining signals) from two images (e.g., one associated with an antibody of the present disclosure and the other associated with a reference antibody) such that one of skill in the art would consider the difference between the two values or the two images to be of little or no biological and/or statistical significance within the context of the biological characteristic measured by the values (e.g., $K_D$ values). For example, the difference between the two values may be less than about 50%, less than about 40%, less than about 30%, less than about 20%, less than about 10%, or less than about 5%, as a function of the value for the reference antibody.

The phrase "substantially increased," "substantially reduced," or "substantially different," as used herein, denotes a sufficiently high degree of difference between two numeric values or signals (e.g. IHC staining signals) from two images (e.g., one associated with an antibody of the present disclosure and the other associated with a reference antibody) such that one of skill in the art would consider the difference between the two values or the two images to be of statistical significance within the context of the biological characteristic measured by the values. For example, the difference between said two values can be greater than about 10%, greater than about 20%, greater than about 30%, greater than about 40%, or greater than about 50%, as a function of the value for the reference antibody.

Antibody "effector functions" refer to those biological activities attributable to the Fc region (e.g., a native sequence Fc region or amino acid sequence variant Fc region) of an antibody, and vary with the antibody isotype. Examples of antibody effector functions include: C1q binding; CDC; Fc receptor binding; ADCC; phagocytosis; and B cell activation.

The term "effective amount" as used herein refers to the amount of an antibody or pharmaceutical composition provided herein which is sufficient to result in the desired outcome.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; etc. Such effector functions generally require the Fc region to be combined with a binding region or binding domain (e.g., an antibody variable region or domain) and can be assessed using various assays as disclosed.

A "native sequence Fc region" comprises an amino acid sequence identical to the amino acid sequence of an Fc region found in nature, and not manipulated, modified, and/or changed (e.g., isolated, purified, selected, including or combining with other sequences such as variable region sequences) by a human. Native sequence human IgG1 Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof. For example, a native human IgG1 Fc region amino acid sequence is provided below (SEQ ID NO:35).

A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith.

The term "variant" when used in relation to Nectin-4 or to an anti-Nectin-4 antibody may refer to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified sequence. For example, a Nectin-4 variant may result from one or more (such as, for example, about 1 to about 25, about 1 to about 20, about 1 to about 15, about 1 to about 10, or about 1 to about 5) changes to an amino acid sequence of a native Nectin-4. Also by way of example, a variant of an anti-Nectin-4 antibody may result from one or more (such as, for example, about 1 to about 25, about 1 to about 20, about 1 to about 15, about 1 to about 10, or about 1 to about 5) changes to an amino acid sequence of a native or previously unmodified anti-Nectin-4 antibody. Variants may be naturally occurring, such as allelic or splice variants, or may be artificially constructed. Polypeptide variants may be prepared from the corresponding nucleic acid molecules encoding the variants. In specific embodiments, the Nectin-4 variant or anti-Nectin-4 antibody variant at least retains specific binding to Nectin-4 in comparison to a reference antibody. In certain embodiments, the variant is encoded by a single nucleotide polymorphism (SNP) variant of a nucleic acid molecule that encodes Nectin-4 or anti-Nectin-4 antibody VH or VL regions or subregions, such as one or more CDRs.

The term "vector" refers to a substance that is used to carry or include a nucleic acid sequence, including for example, a nucleic acid sequence encoding an anti-Nectin-4 antibody as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product (e.g., an anti-Nectin-4 antibody as described herein), and it is further understood that expression levels can be optimized to obtain sufficient expression using methods well known in the art.

A Nectin-4 polypeptide "extracellular domain" or "ECD" refers to a form of the Nectin-4 polypeptide that is essentially free of the transmembrane and cytoplasmic domains. For example, a Nectin-4 polypeptide ECD may have less than 1% of such transmembrane and/or cytoplasmic domains and can have less than 0.5% of such domains.

The term "identity" refers to a relationship between the sequences of two or more polypeptide molecules or two or more nucleic acid molecules, as determined by aligning and comparing the sequences. "Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALIGN (DNAStar, Inc.) software. Those skilled in the art can determine appropriate parameters for aligning sequences, including any algorithms needed to achieve maximal alignment over the full length of the sequences being compared.

A "modification" of an amino acid residue/position refers to a change of a primary amino acid sequence as compared to a starting amino acid sequence, wherein the change results from a sequence alteration involving said amino acid residue/position. For example, typical modifications include substitution of the residue with another amino acid (e.g., a conservative or non-conservative substitution), insertion of one or more (e.g., generally fewer than 5, 4, or 3) amino acids adjacent to said residue/position, and/or deletion of said residue/position.

An "epitope" is the site on the surface of an antigen molecule to which a single antibody molecule binds, such as a localized region on the surface of an antigen, such as a Nectin-4 polypeptide, a Nectin-4 polypeptide fragment, that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits an antibody response in an animal. An epitope having antigenic activity is a portion of a polypeptide to which an antibody binds as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. Induced epitopes are formed when the three dimensional structure of the protein is in an altered conformation, such as following activation or binding of another protein or ligand. In certain embodiments, a Nectin-4 epitope is a three-dimensional surface feature of a Nectin-4 polypeptide. In other embodiments, a Nectin-4 epitope is linear feature of a Nectin-4 polypeptide. Generally an antigen has several or many different epitopes and may react with many different antibodies.

An antibody binds "an epitope," "essentially the same epitope," or "the same epitope" as a reference antibody, when the two antibodies recognize identical, overlapping, or adjacent epitopes in a three-dimensional space. The most widely used and rapid methods for determining whether two antibodies bind to identical, overlapping, or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies is measured using radioactive, fluorescent, or enzyme labels.

"Epitope mapping" is the process of identifying the binding sites, or epitopes, of antibodies on their target antigens. "Epitope binning" is the process of grouping antibodies based on the epitopes they recognize. More particularly, epitope binning comprises methods and systems for discriminating the epitope recognition properties of different antibodies, using competition assays combined with computational processes for clustering antibodies based on their epitope recognition properties and identifying antibodies having distinct binding specificities.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™. The term "carrier" can also refer to a diluent, adjuvant (e.g., Freund's adjuvant (complete or incomplete)), excipient, or vehicle. Such carriers, including pharmaceutical carriers, can be sterile liquids, such as water and oils, including those of petroleum, animal, vegetable, or synthetic origin, such as peanut oil, soybean oil, mineral oil, sesame oil, and the like. Water is an exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like. Oral compositions, including formulations, can include standard carriers such as pharmaceutical grades of mannitol, lactose, starch, magnesium stearate, sodium saccharine, cellulose, magnesium carbonate, etc. Examples of suitable pharmaceutical carriers are described in Remington and Gennaro, *Remington's Pharmaceutical Sciences* (18th ed. 1990). Compositions, including pharmaceutical compounds, may contain an anti-Nectin-4 antibody, for example, in isolated or purified form, together with a suitable amount of carriers.

The term "pharmaceutically acceptable" as used herein means being approved by a regulatory agency of the Federal or a state government, or listed in *United States Pharmacopeia, European Pharmacopeia*, or other generally recognized Pharmacopeia for use in animals, and more particularly in humans.

"Polyclonal antibodies" as used herein refer to an antibody population generated in an immunogenic response to a protein having many epitopes and thus includes a variety of different antibodies directed to the same or different epitopes within the protein. Methods for producing polyclonal antibodies are known in the art (See, e.g., *Short Protocols in Molecular Biology* (Ausubel et al. eds., 5th ed. 2002)).

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces an anti-Nectin-4 antibody of the present disclosure may include a parent hybridoma cell, as well as bacterial and eukaryotic host cells into which nucleic acids encoding the antibodies have been introduced. Suitable host cells are disclosed below.

Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

The term "recombinant antibody" refers to an antibody that is prepared, expressed, created, or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor et al., 1992, Nucl. Acids Res. 20:6287-95), or antibodies prepared, expressed, created, or isolated by any other means that involves splicing of immunoglobulin gene sequences to other DNA sequences. Such recombinant antibodies can have variable and constant regions, including those derived from human germline immunoglobulin sequences (See Kabat et al., supra). In certain embodiments, however, such recombinant antibodies may be subjected to in vitro mutagenesis (or, when an animal transgenic for human Ig sequences is used, in vivo somatic mutagenesis), thus the amino acid sequences of the VH and VL regions of the recombinant antibodies are sequences that, while derived from and related to human germline VH and VL sequences, may not naturally exist within the human antibody germline repertoire in vivo.

The terms "subject" and "patient" may be used interchangeably. As used herein, in certain embodiments, a subject is a mammal, such as a non-primate (e.g., cow, pig, horse, cat, dog, rat, etc.) or a primate (e.g., monkey and human). In specific embodiments, the subject is a human. In one embodiment, the subject is a mammal, e.g., a human, diagnosed with a condition or disorder provided herein. In another embodiment, the subject is a mammal, e.g., a human, at risk of developing a condition or disorder provided herein.

"Substantially all" refers to at least about 60%, at least about 65%, at least about 70%, at least about 75%, at least about 80%, at least about 85%, at least about 90%, at least about 95%, at least about 98%, at least about 99%, or about 100%.

The term "detectable probe" refers to a composition that provides a detectable signal. The term includes, without limitation, any fluorophore, chromophore, radiolabel, enzyme, antibody or antibody fragment, and the like, that provide a detectable signal via its activity.

The term "detectable agent" refers to a substance that can be used to ascertain the existence or presence of a desired molecule, such as an anti-Nectin-4 antibody as described herein, in a sample or subject. A detectable agent can be a substance that is capable of being visualized or a substance that is otherwise able to be determined and/or measured (e.g., by quantitation).

The term "diagnostic agent" refers to a substance administered to a subject that aids in the diagnosis of a disease, disorder, or conditions. Such substances can be used to reveal, pinpoint, and/or define the localization of a disease causing process. In certain embodiments, a diagnostic agent includes the anti-Nectin-4 antibody or a fragment thereof as described herein that when either alone or conjugated to a substance, and administered to a subject or contacted with a sample from a subject, aids in the diagnosis of a Nectin-4-mediated disease.

The term "encoding nucleic acid" or grammatical equivalents thereof as it is used in reference to nucleic acid molecule refers to a nucleic acid molecule in its native state or when manipulated by methods well known to those skilled in the art that can be transcribed to produce mRNA, which is then translated into a polypeptide and/or a fragment thereof. The antisense strand is the complement of such a nucleic acid molecule, and the encoding sequence can be deduced therefrom.

The term "excipient" refers to an inert substance which is commonly used as a diluent, vehicle, preservative, binder, or stabilizing agent, and includes, but is not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.), and polyols (e.g., mannitol, sorbitol, etc.). See, also, Remington and Gennaro, *Remington's Pharmaceutical Sciences* (18th ed. 1990), which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, Nectin-4 fragments or anti-Nectin-4 antibody fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, at least 225, at least 250, at least 275, at least 300, at least 325, at least 350, at least 375, at least 400, at least 425, at least 450, at least 475, at least 500, at least 525, or at least 550 contiguous amino acid residues of the amino acid sequence of a Nectin-4 polypeptide or an anti-Nectin-4 antibody. In a specific embodiment, a fragment of a Nectin-4 polypeptide or an anti-Nectin-4 antibody retains at least 1, at least 2, at least 3, or more functions of the polypeptide or antibody.

The terms "about" and "approximately" mean within 20%, within 15%, within 10%, within 9%, within 8%, within 7%, within 6%, within 5%, within 4%, within 3%, within 2%, within 1%, or less of a given value or range.

"Administer" or "administration" refers to the act of injecting or otherwise physically delivering a substance as it exists outside the body (e.g., an anti-Nectin-4 antibody as described herein) into a patient, such as by mucosal, intradermal, intravenous, intramuscular delivery, and/or any other method of physical delivery described herein or known in the art.

In the context of a polypeptide, the term "analog" as used herein refers to a polypeptide that possesses a similar or identical function as a Nectin-4 polypeptide, a fragment of a Nectin-4 polypeptide, or an anti-Nectin-4 antibody but does not necessarily comprise a similar or identical amino acid sequence of a Nectin-4 polypeptide, a fragment of a Nectin-4 polypeptide, or an anti-Nectin-4 antibody, or possess a similar or identical structure of a Nectin-4 polypeptide, a fragment of a Nectin-4 polypeptide, or an anti-Nectin-4 antibody. A polypeptide that has a similar amino acid sequence refers to a polypeptide that satisfies at least one of the followings: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a Nectin-4 polypeptide, a fragment of a Nectin-4 polypeptide, or an anti-Nectin-4 antibody described herein; (b) a polypeptide encoded by a nucleotide sequence that hybridizes under stringent conditions to a nucleotide sequence encoding a Nectin-4 polypeptide, a fragment of a Nectin-4 polypeptide, or an anti-Nectin-4 antibody (or VH or VL region thereof) described herein at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al., *Molecular Cloning: A Laboratory Manual* (2001); and Maniatis et al., *Molecular Cloning: A Laboratory Manual* (1982)); or (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a Nectin-4 polypeptide, a fragment of a Nectin-4 polypeptide, or an anti-Nectin-4 antibody (or VH or VL region thereof) described herein. A polypeptide with similar structure to a Nectin-4 polypeptide, a fragment of a Nectin-4 polypeptide, or an anti-Nectin-4 antibody described herein refers to a polypeptide that has a similar secondary, tertiary, or quaternary structure of a Nectin-4 polypeptide, a fragment of a Nectin-4 polypeptide, or an anti-Nectin-4 antibody described herein. The structure of a polypeptide can be determined by methods known to those skilled in the art, including but not limited to, X-ray crystallography, nuclear magnetic resonance, and crystallographic electron microscopy.

In the context of a polypeptide, the term "derivative" as used herein refers to a polypeptide that comprises an amino acid sequence of a Nectin-4 polypeptide, a fragment of a Nectin-4 polypeptide, or an antibody that binds to a Nectin-4 polypeptide which has been altered by the introduction of amino acid residue substitutions, deletions, or additions. The term "derivative" as used herein also refers to a Nectin-4 polypeptide, a fragment of a Nectin-4 polypeptide, or an antibody that binds to a Nectin-4 polypeptide which has been chemically modified, e.g., by the covalent attachment of any type of molecule to the polypeptide. For example, but not by way of limitation, a Nectin-4 polypeptide, a fragment of a Nectin-4 polypeptide, or an anti-Nectin-4 antibody may be chemically modified, e.g., by glycosylation, acetylation, pegylation, phosphorylation, amidation, derivatization by known protecting/blocking groups, proteolytic cleavage, chemical cleavage, formulation, metabolic synthesis of tunicamycin, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. Further, a derivative of a Nectin-4 polypeptide, a fragment of a Nectin-4 polypeptide, or an anti-Nectin-4 antibody may contain one or more non-classical amino acids. A polypeptide derivative possesses a similar or identical function as a Nectin-4 polypeptide, a fragment of a Nectin-4 polypeptide, or an anti-Nectin-4 antibody described herein.

The term "composition" is intended to encompass a product containing the specified ingredients (e.g., an antibody provided herein) in, optionally, the specified amounts.

As used herein, the terms "prevent," "preventing," and "prevention" refer to the total or partial inhibition of the development, recurrence, onset or spread of a Nectin-4-mediated disease and/or symptom related thereto, resulting from the administration of a therapy or combination of therapies provided herein (e.g., a combination of prophylactic or therapeutic agents, such as an antibody provided herein).

As used herein, the term "prophylactic agent" refers to any agent that can totally or partially inhibit the development, recurrence, onset or spread of a Nectin-4-mediated disease and/or symptom related thereto in a subject. In certain embodiments, the term "prophylactic agent" refers to an antibody provided herein. In certain other embodiments, the term "prophylactic agent" refers to an agent other than an antibody provided herein. In some embodiments, a prophylactic agent is an agent which is known to be useful to or has been or is currently being used to prevent a Nectin-4-mediated disease and/or a symptom related thereto or impede the onset, development, progression and/or severity of a Nectin-4-mediated disease and/or a symptom related thereto. In specific embodiments, the prophylactic agent is a fully human anti-Nectin-4 antibody, such as a fully human anti-Nectin-4 monoclonal antibody.

In certain embodiments, a "prophylactically effective serum titer" is the serum titer in a subject, such as a human, that totally or partially inhibits the development, recurrence, onset or spread of a Nectin-4-mediated disease and/or symptom related thereto in said subject.

A "Nectin-4-mediated disease" and "Nectin-4-mediated disorder" are used herein interchangeably and refer to any disease that is completely or partially caused by, is the result of, or correlates with Nectin-4. In certain embodiments, Nectin-4 is aberrantly (e.g., highly) expressed on the surface of a cell. In some embodiments, Nectin-4 may be aberrantly upregulated on a particular cell type. In other embodiments, normal, aberrant or excessive cell signaling is caused by binding of Nectin-4 to a Nectin-4 ligand. In some embodiments, Nectin-4-mediated disease is a disease in which Nectin-4 can be used as a biomarker in a subject, e.g. a human. In some embodiments, Nectin-4-mediated disease is a disease in which Nectin-4 expression can reflect disease progression or prognosis in a subject, e.g. a human. In certain embodiments, the Nectin-4 ligand is a Nectin-4 receptor, for example, that is expressed on the surface of a cell.

The term "serum titer" as used herein refers to an average serum titer in a population of least 10, at least 20, at least 30 or at least 40 subjects up to about 100, 1000 or more.

As used herein, the term "side effects" encompasses unwanted and adverse effects of a therapy (e.g., a prophylactic or therapeutic agent). Unwanted effects are not necessarily adverse. An adverse effect from a therapy (e.g., a prophylactic or therapeutic agent) might be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspnea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* ($60^{th}$ ed., 2006).

As used herein, the term "therapeutic agent" refers to any agent that can be used in the treatment, management or amelioration of a Nectin-4-mediated disease and/or a symptom related thereto. In certain embodiments, the term "therapeutic agent" refers to an antibody provided herein. In certain other embodiments, the term "therapeutic agent" refers to an agent other than an antibody provided herein. In some embodiments, a therapeutic agent is an agent which is known to be useful for, or has been or is currently being used for the treatment, management or amelioration of a Nectin-4-mediated disease or one or more symptoms related thereto.

The combination of therapies (e.g., use of prophylactic or therapeutic agents) which is more effective than the additive effects of any two or more single therapies. For example, a synergistic effect of a combination of prophylactic and/or therapeutic agents is more effective than the single agent alone and/or permits the use of lower dosages of one or more of the agents and/or less frequent administration of said agents to a subject with a Nectin-4-mediated disease. The ability to utilize lower dosages of prophylactic or therapeutic therapies and/or to administer said therapies less frequently reduces the toxicity associated with the administration of said therapies to a subject without reducing the efficacy of said therapies in the prevention, management, treatment or amelioration of a Nectin-4-mediated disease. In addition, a synergistic effect can result in improved efficacy of therapies in the prevention, or in the management, treatment or amelioration of a Nectin-4-mediated disease. Finally, synergistic effect of a combination of therapies (e.g., prophylactic or therapeutic agents) may avoid or reduce adverse or unwanted side effects associated with the use of any single therapy.

In certain embodiments, a "therapeutically effective serum titer" is the serum titer in a subject, such as a human, that reduces the severity, the duration and/or the symptoms associated with a Nectin-4-mediated disease in said subject.

As used herein, the term "therapy" refers to any protocol, method and/or agent that can be used in the prevention, management, treatment and/or amelioration of a Nectin-4-mediated disease. In certain embodiments, the terms "therapies" and "therapy" refer to a biological therapy, supportive therapy, and/or other therapies useful in the prevention, management, treatment and/or amelioration of a Nectin-4-mediated disease known to one of skill in the art such as medical personnel.

As used herein, the terms "treat," "treatment" and "treating" refer to the reduction or amelioration of the progression, severity, and/or duration of a Nectin-4-mediated disease resulting from the administration of one or more therapies (including, but not limited to, the administration of one or more prophylactic or therapeutic agents, such as an antibody provided herein).

As used herein, the terms "manage," "managing," and "management" refer to the beneficial effects that a subject derives from a therapy (e.g., a prophylactic or therapeutic agent), which does not result in a cure of a condition associated with Nectin-4. In certain embodiments, a subject is administered one or more therapies (e.g., prophylactic or therapeutic agents, such as an antibody described herein) to "manage" a condition or disorder described herein, one or more symptoms thereof, so as to prevent the progression or worsening of the condition or disorder.

As used herein, the terms "prevent," "preventing," and "prevention" refer to the total or partial inhibition of the development, recurrence, onset or spread of a Nectin-4-mediated disease and/or symptom related thereto, resulting from the administration of a therapy or combination of therapies provided herein (e.g., a combination of prophylactic or therapeutic agents, such as an antibody of the invention).

As used herein, "administer" or "administration" refers to the act of injecting or otherwise physically delivering a substance (e.g., an anti-Nectin-4 antibody provided herein or an antigen-binding fragment thereof) to a subject or a patient (e.g., human), such as by mucosal, topical, intradermal, parenteral, intravenous, subcutaneous, intramuscular delivery and/or any other method of physical delivery described herein or known in the art.

As used herein, the terms "effective amount" or "therapeutically effective amount" refer to an amount of a therapy (e.g., an antibody or pharmaceutical composition provided herein) which is sufficient to reduce and/or ameliorate the severity and/or duration of a given condition, disorder or disease and/or a symptom related thereto. These terms also encompass an amount necessary for the reduction, slowing, or amelioration of the advancement or progression of a given disease, reduction, slowing, or amelioration of the recurrence, development or onset of a given disease, and/or to improve or enhance the prophylactic or therapeutic effect(s) of another therapy (e.g., a therapy other than an anti-Nectin-4 antibody provided herein). In some embodiments, "effective amount" as used herein also refers to the amount of an antibody described herein to achieve a specified result.

The terms "stability" and "stable" as used herein in the context of a liquid formulation comprising an antibody that immunospecifically binds to a Nectin-4 antigen refer to the resistance of the antibody in the formulation to thermal and chemical unfolding, aggregation, degradation or fragmentation under given manufacture, preparation, transportation and storage conditions. The "stable" formulations provided herein retain biological activity equal to or more than 80%, 85%, 90%, 95%, 98%, 99%, or 99.5% under given manufacture, preparation, transportation and storage conditions. The stability of the antibody can be assessed by degrees of aggregation, degradation or fragmentation by methods known to those skilled in the art, including but not limited to reduced Capillary Gel Electrophoresis (rCGE), Sodium Dodecyl Sulfate Polyacrylamide Gel Electrophoresis (SDS-PAGE) and HPSEC, compared to a reference antibody. The overall stability of a formulation comprising an antibody that immunospecifically binds to a Nectin-4 antigen can be assessed by various immunological assays including, for example, ELISA and radioimmunoassay using the specific epitope of Nectin-4. In some exemplary formulation, the anti-Nectin-4 antibody can be stable for two month, four months, six months, eight months, ten months, one year, eighteen months, two years, three years or longer.

The term "substantially free of surfactant" as used herein refers to a formulation of an antibody that immunospecifically binds to a Nectin-4 antigen, said formulation containing less than 0.0005%, less than 0.0003%, or less than 0.0001% of surfactants and/or less than 0.0005%, less than 0.0003%, or less than 0.0001% of surfactants.

The term "substantially free of salt" as used herein refers to a formulation of an antibody that immunospecifically binds to a Nectin-4 antigen, said formulation containing less than 0.0005%, less than 0.0003%, or less than 0.0001% of inorganic salts.

The term "inorganic salt" as used herein refers to any compounds containing no carbon that result from replacement of part or all of the acid hydrogen or an acid by a metal or a group acting like a metal and are often used as a tonicity adjusting compound in pharmaceutical compositions and preparations of biological materials. The most common inorganic salts are NaCl, KCl, $NaH_2PO_4$, etc.

The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials.

8. COMPOSITIONS AND METHODS OF MAKING THE SAME

Provided herein are antibodies that immunospecifically bind to a Nectin-4 polypeptide, a Nectin-4 polypeptide fragment, or a Nectin-4 epitope. Also provided are isolated nucleic acids encoding antibodies that immunospecifically bind to a Nectin-4 polypeptide, a Nectin-4 polypeptide fragment, or a Nectin-4 epitope. Further provided are vectors and host cells comprising nucleic acids encoding antibodies that immunospecifically bind to a Nectin-4 polypeptide, a Nectin-4 polypeptide fragment, or a Nectin-4 epitope. Also provided are methods of making antibodies that that immunospecifically bind to a Nectin-4 polypeptide, a Nectin-4 polypeptide fragment, or a Nectin-4 epitope.

In certain embodiments, the antibodies provided herein bind to human and/or cyno Nectin-4. In one embodiment, the Nectin-4 antibodies bind to human Nectin-4. In one embodiment, the Nectin-4 antibodies bind to cyno Nectin-4. In one embodiment, the Nectin-4 antibodies bind to both human Nectin-4 and cyno Nectin-4. In other embodiments, the antibodies provided herein do not bind to rodent Nectin-4.

In some embodiments, the anti-Nectin-4 antibodies bind to the extracellular domain (ECD) of Nectin-4. In certain embodiments, the anti-Nectin-4 antibodies bind to an epitope in the ECD of Nectin-4, which is distinct from the Nectin-4 ligand binding site.

Also provided are antibodies that competitively block an anti-Nectin-4 antibody provided herein from binding to a Nectin-4 polypeptide.

Also provided are antibodies that compete for binding to a Nectin-4 polypeptide with an anti-Nectin-4 antibody provided herein.

In some embodiments, the anti-Nectin-4 antibodies do not block the binding of Nectin-4 ligand to a Nectin-4 polypeptide.

In some embodiments, the anti-Nectin-4 antibodies do not compete with Nectin-4 ligand for binding to a Nectin-4 polypeptide.

In certain embodiments, binding of Nectin-4 ligand to Nectin-4 is not inhibited by the antibody.

The anti-Nectin-4 antibodies provided herein can also be conjugated or recombinantly fused, e.g., to a diagnostic agent, a detectable agent, and/or an agent. Further provided are compositions comprising an anti-Nectin-4 antibody.

Also provided herein are isolated nucleic acid molecules encoding an immunoglobulin heavy chain, light chain, VH region, VL region, VH CDR1, VH CDR2, VH CDR3, VL CDR1, VL CDR2, and/or VL CDR3 of anti-Nectin-4 antibodies that bind to a Nectin-4 polypeptide, a Nectin-4 polypeptide fragment, a Nectin-4 peptide, or a Nectin-4 epitope.

Further provided are vectors and host cells comprising nucleic acid molecules encoding anti-Nectin-4 antibodies that bind to a Nectin-4 polypeptide, a Nectin-4 polypeptide fragment, a Nectin-4 peptide, or a Nectin-4 epitope. Also provided are methods of making antibodies that bind to a Nectin-4 polypeptide, a Nectin-4 polypeptide fragment, a Nectin-4 peptide, or a Nectin-4 epitope.

In one embodiment, the present disclosure provides anti-Nectin-4 antibodies that may find use herein as diagnostic agents. Exemplary antibodies include polyclonal, monoclonal, humanized, human, and heteroconjugate antibodies, as well as variants thereof having improved affinity or other properties.

9. ANTI-NECTIN-4 ANTIBODIES

Antibodies provided herein, but are not limited to, synthetic antibodies, monoclonal antibodies, recombinantly produced antibodies, human antibodies, humanized antibodies, chimeric antibodies, bispecific antibodies, intrabodies, single-chain Fvs (scFv), camelized antibodies, Fab fragments, F(ab') fragments, disulfide-linked Fvs (sdFv), anti-idiotypic (anti-Id) antibodies, and epitope-binding fragments of any of the above.

In particular, antibodies provided herein include immunoglobulin molecules and immunologically active portions of immunoglobulin molecules, i.e., molecules that contain an antigen binding site that immunospecifically binds to a Nectin-4 antigen. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody, such as an IgG1 antibody.

Variants and derivatives of antibodies include antibody fragments that retain the ability to specifically bind to an epitope. Exemplary fragments include Fab fragments (an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')₂ (two Fab' molecules joined by interchain disulfide bonds in the hinge regions of the heavy chains; the Fab' molecules may be directed toward the same or different epitopes); a single chain Fab chain comprising a variable region, also known as, a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, an antibody provided herein comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in *The Pharmacology of Monoclonal Antibodies*, vol. 113, Rosenburg and Moore eds. Springer-Verlag, New York, pp. 269-315 (1994).

The antibodies provided herein may be from any animal origin including birds and mammals (e.g., human, murine, donkey, sheep, rabbit, goat, guinea pig, camel, horse, or chicken). In certain embodiments, the antibodies provided herein are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In certain embodiments, the antibodies are fully human antibodies, such as fully human antibodies that immunospecifically bind a Nectin-4 polypeptide, a Nectin-4 polypeptide fragment, or a Nectin-4 epitope. Such fully human antibodies would be advantageous over fully mouse (or other full or partial non-human species antibodies), humanized antibodies, or chimeric antibodies to minimize the development of unwanted or unneeded side effects, such as immune responses directed toward non-fully human antibodies (e.g., anti-Nectin-4 antibodies derived from other species) when administered to the subject.

In one embodiment, the antibody provided herein can include a bispecific antibody or antigen binding fragment thereof having two antibodies or antigen binding fragment thereof, each of which is directed to a different epitope on Nectin-4.

In some embodiments, the antibodies provided herein are monospecific for a given epitope of a Nectin-4 polypeptide and do not immunospecifically bind to other epitopes.

In some embodiments, provided herein are antibodies that bind to Nectin-4, including a Nectin-4 polypeptide, a Nectin-4 polypeptide fragment, a Nectin-4 peptide, or a Nectin-4 epitope. In one embodiment, an antibody provided herein binds to human Nectin-4. In another embodiment, an antibody provided herein binds to cyno Nectin-4. In another embodiment, an antibody provided herein binds to human Nectin-4 and cyno Nectin-4. In some embodiments, the anti-Nectin-4 antibodies do not block the binding of Nectin-4 ligand to a Nectin-4 polypeptide. In other embodiments, the anti-Nectin-4 antibodies are humanized antibodies (e.g., comprising human constant regions) that bind Nectin-4, including a Nectin-4 polypeptide, a Nectin-4 polypeptide fragment, a Nectin-4 peptide, or a Nectin-4 epitope.

In one embodiment, antibodies of the compositions comprising the antibodies and methods of using the antibodies provided herein include an M22-321b41.1 antibody. Also provided herein are hybridomas that produce M22-321b41.1 antibody. In some embodiments, M22-321b41.1 antibody is produced from M22-321b41.1 hybridoma cell line. In some embodiments, M22-321b41.1 antibody has murine IgG2a/kappa isotype.

M22-321b41.1 is a hybridoma cell line of mouse origin. M22-321b41.1 hybridoma cell line was deposited on Jun. 13, 2017 (ATCC Accession Nos. PTA-124245).

In certain embodiments, the anti-Nectin-4 antibody comprises a VH region, VL region, VH CDR1, VH CDR2, VH CDR3, VL CDR1, VL CDR2, and/or VL CDR3 of the murine monoclonal antibody described herein, such as an amino acid sequence depicted in Table 1. Accordingly, in some embodiments, the isolated antibody or functional fragment thereof provided herein comprises one, two, and/or three heavy chain CDRs and/or one, two, and/or three light chain CDRs from the anti-Nectin-4 antibody M22-321b41.1.

TABLE 1

Antibody M22-321b41.1 CDR Sequences

| | | Exemplary | Kabat | Chothia | Contact |
|---|---|---|---|---|---|
| VL CDR Seq. | VL CDR1 | RSSKSLLHSNGITYLY (SEQ ID NO: 7) | RSSKSLLHSNGITYLY (SEQ ID NO: 7) | RSSKSLLHSNGITYLY (SEQ ID NO: 7) | ITYLYWY (SEQ ID NO: 8) |
| | VL CDR2 | LLIYHMSNLAS (SEQ ID NO: 9) | HMSNLAS (SEQ ID NO: 10) | HMSNLAS (SEQ ID NO: 10) | LLIYHMSNLA (SEQ ID NO: 11) |
| | VL CDR3 | AQNLELPFT (SEQ ID NO: 12) | AQNLELPFT (SEQ ID NO: 12) | AQNLELPFT (SEQ ID NO: 12) | AQNLELPF (SEQ ID NO: 13) |
| VH CDR Seq. | VH CDR1 | GYTFTTYWMQ (SEQ ID NO: 14) | TYWMQ (SEQ ID NO: 15) | GYTFTTY (SEQ ID NO: 16) | TTYWMQ (SEQ ID NO: 17) |

TABLE 1-continued

Antibody M22-321b41.1 CDR Sequences

| | Exemplary | Kabat | Chothia | Contact |
|---|---|---|---|---|
| VH CDR2 | WIGSIYPGDGDTRYTQKS (SEQ ID NO: 18) | IYPGDGDTRYTQKFKG (SEQ ID NO: 19) | YPGDGD (SEQ ID NO: 20) | WIGSIYPGDGDTR (SEQ ID NO: 21) |
| VH CDR3 | AREYYGLDY (SEQ ID NO: 22) | EYYGLDY (SEQ ID NO: 23) | EYYGLDY (SEQ ID NO: 23) | AREYYGLD |

VL Sequence:
DIVMTQAAFSNPVTLGTSASISCRSSKSLLHSNGITYLYWYLQKPGQSPQLLIYHMSNLASGVPDRFTSSGSGTD

FTLRISRVEAEDVGVYYCAQNLELPFTFGGGTKLETKRADAAPTVSIFPPSSEQLTSG (SEQ ID NO: 3)

VH Sequence:
QVQLQQSGAELARPGASVKLSCKASGYTFTTYWMQWVKQRPGQGLEWIGSIYPGDGDTRYTQKFKGKATLT

ADKSSSTAYIQLSTLASEDSAVYYCAREYYGLDYWGQGTTLTVSSAKTTAPSVYPLAPVCGDTTG (SEQ ID NO: 4)

In some embodiments, an antibody provided herein comprises or consists of six CDRs, for example, VH CDR1, VH CDR2, VH CDR3, VL CDR1, VL CDR2, and/or VL CDR3 identified in Tables 1. In some embodiments, an antibody provided herein can comprise fewer than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3 identified in Table 1. In some embodiments, the antibody comprises or consists of one, two, three, four, or five CDRs selected from the group consisting of VH CDR1, VH CDR2, VH CDR3, VL CDR1, VL CDR2, and/or VL CDR3 of the monoclonal antibody M22-321b41.1.

In some embodiments, the antibodies provided herein comprise one or more (e.g., one, two, or three) VH CDRs listed in Table 1. In other embodiments, the antibodies provided herein comprise one or more (e.g., one, two, or three) VL CDRs listed in Table 1. In yet other embodiments, the antibodies provided herein comprise one or more (e.g., one, two, or three) VH CDRs listed in Table 1 and one or more VL CDRs listed in Table 1. Accordingly, in some embodiments, the antibodies comprise a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14). In some embodiments, the antibodies comprise a VH CDR2 having an amino acid sequence selected from a group consisting of Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18). In some embodiments, the antibodies comprise a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22). In some embodiments, the antibodies comprise a VH CDR1 and/or a VH CDR2 and/or a VH CDR3 independently selected from any one of the VH CDR1, VH CDR2, VH CDR3 amino acid sequence(s) as depicted in Table 1. In some embodiments, the antibodies comprise a VL CDR1 having an amino acid sequence selected from a group of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7). In another embodiment, the antibodies comprise a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In some embodiments, the antibodies comprise a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In some embodiments, the antibodies comprise a VL CDR1 and/or a VL CDR2 and/or a VL CDR3 independently selected from any one of the VL CDR1, VL CDR2, VL CDR3 amino acid sequences as depicted in Table 1.

In certain embodiments, the antibodies provided herein comprise a VH region comprising: (1) a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); (2) a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); and (3) a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL region comprising: (1) a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); (2) a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and (3) a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12).

In some embodiments, the antibodies provided herein comprise a VH region comprising: (1) a VH CDR1 having an amino acid sequence selected from a group consisting of Kabat VH CDR1 (SEQ ID NO:15), Chothia VH CDR1

(SEQ ID NO:16), Contact VH CDR1 (SEQ ID NO:17), and Exemplary VH CDR1 (SEQ ID NO:14); (2) a VH CDR2 having an amino acid sequence selected from a group consisting of: Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); and (3) a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22).

In other embodiments, the antibodies provided herein comprise a VL region comprising: (1) a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); (2) a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and (3) a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12).

Also provided herein are antibodies comprising one or more (e.g., one, two, or three) VH CDRs and one or more (e.g., one, two, or three) VL CDRs listed in Table 1. In particular, provided herein is an antibody comprising a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); and a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7). In one embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In other embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); and a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7). In some embodiments, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In one embodiment, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7). In other embodiments, the antibody comprises a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In some embodiments, the antibody comprises a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); and a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7). In one embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In other embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7). In some embodiments, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In one embodiment, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7). In other embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In some embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In one embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In other embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In some embodiments, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In one embodiment, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In other embodiments, the antibody comprises a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In some embodiments, the antibody comprises a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7). In one embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In other embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In some embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In one embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In other embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In some embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In one embodiment, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In other embodiments, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9). In some embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In one embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In other embodiments, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In some embodiments, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VH CDR3 having an amino acid sequence selected from a group consisting of Kabat VH CDR3 (SEQ ID NO:23), Chothia VH CDR3 (SEQ ID NO:23), Contact VH CDR3 (SEQ ID NO:24), and Exemplary VH CDR3 (SEQ ID NO:22); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises a VH CDR1 having an amino acid sequence selected from a group consisting of Kabat VH CDR1 (SEQ ID NO:15), Chothia VH CDR1 (SEQ ID NO:16), Contact VH CDR1 (SEQ ID NO:17), and Exemplary VH CDR1 (SEQ ID NO:14); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In one embodiment, the antibody comprises a VH CDR2 having an amino acid sequence selected from a group consisting of. Kabat VH CDR2 (SEQ ID NO:19), Chothia VH CDR2 (SEQ ID NO:20), Contact VH CDR2 (SEQ ID NO:21), and Exemplary VH CDR2 (SEQ ID NO:18); a VL CDR1 having an amino acid sequence selected from a group consisting of Kabat VL CDR1 (SEQ ID NO:7), Chothia VL CDR1 (SEQ ID NO:7), Contact VL CDR1 (SEQ ID NO:8), and Exemplary VL CDR1 (SEQ ID NO:7); a VL CDR2 having an amino acid sequence selected from a group consisting of Kabat VL CDR2 (SEQ ID NO:10), Chothia VL CDR2 (SEQ ID NO:10), Contact VL CDR2 (SEQ ID NO:11), and Exemplary VL CDR2 (SEQ ID NO:9); and a VL CDR3 having an amino acid sequence selected from a group consisting of Kabat VL CDR3 (SEQ ID NO:12), Chothia VL CDR3 (SEQ ID NO:12), Contact VL CDR3 (SEQ ID NO:13), and Exemplary VL CDR3 (SEQ ID NO:12). In another embodiment, the antibody comprises any combination thereof the VH CDRs and VL CDRs listed in Table 1.

Framework regions described herein are determined based upon the boundaries of the CDR numbering system. In other words, if the CDRs are determined by, e.g., Kabat, IMGT, or Chothia, then the framework regions are the amino acid residues surrounding the CDRs in the variable region in the format, from the N-terminus to C-terminus: FR1-CDR1-FR2-CDR2-FR3-CDR3-FR4. For example, FR1 is defined as the amino acid residues N-terminal to the CDR1 amino acid residues as defined by, e.g., the Kabat numbering system, the IMGT numbering system, or the Chothia numbering system, FR2 is defined as the amino acid residues between CDR1 and CDR2 amino acid residues as defined by, e.g., the Kabat numbering system, the IMGT numbering system, or the Chothia numbering system, FR3 is defined as the amino acid residues between CDR2 and CDR3 amino acid residues as defined by, e.g., the Kabat numbering system, the IMGT numbering system, or the Chothia numbering system, and FR4 is defined as the amino acid residues C-terminal to the CDR3 amino acid residues as defined by, e.g., the Kabat numbering system, the IMGT numbering system, or the Chothia numbering system.

In some embodiments, the isolated antibody or functional fragment thereof provided herein further comprises one, two, three, and/or four heavy chain FRs and/or one, two, three, and/or four light chain FRs from antibody M22-321b41.1 as shown in Table 2.

TABLE 2

M22-321b41.1 VL and VH FR Amino Acid Sequences

| Antibody | FR1 | FR2 | FR3 | FR4 |
|---|---|---|---|---|
| VL | DIVMTQAAFSNPVTLGTSASISC (SEQ ID NO: 25) | WYLQKPGQSPQLLIYGVPDRFTSSGSGTDFTLRIS- (SEQ ID NO: 26) | RVEAEDVGVYYC (SEQ ID NO: 27) | FGGGTKLETKR (SEQ ID NO: 28) |
| VH | QVQLQQSGAELARPGASVKLSCKASGYTFT (SEQ ID NO: 29) | WVKQRPGQGLEWIG (SEQ ID NO: 30) | KATLTADKSSSTAYIQLST-LASEDSAVYYCAR (SEQ ID NO: 31) | WGQGTTLTVSS (SEQ ID NO: 32) |

In certain embodiments, the isolated antibody or functional fragment thereof provided herein further comprises one, two, three, and/or four heavy chain FRs from antibody M22-321b41.1 as shown in Table 2. In some embodiments, the antibody heavy chain FR(s) is from the antibody M22-321b41.1.

In some embodiments, the isolated antibody or functional fragment thereof provided herein further comprises one, two, three, and/or four light chain FRs from antibody M22-321b41.1 as shown in Table 2. In some embodiments, the antibody light chain FR(s) is from the antibody M22-321b41.1.

In certain embodiments, an antibody of fragment thereof described herein comprises a VH region that comprises: (1) a VH FR1 having an amino acid of SEQ ID NO:29; (2) a VH FR2 having an amino acid sequence of SEQ ID NO:30; (3) a VH FR3 having an amino acid sequence of SEQ ID NO:31; and/or (4) a VH FR4 having an amino acid sequence of SEQ ID NO:32. In specific embodiments, the antibody comprises a VH region comprising all four of the above-referenced VH FR1, VH FR2, VH FR3, and VH FR4.

Accordingly, in one embodiment, the humanized antibody comprises a VH region that includes a VH FR1 having an amino acid sequence of SEQ ID NO:29. In some embodiments, the humanized antibody comprises a VH region that includes a VH FR2 having an amino acid sequence of SEQ ID NO:30. In one embodiment, the humanized antibody comprises a VH region that includes a VH FR3 having an amino acid sequence of SEQ ID NO:31. In other embodiments, the humanized antibody comprises a VH region that includes a VH FR4 having an amino acid sequence of SEQ ID NO:32.

In some embodiments, the VL region comprises: (1) a VL FR1 having an amino acid sequence of SEQ ID NO:25; (2) a VL FR2 having an amino acid sequence of SEQ ID NO:26; (3) a VL FR3 having an amino acid sequence of SEQ ID NO:27; and/or (4) a VL FR4 having an amino acid sequence of SEQ ID NO:28.

Accordingly, in some embodiments, the humanized antibody comprises a VL region that includes a VL FR1 having an amino acid sequence of SEQ ID NO:25. In certain embodiments, the humanized antibody comprises a VL region that includes a VL FR2 having an amino acid sequence of SEQ ID NO:26. In one embodiment, the humanized antibody comprises a VL region that includes a VL FR3 having an amino acid sequence of SEQ ID NO:27. In yet other embodiments, the humanized antibody comprises a VL region that includes a VL FR4 having an amino acid sequence of SEQ ID NO:28.

In some embodiments, an antibody of fragment thereof comprises a VH region and a VL region, wherein the VH region comprises: (1) a VH FR1 having an amino acid sequence of SEQ ID NO:29; (2) a VH FR2 having an amino acid sequence of SEQ ID NO:30; (3) a VH FR3 having an amino acid sequence of SEQ ID NO:31; and/or (4) a VH FR4 having an amino acid sequence of SEQ ID NO:32; and wherein the VL region comprises: (1) a VL FR1 having an amino acid sequence of SEQ ID NO:25; (2) a VL FR2 having an amino acid sequence of SEQ ID NO:26; (3) a VL FR3 having an amino acid sequence of SEQ ID NO:27; and/or (4) a VL FR4 having an amino acid sequence of SEQ ID NO:28. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

Also provided herein are antibodies comprising one or more (e.g., one, two, three, or four) VH FRs and one or more (e.g., one, two, three, or four) VL FRs listed in Table 2. In particular, provided herein is an antibody comprising a VH FR1 (SEQ ID NO:29) and a VL FR1 (SEQ ID NO:25). In one embodiment, the antibody comprises a VH FR1 (SEQ ID NO:29) and a VL FR2 (SEQ ID NO:26). In some embodiments, the antibody comprises a VH FR1 (SEQ ID NO:29) and a VL FR3 (SEQ ID NO:27). In another embodiment, the antibody comprises a VH FR1 (SEQ ID NO:29) and a VL FR4 (SEQ ID NO:28). In other embodiments, the antibody comprises a VH FR2 (SEQ ID NO:30) and a VL FR1 (SEQ ID NO:25). In one embodiment, the antibody comprises a VH FR2 (SEQ ID NO:30) and a VL FR2 (SEQ ID NO:26). In some embodiments, the antibody comprises a VH FR2 (SEQ ID NO:30) and a VL FR3 (SEQ ID NO:27). In another embodiment, the antibody comprises a VH FR2 (SEQ ID NO:30) and a VL FR4 (SEQ ID NO:28). In one embodiment, the antibody comprises a VH FR3 (SEQ ID NO:31) and a VL FR1 (SEQ ID NO:25). In other embodiments, the antibody comprises a VH FR3 (SEQ ID NO:31) and a VL FR2 (SEQ ID NO:26). In another embodiment, the antibody comprises a VH FR3 (SEQ ID NO:31) and a VL FR3 (SEQ ID NO:27). In some embodiments, the antibody comprises a VH FR3 (SEQ ID NO:31) and a VL FR4 (SEQ ID NO:28). In one embodiment, the antibody comprises a VH FR4 (SEQ ID NO:32) and a VL FR1 (SEQ ID NO:25). In another embodiment, the antibody comprises a VH FR4 (SEQ ID NO:32) and a VL FR2 (SEQ ID NO:26). In one embodiment, the antibody comprises a VH FR4 (SEQ ID NO:32) and a VL FR3 (SEQ ID NO:27). In some embodiments, the antibody comprises a VH FR4 (SEQ ID NO:32) and a VL FR4 (SEQ ID NO:28). In another embodiment, the antibody comprises a VH FR1 (SEQ ID NO:29), a VH FR2 (SEQ ID NO:30), and a VL FR1 (SEQ ID NO:25). In other embodiments, the antibody comprises a VH FR1 (SEQ ID NO:29), a VH FR2 (SEQ ID NO:30), and a VL FR2 (SEQ ID NO:26). In one embodiment, the antibody comprises a VH FR1 (SEQ ID NO:29), a VH FR2 (SEQ ID NO:30), and a VL FR3 (SEQ ID NO:27). In another embodiment, the antibody comprises a VH FR1 (SEQ ID NO:29), a VH FR2 (SEQ ID NO:30), and a VL FR4 (SEQ ID NO:28). In some embodiments, the antibody comprises a VH FR2 (SEQ ID NO:30), a VH FR3 (SEQ ID NO:31), and a VL FR1 (SEQ ID NO:25). In one embodiment, the antibody comprises a VH FR2 (SEQ ID NO:30), a VH FR3 (SEQ ID NO:31), and a VL FR2 (SEQ ID NO:26). In another embodiment, the antibody comprises a VH FR2 (SEQ ID NO:30), a VH FR3 (SEQ ID NO:31), and a VL FR3 (SEQ ID NO:27). In other embodiments, the antibody comprises a VH FR2 (SEQ ID NO:30), a VH FR3 (SEQ ID NO:31), and a VL FR4 (SEQ ID NO:28). In some embodiments, the antibody comprises a VH FR1 (SEQ ID NO:29), a VL FR1 (SEQ ID NO:25), and a VL FR2 (SEQ ID NO:26). In another embodiment, the antibody comprises a VH FR1 (SEQ ID NO:29), a VL FR1 (SEQ ID NO:25), and a VL FR3 (SEQ ID NO:27). In one embodiment, the antibody comprises a VH FR1 (SEQ ID NO:29), a VL FR1 (SEQ ID NO:25), and a VL FR4 (SEQ ID NO:28). In one embodiment, the antibody comprises a VH FR1 (SEQ ID NO:29), a VL FR2 (SEQ ID NO:26) and a VL FR3 (SEQ ID NO:27). In another embodiment, the antibody comprises a VH FR1 (SEQ ID NO:29), a VL FR2 (SEQ ID NO:26) and a VL FR4 (SEQ ID NO:28). In some embodiments, the antibody comprises a VH FR1 (SEQ ID NO:29), a VL FR3 (SEQ ID NO:27), and a VL FR4 (SEQ ID NO:28). In other embodiments, the antibody comprises a VH FR2 (SEQ ID NO:30), a VL FR1 (SEQ ID NO:25), and a VL FR2 (SEQ ID NO:26). In another embodiment, the antibody comprises a VH FR2 (SEQ ID NO:30), a VL FR1 (SEQ ID NO:25), and a VL FR3 (SEQ ID NO:27). In one embodiment, the antibody comprises a VH FR2 (SEQ ID NO:30), a VL FR1 (SEQ ID NO:25), and a VL FR4 (SEQ ID NO:28). In some embodiments, the antibody comprises a VH FR2 (SEQ ID NO:30), a VL FR2 (SEQ ID NO:26) and a VL FR3 (SEQ ID NO:27). In another embodiment, the antibody comprises a VH FR2 (SEQ ID NO:30), a VL FR2 (SEQ ID NO:26) and a VL FR4 (SEQ ID NO:28). In one embodiment, the antibody comprises a VH FR2 (SEQ ID NO:30), a VL FR3 (SEQ ID NO:27), and a VL FR4 (SEQ ID NO:28). In another embodiment, the antibody comprises a VH FR3 (SEQ ID NO:31), a VL FR1 (SEQ ID NO:25), and a VL FR2 (SEQ ID NO:26). In other embodiments, the antibody comprises a VH FR3 (SEQ ID NO:31), a VL FR1 (SEQ ID NO:25), and a VL FR3 (SEQ ID NO:27). In some embodiments, the antibody comprises a VH FR3 (SEQ ID NO:31), a VL FR1 (SEQ ID NO:25), and a VL FR4 (SEQ ID NO:28). In another embodiment, the antibody comprises a VH FR3 (SEQ ID NO:31), a VL FR2 (SEQ ID NO:26) and a VL FR3 (SEQ ID NO:27). In one embodiment, the antibody comprises a VH FR3 (SEQ ID NO:31), a VL FR2 (SEQ ID NO:26) and a VL FR4 (SEQ ID NO:28). In one embodiment, the antibody comprises a VH FR3 (SEQ ID NO:31), a VL FR3 (SEQ ID NO:27), and a VL FR4 (SEQ ID NO:28). In another embodiment, the antibody comprises a VH FR4 (SEQ ID NO:32), a VL FR1 (SEQ ID NO:25), and a VL FR2 (SEQ ID NO:26). In some embodiments, the antibody comprises a VH FR4 (SEQ ID NO:32), a VL FR1 (SEQ ID NO:25), and a VL FR3 (SEQ ID NO:27). In other embodiments, the antibody comprises a VH FR4 (SEQ ID NO:32), a VL FR1 (SEQ ID NO:25), and a VL FR4 (SEQ ID NO:28). In another embodiment, the antibody comprises a VH FR4 (SEQ ID NO:32), a VL FR2 (SEQ ID NO:26) and a VL FR3 (SEQ ID NO:27). In one embodiment, the antibody comprises a VH FR4 (SEQ ID NO:32), a VL FR2 (SEQ ID NO:26) and a VL FR4 (SEQ ID NO:28). In some embodiments, the antibody comprises a VH FR4 (SEQ ID NO:32), a VL FR3 (SEQ ID NO:27), and a VL FR4 (SEQ ID NO:28). In another embodiment, the antibody comprises a VH FR1 (SEQ ID NO:29), a VH FR2 (SEQ ID NO:30), a VH FR3 (SEQ ID NO:31), and a VL FR1 (SEQ ID NO:25). In one embodiment, the antibody comprises a VH FR1 (SEQ ID NO:29), a VH FR2 (SEQ ID NO:30), a VH FR3 (SEQ ID NO:31), and a VL FR2 (SEQ ID NO:26). In other embodiments, the antibody comprises a VH FR1 (SEQ ID NO:29), a VH FR2 (SEQ ID NO:30), a VH FR3 (SEQ ID NO:31), and a VL FR3 (SEQ ID NO:27). In another embodiment, the antibody comprises a VH FR1 (SEQ ID NO:29), a VH FR2 (SEQ ID NO:30), a VH FR3 (SEQ ID NO:31), and a VL FR4 (SEQ ID NO:28). In some embodiments, the antibody comprises a VH FR1 (SEQ ID NO:29), a VH FR2 (SEQ ID NO:30), a VH FR4 (SEQ ID NO:32), and a VL FR1 (SEQ ID NO:25). In one embodiment, the antibody comprises a VH FR1 (SEQ ID NO:29), a VH FR2 (SEQ ID NO:30), a VH FR4 (SEQ ID NO:32), and a VL FR2 (SEQ ID NO:26). In another embodiment, the antibody comprises a VH FR1 (SEQ ID NO:29), a VH FR2 (SEQ ID NO:30), a VH FR4 (SEQ ID NO:32), and a VL FR3 (SEQ ID NO:27). In one embodiment, the antibody comprises a VH FR1 (SEQ ID NO:29), a VH FR2 (SEQ ID NO:30), a VH FR4 (SEQ ID NO:32), and a VL FR4 (SEQ ID NO:28). In some embodiments, the antibody comprises a VH FR1 (SEQ ID NO:29), a VH FR3 (SEQ ID NO:31), a VH FR4 (SEQ ID NO:32), and a VL FR1 (SEQ ID NO:25). In another embodiment, the antibody comprises a VH FR1 (SEQ ID NO:29), a VH FR3 (SEQ ID NO:31), a VH FR4 (SEQ ID NO:32), and a VL FR2 (SEQ ID NO:26). In other embodiments, the antibody comprises a VH FR1 (SEQ ID NO:29), VH FR3 (SEQ ID NO:31), a VH FR4 (SEQ ID NO:32), and a VL FR3 (SEQ ID NO:27). In one embodiment, the antibody comprises a VH FR1 (SEQ ID NO:29), a VH FR3 (SEQ ID NO:31), a VH FR4 (SEQ ID NO:32), and a VL FR4 (SEQ ID NO:28). In another embodiment, the antibody comprises a VH FR2 (SEQ ID NO:30), a VH FR3 (SEQ ID NO:31), a VH FR4 (SEQ ID NO:32), and a VL FR1 (SEQ ID NO:25). In some embodiments, the antibody comprises a VH FR2 (SEQ ID NO:30), a VH FR3 (SEQ ID NO:31), a VH FR4 (SEQ ID NO:32), and a VL FR2 (SEQ ID NO:26). In one embodiment, the antibody comprises a VH FR2 (SEQ ID NO:30), VH FR3 (SEQ ID NO:31), a VH FR4 (SEQ ID NO:32), and a VL FR3 (SEQ ID NO:27). In another embodiment, the antibody comprises a VH FR2 (SEQ ID NO:30), a VH FR3 (SEQ ID NO:31), a VH FR4 (SEQ ID NO:32), and a VL FR4 (SEQ ID NO:28). In other embodiments, the antibody comprises a VH FR1 (SEQ ID NO:29), a VH FR2 (SEQ ID NO:30), a VL FR1 (SEQ ID NO:25), and a VL FR2 (SEQ ID NO:26). In some embodiments, the antibody comprises a VH FR1 (SEQ ID NO:29), a VH FR2 (SEQ ID NO:30), a VL FR1 (SEQ ID NO:25), and a VL FR3 (SEQ ID NO:27). In another embodiment, the antibody comprises a VH FR1 (SEQ ID NO:29), a VH FR2 (SEQ ID NO:30), a VL FR1 (SEQ ID NO:25), and a VL FR4 (SEQ ID NO:28). In one embodiment, the antibody comprises a VH FR1 (SEQ ID NO:29), a VH FR2 (SEQ ID NO:30), a VL FR2 (SEQ ID NO:26), and a VL FR3 (SEQ ID NO: 27). In one embodiment, the antibody comprises a VH FR1 (SEQ ID NO:29), a VH FR2 (SEQ ID NO:30), a VL FR2 (SEQ ID NO:26), and a VL FR4 (SEQ ID NO:28). In another embodiment, the antibody comprises a VH FR1 (SEQ ID NO:29), a VH FR2 (SEQ ID NO:30), a VL FR3 (SEQ ID NO:27), and a VL FR4 (SEQ ID NO:28). In some embodiments, the antibody comprises a VH FR1 (SEQ ID NO:29), a VH FR3 (SEQ ID NO:31), a VL FR1 (SEQ ID NO:25), and a VL FR2 (SEQ ID NO:26). In other embodiments, the antibody comprises a VH FR1 (SEQ ID NO:29), a VH FR3 (SEQ ID NO:31), a VL FR1 (SEQ ID NO:25), and a VL FR3 (SEQ ID NO:27). In another embodiment, the antibody comprises a VH FR1 (SEQ ID NO:29), a VH FR3 (SEQ ID NO:31), a VL FR1 (SEQ ID NO:25), and a VL FR4 (SEQ ID NO:28). In one embodiment, the antibody comprises a VH FR1 (SEQ ID NO:29), a VH FR3 (SEQ ID NO:31), a VL FR2 (SEQ ID NO:26), and a VL FR3 (SEQ ID NO:27). In some embodiments, the antibody comprises a VH FR1 (SEQ ID NO:29), a VH FR3 (SEQ ID NO:31), a VL FR2 (SEQ ID NO:26), and a VL FR4 (SEQ ID NO:28). In another embodiment, the antibody comprises a VH FR1 (SEQ ID NO:29), a VH FR3 (SEQ ID NO:31), a VL FR3 (SEQ ID NO:27), and a VL FR4 (SEQ ID NO:28). In one embodiment, the antibody comprises a VH FR1 (SEQ ID NO:29), a VH FR4 (SEQ ID NO:32), a VL FR1 (SEQ ID NO:25), and a VL FR2 (SEQ ID NO:26). In other embodiments, the antibody comprises a VH FR1 (SEQ ID NO:29), a VH FR4 (SEQ ID NO:32), a VL FR1 (SEQ ID NO:25), and a VL FR3 (SEQ ID NO:27). In another embodiment, the antibody comprises a VH FR1 (SEQ ID NO:29), a VH FR4 (SEQ ID NO:32), a VL FR1 (SEQ ID NO:25), and a VL FR4 (SEQ ID NO:28). In some embodiments, the antibody comprises a VH FR1 (SEQ ID NO:29), a VH FR4 (SEQ ID NO:32), a VL FR2 (SEQ ID NO:26), and a VL FR3 (SEQ ID NO:27). In one embodiment, the antibody comprises a VH FR1 (SEQ ID NO:29), a VH FR4 (SEQ ID NO:32), a VL FR2 (SEQ ID NO:26), and a VL FR4 (SEQ ID NO:28). In another embodiment, the antibody comprises a VH FR1 (SEQ ID NO:29), a VH FR4 (SEQ ID NO:32), a VL FR3 (SEQ ID NO:27), and a VL FR4 (SEQ ID NO:28). In one embodiment, the antibody comprises a VH FR2 (SEQ ID NO:30), a VH FR3 (SEQ ID NO:31), a VL FR1 (SEQ ID NO:25), and a VL FR2 (SEQ ID NO:26). In some embodiments, the antibody comprises a VH FR2 (SEQ ID NO:30), a VH FR3 (SEQ ID NO:31), a VL FR1 (SEQ ID NO:25), and a VL FR3 (SEQ ID NO:27). In another embodiment, the antibody comprises a VH FR2 (SEQ ID NO:30), a VH FR3 (SEQ ID NO:31), a VL FR1 (SEQ ID NO:25), and a VL FR4

(SEQ ID NO:28). In other embodiments, the antibody comprises a VH FR2 (SEQ ID NO:30), a VH FR3 (SEQ ID NO:31), a VL FR2 (SEQ ID NO:26), and a VL FR3 (SEQ ID NO:27). In one embodiment, the antibody comprises a VH FR2 (SEQ ID NO:30), a VH FR3 (SEQ ID NO:31), a VL FR2 (SEQ ID NO:26), and a VL FR4 (SEQ ID NO:28). In another embodiment, the antibody comprises a VH FR2 (SEQ ID NO:30), a VH FR3 (SEQ ID NO:31), a VL FR3 (SEQ ID NO:27), and a VL FR4 (SEQ ID NO:28). In some embodiments, the antibody comprises a VH FR2 (SEQ ID NO:30), a VH FR4 (SEQ ID NO:32), a VL FR1 (SEQ ID NO:25), and a VL FR2 (SEQ ID NO:26). In one embodiment, the antibody comprises a VH FR2 (SEQ ID NO:30), a VH FR4 (SEQ ID NO:32), a VL FR1 (SEQ ID NO:25), and a VL FR3 (SEQ ID NO:27). In another embodiment, the antibody comprises a VH FR2 (SEQ ID NO:30), a VH FR4 (SEQ ID NO:32), a VL FR1 (SEQ ID NO:25), and a VL FR4 (SEQ ID NO:28). In other embodiments, the antibody comprises a VH FR2 (SEQ ID NO:30), a VH FR4 (SEQ ID NO:32), a VL FR2 (SEQ ID NO:26), and a VL FR3 (SEQ ID NO:27). In some embodiments, the antibody comprises a VH FR2 (SEQ ID NO:30), a VH FR4 (SEQ ID NO:32), a VL FR2 (SEQ ID NO:26), and a VL FR4 (SEQ ID NO:28). In another embodiment, the antibody comprises a VH FR2 (SEQ ID NO:30), a VH FR4 (SEQ ID NO:32), a VL FR3 (SEQ ID NO:27), and a VL FR4 (SEQ ID NO:28). In one embodiment, the antibody comprises a VH FR3 (SEQ ID NO:31), a VH FR4 (SEQ ID NO:32), a VL FR1 (SEQ ID NO:25), and a VL FR2 (SEQ ID NO:26). In one embodiment, the antibody comprises a VH FR3 (SEQ ID NO:31), a VH FR4 (SEQ ID NO:32), a VL FR1 (SEQ ID NO:25), and a VL FR3 (SEQ ID NO:27). In another embodiment, the antibody comprises a VH FR3 (SEQ ID NO:31), a VH FR4 (SEQ ID NO:32), a VL FR1 (SEQ ID NO:25), and a VL FR4 (SEQ ID NO:28). In some embodiments, the antibody comprises a VH FR3 (SEQ ID NO:31), a VH FR4 (SEQ ID NO:32), a VL FR2 (SEQ ID NO:26), and a VL FR3 (SEQ ID NO:27). In other embodiments, the antibody comprises a VH FR3 (SEQ ID NO:31), a VH FR4 (SEQ ID NO:32), a VL FR2 (SEQ ID NO:26), and a VL FR4 (SEQ ID NO:28). In another embodiment, the antibody comprises a VH FR3 (SEQ ID NO:31), a VH FR4 (SEQ ID NO:32), a VL FR3 (SEQ ID NO:27), and a VL FR4 (SEQ ID NO:28). In one embodiment, the antibody comprises a VH FR1 (SEQ ID NO:29), a VL FR1 (SEQ ID NO:25), a VL FR2 (SEQ ID NO:26), and a VL FR3 (SEQ ID NO:27). In some embodiments, the antibody comprises a VH FR1 (SEQ ID NO:29), a VL FR1 (SEQ ID NO:25), a VL FR2 (SEQ ID NO:26), and a VL FR4 (SEQ ID NO:28). In another embodiment, the antibody comprises a VH FR1 (SEQ ID NO:29), a VL FR1 (SEQ ID NO:25), a VL FR3 (SEQ ID NO:27), and a VL FR4 (SEQ ID NO:28). In one embodiment, the antibody comprises a VH FR1 (SEQ ID NO:29), a VL FR2 (SEQ ID NO:26), a VL FR3 (SEQ ID NO:27), and a VL FR4 (SEQ ID NO:28). In other embodiments, the antibody comprises a VH FR2 (SEQ ID NO:30), a VL FR1 (SEQ ID NO:25), a VL FR2 (SEQ ID NO:26), and a VL FR3 (SEQ ID NO:27). In another embodiment, the antibody comprises a VH FR2 (SEQ ID NO:30), a VL FR1 (SEQ ID NO:25), a VL FR2 (SEQ ID NO:26), and a VL FR4 (SEQ ID NO:28). In some embodiments, the antibody comprises a VH FR2 (SEQ ID NO:30), a VL FR1 (SEQ ID NO:25), a VL FR3 (SEQ ID NO:27), and a VL FR4 (SEQ ID NO:28). In one embodiment, the antibody comprises a VH FR2 (SEQ ID NO:30), a VL FR2 (SEQ ID NO:26), a VL FR3 (SEQ ID NO:27), and a VL FR4 (SEQ ID NO:28). In another embodiment, the antibody comprises a VH FR3 (SEQ ID NO:31), a VL FR1 (SEQ ID NO:25), a VL FR2 (SEQ ID NO:26), and a VL FR3 (SEQ ID NO:27). In one embodiment, the antibody comprises a VH FR3 (SEQ ID NO:31), a VL FR1 (SEQ ID NO:25), a VL FR2 (SEQ ID NO:26), and a VL FR4 (SEQ ID NO:28). In some embodiments, the antibody comprises a VH FR3 (SEQ ID NO:31), a VL FR1 (SEQ ID NO:25), a VL FR3 (SEQ ID NO:27), and a VL FR4 (SEQ ID NO:28). In another embodiment, the antibody comprises a VH FR3 (SEQ ID NO:31), a VL FR2 (SEQ ID NO:26), a VL FR3 (SEQ ID NO:27), and a VL FR4 (SEQ ID NO:28). In other embodiments, the antibody comprises a VH FR4 (SEQ ID NO:32), a VL FR1 (SEQ ID NO:25), a VL FR2 (SEQ ID NO:26), and a VL FR3 (SEQ ID NO:27). In one embodiment, the antibody comprises a VH FR4 (SEQ ID NO:32), a VL FR1 (SEQ ID NO:25), a VL FR2 (SEQ ID NO:26), and a VL FR4 (SEQ ID NO:28). In another embodiment, the antibody comprises a VH FR4 (SEQ ID NO:32), a VL FR1 (SEQ ID NO:25), a VL FR3 (SEQ ID NO:27), and a VL FR4 (SEQ ID NO:28). In some embodiments, the antibody comprises a VH FR4 (SEQ ID NO:32), a VL FR2 (SEQ ID NO:26), a VL FR3 (SEQ ID NO:27), and a VL FR4 (SEQ ID NO:28). In one embodiment, the antibody comprises a VH FR1 (SEQ ID NO:29), a VH FR2 (SEQ ID NO:30), a VH FR3 (SEQ ID NO:31), a VH FR4 (SEQ ID NO:32), and a VL FR1 (SEQ ID NO:25). In another embodiment, the antibody comprises a VH FR1 (SEQ ID NO:29), a VH FR2 (SEQ ID NO:30), a VH FR3 (SEQ ID NO:31), a VH FR4 (SEQ ID NO:32), and a VL FR2 (SEQ ID NO:26). In other embodiments, the antibody comprises a VH FR1 (SEQ ID NO:29), a VH FR2 (SEQ ID NO:30), a VH FR3 (SEQ ID NO:31), a VH FR4 (SEQ ID NO:32), and a VL FR3 (SEQ ID NO:27). In some embodiments, the antibody comprises a VH FR1 (SEQ ID NO:29), a VH FR2 (SEQ ID NO:30), a VH FR3 (SEQ ID NO:31), a VH FR4 (SEQ ID NO:32), and a VL FR4 (SEQ ID NO:28). In another embodiment, the antibody comprises a VH FR1 (SEQ ID NO:29), a VH FR2 (SEQ ID NO:30), a VH FR3 (SEQ ID NO:31), a VL FR1 (SEQ ID NO:25), and a VL FR2 (SEQ ID NO:26). In one embodiment, the antibody comprises a VH FR1 (SEQ ID NO:29), a VH FR2 (SEQ ID NO:30), a VH FR3 (SEQ ID NO:31), a VL FR1 (SEQ ID NO:25), and a VL FR3 (SEQ ID NO:27). In one embodiment, the antibody comprises a VH FR1 (SEQ ID NO:29), a VH FR2 (SEQ ID NO:30), a VH FR3 (SEQ ID NO:31), a VL FR1 (SEQ ID NO:25), and a VL FR4 (SEQ ID NO:28). In another embodiment, the antibody comprises a VH FR1 (SEQ ID NO:29), a VH FR2 (SEQ ID NO:30), a VH FR3 (SEQ ID NO:31), a VL FR2 (SEQ ID NO:26), and a VL FR3 (SEQ ID NO:27). In some embodiments, the antibody comprises a VH FR1 (SEQ ID NO:29), a VH FR2 (SEQ ID NO:30), a VH FR3 (SEQ ID NO:31), a VL FR2 (SEQ ID NO:26), and a VL FR4 (SEQ ID NO:28). In other embodiments, the antibody comprises a VH FR1 (SEQ ID NO:29), a VH FR2 (SEQ ID NO:30), a VH FR3 (SEQ ID NO:31), a VL FR3 (SEQ ID NO:27), and a VL FR4 (SEQ ID NO:28). In another embodiment, the antibody comprises a VH FR1 (SEQ ID NO:29), a VH FR2 (SEQ ID NO:30), a VH FR4 (SEQ ID NO:32), a VL FR1 (SEQ ID NO:25), and a VL FR2 (SEQ ID NO:26). In one embodiment, the antibody comprises a VH FR1 (SEQ ID NO:29), a VH FR2 (SEQ ID NO:30), a VH FR4 (SEQ ID NO:32), a VL FR1 (SEQ ID NO:25), and a VL FR3 (SEQ ID NO:27). In some embodiments, the antibody comprises a VH FR1 (SEQ ID NO:29), a VH FR2 (SEQ ID NO:30), a VH FR4 (SEQ ID NO:32), a VL FR1 (SEQ ID NO:25), and a VL FR4 (SEQ ID NO:28). In another embodiment, the antibody comprises a VH FR1 (SEQ ID NO:29), a VH FR2 (SEQ ID NO:30), a VH FR4 (SEQ ID NO:32), a VL FR2

(SEQ ID NO:26), and a VL FR3 (SEQ ID NO:27). In one embodiment, the antibody comprises a VH FR1 (SEQ ID NO:29), a VH FR2 (SEQ ID NO:30), a VH FR4 (SEQ ID NO:32), a VL FR2 (SEQ ID NO:26), and a VL FR4 (SEQ ID NO:28). In other embodiments, the antibody comprises a VH FR1 (SEQ ID NO:29), a VH FR2 (SEQ ID NO:30), a VH FR4 (SEQ ID NO:32), a VL FR3 (SEQ ID NO:27), and a VL FR4 (SEQ ID NO:28). In another embodiment, the antibody comprises a VH FR1 (SEQ ID NO:29), a VH FR3 (SEQ ID NO:31), a VH FR4 (SEQ ID NO:32), a VL FR1 (SEQ ID NO:25), and a VL FR2 (SEQ ID NO:26). In some embodiments, the antibody comprises a VH FR1 (SEQ ID NO:29), a VH FR3 (SEQ ID NO:31), a VH FR4 (SEQ ID NO:32), a VL FR1 (SEQ ID NO:25), and a VL FR3 (SEQ ID NO:27). In one embodiment, the antibody comprises a VH FR1 (SEQ ID NO:29), a VH FR3 (SEQ ID NO:31), a VH FR4 (SEQ ID NO:32), a VL FR1 (SEQ ID NO:25), and a VL FR4 (SEQ ID NO:28). In another embodiment, the antibody comprises a VH FR1 (SEQ ID NO:29), a VH FR3 (SEQ ID NO:31), a VH FR4 (SEQ ID NO:32), a VL FR2 (SEQ ID NO:26), and a VL FR3 (SEQ ID NO:27). In one embodiment, the antibody comprises a VH FR1 (SEQ ID NO:29), a VH FR3 (SEQ ID NO:31), a VH FR4 (SEQ ID NO:32), a VL FR2 (SEQ ID NO:26), and a VL FR4 (SEQ ID NO:28). In some embodiments, the antibody comprises a VH FR1 (SEQ ID NO:29), a VH FR3 (SEQ ID NO:31), a VH FR4 (SEQ ID NO:32), a VL FR3 (SEQ ID NO:27), and a VL FR4 (SEQ ID NO:28). In another embodiment, the antibody comprises a VH FR2 (SEQ ID NO:30), a VH FR3 (SEQ ID NO:31), a VH FR4 (SEQ ID NO:32), a VL FR1 (SEQ ID NO:25), and a VL FR2 (SEQ ID NO:26). In other embodiments, the antibody comprises a VH FR2 (SEQ ID NO:30), a VH FR3 (SEQ ID NO:31), a VH FR4 (SEQ ID NO:32), a VL FR1 (SEQ ID NO:25), and a VL FR3 (SEQ ID NO:27). In one embodiment, the antibody comprises a VH FR2 (SEQ ID NO:30), a VH FR3 (SEQ ID NO:31), a VH FR4 (SEQ ID NO:32), a VL FR1 (SEQ ID NO:25), and a VL FR4 (SEQ ID NO:28). In another embodiment, the antibody comprises a VH FR2 (SEQ ID NO:30), a VH FR3 (SEQ ID NO:31), a VH FR4 (SEQ ID NO:32), a VL FR2 (SEQ ID NO:26), and a VL FR3 (SEQ ID NO:27). In some embodiments, the antibody comprises a VH FR2 (SEQ ID NO:30), a VH FR3 (SEQ ID NO:31), a VH FR4 (SEQ ID NO:32), a VL FR2 (SEQ ID NO:26), and a VL FR4 (SEQ ID NO:28). In one embodiment, the antibody comprises a VH FR2 (SEQ ID NO:30), a VH FR3 (SEQ ID NO:31), a VH FR4 (SEQ ID NO:32), a VL FR3 (SEQ ID NO:27), and a VL FR4 (SEQ ID NO:28). In another embodiment, the antibody comprises a VH FR1 (SEQ ID NO:29), a VH FR2 (SEQ ID NO:30), a VL FR1 (SEQ ID NO:25), a VL FR2 (SEQ ID NO:26), and a VL FR3 (SEQ ID NO:27). In other embodiments, the antibody comprises a VH FR1 (SEQ ID NO:29), a VH FR2 (SEQ ID NO:30), a VL FR1 (SEQ ID NO:25), a VL FR2 (SEQ ID NO:26), and a VL FR4 (SEQ ID NO:28). In some embodiments, the antibody comprises a VH FR1 (SEQ ID NO:29), a VH FR2 (SEQ ID NO:30), a VL FR1 (SEQ ID NO:25), a VL FR3 (SEQ ID NO:27), and a VL FR4 (SEQ ID NO:28). In another embodiment, the antibody comprises a VH FR1 (SEQ ID NO:29), a VH FR2 (SEQ ID NO:30), a VL FR2 (SEQ ID NO:26), a VL FR3 (SEQ ID NO:27), and a VL FR4 (SEQ ID NO:28). In one embodiment, the antibody comprises a VH FR1 (SEQ ID NO:29), a VH FR3 (SEQ ID NO:31), a VL FR1 (SEQ ID NO:25), a VL FR2 (SEQ ID NO:26), and a VL FR3 (SEQ ID NO:27). In one embodiment, the antibody comprises a VH FR1 (SEQ ID NO:29), a VH FR3 (SEQ ID NO:31), a VL FR1 (SEQ ID NO:25), a VL FR2 (SEQ ID NO:26), and a VL FR4 (SEQ ID NO:28). In another embodiment, the antibody comprises a VH FR1 (SEQ ID NO:29), a VH FR3 (SEQ ID NO:31), a VL FR1 (SEQ ID NO:25), a VL FR3 (SEQ ID NO:27), and a VL FR4 (SEQ ID NO:28). In some embodiments, the antibody comprises a VH FR1 (SEQ ID NO:29), a VH FR3 (SEQ ID NO:31), a VL FR2 (SEQ ID NO:26), a VL FR3 (SEQ ID NO:27), and a VL FR4 (SEQ ID NO:28). In other embodiments, the antibody comprises a VH FR1 (SEQ ID NO:29), a VH FR4 (SEQ ID NO:32), a VL FR1 (SEQ ID NO:25), a VL FR2 (SEQ ID NO:26), and a VL FR3 (SEQ ID NO:27). In another embodiment, the antibody comprises a VH FR1 (SEQ ID NO:29), a VH FR4 (SEQ ID NO:32), a VL FR1 (SEQ ID NO:25), a VL FR2 (SEQ ID NO:26), and a VL FR4 (SEQ ID NO:28). In one embodiment, the antibody comprises a VH FR1 (SEQ ID NO:29), a VH FR4 (SEQ ID NO:32), a VL FR1 (SEQ ID NO:25), a VL FR3 (SEQ ID NO:27), and a VL FR4 (SEQ ID NO:28). In some embodiments, the antibody comprises a VH FR1 (SEQ ID NO:29), a VH FR4 (SEQ ID NO:32), a VL FR2 (SEQ ID NO:26), a VL FR3 (SEQ ID NO:27), and a VL FR4 (SEQ ID NO:28). In another embodiment, the antibody comprises a VH FR2 (SEQ ID NO:30), a VH FR3 (SEQ ID NO:31), a VL FR1 (SEQ ID NO:25), a VL FR2 (SEQ ID NO:26), and a VL FR3 (SEQ ID NO:27). In one embodiment, the antibody comprises a VH FR2 (SEQ ID NO:30), a VH FR3 (SEQ ID NO:31), a VL FR1 (SEQ ID NO:25), a VL FR2 (SEQ ID NO:26), and a VL FR4 (SEQ ID NO:28). In other embodiments, the antibody comprises a VH FR2 (SEQ ID NO:30), a VH FR3 (SEQ ID NO:31), a VL FR1 (SEQ ID NO:25), a VL FR3 (SEQ ID NO:27), and a VL FR4 (SEQ ID NO:28). In another embodiment, the antibody comprises a VH FR2 (SEQ ID NO:30), a VH FR3 (SEQ ID NO:31), a VL FR2 (SEQ ID NO:26), a VL FR3 (SEQ ID NO:27), and a VL FR4 (SEQ ID NO:28). In some embodiments, the antibody comprises a VH FR2 (SEQ ID NO:30), a VH FR4 (SEQ ID NO:32), a VL FR1 (SEQ ID NO:25), a VL FR2 (SEQ ID NO:26), and a VL FR3 (SEQ ID NO:27). In one embodiment, the antibody comprises a VH FR2 (SEQ ID NO:30), a VH FR4 (SEQ ID NO:32), a VL FR1 (SEQ ID NO:25), a VL FR2 (SEQ ID NO:26), and a VL FR4 (SEQ ID NO:28). In another embodiment, the antibody comprises a VH FR2 (SEQ ID NO:30), a VH FR4 (SEQ ID NO:32), a VL FR1 (SEQ ID NO:25), a VL FR3 (SEQ ID NO:27), and a VL FR4 (SEQ ID NO:28). In one embodiment, the antibody comprises a VH FR2 (SEQ ID NO:30), a VH FR4 (SEQ ID NO:32), a VL FR2 (SEQ ID NO:26), a VL FR3 (SEQ ID NO:27), and a VL FR4 (SEQ ID NO:28). In some embodiments, the antibody comprises a VH FR3 (SEQ ID NO:31), a VH FR4 (SEQ ID NO:32), a VL FR1 (SEQ ID NO:25), a VL FR2 (SEQ ID NO:26), and a VL FR3 (SEQ ID NO:27). In another embodiment, the antibody comprises a VH FR3 (SEQ ID NO:31), a VH FR4 (SEQ ID NO:32), a VL FR1 (SEQ ID NO:25), a VL FR2 (SEQ ID NO:26), and a VL FR4 (SEQ ID NO:28). In other embodiments, the antibody comprises a VH FR3 (SEQ ID NO:31), a VH FR4 (SEQ ID NO:32), a VL FR1 (SEQ ID NO:25), a VL FR3 (SEQ ID NO:27), and a VL FR4 (SEQ ID NO:28). In one embodiment, the antibody comprises a VH FR3 (SEQ ID NO:31), a VH FR4 (SEQ ID NO:32), a VL FR2 (SEQ ID NO:26), a VL FR3 (SEQ ID NO:27), and a VL FR4 (SEQ ID NO:28). In another embodiment, the antibody comprises a VH FR1 (SEQ ID NO:29), a VL FR1 (SEQ ID NO:25), a VL FR2 (SEQ ID NO:26), a VL FR3 (SEQ ID NO:27), and a VL FR4 (SEQ ID NO:28). In some embodiments, the antibody comprises a VH FR2 (SEQ ID NO:30), a VL FR1 (SEQ ID NO:25), a VL FR2 (SEQ ID NO:26), a VL FR3 (SEQ ID NO:27), and a VL FR4 (SEQ ID NO:28). In one embodiment, the antibody comprises a VH FR3 (SEQ ID NO:31), a VL FR1 (SEQ ID NO:25), a VL FR2 (SEQ ID NO:26), a VL FR3 (SEQ ID NO:27), and a VL FR4 (SEQ ID NO:28). In another embodiment, the antibody comprises a VH FR4 (SEQ ID NO:32), a VL FR1 (SEQ ID NO:25), a VL FR2 (SEQ ID NO:26), a VL FR3 (SEQ ID NO:27), and a VL FR4 (SEQ ID NO:28). In other embodiments, the antibody comprises a VH FR1 (SEQ ID NO:29), a VH FR2 (SEQ ID NO:30), a VH FR3 (SEQ ID NO:31), a VH FR4 (SEQ ID NO:32), a VL FR1 (SEQ ID NO:25), and a VL FR2 (SEQ ID NO:26). In some embodiments, the antibody comprises a VH FR1 (SEQ ID NO:29), a VH FR2 (SEQ ID NO:30), a VH FR3 (SEQ ID NO:31), a VH FR4 (SEQ ID NO:32), a VL FR1 (SEQ ID NO:25), and a VL FR3 (SEQ ID NO:27). In another embodiment, the antibody comprises a VH FR1 (SEQ ID NO:29), a VH FR2 (SEQ ID NO:30), a VH FR3 (SEQ ID NO:31), a VH FR4 (SEQ ID NO:32), a VL FR1 (SEQ ID NO:25), and a VL FR4 (SEQ ID NO:28). In one embodiment, the antibody comprises a VH FR1 (SEQ ID NO:29), a VH FR2 (SEQ ID NO:30), a VH FR3 (SEQ ID NO:31), a VH FR4 (SEQ ID NO:32), a VL FR2 (SEQ ID NO:26), and a VL FR3 (SEQ ID NO:27). In one embodiment, the antibody comprises a VH FR1 (SEQ ID NO:29), a VH FR2 (SEQ ID NO:30), a VH FR3 (SEQ ID NO:31), a VH FR4 (SEQ ID NO:32), a VL FR2 (SEQ ID NO:26), and a VL FR4 (SEQ ID NO:28). In another embodiment, the antibody comprises a VH FR1 (SEQ ID NO:29), a VH FR2 (SEQ ID NO:30), a VH FR3 (SEQ ID NO:31), a VH FR4 (SEQ ID NO:32), a VL FR3 (SEQ ID NO:27), and a VL FR4 (SEQ ID NO:28). In some embodiments, the antibody comprises a VH FR1 (SEQ ID NO:29), a VH FR2 (SEQ ID NO:30), a VH FR3 (SEQ ID NO:31), a VL FR1 (SEQ ID NO:25), a VL FR2 (SEQ ID NO:26), and a VL FR3 (SEQ ID NO:27). In other embodiments, the antibody comprises a VH FR1 (SEQ ID NO:29), a VH FR2 (SEQ ID NO:30), a VH FR3 (SEQ ID NO:31), a VL FR1 (SEQ ID NO:25), a VL FR2 (SEQ ID NO:26), and a VL FR4 (SEQ ID NO:28). In another embodiment, the antibody comprises a VH FR1 (SEQ ID NO:29), a VH FR2 (SEQ ID NO:30), a VH FR3 (SEQ ID NO:31), a VL FR1 (SEQ ID NO:25), a VL FR3 (SEQ ID NO:27), and a VL FR4 (SEQ ID NO:28). In one embodiment, the antibody comprises a VH FR1 (SEQ ID NO:29), a VH FR2 (SEQ ID NO:30), a VH FR3 (SEQ ID NO:31), a VL FR2 (SEQ ID NO:26), a VL FR3 (SEQ ID NO:27), and a VL FR4 (SEQ ID NO:28). In some embodiments, the antibody comprises a VH FR1 (SEQ ID NO:29), a VH FR2 (SEQ ID NO:30), a VH FR4 (SEQ ID NO:32), a VL FR1 (SEQ ID NO:25), a VL FR2 (SEQ ID NO:26), and a VL FR3 (SEQ ID NO:27). In another embodiment, the antibody comprises a VH FR1 (SEQ ID NO:29), a VH FR2 (SEQ ID NO:30), a VH FR4 (SEQ ID NO:32), a VL FR1 (SEQ ID NO:25), a VL FR2 (SEQ ID NO:26), and a VL FR4 (SEQ ID NO:28). In one embodiment, the antibody comprises a VH FR1 (SEQ ID NO:29), a VH FR2 (SEQ ID NO:30), a VH FR4 (SEQ ID NO:32), a VL FR1 (SEQ ID NO:25), a VL FR3 (SEQ ID NO:27), and a VL FR4 (SEQ ID NO:28). In other embodiments, the antibody comprises a VH FR1 (SEQ ID NO:29), a VH FR2 (SEQ ID NO:30), a VH FR4 (SEQ ID NO:32), a VL FR2 (SEQ ID NO:26), a VL FR3 (SEQ ID NO:27), and a VL FR4 (SEQ ID NO:28). In another embodiment, the antibody comprises a VH FR1 (SEQ ID NO:29), a VH FR3 (SEQ ID NO:31), a VH FR4 (SEQ ID NO:32), a VL FR1 (SEQ ID NO:25), a VL FR2 (SEQ ID NO:26), and a VL FR3 (SEQ ID NO:27). In some embodiments, the antibody comprises a VH FR1 (SEQ ID NO:29), a VH FR3 (SEQ ID NO:31), a VH FR4 (SEQ ID NO:32), a VL FR1 (SEQ ID NO:25), a VL FR2 (SEQ ID NO:26), and a VL FR4 (SEQ ID NO:28). In one embodiment, the antibody comprises a VH FR1 (SEQ ID NO:29), a VH FR3 (SEQ ID NO:31), a VH FR4 (SEQ ID NO:32), a VL FR1 (SEQ ID NO:25), a VL FR3 (SEQ ID NO:27), and a VL FR4 (SEQ ID NO:28). In another embodiment, the antibody comprises a VH FR1 (SEQ ID NO:29), a VH FR3 (SEQ ID NO:31), a VH FR4 (SEQ ID NO:32), a VL FR2 (SEQ ID NO:26), a VL FR3 (SEQ ID NO:27), and a VL FR4 (SEQ ID NO:28). In one embodiment, the antibody comprises a VH FR2 (SEQ ID NO:30), a VH FR3 (SEQ ID NO:31), a VH FR4 (SEQ ID NO:32), a VL FR1 (SEQ ID NO:25), a VL FR2 (SEQ ID NO:26), and a VL FR3 (SEQ ID NO:27). In some embodiments, the antibody comprises a VH FR2 (SEQ ID NO:30), a VH FR3 (SEQ ID NO:31), a VH FR4 (SEQ ID NO:32), a VL FR1 (SEQ ID NO:25), a VL FR2 (SEQ ID NO:26), and a VL FR4 (SEQ ID NO:28). In another embodiment, the antibody comprises a VH FR2 (SEQ ID NO:30), a VH FR3 (SEQ ID NO:31), a VH FR4 (SEQ ID NO:32), a VL FR1 (SEQ ID NO:25), a VL FR3 (SEQ ID NO:27), and a VL FR4 (SEQ ID NO:28). In other embodiments, the antibody comprises a VH FR2 (SEQ ID NO:30), a VH FR3 (SEQ ID NO:31), a VH FR4 (SEQ ID NO:32), a VL FR2 (SEQ ID NO:26), a VL FR3 (SEQ ID NO:27), and a VL FR4 (SEQ ID NO:28). In one embodiment, the antibody comprises a VH FR1 (SEQ ID NO:29), a VH FR2 (SEQ ID NO:30), a VL FR1 (SEQ ID NO:25), a VL FR2 (SEQ ID NO:26), a VL FR3 (SEQ ID NO:27), and a VL FR4 (SEQ ID NO:28). In another embodiment, the antibody comprises a VH FR1 (SEQ ID NO:29), a VH FR3 (SEQ ID NO:31), a VL FR1 (SEQ ID NO:25), a VL FR2 (SEQ ID NO:26), a VL FR3 (SEQ ID NO:27), and a VL FR4 (SEQ ID NO:28). In some embodiments, the antibody comprises a VH FR1 (SEQ ID NO:29), a VH FR4 (SEQ ID NO:32), a VL FR1 (SEQ ID NO:25), a VL FR2 (SEQ ID NO:26), a VL FR3 (SEQ ID NO:27), and a VL FR4 (SEQ ID NO:28). In one embodiment, the antibody comprises a VH FR2 (SEQ ID NO:30), a VH FR3 (SEQ ID NO:31), a VL FR1 (SEQ ID NO:25), a VL FR2 (SEQ ID NO:26), a VL FR3 (SEQ ID NO:27), and a VL FR4 (SEQ ID NO:28). In another embodiment, the antibody comprises a VH FR2 (SEQ ID NO:30), a VH FR4 (SEQ ID NO:32), a VL FR1 (SEQ ID NO:25), a VL FR2 (SEQ ID NO:26), a VL FR3 (SEQ ID NO:27), and a VL FR4 (SEQ ID NO:28). In other embodiments, the antibody comprises a VH FR3 (SEQ ID NO:31), a VH FR4 (SEQ ID NO:32), a VL FR1 (SEQ ID NO:25), a VL FR2 (SEQ ID NO:26), a VL FR3 (SEQ ID NO:27), and a VL FR4 (SEQ ID NO:28). In some embodiments, the antibody comprises a VH FR1 (SEQ ID NO:29), a VH FR2 (SEQ ID NO:30), a VH FR3 (SEQ ID NO:31), a VH FR4 (SEQ ID NO:32), a VL FR1 (SEQ ID NO:25), a VL FR2 (SEQ ID NO:26), and a VL FR3 (SEQ ID NO:27). In another embodiment, the antibody comprises a VH FR1 (SEQ ID NO:29), a VH FR2 (SEQ ID NO:30), a VH FR3 (SEQ ID NO:31), a VH FR4 (SEQ ID NO:32), a VL FR1 (SEQ ID NO:25), a VL FR2 (SEQ ID NO:26), and a VL FR4 (SEQ ID NO:28). In one embodiment, the antibody comprises a VH FR1 (SEQ ID NO:29), a VH FR2 (SEQ ID NO:30), a VH FR3 (SEQ ID NO:31), a VH FR4 (SEQ ID NO:32), a VL FR1 (SEQ ID NO:25), a VL FR3 (SEQ ID NO:27), and a VL FR4 (SEQ ID NO:28). In one embodiment, the antibody comprises a VH FR1 (SEQ ID NO:29), a VH FR2 (SEQ ID NO:30), a VH FR3 (SEQ ID NO:31), a VH FR4 (SEQ ID NO:32), a VL FR2 (SEQ ID NO:26), a VL FR3 (SEQ ID NO:27), and a VL FR4 (SEQ ID NO:28). In another embodiment, the antibody comprises a VH FR1 (SEQ ID NO:29), a VH FR2 (SEQ ID NO:30), a VH FR3 (SEQ ID NO:31), a VL FR1 (SEQ ID NO:25), a VL FR2

(SEQ ID NO:26), a VL FR3 (SEQ ID NO:27), and a VL FR4 (SEQ ID NO:28). In some embodiments, the antibody comprises a VH FR1 (SEQ ID NO:29), a VH FR2 (SEQ ID NO:30), a VH FR4 (SEQ ID NO:32), a VL FR1 (SEQ ID NO:25), a VL FR2 (SEQ ID NO:26), a VL FR3 (SEQ ID NO:27), and a VL FR4 (SEQ ID NO:28). In other embodiments, the antibody comprises a VH FR1 (SEQ ID NO:29), a VH FR3 (SEQ ID NO:31), a VH FR4 (SEQ ID NO:32), a VL FR1 (SEQ ID NO:25), a VL FR2 (SEQ ID NO:26), a VL FR3 (SEQ ID NO:27), and a VL FR4 (SEQ ID NO:28). In one embodiment, the antibody comprises a VH FR2 (SEQ ID NO:30), a VH FR3 (SEQ ID NO:31), a VH FR4 (SEQ ID NO:32), a VL FR1 (SEQ ID NO:25), a VL FR2 (SEQ ID NO:26), a VL FR3 (SEQ ID NO:27), and a VL FR4 (SEQ ID NO:28). In some embodiments, the antibody comprises any combination thereof the VH FRs (SEQ ID NOS:29-32) and the VL FRs (SEQ ID NOS:25-28) listed in Table 2.

In some embodiments, the antibodies provided herein comprise a VH region or VH domain. In other embodiments, the antibodies provided herein comprise a VL region or VL domain. In certain embodiments, the antibodies provided herein have a combination of (i) a VH domain or VH region; and/or (ii) a VL domain or VL region. In yet other embodiments, the antibodies provided herein have a combination of (i) a VH domain or VH region; and/or (ii) a VL domain or VL region selected from the group consisting of SEQ ID NOS:3 and 4 as set forth in Table 1.

In certain embodiments, the antibodies provided herein comprise a VH region comprising: (1) a VH CDR1 having an amino acid sequence of SEQ ID NO:15; (2) a VH CDR2 having an amino acid sequence of SEQ ID NO:19; and (3) a VH CDR3 having an amino acid sequence of SEQ ID NO:23; and a VL region selected from the group consisting of SEQ ID NO:3 as set forth in Table 1.

In other embodiments, the antibodies provided herein comprise a VH region selected from the group consisting of SEQ ID NO:4 as set forth in Table 1; and a VL region comprising: (1) a VL CDR1 having an amino acid sequence of SEQ ID NO:7; (2) a VL CDR2 having an amino acid sequence of SEQ ID NO:10; and (3) a VL CDR3 having an amino acid sequence of SEQ ID NO:12.

Also provided herein are isolated nucleic acid molecules encoding an immunoglobulin heavy chain, light chain, VH region, VL region, VH CDR1, VH CDR2, VH CDR3, VL CDR1, VL CDR2, and/or VL CDR3 of anti-Nectin-4 antibodies that bind to a Nectin-4 polypeptide, a Nectin-4 polypeptide fragment, a Nectin-4 peptide, or a Nectin-4 epitope. The exemplary nucleic acid sequences for the VL region, light chain, the VH region, and heavy chain of antibody M22-321b41.1 are shown in Tables 3-4.

TABLE 3

VL Nucleic Acid Sequences

| Antibody | Nucleotide sequences |
| --- | --- |
| DNA sequence for M22-321b41.1 VL region | GATATTGTGATGACGCAGGCTGCATTCTCCAATCCAGTCACTCTTGGAACATC AGCTTCCATCTCCTGCAGGTCTAGTAAGAGTCTCCTACATAGTAATGGCATCA CTTATTTGTATTGGTATCTGCAGAAGCCAGGCCAGTCTCCTCAGCTCCTGATT TATCATATGTCCAACCTTGCCTCAGGAGTCCCAGACAGGTTCACTAGCAGTG GGTCAGGAACTGATTTCACACTGAGAATCAGCAGAGTGGAGGCTGAGGATGT GGGTGTTTATTACTGCGCTCAAAATCTAGAACTTCCGTTCACGTTCGGAGGGG GGACCAAGCTGGAAACAAAACGGGCTGATGCTGCACCAACTGTATCCATCTT CCCACCATCCAGTGAGCAGTTAACATCTGGA (SEQ ID NO:37) |
| DNA sequence for M22-321b41.1 Light Chain | GATATTGTGATGACGCAGGCTGCATTCTCCAATCCAGTCACTCTTGGAACATC AGCTTCCATCTCCTGCAGGTCTAGTAAGAGTCTCCTACATAGTAATGGCATCA CTTATTTGTATTGGTATCTGCAGAAGCCAGGCCAGTCTCCTCAGCTCCTGATT TATCATATGTCCAACCTTGCCTCAGGAGTCCCAGACAGGTTCACTAGCAGTG GGTCAGGAACTGATTTCACACTGAGAATCAGCAGAGTGGAGGCTGAGGATGT GGGTGTTTATTACTGCGCTCAAAATCTAGAACTTCCGTTCACGTTCGGAGGGG GGACCAAGCTGGAAACAAAACGGGCTGATGCTGCACCAACTGTATCCATCTT CCCACCATCCAGTGAGCAGTTAACATCTGGAGGTGCCTCAGTCGTGTGCTTCT TGAACAACTTCTACCCCAAAGACATCAATGTCAAGTGGAAGATTGATGGCAG TGAACGACAAAATGGCGTCCTGAACAGTTGGACTGATCAGGACAGCAAAGA CAGCACCTACAGCATGAGCAGCACCCTCACGTTGACCAAGGACGAGTATGAA CGACTAACAGCTATACCTGTGAGGCCACTCACAAGACATCAACTTCACCCA TTGTCAAGACCTTCAACAGGAATGAGTGT (SEQ ID NO:39) |

TABLE 4

VH Nucleic Acid Sequences

| Antibody | Nucleotide sequences |
| --- | --- |
| DNA sequence for M22-321b41.1 VH region | CAGGTTCAGCTCCAGCAGTCTGGGGCTGAGCTGGCAAGACCTGGGGCTTCAG TGAAATTGTCCTGCAAGGCTTCTGGCTATACCTTTACTACCTACTGGATGCAG TGGGTAAAACAGAGGCCTGGACAGGGTCTGGAATGGATTGGGTCTATTTATC CTGGAGATGGTGATACTAGGTACACTCAGAAGTTCAAGGGCAAGGCCACATT GACTGCAGATAAATCCTCCAGCACAGCCTACATTCAACTCAGCACCTTGGCA TCTGAGGACTCTGCGGTCTATTACTGTGCAAGAGAATACTACGGTCTTGACTA CTGGGGCCAAGGCACCACTCTCACAGTCTCCTCAGCCAAAACAACAGCCCCA TCGGTCTATCCACTGGCCCCTGTGTGTGGAGATACAACTGGC (SEQ ID NO: 38) |

TABLE 4-continued

VH Nucleic Acid Sequences

| Antibody | Nucleotide sequences |
|---|---|
| DNA sequence for M22-321b41.1 Heavy Chain | CAGGTTCAGCTCCAGCAGTCTGGGGCTGAGCTGGCAAGACCTGGGGCTTCAG<br>TGAAATTGTCCTGCAAGGCTTCTGGCTATACCTTTACTACCTACTGGATGCAG<br>TGGGTAAAACAGAGGCCTGGACAGGGTCTGGAATGGATTGGGTCTATTTATC<br>CTGGAGATGGTGATACTAGGTACACTCAGAAGTTCAAGGGCAAGGCCACATT<br>GACTGCAGATAAATCCTCCAGCACAGCCTACATTCAACTCAGCACCTTGGCA<br>TCTGAGGACTCTGCCGGTCTATTACTGTGCAAGAGAATACTACGGTCTTGACTA<br>CTGGGGCCAAGGCACCACTCTCACAGTCTCCTCAGCCAAAACAACAGCCCCA<br>TCGGTCTATCCACTGGCCCCTGTGTGTGGAGATACAACTGGCTCCTCGGTGAC<br>TCTAGGATGCCTGGTCAAGGGTTATTTCCCTGAGCCAGTGACCTTGACCTGGA<br>ACTCTGGATCCCTGTCCAGTGGTGTGCACACCTTCCCAGCTGTCCTGCAGTCT<br>GACCTCTACACCCTCAGCAGCTCAGTGACTGTAACCTCGAGCACCTGGCCCA<br>GCCAGTCCATCACCTGCAATGTGGCCCACCCGGCAAGCAGCACCAAGGTGGA<br>CAAGAAAATTGAGCCCAGAGGGCCCACAATCAAGCCCTGTCCTCCATGCAAA<br>TGCCCAGCACCTAACCTCTTGGGTGGACCATCCGTCTTCATCTTCCCTCCAAA<br>GATCAAGGATGTACTCATGATCTCCCTGAGCCCCATAGTCACATGTGTGGTG<br>GTGGATGTGAGCGAGGATGACCCAGATGTCCAGATCAGCTGGTTTGTGAACA<br>ACGTGGAAGTACACACAGCTCAGACACAAACCCATAGAGAGGATTACAACA<br>GTACTCTCCGGGTGGTCAGTGCCCTCCCCATCCAGCACCAGGACTGGATGAG<br>TGGCAAGGAGTTCAAATGCAAGGTCAACAACAAAGACCTCCCAGCGCCCATC<br>GAGAGAACCATCTCAAAACCCAAAGGGTCAGTAAGAGCTCCACAGGTATAT<br>GTCTTGCCTCCACCAGAAGAAGAGATGACTAAGAAACAGGTCACTCTGACCT<br>GCATGGTCACAGACTTCATGCCTGAAGACATTTACGTGGAGTGGACCAACAA<br>CGGGAAAACAGAGCTAAACTACAAGAACACTGAACCAGTCCTGGACTCTGA<br>TGGTTCTTACTTCATGTACAGCAAGCTGAGAGTGGAAAAGAAGAACTGGGTG<br>GAAAGAAATAGCTACTCCTGTTCAGTGGTCCACGAGGGTCTGCACAATCACC<br>ACACGACTAAGAGCTTCTCCCGGACTCCGGGTAAA (SEQ ID NO: 40) |

In some embodiments, an antibody provided herein has a VH and a VL amino acid sequence of antibody M22-321b41.1. In some embodiments, an antibody comprises a VH amino acid sequence of SEQ ID NO:4, and a VL amino acid sequence of SEQ ID NO:3.

In certain embodiments, an antibody or antigen-binding fragment thereof described herein, which specifically binds to a Nectin-4 polypeptide (e.g., an ECD of Nectin-4, for example human Nectin-4), comprises a light chain and a heavy chain, wherein the light chain comprises a constant region having an amino acid sequence of:

(SEQ ID NO: 33)
GASVVCFLNNFYPKDINVKWKIDGSERQNGVLNSWTDQDSKDSTYSMSS

TLTLTKDEYERHNSYTCEATHKTSTSPIVKTFNRNEC.

In certain embodiments, an antibody or antigen-binding fragment thereof described herein, which specifically binds to a Nectin-4 polypeptide (e.g., an ECD of Nectin-4, for example human Nectin-4), comprises a light chain and a heavy chain, wherein the heavy chain comprises a constant region having an amino acid sequence of:

SSVTLGCLVKGYFPEPVTLTWNSGSLSSGVHTFPAVLQSDLYTLSSSVT

VTSSTWPSQSITCNVAHPASSTKVDKKIEPRGPTIKPCPPCKCPAPNLL

GGPSVFIFPPKIKDVLMISLSPIVTCVVVDVSEDDPDVQISWFVNNVEV

HTAQTQTHREDYNSTLRVVSALPIQHQDWMSGKEFKCKVNNKDLPAPIE

RTISKPKGSVRAPQVYVLPPPEEEMTKKQVTLTCMVTDFMPEDIYVEWT

NNGKTELNYKNTEPVLDSDGSYFMYSKLRVEKKNWVERNSYSCSVVHEG

LHNHHTTKSFSRTPGK (SEQ ID NO: 34).

In other embodiments, an antibody or antigen-binding fragment thereof described herein, which specifically binds to a Nectin-4 polypeptide (e.g., an ECD of Nectin-4, for example human Nectin-4), comprises a light chain and a heavy chain, wherein the heavy chain comprises a human IgG1 Fc region having an amino acid sequence of:

PRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDW

MSGKEFKCKVNNKDLPAPIERTISKPKGSVRAPQVYVLPPPEEEMTKKQ

VTLTCMVTDFMPEDIYVEWTNNGKTELNYKNTEPVLDSDGSYFMYSKLR

VEKKNWVERNSYSCSVVHEGLHNHEITTKSFSRTPGK (SEQ ID NO: 35).

In some embodiments, an antibody or antigen-binding fragment thereof described herein, which specifically binds to a Nectin-4 polypeptide (e.g., an ECD of Nectin-4, for example human Nectin-4), comprises a light chain and a heavy chain, wherein the heavy chain does not comprise a human IgG1 Fc region having an amino acid sequence of SEQ ID NO:35.

In still another embodiment, an antibody or antigen-binding fragment thereof described herein, which specifically binds to a Nectin-4 polypeptide (e.g., an ECD of Nectin-4, for example human Nectin-4), comprises a light chain and a heavy chain, wherein the light chain comprises a constant region having an amino acid sequence of SEQ ID NO:33; and the heavy chain comprises an Fc region having an amino acid sequence of SEQ ID NO:35.

In certain embodiments, an antibody described herein, which specifically binds to a Nectin-4 polypeptide (e.g., an ECD of Nectin-4, for example human Nectin-4), comprises a light chain and a heavy chain, wherein the light chain comprises an amino acid sequence as follows:

DIVNITQAAFSNPVTLGTSASISCRSSKSLLHSNGITYLYWYLQKPGQS

PQLLIYHMSNLASGVPDRFTSSGSGTDFTLRISRVEAEDVGVYYCAQNL

ELPFTFGGGTKLETKRADAAPTVSIFPPSSEQLTSGGASVVCFLNNFYP

KDINVKWKIDGSERQNGVLNSWTDQDSKDSTYSMSSTLTLTKDEYERHN

SYTCEATHKTSTSPIVKTFNRNEC (SEQ ID NO: 5).

In some embodiments, an antibody described herein, which specifically binds to a Nectin-4 polypeptide (e.g., an ECD of Nectin-4, for example human Nectin-4), comprises a light chain and a heavy chain, wherein the heavy chain comprises an amino acid sequence as follows:

QVQLQQSGAELARPGASVKLSCKASGYTFTTYWMQWVKQRPGQGLEWIG

STYPGDGDTRYTQKFKGKATLTADKSSSTAYIQLSTLASEDSAVYYCAR

EYYGLDYWGQGTTLTVSSAKTTAPSVYPLAPVCGDTTGSSVTLGCLVKG

YFPEPVTLTWNSGSLSSGVHTFPAVLQSDLYTLSSSVTVTSSTWPSQSI

TCNVAHPASSTKVDKKIEPRGPTIKPCPPCKCPAPNLLGGPSVFIFPPK

IKDVLMISLSPIVTCVVVDVSEDDPDVQISWFVNNVEVHTAQTQTHRED

YNSTLRVVSALPIQHQDWMSGKEFKCKVNNKDLPAPIERTISKPKGSVR

APQVYVLPPPEEEMTKKQVTLTCMVTDFMPEDIYVEWTNNGKTELNYKN

TEPVLDSDGSYFMYSKLRVEKKNWVERNSYSCSVVHEGLHNHHTTKSFS

RTPGK (SEQ ID NO: 6).

In one particular embodiment, an antibody described herein, which specifically binds to a Nectin-4 polypeptide (e.g., an ECD of Nectin-4, for example human Nectin-4), comprises a light chain and a heavy chain, wherein (i) the light chain comprises an amino acid sequence of SEQ ID NO:5; and (ii) the heavy chain comprises an amino acid sequence of SEQ ID NO:6.

In yet another aspect, antibodies are provided that compete with one of the exemplified antibodies or functional fragments for binding to Nectin-4. Such antibodies may also bind to the same epitope as one of the herein exemplified antibodies, or an overlapping epitope. Antibodies and fragments that compete with or bind to the same epitope as the exemplified antibodies are expected to show similar functional properties. The exemplified antigen-binding proteins and fragments include those with the VH and VL regions, and CDRs provided herein, including those in Table 1. Thus, as a specific example, the antibodies that are provided include those that compete with an antibody comprising: (a) 1, 2, 3, 4, 5, or all 6 of the CDRs listed for an antibody listed in Table 1; (b) a VH and a VL selected from the VH and the VL regions listed for an antibody listed in Table 1; or (c) two light chains and two heavy chains comprising a VH and a VL as specified for an antibody listed in Table 1. In some embodiments, the antibody is antibody M22-321b41.1.

In certain embodiments, an antibody described herein or an antigen-binding fragment thereof comprises amino acid sequences with certain percent identity relative to antibody M22-321b41.1.

The determination of percent identity between two sequences (e.g., amino acid sequences or nucleic acid sequences) can be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and) (BLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the) (BLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of)(BLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO:3, wherein the antibody immunospecifically binds to Nectin-4. In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO:3, wherein the antibody immunospecifically binds to Nectin-4, and wherein the antibody comprises CDRs (e.g., VL CDRs 1-3) that are identical to the CDRs (e.g., VL CDRs 1-3) of antibody M22-321b41.1.

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO:3, wherein the antibody immunospecifically binds to Nectin-4. In a particular embodiment, the antibody comprises VL CDRs that are identical to the VL CDRs of antibody M22-321b41.1.

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO:4, wherein the antibody immunospecifically binds to Nectin-4. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO:4, wherein the antibody immunospecifically binds to Nectin-4, and wherein the antibody comprises CDRs (e.g., VH CDRs 1-3) that are identical to the CDRs (e.g., VH CDRs 1-3) of antibody M22-321b41.1.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO:4, wherein the antibody immunospecifically binds to Nectin-4. In specific embodiments, such an antibody comprises CDRs (e.g., VH CDRs 1-3) identical to the CDRs (e.g., VH CDRs 1-3) of antibody M22-321b41.1.

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO:3, and (ii) a VH domain having at least 80%, at least 85%, at least 90%, at least 95%, or at least 98% sequence identity to the amino acid sequence of SEQ ID NO:4, respectively, wherein the antibody immunospecifically binds to Nectin-4. In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody M22-321b41.1.

In another aspect, antibodies or antigen-binding fragments thereof provided herein bind to a region, including an epitope, of human Nectin-4. For example, in some embodiments, an antibody provided herein binds to a region of human Nectin-4 (SEQ ID NO:1) comprising amino acid residues 31-346 (SEQ ID NO:2), a region of human Nectin-4 (SEQ ID NO:1) comprising amino acid residues 1-150 (SEQ ID NO:45), or a region of human Nectin-4 (SEQ ID NO:1) comprising amino acid residues 31-150 (SEQ ID NO:46) of human Nectin-4. In still another aspect, antibodies provided herein bind to a specific epitope of human Nectin-4. Amino acid sequence of amino acid residues 31-346 of human Nectin-4 (SEQ ID NO:1) is: AGELETSDVVTVVLGQDAK-LPCFYRGDSGEQVGQVAWARVDAGEGAQELALLHS-KYG LHVSPAYEGRVEQPPPPRNPLDGSVLLRNAVQADE-GEYECRVSTFPAGSFQARLRLRVL VPPLPSLNPGPA-LEEGQGLTLAASCTAEGSPAPSVTWDTE-VKGTTSSRSFKHSRSAAVTS EFHLVPSRSMNGQPLTCVVSHPGLLQDQRITHILHVS-FLAEASVRGLEDQNLWHIGREG AMLKCLSEGQPPPSYNWTRLDG-PLPSGVRVDGDTLGFPPLTTEHSGIYVCHVSNEFSSRD SQVTVDVLDPQEDSGKQVDLV (SEQ ID NO:2). Amino acid sequence of amino acid residues 1-150 of human Nectin-4 (SEQ ID NO:1) is: MPLSLGAEMWG-PEAWLLLLLLLASFTGRCPAGE-LETSDVVTVVLGQDAKLPCFYRGDS GEQVGQVAWARVDAGEGAQELALLHSKYGLHVS-PAYEGRVEQPPPPRNPLDGSVLLR NAVQADEGEYE-CRVSTFPAGSFQARLRLRVLVPPL (SEQ ID NO:45). Amino acid sequence of amino acid residues 31-150 of human Nectin-4 (SEQ ID NO:1) is:

AGELETSDVVTVVLGQDAKLPCFYRGDSGEQVGQVAWARVDAGEGAQE

LALLHSKYGLHVSPAYEGRVEQPPPPRNPLDGSVLLRNAVQADEGEYEC

RVSTFPAGSFQARLRLRVLVPPL (SEQ ID NO: 46)

In some embodiments, the antibodies provided herein bind to a Nectin-4 epitope that is a three-dimensional surface feature of a Nectin-4 polypeptide (e.g., in a multimeric form of a Nectin-4 polypeptide). A region of a Nectin-4 polypeptide contributing to an epitope may be contiguous amino acids of the polypeptide or the epitope may come together from two or more non-contiguous regions of the polypeptide. A Nectin-4 epitope may be present in (a) the multimeric form ("a multimeric Nectin-4 epitope") of Nectin-4, (b) the monomeric form ("a monomeric Nectin-4 epitope") of Nectin-4, (c) both the multimeric and monomeric form of Nectin-4, (d) the multimeric form, but not the monomeric form of Nectin-4, or (e) the monomeric form, but not the multimeric form of Nectin-4. For example, in some embodiments, the epitope is only present or available for binding in the multimeric (native) form, but is not present or available for binding in the monomeric (denatured) form by an anti-Nectin-4 antibody. In other embodiments, the Nectin-4 epitope is linear feature of the Nectin-4 polypeptide (e.g., in a multimeric form or monomeric form of the Nectin-4 polypeptide). Antibodies provided herein may immunospecifically bind to (a) an epitope of the monomeric form of Nectin-4, (b) an epitope of the multimeric form of Nectin-4, (c) an epitope of the monomeric but not the multimeric form of Nectin-4, (d) an epitope of the multimeric but not the monomeric form of Nectin-4, or (e) both the monomeric form and the multimeric form of Nectin-4.

Also provided herein are antibodies that bind the same or an overlapping epitope of Nectin-4 (e.g., an epitope located in an ECD of human Nectin-4) as the antibody M22-321b41.1 described herein, for example, antibodies that compete (e.g., in a dose dependent manner) for binding to Nectin-4 (e.g., an ECD of human Nectin-4) with the antibody M22-321b41.1 described herein, or that competitively inhibit (e.g., in a dose dependent manner) the antibody M22-321b41.1 described herein from binding to Nectin-4 (e.g., an epitope located on the ECD of human Nectin-4).

In a specific aspect, also provided herein are antibodies that bind the same or an overlapping epitope of Nectin-4 (e.g., an epitope located in an ECD of human Nectin-4) as the antibody M22-321b41.1.

Antibodies that bind to the same or overlapping epitopes of Nectin-4 (e.g., an epitope located in an ECD of human Nectin-4) can be identified using routine techniques such as those utilized in the examples presented herein. An immunoassay, for example, used to demonstrate the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as Nectin-4. Numerous types of competitive binding assays are known, for example: solid phase direct or indirect radioimmunoassay (MA), solid phase direct or indirect enzyme immunoassay (EIA), sandwich competition assay (see Stahli et al., (1983) Methods in Enzymology 9:242); solid phase direct biotin-avidin EIA (see Kirkland et al., (1986) J. Immunol. 137:3614); solid phase direct labeled assay, solid phase direct labeled sandwich assay (see Harlow and Lane, (1988)

Antibodies: A Laboratory Manual, Cold Spring Harbor Press); solid phase direct label MA using I-125 label (see Morel et al., (1988) Mol. Immunol. 25(1):7); solid phase direct biotin-avidin EIA (Cheung et al., (1990) Virology 176:546); and direct labeled RIA. (Moldenhauer et al., (1990) Scand J. Immunol. 32:77). Typically, such an assay involves the use of purified antigen (e.g., Nectin-4, such as an ECD of human Nectin-4) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener et al., J. Immunol., 1983, 130:2308-2315; Wagener et al., J. Immunol. Methods, 1984, 68:269-274; Kuroki et al., Cancer Res., 1990, 50:4872-4879; Kuroki et al., Immunol. Invest., 1992, 21:523-538; Kuroki et al., Hybridoma, 1992, 11:391-407, and *Using Antibodies: A Laboratory Manual*, Ed Harlow and David Lane editors (Cold Springs Harbor Laboratory Press, Cold Springs Harbor, N.Y., 1999), pp. 386-389.

In certain aspects, competition binding assays can be used to determine whether binding of an antibody is competitively inhibited, e.g., in a dose dependent manner, by another antibody, thereby signaling that the antibodies bind essentially the same epitope, or overlapping epitopes, e.g., sterically overlapping epitopes. Such competition binding assays can include, for example, competition ELISA assays, which can be configured in all number of different formats, using either labeled antigen or labeled antibody. In a particular embodiment, an antibody can be tested in competition binding assays with the antibody M22-321b41.1 described herein, or a chimeric or Fab antibody thereof, or an antibody comprising VH CDRs and VL CDRs of the antibody M22-321b41.1.

In specific aspects, provided herein is an antibody which competitively blocks (e.g., in a dose dependent manner) binding of antibodies comprising the amino acid sequences described herein for specific binding to a Nectin-4 polypeptide (e.g., an ECD of Nectin-4, for example human Nectin-4), as determined using assays known to one of skill in the art or described herein (e.g., ELISA competitive assays). In specific aspects, provided herein is an antibody which competes (e.g., in a dose dependent manner) for specific binding to a Nectin-4 polypeptide (e.g., an ECD of Nectin-4, for example human Nectin-4), with an antibody comprising the amino acid sequences described herein (e.g., VL and/or VH amino acid sequences of the antibody M22-321b41.1), as determined using assays known to one of skill in the art or described herein (e.g., ELISA competitive assays).

In specific aspects, provided herein is an antibody which competes (e.g., in a dose dependent manner) for specific binding to a Nectin-4 polypeptide (e.g., an ECD of Nectin-4, for example human Nectin-4), with the antibody M22-321b41.1.

In specific aspects, provided herein is an antibody which competes (e.g., in a dose dependent manner) for specific binding to a Nectin-4 polypeptide (e.g., an ECD of Nectin-4, for example human Nectin-4), with an antibody comprising a VL chain region having the amino acid sequence of SEQ ID NO:3, and a VH chain region having the amino acid sequence of SEQ ID NO:4.

In a specific aspect, also provided herein are antibodies (i) that compete (e.g., in a dose dependent manner) for specific binding to an epitope of a Nectin-4 polypeptide (e.g., an epitope of an ECD of human Nectin-4), with any the antibody M22-321b41.1, and (ii) that are capable of specifically bind to Nectin-4 in an IHC assay.

In a specific embodiment, an antibody described herein is one that is competitively blocked (e.g., in a dose dependent manner) by an antibody that specifically binds Nectin-4 and comprises a VL chain region having the amino acid sequence of SEQ ID NO:3 and a VH chain region having the amino acid sequence of SEQ ID NO:4, for specific binding to a Nectin-4 polypeptide (e.g., an ECD of Nectin-4, for example human Nectin-4).

In a specific aspect, also provided herein are antibodies (i) that competitively block (e.g., in a dose dependent manner) the antibody M22-321b41.1 for specific binding to an epitope of a Nectin-4 polypeptide (e.g., an epitope of an ECD of human Nectin-4), and (ii) that are capable of specifically bind to Nectin-4 in an IHC assay.

In specific aspects, provided herein is an antibody, or an antigen-binding fragment thereof, which immunospecifically binds to the same epitope as that of the antibody M22-321b41.1 comprising the amino acid sequences described herein for specific binding to a Nectin-4 polypeptide (e.g., an ECD of Nectin-4, for example human Nectin-4). Assays known to one of skill in the art or described herein (e.g., ELISA assays) can be used to determine if two antibodies bind to the same epitope.

In a specific embodiment, an antibody described herein, or an antigen-binding fragment thereof, immunospecifically binds to the same epitope as that of the antibody M22-321b41.1 that specifically binds Nectin-4 and comprises a VL chain region having the amino acid sequence of SEQ ID NO:3 and a VH chain region having the amino acid sequence of SEQ ID NO:4.

In a specific aspect, also provided herein are antibodies (i) that immunospecifically binds the same epitope of a Nectin-4 polypeptide (e.g., an epitope of an ECD of human Nectin-4) as that of the antibody M22-321b41.1; and (ii) that are capable of specifically bind to Nectin-4 in an IHC assay.

In certain embodiments, the antibody or antigen-binding fragment thereof, when bound to Nectin-4, binds to at least one of residues 31-346 within an amino acid sequence of SEQ ID NO:1. In some embodiments, the antibody or antigen-binding fragment thereof, when bound to Nectin-4, binds to at least one of residues 31-75 within an amino acid sequence of SEQ ID NO:1. In other embodiments, the antibody or antigen-binding fragment thereof, when bound to Nectin-4, binds to at least one of residues 75-125 within an amino acid sequence of SEQ ID NO:1. In some embodiments, the antibody or antigen-binding fragment thereof, when bound to Nectin-4, binds to at least one of residues 100-150 within an amino acid sequence of SEQ ID NO:1. In other embodiments, the antibody or antigen-binding fragment thereof, when bound to Nectin-4, binds to at least one of residues 125-175 within an amino acid sequence of SEQ ID NO:1. In some embodiments, the antibody or antigen-binding fragment thereof, when bound to Nectin-4, binds to at least one of residues 150-200 within an amino acid sequence of SEQ ID NO:1. In other embodiments, the antibody or antigen-binding fragment thereof, when bound to Nectin-4, binds to at least one of residues 175-225 within an amino acid sequence of SEQ ID NO:1. In some embodiments, the antibody or antigen-binding fragment thereof, when bound to Nectin-4, binds to at least one of residues 200-250 within an amino acid sequence of SEQ ID NO:1. In other embodiments, the antibody or antigen-binding fragment thereof, when bound to Nectin-4, binds to at least one of residues 225-275 within an amino acid sequence of SEQ ID NO:1. In some embodiments, the antibody or antigen-binding fragment thereof, when bound to Nectin-4, binds to at least one of residues 250-300 within an amino acid sequence of SEQ ID NO:1. In other embodiments, the antibody or antigen-binding fragment thereof, when bound to Nectin-4, binds to at least one of residues 275-325 within an amino acid sequence of SEQ ID NO:1. In some embodiments, the antibody or antigen-binding fragment thereof, when bound to Nectin-4, binds to at least one of residues 300-346 within an amino acid sequence of SEQ ID NO:1.

In certain embodiments, the antibody or antigen-binding fragment thereof, when bound to Nectin-4, binds to at least one of residues 1-150 within an amino acid sequence of SEQ ID NO:1. In some embodiments, the antibody or antigen-binding fragment thereof, when bound to Nectin-4, binds to at least one of residues 31-150 within an amino acid sequence of SEQ ID NO:1. In other embodiments, the antibody or antigen-binding fragment thereof, when bound to Nectin-4, binds to at least one of residues 1-10 within an amino acid sequence of SEQ ID NO:1. In some embodiments, the antibody or antigen-binding fragment thereof, when bound to Nectin-4, binds to at least one of residues 5-15 within an amino acid sequence of SEQ ID NO:1. In other embodiments, the antibody or antigen-binding fragment thereof, when bound to Nectin-4, binds to at least one of residues 10-20 within an amino acid sequence of SEQ ID NO:1. In some embodiments, the antibody or antigen-binding fragment thereof, when bound to Nectin-4, binds to at least one of residues 15-25 within an amino acid sequence of SEQ ID NO:1. In other embodiments, the antibody or antigen-binding fragment thereof, when bound to Nectin-4, binds to at least one of residues 20-30 within an amino acid sequence of SEQ ID NO:1. In some embodiments, the antibody or antigen-binding fragment thereof, when bound to Nectin-4, binds to at least one of residues 25-35 within an amino acid sequence of SEQ ID NO:1. In other embodiments, the antibody or antigen-binding fragment thereof, when bound to Nectin-4, binds to at least one of residues 30-40 within an amino acid sequence of SEQ ID NO:1. In some embodiments, the antibody or antigen-binding fragment thereof, when bound to Nectin-4, binds to at least one of residues 35-45 within an amino acid sequence of SEQ ID NO:1. In other embodiments, the antibody or antigen-binding fragment thereof, when bound to Nectin-4, binds to at least one of residues 40-50 within an amino acid sequence of SEQ ID NO:1. In some embodiments, the antibody or antigen-binding fragment thereof, when bound to Nectin-4, binds to at least one of residues 45-55 within an amino acid sequence of SEQ ID NO:1. In other embodiments, the antibody or antigen-binding fragment thereof, when bound to Nectin-4, binds to at least one of residues 50-60 within an amino acid sequence of SEQ ID NO:1. In some embodiments, the antibody or antigen-binding fragment thereof, when bound to Nectin-4, binds to at least one of residues 65-75 within an amino acid sequence of SEQ ID NO:1. In other embodiments, the antibody or antigen-binding fragment thereof, when bound to Nectin-4, binds to at least one of residues 70-80 within an amino acid sequence of SEQ ID NO:1. In some embodiments, the antibody or antigen-binding fragment thereof, when bound to Nectin-4, binds to at least one of residues 75-85 within an amino acid sequence of SEQ ID NO:1. In other embodiments, the antibody or antigen-binding fragment thereof, when bound to Nectin-4, binds to at least one of residues 80-90 within an amino acid sequence of SEQ ID NO:1. In some embodiments, the antibody or antigen-binding fragment thereof, when bound to Nectin-4, binds to at least one of residues 85-95 within an amino acid sequence of SEQ ID NO:1. In other embodiments, the antibody or antigen-binding fragment thereof, when bound to Nectin-4, binds to at least one of residues 90-100 within an amino acid sequence of SEQ ID NO:1. In some embodiments, the antibody or antigen-binding fragment thereof, when bound to Nectin-4, binds to at least one of residues 95-105 within an amino acid sequence of SEQ ID NO:1. In other embodiments, the antibody or antigen-binding fragment thereof, when bound to Nectin-4, binds to at least one of residues 100-110 within an amino acid sequence of SEQ ID NO:1. In some embodiments, the antibody or antigen-binding fragment thereof, when bound to Nectin-4, binds to at least one of residues 105-115 within an amino acid sequence of SEQ ID NO:1. In other embodiments, the antibody or antigen-binding fragment thereof, when bound to Nectin-4, binds to at least one of residues 110-120 within an amino acid sequence of SEQ ID NO:1. In some embodiments, the antibody or antigen-binding fragment thereof, when bound to Nectin-4, binds to at least one of residues 115-125 within an amino acid sequence of SEQ ID NO:1. In other embodiments, the antibody or antigen-binding fragment thereof, when bound to Nectin-4, binds to at least one of residues 120-130 within an amino acid sequence of SEQ ID NO:1. In some embodiments, the antibody or antigen-binding fragment thereof, when bound to Nectin-4, binds to at least one of residues 125-135 within an amino acid sequence of SEQ ID NO:1. In other embodiments, the antibody or antigen-binding fragment thereof, when bound to Nectin-4, binds to at least one of residues 130-140 within an amino acid sequence of SEQ ID NO:1. In some embodiments, the antibody or antigen-binding fragment thereof, when bound to Nectin-4, binds to at least one of residues 135-145 within an amino acid sequence of SEQ ID NO:1. In other embodiments, the antibody or antigen-binding fragment thereof, when bound to Nectin-4, binds to at least one of residues 140-150 within an amino acid sequence of SEQ ID NO:1.

Any combination of two, three, four, five, six, seven, eight, nine, ten or more of the above-referenced amino acid Nectin-4 binding sites is also contemplated.

In certain embodiments, the antibodies specifically bind to an epitope of an ECD of human Nectin-4 that is distinct from the Nectin-4 ligand binding site. In certain embodiments, binding of Nectin-4 ligand to Nectin-4 is not inhibited by the antibody.

In one aspect, provided herein are antibodies that specifically bind to Nectin-4. In certain embodiments, provided herein are antibodies that specifically bind to an ECD of human Nectin-4.

In certain embodiments, the antibodies that specifically bind to Nectin-4 bind to an ECD of human Nectin-4, or an epitope of an ECD of human Nectin-4 thereof. In certain embodiments, the antibodies specifically bind to an epitope of an ECD of human Nectin-4 that is distinct from the Nectin-4 ligand binding site.

Nectin-4 activity can relate to any activity of Nectin-4 such as those known or described in the art. Non-limiting examples of Nectin-4 activity include: Nectin-4 receptor dimerization, Nectin-4 receptor heterodimerization with other receptors, Nectin-4 receptor phosphorylation, signaling downstream of the Nectin-4 receptor, cell proliferation such as Nectin-4 ligand-induced enhancement of cell proliferation (e.g., cancer cell proliferation), or cell survival (e.g., cancer cells), Nectin-4 ligand induced anti-apoptosis. Nectin-4 activity or Nectin-4 function are used interchangeably herein. In certain aspects, Nectin-4 activity is induced by Nectin-4 ligand binding to Nectin-4 receptor. In certain embodiments, an increase in Nectin-4 activity or signaling can occur, in the absence of Nectin-4 ligand binding Nectin-4 receptor, due to high (or overexpression) expression of Nectin-4 receptors. High or overexpression of Nectin-4 in a cell refers to an expression level which is at least about 10%, 20%, 30%, 40%, 50%, 60%, 70%, 80%, 90%, 100%, 150%, 200%, 250%, 300%, 400%, or 500% more than the expression level of a reference cell known to have normal Nectin-4 expression or Nectin-4 activity or more than the average expression level of Nectin-4 in a population of cells or samples known to have normal Nectin-4 expression or Nectin-4 activity. Expression levels of Nectin-4 can be assessed by methods described herein or known to one of skill in the art (e.g., Western blotting, ELISA, or IHC).

10. POLYCLONAL ANTIBODIES

The antibodies of the present disclosure may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a Nectin-4 polypeptide or a fusion protein thereof. It may be useful to conjugate the immunizing agent to a protein known to be immunogenic in the mammal being immunized or to immunize the mammal with the protein and one or more adjuvants. Examples of such immunogenic proteins include, but are not limited to, keyhole limpet hemocyanin, serum albumin, bovine thyroglobulin, and soybean trypsin inhibitor. Examples of adjuvants which may be employed include Ribi, CpG, Poly 1C, Freund's complete adjuvant, and MPL-TDM adjuvant (monophosphoryl Lipid A, synthetic trehalose dicorynomycolate). The immunization protocol may be selected by one skilled in the art without undue experimentation. The mammal can then be bled, and the serum assayed for Nectin-4 antibody titer. If desired, the mammal can be boosted until the antibody titer increases or plateaus. Additionally or alternatively, lymphocytes may be obtained from the immunized animal for fusion and preparation of monoclonal antibodies from hybridoma as described below.

11. MONOCLONAL ANTIBODIES

The antibodies of the present disclosure may alternatively be monoclonal antibodies. Monoclonal antibodies may be made using the hybridoma method first described by Kohler et al., 1975, Nature 256:495-97, or may be made by recombinant DNA methods (see, e.g., U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice* 59-103 (1986)).

The hybridoma cells thus prepared are seeded and grown in a suitable culture medium which, in certain embodiments, contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which prevent the growth of HGPRT-deficient cells.

Exemplary fusion partner myeloma cells are those that fuse efficiently, support stable high-level production of antibody by the selected antibody-producing cells, and are sensitive to a selective medium that selects against the unfused parental cells. Exemplary myeloma cell lines are murine myeloma lines, such as SP-2 and derivatives, for example, X63-Ag8-653 cells available from the American Type Culture Collection (Manassas, Va.), and those derived from MOPC-21 and MPC-11 mouse tumors available from the Salk Institute Cell Distribution Center (San Diego, Calif.). Human myeloma and mouse-human heteromyeloma cell lines also have been described for the production of human monoclonal antibodies (Kozbor, 1984, Immunol. 133:3001-05; and Brodeur et al., *Monoclonal Antibody Production Techniques and Applications* 51-63 (1987)).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as RIA or ELISA. The binding affinity of the monoclonal antibody can, for example, be determined by the Scatchard analysis described in Munson et al., 1980, Anal. Biochem. 107:220-39.

Once hybridoma cells that produce antibodies of the desired specificity, affinity, and/or activity are identified, the clones may be subcloned by limiting dilution procedures and grown by standard methods (Goding, supra). Suitable culture media for this purpose include, for example, DMEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells can serve as a source of such DNA. Once isolated, the DNA may be placed into expression vectors, which are then transfected into host cells, such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., 1993, Curr. Opinion in Immunol. 5:256-62 and Plückthun, 1992, Immunol. Revs. 130:151-88.

In some embodiments, an antibody that binds a Nectin-4 epitope comprises an amino acid sequence of a VH domain and/or an amino acid sequence of a VL domain encoded by a nucleotide sequence that hybridizes to (1) the complement of a nucleotide sequence encoding any one of the VH and/or VL domain described herein under stringent conditions (e.g., hybridization to filter-bound DNA in 6× sodium chloride/sodium citrate (SSC) at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art. See, e.g., *Current Protocols in Molecular Biology Vol. I*, 6.3.1-6.3.6 and 2.10.3 (Ausubel et al. eds., 1989).

In some embodiments, an antibody that binds a Nectin-4 epitope comprises an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in Table 1 under stringent conditions (e.g., hybridization to filter-bound DNA in 6×SSC at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, e.g., Ausubel et al., supra).

In a further embodiment, monoclonal antibodies or antibody fragments can be isolated from antibody phage libraries generated using the techniques described in, for example, *Antibody Phage Display: Methods and Protocols* (O'Brien and Aitken eds., 2002). In phage display methods, functional antibody domains are displayed on the surface of phage particles which carry the polynucleotide sequences encoding them. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

In principle, synthetic antibody clones are selected by screening phage libraries containing phages that display various fragments of antibody variable region (Fv) fused to phage coat protein. Such phage libraries are screened against the desired antigen. Clones expressing Fv fragments capable of binding to the desired antigen are adsorbed to the antigen and thus separated from the non-binding clones in the library. The binding clones are then eluted from the antigen and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., 1994, Ann. Rev. Immunol. 12:433-55.

Repertoires of VH and VL genes can be separately cloned by PCR and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., 1993, EMBO J 12:725-34. Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, 1992, J. Mol. Biol. 227:381-88.

Screening of the libraries can be accomplished by various techniques known in the art. For example, Nectin-4 (e.g., a Nectin-4 polypeptide, fragment, or epitope) can be used to coat the wells of adsorption plates, expressed on host cells affixed to adsorption plates or used in cell sorting, conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., 1990, Proteins 8:309-14 and WO 92/09690, and by use of a low coating density of antigen as described in Marks et al., 1992, Biotechnol. 10:779-83.

Anti-Nectin-4 antibodies can be obtained by designing a suitable antigen screening procedure to select for the phage clone of interest followed by construction of a full length anti-Nectin-4 antibody clone using VH and/or VL sequences (e.g., the Fv sequences), or various CDR sequences from VH and VL sequences, from the phage clone of interest and suitable constant region (e.g., Fc) sequences described in Kabat et al., supra.

Antibodies described herein can also, for example, include chimeric antibodies. A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415.

Antibodies or antigen-binding fragments produced using techniques such as those described herein can be isolated using standard, well known techniques. For example, antibodies or antigen-binding fragments can be suitably separated from, e.g., culture medium, ascites fluid, serum, cell lysate, synthesis reaction material or the like by conventional immunoglobulin purification procedures such as, for example, protein A-Sepharose, hydroxylapatite chromatography, gel electrophoresis, dialysis, or affinity chromatography. As used herein, an "isolated" or "purified" antibody is substantially free of cellular material or other proteins from the cell or tissue source from which the antibody is derived, or substantially free of chemical precursors or other chemicals when chemically synthesized.

12. ANTIBODY FRAGMENTS

The present disclosure provides antibodies and antibody fragments that bind to Nectin-4. In certain circumstances there are advantages of using antibody fragments, rather than whole antibodies. The smaller size of the fragments allows for rapid clearance, and may lead to improved access to cells, tissues, or organs. For a review of certain antibody fragments, see Hudson et al., 2003, Nature Med. 9:129-34.

Various techniques have been developed for the production of antibody fragments. Traditionally, these fragments were derived via proteolytic digestion of intact antibodies (see, e.g., Morimoto et al., 1992, J. Biochem. Biophys. Methods 24:107-17; and Brennan et al., 1985, Science 229:81-83). However, these fragments can now be produced directly by recombinant host cells. Fab, Fv, and scFv antibody fragments can all be expressed in and secreted from *E. coli* or yeast cells, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., 1992, Bio/Technology 10:163-67). According to another approach, F(ab')$_2$ fragments can be isolated directly from recombinant host cell culture. Fab and F(ab')$_2$ fragment with increased in vivo half-life comprising salvage receptor binding epitope residues are described in, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894 and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv (See, e.g., Borrebaeck ed., supra). The antibody fragment may also be a "linear antibody," for example, as described in the references cited above.

Smaller antibody-derived binding structures are the separate variable domains (V domains) also termed single variable domain antibodies (sdAbs). Certain types of organisms, the camelids and cartilaginous fish, possess high affinity single V-like domains mounted on an Fc equivalent domain structure as part of their immune system. (Woolven et al., 1999, Immunogenetics 50: 98-101; and Streltsov et al., 2004, Proc Natl Acad Sci USA. 101:12444-49). The V-like domains (called VhH in camelids and V-NAR in sharks) typically display long surface loops, which allow penetration of cavities of target antigens. They also stabilize isolated VH domains by masking hydrophobic surface patches.

These VhH and V-NAR domains have been used to engineer sdAbs. Human V domain variants have been designed using selection from phage libraries and other approaches that have resulted in stable, high binding VL- and VH-derived domains.

Antibodies provided herein include, but are not limited to, immunoglobulin molecules and immunologically active portions of immunoglobulin molecules, for example, molecules that contain an antigen binding site that bind to a Nectin-4 epitope. The immunoglobulin molecules provided herein can be of any class (e.g., IgG, IgE, IgM, IgD, and IgA) or any subclass (e.g., IgG1, IgG2, IgG3, IgG4, IgA1, and IgA2) of immunoglobulin molecule.

Variants and derivatives of antibodies include antibody functional fragments that retain the ability to bind to a Nectin-4 epitope. Exemplary functional fragments include Fab fragments (e.g., an antibody fragment that contains the antigen-binding domain and comprises a light chain and part of a heavy chain bridged by a disulfide bond); Fab' (e.g., an antibody fragment containing a single antigen-binding domain comprising an Fab and an additional portion of the heavy chain through the hinge region); F(ab')$_2$ (e.g., two Fab' molecules joined by interchain disulfide bonds in the hinge regions of the heavy chains; the Fab' molecules may be directed toward the same or different epitopes); a single chain comprising a variable region, also known as, scFv (e.g., the variable, antigen-binding determinative region of a single light and heavy chain of an antibody linked together by a chain of 10-25 amino acids); a disulfide-linked Fv, or dsFv (e.g., the variable, antigen-binding determinative region of a single light and heavy chain of an antibody linked together by a disulfide bond); a camelized VH (e.g., the variable, antigen-binding determinative region of a single heavy chain of an antibody in which some amino acids at the VH interface are those found in the heavy chain of naturally occurring camel antibodies).

13. HUMANIZED ANTIBODIES

Antibodies described herein can, for example, include humanized antibodies, e.g., deimmunized or composite human antibodies.

A humanized antibody can comprise human constant region sequences. In certain embodiments, a humanized antibody can be selected from any class of immunoglobulins, including IgM, IgG, IgD, IgA and IgE, and any isotype, including IgG$_1$, IgG$_2$, IgG$_3$ and IgG$_4$. In certain embodiments, a humanized antibody can comprise kappa or lambda light chain constant sequences.

Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp): 5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

In some embodiments, antibodies provided herein can be humanized antibodies that bind Nectin-4, including human Nectin-4. For example, humanized antibodies of the present disclosure may comprise one or more CDRs as shown in Table 1. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., 1986, Nature 321:522-25; Riechmann et al., 1988, Nature 332: 323-27; and Verhoeyen et al., 1988, Science 239:1534-36), by substituting hypervariable region sequences for the corresponding sequences of a human antibody.

In some cases, the humanized antibodies are constructed by CDR grafting, in which the amino acid sequences of the six CDRs of the parent non-human antibody (e.g., rodent) are grafted onto a human antibody framework. For example, Padlan et al. determined that only about one third of the residues in the CDRs actually contact the antigen, and termed these the "specificity determining residues," or SDRs (Padlan et al., 1995, FASEB J. 9:133-39). In the technique of SDR grafting, only the SDR residues are grafted onto the human antibody framework (see, e.g., Kashmiri et al., 2005, Methods 36:25-34).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence that is closest to that of the rodent may be selected as the human framework for the humanized antibody (Sims et al., 1993, J. Immunol. 151:2296-308; and Chothia et al., 1987, J. Mol. Biol. 196:901-17). Another method uses a particular framework derived from the consensus sequence of all human antibodies of a particular subgroup of light or heavy chains. The same framework may be used for several different humanized antibodies (Carter et al., 1992, Proc. Natl. Acad. Sci. USA 89:4285-89; and Presta et al., 1993, J. Immunol. 151:2623-32). In some cases, the framework is derived from the consensus sequences of the most abundant human subclasses, $V_L6$ subgroup I ($V_L6I$) and VH subgroup III ($V_HIII$). In another method, human germline genes are used as the source of the framework regions.

In an alternative paradigm based on comparison of CDRs, called superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., 2002, J. Immunol. 169:1119-25).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, 2000, Protein Eng. 13:819-24), Modeller (Sali and Blundell, 1993, J. Mol. Biol. 234:779-815), and Swiss PDB Viewer (Guex and Peitsch, 1997, Electrophoresis 18:2714-23). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes, and the differences are scored as HSC. The target sequence is then humanized by maximizing its HSC rather than using a global identity measure to generate multiple diverse humanized variants (Lazar et al., 2007, Mol. Immunol. 44:1986-98).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome, and yeast display libraries as well as by bacterial colony screening (see, e.g., Hoogenboom, 2005, Nat. Biotechnol. 23:1105-16; Dufner et al., 2006, Trends Biotechnol. 24:523-29; Feldhaus et al., 2003, Nat. Biotechnol. 21:163-70; and Schlapschy et al., 2004, Protein Eng. Des. Sel. 17:847-60).

In the FR library approach, a collection of residue variants are introduced at specific positions in the FR followed by screening of the library to select the FR that best supports the grafted CDR. The residues to be substituted may include some or all of the "Vernier" residues identified as potentially contributing to CDR structure (see, e.g., Foote and Winter, 1992, J. Mol. Biol. 224:487-99), or from the more limited set of target residues identified by Baca et al. (1997, J. Biol. Chem. 272:10678-84).

In FR shuffling, whole FRs are combined with the non-human CDRs instead of creating combinatorial libraries of selected residue variants (see, e.g., Dall'Acqua et al., 2005, Methods 36:43-60). The libraries may be screened for binding in a two-step process, first humanizing VL, followed by VH. Alternatively, a one-step FR shuffling process may be used. Such a process has been shown to be more efficient than the two-step screening, as the resulting antibodies exhibited improved biochemical and physicochemical properties including enhanced expression, increased affinity, and thermal stability (see, e.g., Damschroder et al., 2007, Mol. Immunol. 44:3049-60).

The "humaneering" method is based on experimental identification of essential minimum specificity determinants (MSDs) and is based on sequential replacement of non-human fragments into libraries of human FRs and assessment of binding. It begins with regions of the CDR3 of non-human VH and VL chains and progressively replaces other regions of the non-human antibody into the human FRs, including the CDR1 and CDR2 of both VH and VL. This methodology typically results in epitope retention and identification of antibodies from multiple subclasses with distinct human V-segment CDRs. Humaneering allows for isolation of antibodies that are 91-96% homologous to human germline gene antibodies (see, e.g., Alfenito, Cambridge Healthtech Institute's Third Annual PEGS, The Protein Engineering Summit, 2007).

The "human engineering" method involves altering a non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk," "moderate risk," or "high risk" residues. The classification is performed using a global risk/reward calculation that evaluates the predicted benefits of making particular substitution (e.g., for immunogenicity in humans) against the risk that the substitution will affect the resulting antibody's folding. The particular human amino acid residue to be substituted at a given position (e.g., low or moderate risk) of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., 1994, Protein Engineering 7:805-14; U.S. Pat. Nos. 5,766,886; 5,770,196; 5,821,123; and 5,869,619; and PCT Publication WO 93/11794.

A composite human antibody can be generated using, for example, Composite Human Antibody™ technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody. Such antibodies can comprise human constant region sequences, e.g., human light chain and/or heavy chain constant regions.

A deimmunized antibody is an antibody in which T-cell epitopes have been removed. Methods for making deimmunized antibodies have been described. See, e.g., Jones et al., Methods Mol Biol. 2009; 525:405-23, xiv, and De Groot et al., Cell. Immunol. 244:148-153(2006)). Deimmunized antibodies comprise T-cell epitope-depleted variable regions and human constant regions. Briefly, VH and VL of an antibody are cloned and T-cell epitopes are subsequently identified by testing overlapping peptides derived from the VH and VL of the antibody in a T cell proliferation assay. T cell epitopes are identified via in silico methods to identify peptide binding to human MEW class II. Mutations are introduced in the VH and VL to abrogate binding to human MHC class II. Mutated VH and VL are then utilized to generate the deimmunized antibody.

14. HUMAN ANTIBODIES

In specific embodiments, the antibody is a fully human anti-human antibody. Fully human antibodies may be produced by any method known in the art. Human anti-Nectin-4 antibodies can be constructed by combining Fv clone variable domain sequence(s) selected from human-derived phage display libraries with known human constant domain sequences(s). Alternatively, human monoclonal anti-Nectin-4 antibodies of the present disclosure can be made by the hybridoma method. Human myeloma and mouse-human heteromyeloma cell lines for the production of human monoclonal antibodies have been described, for example, by Kozbor, 1984, J. Immunol. 133:3001-05; Brodeur et al., *Monoclonal Antibody Production Techniques and Applications* 51-63 (1987); and Boerner et al., 1991, J. Immunol. 147:86-95.

It is also possible to produce transgenic animals (e.g., mice) that are capable, upon immunization, of producing a full repertoire of human antibodies in the absence of endogenous immunoglobulin production. Transgenic mice that express human antibody repertoires have been used to generate high-affinity human sequence monoclonal antibodies against a wide variety of potential drug targets (see, e.g., Jakobovits, A., 1995, Curr. Opin. Biotechnol. 6(5):561-66; Bruggemann and Taussing, 1997, Curr. Opin. Biotechnol. 8(4):455-58; U.S. Pat. Nos. 6,075,181 and 6,150,584; and Lonberg et al., 2005, Nature Biotechnol. 23:1117-25).

Alternatively, the human antibody may be prepared via immortalization of human B lymphocytes producing an antibody directed against a target antigen (e.g., such B lymphocytes may be recovered from an individual or may have been immunized in vitro) (see, e.g., Cole et al., *Monoclonal Antibodies and Cancer Therapy* (1985); Boerner et al., 1991, J. Immunol. 147(1):86-95; and U.S. Pat. No. 5,750,373).

Gene shuffling can also be used to derive human antibodies from non-human, for example, rodent, antibodies, where the human antibody has similar affinities and specificities to the starting non-human antibody. According to this method, which is also called "epitope imprinting" or "guided selection," either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone (e.g., the epitope guides (imprints) the choice of the human chain partner). When the process is repeated in order to replace the remaining non-human chain, a human antibody is obtained (see, e.g., PCT WO 93/06213; and Osbourn et al., 2005, Methods 36:61-68). Unlike traditional humanization of non-human antibodies by CDR grafting, this technique provides completely human antibodies, which have no FR or CDR residues of non-human origin. Examples of guided selection to humanize mouse antibodies towards cell surface antigens include the folate-binding protein present on ovarian cancer cells (see, e.g., Figini et al., 1998, Cancer Res. 58:991-96) and CD147, which is highly expressed on hepatocellular carcinoma (see, e.g., Bao et al., 2005, Cancer Biol. Ther. 4:1374-80).

A potential disadvantage of the guided selection approach is that shuffling of one antibody chain while keeping the other constant could result in epitope drift. In order to maintain the epitope recognized by the non-human antibody, CDR retention can be applied (see, e.g., Klimka et al., 2000, Br. J. Cancer. 83:252-60; and Beiboer et al., 2000, J. Mol. Biol. 296:833-49). In this method, the non-human VH CDR3 is commonly retained, as this CDR may be at the center of the antigen-binding site and may be the most important region of the antibody for antigen recognition. In some instances, however, VH CDR3 and $V_L$ CDR3, as well as VH CDR2, VL CDR2, and VL CDR1 of the non-human antibody may be retained.

15. MULTIVALENT ANTIBODIES

A multivalent antibody may be internalized (and/or catabolized) faster than a bivalent antibody by a cell expressing an antigen to which the antibodies bind. The antibodies of the present disclosure can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (e.g., two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (e.g., four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

16. FC ENGINEERING

It may be desirable to modify an anti-Nectin-4 antibody provided herein by Fc engineering. In certain embodiments, the modification to the Fc region of the antibody results in the decrease or elimination of an effector function of the antibody. In certain embodiments, the effector function is ADCC, ADCP, and/or CDC. In some embodiments, the effector function is ADCC. In other embodiments, the effector function is ADCP. In other embodiments, the effector function is CDC. In one embodiment, the effector function is ADCC and ADCP. In one embodiment, the effector function is ADCC and CDC. In one embodiment, the effector function is ADCP and CDC. In one embodiment, the effector function is ADCC, ADCP and CDC. This may be achieved by introducing one or more amino acid substitutions in an Fc region of the antibody.

To increase the serum half life of the antibody, one may incorporate a salvage receptor binding epitope into the antibody (especially an antibody fragment), for example, as described in U.S. Pat. No. 5,739,277. Term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

17. ALTERNATIVE BINDING AGENTS

The present disclosure encompasses non-immunoglobulin binding agents that specifically bind to the same epitope as an anti-Nectin-4 antibody disclosed herein. In some embodiments, a non-immunoglobulin binding agent is identified as an agent that displaces or is displaced by an anti-Nectin-4 antibody of the present disclosure in a competitive binding assay. These alternative binding agents may include, for example, any of the engineered protein scaffolds known in the art. Such scaffolds may comprise one or more CDRs as shown in Table 1. Such scaffolds include, for example, anticalins, which are based upon the lipocalin scaffold, a protein structure characterized by a rigid beta-barrel that supports four hypervariable loops which form the ligand binding site. Novel binding specificities may be engineered by targeted random mutagenesis in the loop regions, in combination with functional display and guided selection (see, e.g., Skerra, 2008, FEBS J. 275:2677-83). Other suitable scaffolds may include, for example, adnectins, or monobodies, based on the tenth extracellular domain of human fibronectin III (see, e.g., Koide and Koide, 2007, Methods Mol. Biol. 352: 95-109); affibodies, based on the Z domain of staphylococcal protein A (see, e.g., Nygren et al., 2008, FEBS J. 275:2668-76); DARPins, based on ankyrin repeat proteins (see, e.g., Stumpp et al., 2008, Drug. Discov. Today 13:695-701); fynomers, based on the SH3 domain of the human Fyn protein kinase (see, e.g., Grabulovski et al., 2007, J. Biol. Chem. 282:3196-204); affitins, based on Sac7d from *Sulfolobus acidolarius* (see, e.g., Krehenbrink et al., 2008, J. Mol. Biol. 383:1058-68); affilins, based on human y-B-crystallin (see, e.g., Ebersbach et al., 2007, J. Mol. Biol. 372:172-85); avimers, based on the A domain of membrane receptor proteins (see, e.g., Silverman et al., 2005, Biotechnol. 23:1556-61); cysteine-rich knottin peptides (see, e.g., Kolmar, 2008, FEBS J. 275:2684-90); and engineered Kunitz-type inhibitors (see, e.g., Nixon and Wood, 2006, Curr. Opin. Drug. Discov. Dev. 9:261-68). For a review, see, for example, Gebauer and Skerra, 2009, Curr. Opin. Chem. Biol. 13:245-55.

18. SCREENING FOR NECTIN-4 SPECIFIC ANTIBODIES

Techniques for generating antibodies have been described above. Antibodies can be further screened or selected for certain biological characteristics, such as their binding specificity for Nectin-4, as desired. Screening for antibodies specific for a target antigen involves two aspects. First, screening the antibodies to identify those that do not bind to or have low binding to a sample that contains no Nectin-4. This aspect of the screening identifies antibodies that specifically recognize and bind Nectin-4, but do not substantially recognize or bind molecules other than Nectin-4. Second, screening the antibodies to identify those that bind strongly or with high affinity to a sample that includes Nectin-4. This aspect of the screening identifies antibodies that have high affinity to Nectin-4 and can give strong detection signals in various assays as described below. Screening for antibodies in both aspects may be accomplished using an immunoassay further described below.

In certain embodiments, the antibodies are initially screened using an ELISA in which microtiter plates are coated with Nectin-4 protein or fragment thereof. The clones of antibodies that do not bind to or bind weakly to immobilized Nectin-4 are eliminated. In some embodiments, antibodies that bind Nectin-4 can be further screened for reactivity in an immunoassay, e.g. ELISA-based assay or western blotting assay, to other Nectin isoforms, for example using microtiter plates coated with Nectin-1, Nectin-2, or Nectin-3. Clones of antibodies that are reactive to another isoform of Nectin are eliminated, and clones of antibodies that are reactive to Nectin-4 only can be selected for further screening.

The anti-Nectin-4 antibodies can be further screened for its binding to negative controls that do not express or express low level of Nectin-4. For such screens, the binding between the various clones of the antibodies and the negative controls can be determined in an immunoassay, e.g. IHC assay, ELISA assay, or immunoblotting assays. Clones of antibodies that are reactive to any negative controls are eliminated. Different negative controls (e.g. different tissues or cell lines negative for Nectin-4 expression) can contain a different set of molecules, therefore multiple negative controls can be used to ensure that the candidate anti-Nectin-4 antibodies are selected against a diverse set of non-Nectin-4 molecules.

The anti-Nectin-4 antibodies can be further screened for binding to positive controls that are known to express Nectin-4. For such screens, the binding between the various clones of the antibodies and the positive controls can be determined in an immunoassay, e.g. IHC assay, ELISA assay, or immunoblotting assays. Clones of antibodies that have strong binding to the positive controls are selected. An anti-Nectin-4 antibody that bind strongly to a positive control and weakly to a negative control can be selected as an antibody specific for Nectin-4. The difference between the amount of an anti-Nectin-4 antibody bound to the positive and the negative controls is the specific binding of that anti-Nectin-4 antibody to Nectin-4. Specific binding can be used as one of the criteria for selecting specific anti-Nectin-4 antibodies. A specific antibody provides high specific binding in an immunoassay described in details below.

In some embodiments, the specificity of the anti-Nectin-4 antibody can be determined by correlating or comparing the anti-Nectin-4 antibody binding to negative and positive references with the known Nectin-4 expression levels in these references that has been determined by other means. The reference Nectin-4 expression can be a positive Nectin-4 control or a negative Nectin-4 control, as described below. The binding of a specific anti-Nectin-4 antibody to a sample or a reference can correlate with or be proportional to the Nectin-4 expression in the sample or the reference. That is, a specific anti-Nectin-4 antibody binds strongly to a sample or a reference that expresses high level of Nectin-4, binds moderately to that expresses intermediate level, binds weakly to that expresses low level, and binds minimally (e.g. binds at approximately the same level as an isotype control antibody would bind) to that expresses no Nectin-4. The known Nectin-4 expression in the negative or positive controls can be determined independently by a qPCR assay described in details below. The known Nectin-4 expression can also be independently determined using any below described immunoassays with an anti-Nectin-4 antibody that have been previously determined to be Nectin-4 specific. Suitable immunoassays for confirming the Nectin-4 expression in the negative and positive controls include, by way of example and without any limitation, an IHC assay, an immunoblotting assay, a FACS assay, or an ELISA, as described in details below. In some embodiments, the Nectin-4 mRNA level may not be zero in the negative control due to the background noise of the assays or due to the biologically insignificant low level of remaining Nectin-4, as described below. Negative Nectin-4 control can be properly considered negative for Nectin-4, for example, when the Nectin-4 mRNA level in a qPCR assay is substantially similar to the level of mRNA detected with a set of non-specific primers, or when the Nectin-4 mRNA level is biologically insignificant in light of the Nectin-4 mRNA level in a positive Nectin-4 control. Similarly, the Nectin-4 detected by immunoassays using another Nectin-4 specific antibody in a negative control may not be zero due to background noise of the assays or due to the biologically insignificant low level of remaining Nectin-4. The background noise can be caused by non-specific interactions between the assay reagents other than the anti-Nectin-4 antibodies and the samples. The negative Nectin-4 control can be properly considered negative for Nectin-4, for example, when the Nectin-4 level in the negative control detected by the Nectin-4 specific antibody is substantially similar to the detection level from an isotype control antibody in the same assay. In some assays, the background noise can account for a substantial percentage of the detected signal in the positive control.

Additionally, positive and negative controls have be identified and published in the literature by persons skilled in the art, including positive and/or negative tissues, cells (including, e.g. cell lines), and pathological samples. Such literature can be readily identified by searching databases such as Pubmed (e.g. using search terms such as Nectin-4, expression, positive, negative, and/or distribution) and analyzing the search hits.

Accordingly, the relative amount of the Nectin-4 specific antibody or antigen-binding fragment thereof bound to a negative control cell with no Nectin-4 expression can be about 50%, 40%, 30%, 20%, 10%, 5%, 4%, 3%, 2%, 1%, 0.5%, 0.3%, 0.2%, 0.1%, 0.05%, 0.03%, 0.01%, 0.001% or less of the amount of the antibody or antigen-binding fragment thereof bound to positive control expressing Nectin-4.

In some embodiments of the antibody or antigen-binding fragment thereof provided herein, the negative or positive Nectin-4 expression in the control cells is independently determined by a qPCR assay, an IHC assay with a second antibody, an immunoblotting assay with a second antibody, a FACS assay with a second antibody, or an ELISA with a second antibody.

In some embodiments of the antibody or antigen-binding fragment thereof provided herein, the amount of the antibody or antigen-binding fragment thereof bound to the cells is determined by an IHC assay, an immunoblotting assay, a FACS assay, or an ELISA.

19. ANTIBODY VARIANTS

In some embodiments, amino acid sequence modification(s) of the antibodies that bind to Nectin-4 or described herein are contemplated. For example, it may be desirable to improve the binding affinity and/or other biological properties of the antibody, including but not limited to specificity, thermostability, expression level, effector functions, glycosylation, reduced immunogenicity, or solubility. Thus, in addition to the anti-Nectin-4 antibodies described herein, it is contemplated that anti-Nectin-4 antibody variants can be prepared. For example, anti-Nectin-4 antibody variants can be prepared by introducing appropriate nucleotide changes into the encoding DNA, and/or by synthesis of the desired antibody or polypeptide. Those skilled in the art who appreciate that amino acid changes may alter post-translational processes of the anti-Nectin-4 antibody, such as changing the number or position of glycosylation sites or altering the membrane anchoring characteristics.

In some embodiments, the glutamine at the first residue can be substituted with pyroglutamate in any of antibodies provided herein that comprises a polypeptide having a first glutamine in its sequence is provided as well. Such substitution occurs naturally at physiological conditions or in vitro or ex vivo in a buffer with a pH about 7. Such substitution can be performed by subjecting the antibody that comprises a polypeptide having a first glutamine to a condition in which cyclization of the first glutamine glutaminyl to form pyroglutamate is favored, for example in a solution of weak acid such as acetate and trifluoroacetate.

In some embodiments, antibodies provided herein are chemically modified, for example, by the covalent attachment of any type of molecule to the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

Variations may be a substitution, deletion, or insertion of one or more codons encoding the antibody or polypeptide that results in a change in the amino acid sequence as compared with the native sequence antibody or polypeptide. Amino acid substitutions can be the result of replacing one amino acid with another amino acid having similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 5 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the full-length or mature native sequence.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for antibody-directed enzyme prodrug therapy) or a polypeptide which increases the serum half-life of the antibody.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Alternatively, conservative (e.g., within an amino acid group with similar properties and/or side chains) substitutions may be made, so as to maintain or not significantly change the properties. Amino acids may be grouped according to similarities in the properties of their side chains (see, e.g., Lehninger, *Biochemistry* 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His(H).

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions entail exchanging a member of one of these classes for another class. Such substituted residues also may be introduced into the conservative substitution sites or, into the remaining (non-conserved) sites. Accordingly, in one embodiment, an antibody or fragment thereof that binds to a Nectin-4 epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a murine monoclonal antibody described herein. In one embodiment, an antibody or fragment thereof that binds to a Nectin-4 epitope comprises an amino acid sequence that is at least 35% identical to the amino acid sequence of a murine monoclonal antibody described herein. In one embodiment, an antibody or fragment thereof that binds to a Nectin-4 epitope comprises an amino acid sequence that is at least 40% identical to the amino acid sequence of a murine monoclonal antibody described herein. In one embodiment, an antibody or fragment thereof that binds to a Nectin-4 epitope comprises an amino acid sequence that is at least 45% identical to the amino acid sequence of a murine monoclonal antibody described herein. In one embodiment, an antibody or fragment thereof that binds to a Nectin-4 epitope comprises an amino acid sequence that is at least 50% identical to the amino acid sequence of a murine monoclonal antibody described herein. In one embodiment, an antibody or fragment thereof that binds to a Nectin-4 epitope comprises an amino acid sequence that is at least 55% identical to the amino acid sequence of a murine monoclonal antibody described herein. In one embodiment, an antibody or fragment thereof that binds to a Nectin-4 epitope comprises an amino acid sequence that is at least 60% identical to the amino acid sequence of a murine monoclonal antibody described herein. In one embodiment, an antibody or fragment thereof that binds to a Nectin-4 epitope comprises an amino acid sequence that is at least 65% identical to the amino acid sequence of a murine monoclonal antibody described herein. In one embodiment, an antibody or fragment thereof that binds to a Nectin-4 epitope comprises an amino acid sequence that is at least 70% identical to the amino acid sequence of a murine monoclonal antibody described herein. In one embodiment, an antibody or fragment thereof that binds to a Nectin-4 epitope comprises an amino acid sequence that is at least 75% identical to the amino acid sequence of a murine monoclonal antibody described herein. In one embodiment, an antibody or fragment thereof that binds to a Nectin-4 epitope comprises an amino acid sequence that is at least 80% identical to the amino acid sequence of a murine monoclonal antibody described herein. In one embodiment, an antibody or fragment thereof that binds to a Nectin-4 epitope comprises an amino acid sequence that is at least 85% identical to the amino acid sequence of a murine monoclonal antibody described herein. In one embodiment, an antibody or fragment thereof that binds to a Nectin-4 epitope comprises an amino acid sequence that is at least 90% identical to the amino acid sequence of a murine monoclonal antibody described herein. In one embodiment, an antibody or fragment thereof that binds to a Nectin-4 epitope comprises an amino acid sequence that is at least 95% identical to the amino acid sequence of a murine monoclonal antibody described herein. In one embodiment, an antibody or fragment thereof that binds to a Nectin-4 epitope comprises an amino acid sequence that is at least 99% identical to the amino acid sequence of a murine monoclonal antibody described herein.

In one embodiment, an antibody or fragment thereof that binds to a Nectin-4 epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in Tables 1-2. In one embodiment, an antibody or fragment thereof that binds to a Nectin-4 epitope comprises an amino acid sequence that is at least 35% identical to an amino acid sequence depicted in Tables 1-2. In one embodiment, an antibody or fragment thereof that binds to a Nectin-4 epitope comprises an amino acid sequence that is at least 40% identical to an amino acid sequence depicted in Tables 1-2. In one embodiment, an antibody or fragment thereof that binds to a Nectin-4 epitope comprises an amino acid sequence that is at least 45% identical to an amino acid sequence depicted in Tables 1-2. In one embodiment, an antibody or fragment thereof that binds to a Nectin-4 epitope comprises an amino acid sequence that is at least 50% identical to an amino acid sequence depicted in Tables 1-2. In one embodiment, an antibody or fragment thereof that binds to a Nectin-4 epitope comprises an amino acid sequence that is at least 55% identical to an amino acid sequence depicted in Tables 1-2. In one embodiment, an antibody or fragment thereof that binds to a Nectin-4 epitope comprises an amino acid sequence that is at least 60% identical to an amino acid sequence depicted in Tables 1-2. In one embodiment, an antibody or fragment thereof that binds to a Nectin-4 epitope comprises an amino acid sequence that is at least 65% identical to an amino acid sequence depicted in Tables 1-2. In one embodiment, an antibody or fragment thereof that binds to a Nectin-4 epitope comprises an amino acid sequence that is at least 70% identical to an amino acid sequence depicted in Tables 1-2. In one embodiment, an antibody or fragment thereof that binds to a Nectin-4 epitope comprises an amino acid sequence that is at least 75% identical to an amino acid sequence depicted in Tables 1-2. In one embodiment, an antibody or fragment thereof that binds to a Nectin-4 epitope comprises an amino acid sequence that is at least 80% identical to an amino acid sequence depicted in Tables 1-2. In one embodiment, an antibody or fragment thereof that binds to a Nectin-4 epitope comprises an amino acid sequence that is at least 85% identical to an amino acid sequence depicted in Tables 1-2. In one embodiment, an antibody or fragment thereof that binds to a Nectin-4 epitope comprises an amino acid sequence that is at least 90% identical to an amino acid sequence depicted in Tables 1-2. In one embodiment, an antibody or fragment thereof that binds to a Nectin-4 epitope comprises an amino acid sequence that is at least 95% identical to an amino acid sequence depicted in Tables 1-2. In one embodiment, an antibody or fragment thereof that binds to a Nectin-4 epitope comprises an amino acid sequence that is at least 99% identical to an amino acid sequence depicted in Tables 1-2.

In yet another embodiment, an antibody or fragment thereof that binds to a Nectin-4 epitope comprises a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a VL CDR amino acid sequence that is at least 35% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a VL CDR amino acid sequence that is at least 40% identical to a VH CDR amino acid sequence depicted in Table 1 and/or a $V_L$ CDR amino acid sequence depicted in Table 1. In yet another embodiment, an antibody or fragment thereof that binds to a Nectin-4 epitope comprises a VH CDR and/or a VL CDR amino acid sequence that is at least 45% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a $V_L$ CDR amino acid sequence that is at least 50% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a VL CDR amino acid sequence that is at least 55% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a VL CDR amino acid sequence that is at least 60% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a VL CDR amino acid sequence that is at least 65% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a VL CDR amino acid sequence that is at least 70% identical to a VH CDR amino acid sequence depicted in Table 1 and/or a $V_L$ CDR amino acid sequence depicted in Table 1. In yet another embodiment, an antibody or fragment thereof that binds to a Nectin-4 epitope comprises a VH CDR and/or a VL CDR amino acid sequence that is at least 75% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a $V_L$ CDR amino acid sequence that is at least 80% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a VL CDR amino acid sequence that is at least 85% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a VL CDR amino acid sequence that is at least 90% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a VL CDR amino acid sequence that is at least 95% identical to a VH CDR amino acid sequence depicted in Table 1 and/or a VL CDR amino acid sequence depicted in Table 1. In yet another embodiment, an antibody or fragment thereof that binds to a Nectin-4 epitope comprises a VH CDR and/or a VL CDR amino acid sequence that is at least 99% identical to a VH CDR amino acid sequence depicted in Table 1 and/or a $V_L$ CDR amino acid sequence depicted in Table 1.

The variations can be made using methods known in the art such as oligonucleotide-mediated (site-directed) mutagenesis, alanine scanning, and PCR mutagenesis. Site-directed mutagenesis (see, e.g., Carter, 1986, Biochem J. 237:1-7; and Zoller et al., 1982, Nucl. Acids Res. 10:6487-500), cassette mutagenesis (see, e.g., Wells et al., 1985, Gene 34:315-23), or other known techniques can be performed on the cloned DNA to produce the anti-Nectin-4 antibody variant DNA.

Any cysteine residue not involved in maintaining the proper conformation of the anti-Nectin-4 antibody also may be substituted, for example, with another amino acid, such as alanine or serine, to improve the oxidative stability of the molecule and to prevent aberrant crosslinking. Conversely, cysteine bond(s) may be added to the anti-Nectin-4 antibody to improve its stability (e.g., where the antibody is an antibody fragment such as an Fv fragment).

In some embodiments, an anti-Nectin-4 antibody molecule of the present disclosure is a "de-immunized" antibody. A "de-immunized" anti-Nectin-4 antibody is an antibody derived from a humanized or chimeric anti-Nectin-4 antibody, which has one or more alterations in its amino acid sequence resulting in a reduction of immunogenicity of the antibody, compared to the respective original non-de-immunized antibody. One of the procedures for generating such antibody mutants involves the identification and removal of T-cell epitopes of the antibody molecule. In a first step, the immunogenicity of the antibody molecule can be determined by several methods, for example, by in vitro determination of T-cell epitopes or in silico prediction of such epitopes, as known in the art. Once the critical residues for T-cell epitope function have been identified, mutations can be made to remove immunogenicity and retain antibody activity. For review, see, for example, Jones et al., 2009, Methods in Molecular Biology 525:405-23.

20. IN VITRO AFFINITY MATURATION

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed as Fab, scFv, or V domain fragments either on the surface of an organism (e.g., phage, bacteria, yeast, or mammalian cell) or in association (e.g., covalently or non-covalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Affinity matured antibodies can have nanomolar or even picomolar affinities for the target antigen.

Phage display is a widespread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and used to infect bacteria to produce phage for further rounds of selection. For review, see, for example, Hoogenboom, 2002, Methods. Mol. Biol. 178:1-37; and Bradbury and Marks, 2004, J. Immunol. Methods 290:29-49.

In a yeast display system (see, e.g., Boder et al., 1997, Nat. Biotech. 15:553-57; and Chao et al., 2006, Nat. Protocols 1:755-68), the antibody may be displayed as single-chain variable fusions (scFv) in which the heavy and light chains are connected by a flexible linker. The scFv is fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the scFv. Expression has been shown to correlate with the stability of the displayed protein, and thus antibodies can be selected for improved stability as well as affinity (see, e.g., Shusta et al., 1999, J. Mol. Biol. 292:949-56). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently "titrated" while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., U.S. Pat. Publication 2003/0186374; and Blaise et al., 2004, Gene 342:211-18).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reverse transcribed back into cDNA, which can then undergo mutagenesis and be used in the next round of selection (see, e.g., Fukuda et al., 2006, Nucleic Acids Res. 34:e127). In mRNA display, a covalent bond between antibody and mRNA is established using puromycin as an adaptor molecule (Wilson et al., 2001, Proc. Natl. Acad. Sci. USA 98:3750-55).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerases, as no library must be transformed after any diversification step.

In a mammalian cell display system (see, e.g., Bowers et al., 2011, Proc Natl Acad Sci USA. 108:20455-60), a fully human library of IgGs is constructed based on germline sequence V-gene segments joined to prerecombined D(J) regions. Full-length V regions for heavy chain and light chain are assembled with human heavy chain and light chain constant regions and transfected into a mammalian cell line (e.g., HEK293). The transfected library is expanded and subjected to several rounds of negative selection against streptavidin (SA)-coupled magnetic beads, followed by a round of positive selection against SA-coupled magnetic beads coated with biotinylated target protein, peptide fragment, or epitope. Positively selected cells are expanded, and then sorted by rounds of FACS to isolate single cell clones displaying antibodies that specifically bind to the target protein, peptide fragment, or epitope. Heavy and light chain pairs from these single cell clones are retransfected with AID for further maturation. Several rounds of mammalian cell display, coupled with AID-triggered somatic hypermutation, generate high specificity, high affinity antibodies.

Diversity may also be introduced into the CDRs or the whole V genes of the antibody libraries in a targeted manner or via random introduction. The former approach includes sequentially targeting all the CDRs of an antibody via a high or low level of mutagenesis or targeting isolated hot spots of somatic hypermutations (see, e.g., Ho et al., 2005, J. Biol. Chem. 280:607-17) or residues suspected of affecting affinity on experimental basis or structural reasons. Diversity may also be introduced by replacement of regions that are naturally diverse via DNA shuffling or similar techniques (see, e.g., Lu et al., 2003, J. Biol. Chem. 278:43496-507; U.S. Pat. Nos. 5,565,332 and 6,989,250). Alternative techniques target hypervariable loops extending into framework-region residues (see, e.g., Bond et al., 2005, J. Mol. Biol. 348:699-709) employ loop deletions and insertions in CDRs or use hybridization-based diversification (see, e.g., U.S. Pat. Publication No. 2004/0005709). Additional methods of generating diversity in CDRs are disclosed, for example, in U.S. Pat. No. 7,985,840. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

Screening of the libraries can be accomplished by various techniques known in the art. For example, Nectin-4 can be immobilized onto solid supports, columns, pins, or cellulose/poly(vinylidene fluoride) membranes/other filters, expressed on host cells affixed to adsorption plates or used in cell sorting, or conjugated to biotin for capture with streptavidin-coated beads or used in any other method for panning display libraries.

For review of in vitro affinity maturation methods, see, e.g., Hoogenboom, 2005, Nature Biotechnology 23:1105-16; Quiroz and Sinclair, 2010, Revista Ingeneria Biomedia 4:39-51; and references therein.

21. MODIFICATIONS OF ANTI-NECTIN-4 ANTIBODIES

Covalent modifications of anti-Nectin-4 antibodies are included within the scope of the present disclosure. Covalent modifications include reacting targeted amino acid residues of an anti-Nectin-4 antibody with an organic derivatizing agent that is capable of reacting with selected side chains or the N- or C-terminal residues of the anti-Nectin-4 antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see, e.g., Creighton, *Proteins: Structure and Molecular Properties* 79-86 (1983)), acetylation of the N-terminal amine, and amidation of any C-terminal carboxyl group.

Other types of covalent modification of the anti-Nectin-4 antibody included within the scope of this present disclosure include altering the native glycosylation pattern of the antibody or polypeptide (see, e.g., Beck et al., 2008, Curr. Pharm. Biotechnol. 9:482-501; and Walsh, 2010, Drug Discov. Today 15:773-80), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640,835; 4,496,689; 4,301,144; 4,670,417; 4,791,192; or 4,179,337.

An anti-Nectin-4 antibody of the present disclosure may also be modified to form chimeric molecules comprising an anti-Nectin-4 antibody fused to another, heterologous polypeptide or amino acid sequence, for example, an epitope tag (see, e.g., Terpe, 2003, Appl. Microbiol. Biotechnol. 60:523-33) or the Fc region of an IgG molecule (see, e.g., Aruffo, *Antibody Fusion Proteins* 221-42 (Chamow and Ashkenazi eds., 1999)).

Also provided herein are fusion proteins comprising an antibody provided herein that binds to a Nectin-4 antigen and a heterologous polypeptide. In some embodiments, the heterologous polypeptide to which the antibody is fused is useful for targeting the antibody to cells having cell surface-expressed Nectin-4.

Also provided herein are panels of antibodies that bind to a Nectin-4 antigen. In specific embodiments, the panels of antibodies have different association rates, different dissociation rates, different affinities for a Nectin-4 antigen, and/or different specificities for a Nectin-4 antigen. In some embodiments, the panels comprise or consist of about 10, about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more.

22. PREPARATION OF ANTI-NECTIN-4 ANTIBODIES

Anti-Nectin-4 antibodies may be produced by culturing cells transformed or transfected with a vector containing anti-Nectin-4 antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression, and purification are further described in Plückthun et al., *Antibody Engineering: Producing antibodies in Escherichia coli: From PCR to fermentation* 203-52 (McCafferty et al. eds., 1996); Kwong and Rader, *E. coli Expression and Purification of Fab Antibody Fragments*, in *Current Protocols in Protein Science* (2009); Tachibana and Takekoshi, *Production of Antibody Fab Fragments in Escherischia coli*, in *Antibody Expression and Production* (Al-Rubeai ed., 2011); and *Therapeutic Monoclonal Antibodies: From Bench to Clinic* (An ed., 2009).

It is, of course, contemplated that alternative methods, which are well known in the art, may be employed to prepare anti-Nectin-4 antibodies. For instance, the appropriate amino acid sequence, or portions thereof, may be produced by direct peptide synthesis using solid-phase techniques (see, e.g., Stewart et al., *Solid-Phase Peptide Synthesis* (1969); and Merrifield, 1963, J. Am. Chem. Soc. 85:2149-54). In vitro protein synthesis may be performed using manual techniques or by automation. Various portions of the anti-Nectin-4 antibody may be chemically synthesized separately and combined using chemical or enzymatic methods to produce the desired anti-Nectin-4 antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

23. IMMUNOCONJUGATES

The present disclosure also provides conjugates comprising any one of the anti-Nectin-4 antibodies of the present disclosure covalently bound by a synthetic linker to one or more non-antibody agents.

In some embodiments, antibodies provided herein are conjugated or recombinantly fused, e.g., to a diagnostic or detectable molecule. The conjugated or recombinantly fused antibodies can be useful, for example, for monitoring or prognosing the onset, development, progression, and/or severity of a Nectin-4-mediated disease.

Such diagnosis and detection can be accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin or avidin/biotin; fluorescent materials, such as, but not limited to, umbelliferone, fluorescein, fluorescein isothiocynate, rhodamine, dichlorotriazinylamine fluorescein, dansyl chloride, or phycoerythrin; luminescent materials, such as, but not limited to, luminol; bioluminescent materials, such as, but not limited to, luciferase, luciferin, or aequorin; chemiluminescent material, such as, but not limited to, an acridinium based compound or a HALOTAG; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga and $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, or $^{117}$Sn; positron emitting metals using various positron emission tomographies; and non-radioactive paramagnetic metal ions.

Also provided herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90, or about 100 amino acids) to generate fusion proteins, as well as uses thereof. In particular, provided herein are fusion proteins comprising an antigen-binding fragment of an antibody provided herein (e.g., a Fab fragment, Fc fragment, Fv fragment, F(ab)$_2$ fragment, a VH domain, a VH CDR, a VL domain, or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses Nectin-4. For example, an antibody that binds to a cell surface receptor expressed by a particular cell type may be fused or conjugated to a modified antibody provided herein.

Moreover, antibodies provided herein can be fused to marker or "tag" sequences, such as a peptide, to facilitate purification. In specific embodiments, the marker or tag amino acid sequence is a hexa-histidine peptide, such as the tag provided in a pQE vector (see, e.g., QIAGEN, Inc.), among others, many of which are commercially available. For example, as described in Gentz et al., 1989, Proc. Natl. Acad. Sci. USA 86:821-24, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767-78), the streptavidin/avidin binding peptide, and the "FLAG" tag.

Methods for fusing or conjugating moieties (including polypeptides) to antibodies are known (see, e.g., Arnon et al., *Monoclonal Antibodies for Immunotargeting of Drugs in Cancer Therapy*, in *Monoclonal Antibodies and Cancer*

*Therapy* 243-56 (Reisfeld et al. eds., 1985); Hellstrom et al., *Antibodies for Drug Delivery, in Controlled Drug Delivery* 623-53 (Robinson et al. eds., 2d ed. 1987); Thorpe, *Antibody Carriers of Cytotoxic Agents in Cancer Therapy: A Review, in Monoclonal Antibodies: Biological and Clinical Applications* 475-506 (Pinchera et al. eds., 1985); *Analysis, Results, and Future Prospective of the Therapeutic Use of Radiolabeled Antibody in Cancer Therapy, in Monoclonal Antibodies for Cancer Detection and Therapy* 303-16 (Baldwin et al. eds., 1985); Thorpe et al., 1982, Immunol. Rev. 62:119-58; U.S. Pat. Nos. 5,336,603; 5,622,929; 5,359,046; 5,349,053; 5,447,851; 5,723,125; 5,783,181; 5,908,626; 5,844,095; and 5,112,946; EP 307,434; EP 367,166; EP 394,827; PCT publications WO 91/06570, WO 96/04388, WO 96/22024, WO 97/34631, and WO 99/04813; Ashkenazi et al., 1991, Proc. Natl. Acad. Sci. USA, 88: 10535-39; Traunecker et al., 1988, Nature, 331:84-86; Zheng et al., 1995, J. Immunol. 154:5590-600; and Vil et al., 1992, Proc. Natl. Acad. Sci. USA 89:11337-41).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of anti-Nectin-4 antibodies as provided herein, including, for example, antibodies with higher affinities and lower dissociation rates (see, e.g., U.S. Pat. Nos. 5,605,793; 5,811,238; 5,830,721; 5,834,252; and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-13). Antibodies, or the encoded antibodies, may be altered by being subjected to random mutagenesis by error-prone PCR, random nucleotide insertion, or other methods prior to recombination. A polynucleotide encoding an antibody provided herein may be recombined with one or more components, motifs, sections, parts, domains, fragments, etc. of one or more heterologous molecules.

An antibody provided herein can also be conjugated to a second antibody to form an antibody heteroconjugate as described, for example, in U.S. Pat. No. 4,676,980.

Antibodies that bind to Nectin-4 as provided herein may also be attached to solid supports, which are particularly useful for immunoassays or purification of the target antigen. Such solid supports include, but are not limited to, glass, cellulose, polyacrylamide, nylon, polystyrene, polyvinyl chloride, or polypropylene.

The linker may be a "cleavable linker" facilitating release of the conjugated agent in the cell, but non-cleavable linkers are also contemplated herein. Linkers for use in the conjugates of the present disclosure include, without limitation, acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers (see, e.g., Chari et al., 1992, Cancer Res. 52:127-31; and U.S. Pat. No. 5,208,020), thioether linkers, or hydrophilic linkers designed to evade multidrug transporter-mediated resistance (see, e.g., Kovtun et al., 2010, Cancer Res. 70:2528-37).

Conjugates of the antibody and agent may be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate). The present disclosure further contemplates that conjugates of antibodies and agents may be prepared using any suitable methods as disclosed in the art (see, e.g., *Bioconjugate Techniques* (Hermanson ed., 2d ed. 2008)).

Conventional conjugation strategies for antibodies and agents have been based on random conjugation chemistries involving the ε-amino group of Lys residues or the thiol group of Cys residues, which results in heterogenous conjugates. Recently developed techniques allow site-specific conjugation to antibodies, resulting in homogeneous loading and avoiding conjugate subpopulations with altered antigen-binding or pharmacokinetics. These include engineering of "thiomabs" comprising cysteine substitutions at positions on the heavy and light chains that provide reactive thiol groups and do not disrupt immunoglobulin folding and assembly or alter antigen binding (see, e.g., Junutula et al., 2008, J. Immunol. Meth. 332: 41-52; and Junutula et al., 2008, Nature Biotechnol. 26:925-32). In another method, selenocysteine is cotranslationally inserted into an antibody sequence by recoding the stop codon UGA from termination to selenocysteine insertion, allowing site specific covalent conjugation at the nucleophilic selenol group of selenocysteine in the presence of the other natural amino acids (see, e.g., Hofer et al., 2008, Proc. Natl. Acad. Sci. USA 105: 12451-56; and Hofer et al., 2009, Biochemistry 48(50): 12047-57).

In other embodiments, provided herein are antibodies conjugated or recombinantly fused to a therapeutic moiety (or one or more therapeutic moieties). The antibody may be conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399, 633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, an antibody provided herein may be conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

The therapeutic moiety or drug conjugated or recombinantly fused to an antibody provided herein that immunospecifically binds to a Nectin-4 antigen should be chosen to achieve the desired prophylactic or therapeutic effect(s). In certain embodiments, the antibody is a modified antibody. A clinician or other medical personnel should consider the following when deciding on which therapeutic moiety or drug to conjugate or recombinantly fuse to an antibody provided herein: the nature of the disease, the severity of the disease, and the condition of the subject.

As used herein, "anti-Nectin-4 antibody drug conjugate" or "anti-Nectin-4 ADC" refers to an anti-Nectin-4 antibody or antigen binding fragment thereof conjugated or recombinantly fused to a therapeutic moiety (or one or more therapeutic moieties), or an anti-Nectin-4 antibody or antigen binding fragment thereof conjugated or recombinantly fused to a therapeutic moiety or drug moiety that modifies a given biological response, as described above.

Provided herein is an anti-Nectin-4 ADC including an anti-Nectin-4 antibody that specifically binds to Nectin-4. Also provided herein is an anti-Nectin-4 ADC including anti-Nectin-4 antibody or antigen binding fragment thereof provided herein.

24. METHODS OF USING THE ANTIBODIES AND COMPOSITIONS

In one aspect, provided herein is a method of inhibiting (e.g., reducing the rate of doubling of the cell numbers, slowing down the rate of increase of the cell numbers, or blocking or preventing the increase of cell numbers) the proliferation of a cell, comprising contacting the cell with an effective amount of an anti-Nectin-4 ADC provided herein.

In one aspect, provided herein are methods of inhibiting the proliferation of a cell, comprising contacting the cell with an anti-Nectin-4 ADC including an anti-Nectin-4 antibody that specifically binds to Nectin-4 (e.g., an ECD of human Nectin-4 or an epitope of an ECD of human Nectin-4) as provided herein. In certain embodiments, the cell is contacted with an effective amount of an anti-Nectin-4 ADC as described herein. In some embodiments, the anti-Nectin-4 ADC binds to an ECD of human Nectin-4. In some embodiments, the anti-Nectin-4 ADC binds to an epitope of an ECD of human Nectin-4. In certain embodiments, the anti-Nectin-4 ADC specifically binds to an epitope of an ECD of human Nectin-4 that is distinct from the Nectin-4 ligand binding site. In some embodiments, the proliferation of a cell is inhibited by at least about 10%. In some embodiments, the proliferation of a cell is inhibited by at least about 15%. In some embodiments, the proliferation of a cell is inhibited by at least about 20%. In some embodiments, the proliferation of a cell is inhibited by at least about 25%. In some embodiments, the proliferation of a cell is inhibited by at least about 30%. In some embodiments, the proliferation of a cell is inhibited by at least about 35%. In some embodiments, the proliferation of a cell is inhibited by at least about 40%. In some embodiments, the proliferation of a cell is inhibited by at least about 45%. In some embodiments, the proliferation of a cell is inhibited by at least about 50%. In some embodiments, the proliferation of a cell is inhibited by at least about 55%. In some embodiments, the proliferation of a cell is inhibited by at least about 60%. In some embodiments, the proliferation of a cell is inhibited by at least about 65%. In some embodiments, the proliferation of a cell is inhibited by at least about 70%. In some embodiments, the proliferation of a cell is inhibited by at least about 75%. In some embodiments, the proliferation of a cell is inhibited by at least about 80%. In some embodiments, the proliferation of a cell is inhibited by at least about 85%. In some embodiments, the proliferation of a cell is inhibited by at least about 90%. In some embodiments, the proliferation of a cell is inhibited by at least about 95%. In some embodiments, the proliferation of a cell is inhibited by at least about 98%. In some embodiments, the proliferation of a cell is inhibited by at least about 99%. In some embodiments, the proliferation of a cell is inhibited by at least about 100%. In certain embodiments, the proliferation of a cell is inhibited by at least about 25% to about 65%. In specific embodiments, the inhibition of the proliferation of a cell is assessed by methods described herein. In some embodiments, the inhibition of the proliferation of a cell is assessed by methods known to one of skill in the art. In certain embodiments, the inhibition of the proliferation of a cell is relative to inhibition of the proliferation of a cell that is not contacted with an anti-Nectin-4 ADC. In certain embodiments, the inhibition of the proliferation of a cell is relative to inhibition of the proliferation of a cell that is contacted with an unrelated antibody (e.g., an antibody that does not specifically bind to Nectin-4), ADC of the unrelated antibody, or an unconjugated anti-Nectin-4 antibody.

25. PHARMACEUTICAL COMPOSITIONS

In one aspect, the present disclosure further provides pharmaceutical compositions comprising at least one anti-Nectin-4 ADC of the present disclosure. In some embodiments, a pharmaceutical composition comprises 1) an anti-Nectin-4 antibody, and 2) a pharmaceutically acceptable carrier.

Pharmaceutical compositions comprising an anti-Nectin-4 ADC are prepared for storage by mixing the anti-Nectin-4 ADC having the desired degree of purity with optional physiologically acceptable carriers, excipients, or stabilizers (see, e.g., Remington, *Remington's Pharmaceutical Sciences* (18th ed. 1980)) in the form of aqueous solutions or lyophilized or other dried forms.

The antibodies of the present disclosure may be formulated in any suitable form for delivery to a target cell/tissue, e.g., as microcapsules or macroemulsions (Remington, supra; Park et al., 2005, Molecules 10:146-61; Malik et al., 2007, Curr. Drug. Deliv. 4:141-51), as sustained release formulations (Putney and Burke, 1998, Nature Biotechnol. 16:153-57), or in liposomes (Maclean et al., 1997, Int. J. Oncol. 11:325-32; Kontermann, 2006, Curr. Opin. Mol. Ther. 8:39-45).

An anti-Nectin-4 ADC provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles, and nanocapsules) or in macroemulsions. Such techniques are disclosed, for example, in Remington, supra.

Various compositions and delivery systems are known and can be used with an anti-Nectin-4 ADC that binds to Nectin-4 as described herein, including, but not limited to, encapsulation in liposomes, microparticles, microcapsules, recombinant cells capable of expressing the anti-Nectin-4 ADC, receptor-mediated endocytosis (see, e.g., Wu and Wu, 1987, J. Biol. Chem. 262:4429-32), construction of a nucleic acid as part of a retroviral or other vector, etc. In another embodiment, a composition can be provided as a controlled release or sustained release system. In one embodiment, a pump may be used to achieve controlled or sustained release (see, e.g., Langer, supra; Sefton, 1987, Crit. Ref. Biomed. Eng. 14:201-40; Buchwald et al., 1980, Surgery 88:507-16; and Saudek et al., 1989, N. Engl. J. Med. 321:569-74). In another embodiment, polymeric materials can be used to achieve controlled or sustained release of a prophylactic or therapeutic agent (e.g., an anti-Nectin-4 ADC as described herein) or a composition provided herein (see, e.g., *Medical Applications of Controlled Release* (Langer and Wise eds., 1974); *Controlled Drug Bioavailability, Drug Product Design and Performance* (Smolen and Ball eds., 1984); Ranger and Peppas, 1983, J. Macromol. Sci. Rev. Macromol. Chem. 23:61-126; Levy et al., 1985, Science 228:190-92; During et al., 1989, Ann. Neurol. 25:351-56; Howard et al., 1989, J. Neurosurg. 71:105-12; U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable.

In yet another embodiment, a controlled or sustained release system can be placed in proximity of a particular target tissue, for example, the nasal passages or lungs, thus requiring only a fraction of the systemic dose (see, e.g., Goodson, *Medical Applications of Controlled Release* Vol. 2, 115-38 (1984)). Controlled release systems are discussed, for example, by Langer, 1990, Science 249:1527-33. Any technique known to one of skill in the art can be used to produce sustained release formulations comprising one or more antibodies that bind to Nectin-4 as described herein (see, e.g., U.S. Pat. No. 4,526,938, PCT publication Nos. WO 91/05548 and WO 96/20698, Ning et al., 1996, Radiotherapy & Oncology 39:179-89; Song et al., 1995, PDA J. of Pharma. Sci. & Tech. 50:372-97; Cleek et al., 1997, Pro. Int'l. Symp. Control. Rel. Bioact. Mater. 24:853-54; and Lam et al., 1997, Proc. Int'l. Symp. Control Rel. Bioact. Mater. 24:759-60).

Therapeutic formulations containing one or more antibodies provided herein provided herein can be prepared for storage by mixing the anti-Nectin-4 ADC having the desired degree of purity with optional physiologically acceptable carriers, excipients or stabilizers (*Remington's Pharmaceutical Sciences* (1990) Mack Publishing Co., Easton, Pa.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibodies provided herein can also, for example, be formulated in liposomes. Liposomes containing the molecule of interest are prepared by methods known in the art, such as described in Epstein et al. (1985) *Proc. Natl. Acad. Sci. USA* 82:3688; Hwang et al. (1980) *Proc. Natl. Acad. Sci. USA* 77:4030; and U.S. Pat. Nos. 4,485,045 and 4,544,545. Liposomes with enhanced circulation time are disclosed in U.S. Pat. No. 5,013,556.

Particularly useful immunoliposomes can be generated by the reverse phase evaporation method with a lipid composition containing phosphatidylcholine, cholesterol and PEG-derivatized phosphatidylethanolamine (PEG-PE). Liposomes are extruded through filters of defined pore size to yield liposomes with the desired diameter. Fab' fragments of an anti-Nectin-4 ADC provided herein can be conjugated to the liposomes as described in Martin et al. (1982) *J. Biol. Chem.* 257:286-288 via a disulfide interchange reaction. A chemotherapeutic agent (such as Doxorubicin) is optionally contained within the liposome; See Gabizon et al., (1989) *J. National Cancer Inst.* 81(19):1484.

Formulations, such as those described herein, can also contain more than one active compound as necessary for the particular indication being treated. In certain embodiments, formulations comprise an anti-Nectin-4 ADC provided herein and one or more active compounds with complementary activities that do not adversely affect each other. Such molecules are suitably present in combination in amounts that are effective for the purpose intended. For example, an anti-Nectin-4 ADC provided herein can be combined with one or more other therapeutic agents. Such combined therapy can be administered to the patient serially or simultaneously or in sequence.

An anti-Nectin-4 ADC provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* (1990) Mack Publishing Co., Easton, Pa.

The formulations to be used for in vivo administration can be sterile. This is readily accomplished by filtration through, e.g., sterile filtration membranes.

Sustained-release preparations can also be prepared. Suitable examples of sustained-release preparations include semipermeable matrices of solid hydrophobic polymers containing the anti-Nectin-4 ADC, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The pharmaceutical compositions provided herein contain therapeutically effective amounts of one or more of the antibodies provided herein, and optionally one or more additional prophylactic of therapeutic agents, in a pharmaceutically acceptable carrier. Such pharmaceutical compositions are useful in the prevention, treatment, management or amelioration of a Nectin-4-mediated disease, or one or more of the symptoms thereof.

Pharmaceutical carriers suitable for administration of the compounds provided herein include any such carriers known to those skilled in the art to be suitable for the particular mode of administration.

In addition, the antibodies provided herein may be formulated as the sole pharmaceutically active ingredient in the composition or may be combined with other active ingredients (such as one or more other prophylactic or therapeutic agents).

The compositions can contain one or more antibodies provided herein. In one embodiment, the antibodies are formulated into suitable pharmaceutical preparations, such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the antibodies described above are formulated into pharmaceutical compositions using techniques and procedures well known in the art (see, e.g., Ansel (1985) *Introduction to Pharmaceutical Dosage Forms*, $4^{th}$ Ed., p. 126).

In the compositions, effective concentrations of one or more antibodies or derivatives thereof is (are) mixed with a suitable pharmaceutical carrier. The concentrations of the compounds in the compositions are effective for delivery of an amount, upon administration, that treats, prevents, or ameliorates a Nectin-4-mediated disease or symptom thereof.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

An anti-Nectin-4 ADC provided herein is included in the pharmaceutically acceptable carrier in an effective amount sufficient to exert a therapeutically useful effect in the absence of undesirable side effects on the patient treated. The therapeutically effective concentration can be determined empirically by testing the compounds in in vitro and in vivo systems using routine methods and then extrapolated therefrom for dosages for humans.

The concentration of anti-Nectin-4 ADC in the pharmaceutical composition will depend on, e.g., the physicochemical characteristics of the anti-Nectin-4 ADC, the dosage schedule, and amount administered as well as other factors known to those of skill in the art.

In one embodiment, a therapeutically effective dosage produces a serum concentration of anti-Nectin-4 ADC of from about 0.1 ng/ml to about 50-100 µg/ml. The pharmaceutical compositions, in another embodiment, provide a dosage of from about 0.001 mg to about 2000 mg of anti-Nectin-4 ADC per kilogram of body weight per day. Pharmaceutical dosage unit forms can be prepared to provide from about 0.01 mg, 0.1 mg or 1 mg to about 500 mg, 1000 mg or 2000 mg, and in one embodiment from about 10 mg to about 500 mg of the anti-Nectin-4 ADC and/or a combination of other optional essential ingredients per dosage unit form.

The anti-Nectin-4 ADC can be administered at once, or may be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the anti-Nectin-4 ADC, the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The anti-Nectin-4 ADC is, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the anti-Nectin-4 ADC sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

In some embodiments, one or more anti-Nectin-4 antibodies provided herein are in a liquid pharmaceutical formulation. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see *Remington's Pharmaceutical Sciences* (1990) Mack Publishing Co., Easton, Pa.

Dosage forms or compositions containing anti-Nectin-4 ADC in the range of 0.005% to 100% with the balance made up from non-toxic carrier can be prepared. Methods for preparation of these compositions are known to those skilled in the art.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules can be hard or soft gelatin capsules, while granules and powders can be provided in non-effervescent or effervescent form with the combination of other ingredients known to those skilled in the art.

In certain embodiments, the formulations are solid dosage forms. In certain embodiments, the formulations are capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The antibodies can be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The anti-Nectin-4 ADC can also be mixed with other active materials which do not impair the desired action, or with materials that supplement the desired action, such as antacids, H2 blockers, and diuretics. The active ingredient is an anti-Nectin-4 ADC or pharmaceutically acceptable derivative thereof as described herein. Higher concentrations, up to about 98% by weight of the active ingredient may be included.

In all embodiments, tablets and capsules formulations can be coated as known by those of skill in the art in order to modify or sustain dissolution of the active ingredient. Thus, for example, they may be coated with a conventional enterically digestible coating, such as phenylsalicylate, waxes and cellulose acetate phthalate.

In some embodiments, the formulations are liquid dosage forms. Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is, in one embodiment, encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The anti-Nectin-4 ADC diffuses through the outer polymeric membrane in a release rate controlling step. The amount of anti-Nectin-4 ADC contained in such parenteral compositions is highly dependent on the specific nature thereof, as well as the activity of the compound and the needs of the subject.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations can be packaged in an ampoule, a vial or a syringe with a needle. All preparations for parenteral administration can be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The anti-Nectin-4 ADC can be suspended in micronized or other suitable form. The form of the resulting mixture depends upon a number of factors, including the intended mode of administration and the solubility of the compound in the selected carrier or vehicle. The effective concentration is sufficient for ameliorating the symptoms of the condition and may be empirically determined.

In other embodiments, the pharmaceutical formulations are lyophilized powders, which can be reconstituted for administration as solutions, emulsions and other mixtures. They may also be reconstituted and formulated as solids or gels.

The lyophilized powder is prepared by dissolving an anti-Nectin-4 ADC provided herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The antibodies provided herein can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration can be manufactured using the same pharmaceutically acceptable substance and by the same methods as for formulations for oral administration.

The antibodies and other compositions provided herein may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, the anti-Nectin-4 antibodies provided herein are targeted (or otherwise administered) to the colon, such as in a patient having or at risk of having a Nectin-4-mediated disease.

In one embodiment, liposomal suspensions, including tissue-targeted liposomes, such as tumor-targeted liposomes, may also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

26. METHODS OF ADMINISTRATION AND DOSING

In a specific embodiment, provided herein is a composition for use in the prevention, management, treatment and/or amelioration of a Nectin-4-mediated disease comprising an anti-Nectin-4 ADC provided herein. In one embodiment, provided herein is a composition for use in the prevention of a Nectin-4-mediated disease, wherein the composition comprises an anti-Nectin-4 ADC provided herein. In one embodiment, provided herein is a composition for use in the management of a Nectin-4-mediated disease, wherein the composition comprises an anti-Nectin-4 ADC provided herein. In one embodiment, provided herein is a composition for use in the treatment of a Nectin-4-mediated disease, wherein the composition comprises an anti-Nectin-4 ADC provided herein. In one embodiment, provided herein is a composition for use in the amelioration of a Nectin-4-mediated disease, wherein the composition comprises an anti-Nectin-4 ADC provided herein. In certain embodiments, the subject is a subject in need thereof. In some embodiments, the subject has the Nectin-4-mediated disease. In other embodiments, the subject is at risk of having the Nectin-4-mediated disease. In some embodiments, the administration results in the prevention, management, treatment or amelioration of the Nectin-4-mediated disease. In one embodiment, the anti-Nectin-4 ADC is an ADC wherein the anti-Nectin-4 antibody is antibody M22-321b41.1.

In one embodiment, provided herein is a composition for use in the prevention, management, treatment and/or amelioration of a symptom of a Nectin-4-mediated disease, wherein the composition comprises an anti-Nectin-4 ADC provided herein. In one embodiment, provided herein is a composition for use in the prevention of a symptom of a Nectin-4-mediated disease, wherein the composition comprises an anti-Nectin-4 ADC provided herein. In one embodiment, provided herein is a composition for use in the management of a symptom of a Nectin-4-mediated disease, wherein the composition comprises an anti-Nectin-4 ADC provided herein. In one embodiment, provided herein is a composition for use in the treatment of a symptom of a Nectin-4-mediated disease, wherein the composition comprises an anti-Nectin-4 ADC provided herein. In one embodiment, provided herein is a composition for use in the amelioration of a symptom of a Nectin-4-mediated disease, wherein the composition comprises an anti-Nectin-4 ADC provided herein. In certain embodiments, the subject is a subject in need thereof. In some embodiments, the subject has the Nectin-4-mediated disease. In other embodiments, the subject is at risk of having the Nectin-4-mediated disease. In some embodiments, the administration results in the prevention, management, treatment or amelioration of the symptom of the Nectin-4-mediated disease. In one embodiment, the Nectin-4 antibody is antibody M22-321b41.1.

In another embodiment, provided herein is a method of preventing, managing, treating and/or ameliorating a Nectin-4-mediated disease in a subject, comprising administering an effective amount of an anti-Nectin-4 ADC provided herein. In one embodiment, provided herein is a method of preventing a Nectin-4-mediated disease in a subject, comprising administering an effective amount of an anti-Nectin-4 ADC provided herein. In one embodiment, provided herein is a method of managing a Nectin-4-mediated disease in a subject, comprising administering an effective amount of an anti-Nectin-4 ADC provided herein. In one embodiment, provided herein is a method of treating a Nectin-4-mediated disease in a subject, comprising administering an effective amount of an anti-Nectin-4 ADC provided herein. In one embodiment, provided herein is a method of ameliorating a Nectin-4-mediated disease in a subject, comprising administering an effective amount of an anti-Nectin-4 ADC provided herein. In certain embodiments, the subject is a subject in need thereof. In some embodiments, the subject has the Nectin-4-mediated disease. In other embodiments, the subject is at risk of having the Nectin-4-mediated disease. In some embodiments, the administration results in the prevention, management, treatment or amelioration of the Nectin-4-mediated disease. In one embodiment, the anti-Nectin-4 ADC is an ADC wherein the anti-Nectin-4 antibody is antibody M22-321b41.1.

In another embodiment, provided herein is a method of preventing, managing, treating and/or ameliorating a symptom of a Nectin-4-mediated disease in a subject, comprising administering an effective amount of an anti-Nectin-4 ADC provided herein. In one embodiment, provided herein is a method of preventing a symptom of a Nectin-4-mediated disease in a subject, comprising administering an effective amount of an anti-Nectin-4 ADC provided herein. In one embodiment, provided herein is a method of managing a symptom of a Nectin-4-mediated disease in a subject, comprising administering an effective amount of an anti-Nectin-4 ADC provided herein. In one embodiment, provided herein is a method of treating a symptom of a Nectin-4-mediated disease in a subject, comprising administering an effective amount of an anti-Nectin-4 ADC provided herein. In one embodiment, provided herein is a method of ameliorating a Nectin-4-mediated disease in a subject, comprising administering an effective amount of an anti-Nectin-4 ADC provided herein. In certain embodiments, the subject is a subject in need thereof. In some embodiments, the subject has the Nectin-4-mediated disease. In other embodiments, the subject is at risk of having the Nectin-4-mediated disease. In some embodiments, the administration results in the prevention, management, treatment or amelioration of the symptom of the Nectin-4-mediated disease. In one embodiment, the anti-Nectin-4 ADC is an ADC wherein the anti-Nectin-4 antibody is antibody M22-321b41.1.

Antibodies provided herein may also be used, for example, to purify, detect, and target Nectin-4 antigens, in both in vitro and in vivo diagnostic and therapeutic methods. For example, the modified antibodies have use in immunoassays for qualitatively and quantitatively measuring levels of Nectin-4 in biological samples. See, e.g., Harlow et al., Antibodies: A Laboratory Manual, (Cold Spring Harbor Laboratory Press, 2nd ed. 1988) (incorporated by reference herein in its entirety).

Also provided herein are methods of preventing, managing, treating and/or ameliorating a Nectin-4-mediated disease by administrating to a subject of an effective amount of an anti-Nectin-4 ADC, or pharmaceutical composition comprising an anti-Nectin-4 ADC provided herein. In one aspect, an anti-Nectin-4 ADC is substantially purified (i.e., substantially free from substances that limit its effect or produce undesired side-effects). In certain embodiments, the antibody in anti-Nectin-4 ADC is a fully human monoclonal antibody, such as a fully human monoclonal antibody. The subject administered a therapy can be a mammal such as non-primate (e.g., cows, pigs, horses, cats, dogs, rats etc.) or a primate (e.g., a monkey, such as a cynomolgus monkey, or a human). In a one embodiment, the subject is a human. In another embodiment, the subject is a human with a Nectin-4-mediated disease.

Various delivery systems are known and can be used to administer a prophylactic or therapeutic agent (e.g., an anti-Nectin-4 ADC provided herein), including, but not limited to, encapsulation in liposomes, microparticles, microcapsules, recombinant cells capable of expressing the anti-Nectin-4 ADC, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent (e.g., an anti-Nectin-4 ADC provided herein), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., an anti-Nectin-4 ADC provided herein), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

In a specific embodiment, it may be desirable to administer a prophylactic or therapeutic agent, or a pharmaceutical composition provided herein locally to the area in need of treatment. This may be achieved by, for example, and not by way of limitation, local infusion, by topical administration (e.g., by intranasal spray), by injection, or by means of an implant, said implant being of a porous, non-porous, or gelatinous material, including membranes, such as sialastic membranes, or fibers. In some embodiments, when administering an anti-Nectin-4 ADC provided herein, care must be taken to use materials to which the anti-Nectin-4 ADC does not absorb.

In another embodiment, a prophylactic or therapeutic agent, or a composition provided herein can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In another embodiment, a prophylactic or therapeutic agent, or a composition provided herein can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an anti-Nectin-4 ADC provided herein) or a composition provided herein (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In an embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the nasal passages or lungs, thus requiring only a fraction of the systemic dose (see, e.g., Goodson, in Medical Applications of Controlled Release, supra, vol. 2, pp. 115-138 (1984)). Controlled release systems are discussed in the review by Langer (1990, Science 249:1527-1533). Any technique known to one of skill in the art can be used to produce sustained release formulations comprising one or more antibodies provided herein. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

In a specific embodiment, where the composition provided herein is a nucleic acid encoding a prophylactic or therapeutic agent (e.g., an anti-Nectin-4 ADC provided herein), the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

In a specific embodiment, a composition provided herein comprises one, two or more antibodies provided herein. In another embodiment, a composition provided herein comprises one, two or more antibodies provided herein and a prophylactic or therapeutic agent other than an anti-Nectin-4 ADC provided herein. In one embodiment, the agents are known to be useful for or have been or are currently used for the prevention, management, treatment and/or amelioration of a Nectin-4-mediated disease. In addition to prophylactic or therapeutic agents, the compositions provided herein may also comprise a carrier.

The compositions provided herein include bulk drug compositions useful in the manufacture of pharmaceutical compositions (e.g., compositions that are suitable for administration to a subject or patient) that can be used in the preparation of unit dosage forms. In an embodiment, a composition provided herein is a pharmaceutical composition. Such compositions comprise a prophylactically or therapeutically effective amount of one or more prophylactic or therapeutic agents (e.g., an antibody provided herein or other prophylactic or therapeutic agent), and a pharmaceutically acceptable carrier. The pharmaceutical compositions can be formulated to be suitable for the route of administration to a subject.

In a specific embodiment, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* (1990) Mack Publishing Co., Easton, Pa. Such compositions will contain a prophylactically or therapeutically effective amount of the anti-Nectin-4 ADC, such as in purified form, together with a suitable amount of carrier so as to provide the form for proper administration to the patient. The formulation should suit the mode of administration.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Such compositions, however, may be administered by a route other than intravenous.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

An antibody or an anti-Nectin-4 ADC provided herein can be packaged in a hermetically sealed container such as an ampoule or sachette indicating the quantity of antibody or anti-Nectin-4 ADC. In one embodiment, the antibody or anti-Nectin-4 ADC is supplied as a dry sterilized lyophilized powder or water free concentrate in a hermetically sealed container and can be reconstituted, e.g., with water or saline to the appropriate concentration for administration to a subject. In certain embodiments, the antibody or anti-Nectin-4 ADC is supplied as a dry sterile lyophilized powder in a hermetically sealed container at a unit dosage of at least 0.1 mg, at least 0.5 mg, at least 1 mg, at least 2 mg, or at least 3 mg, such as at least 5 mg, at least 10 mg, at least 15 mg, at least 25 mg, at least 30 mg, at least 35 mg, at least 45 mg, at least 50 mg, at least 60 mg, at least 75 mg, at least 80 mg, at least 85 mg, at least 90 mg, at least 95 mg, or at least 100 mg. The lyophilized anti-Nectin-4 ADC can be stored at between 2 and 8° C. in its original container and the anti-Nectin-4 ADC can be administered within 12 hours, such as within 6 hours, within 5 hours, within 3 hours, or within 1 hour after being reconstituted. In an alternative embodiment, an antibody or an anti-Nectin-4 ADC is supplied in liquid form in a hermetically sealed container indicating the quantity and concentration of the antibody or the anti-Nectin-4 ADC. In certain embodiments, the liquid form of the antibody or anti-Nectin-4 ADC is supplied in a hermetically sealed container at least 0.1 mg/ml, at least 0.5 mg/ml, or at least 1 mg/ml, and such as at least 5 mg/ml, at least 10 mg/ml, at least 15 mg/ml, at least 25 mg/ml, at least 30 mg/ml, at least 40 mg/ml, at least 50 mg/ml, at least 60 mg/ml, at least 70 mg/ml, at least 80 mg/ml, at least 90 mg/ml, or at least 100 mg/ml.

The compositions provided herein can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a prophylactic or therapeutic agent (e.g., an anti-Nectin-4 ADC provided herein), or a composition provided herein that will be effective in the prevention, management, treatment and/or amelioration of a Nectin-4-mediated disease can be determined by standard clinical techniques.

Accordingly, a dosage of an anti-Nectin-4 ADC or a composition that results in a serum titer of from about 0.1 µg/ml to about 450 µg/ml, and in some embodiments at least 0.1 µg/ml, at least 0.2 µg/ml, at least 0.4 µg/ml, at least 0.5 µg/ml, at least 0.6 µg/ml, at least 0.8 µg/ml, at least 1 µg/ml, at least 1.5 µg/ml, such as at least 2 µg/ml, at least 5 µg/ml, at least 10 µg/ml, at least 15 µg/ml, at least 20 µg/ml, at least 25 µg/ml, at least 30 µg/ml, at least 35 µg/ml, at least 40 µg/ml, at least 50 µg/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for the prevention, management, treatment and/or amelioration of a Nectin-4-mediated disease. In addition, in vitro assays may optionally be employed to help identify optimal dosage ranges. The precise dose to be employed in the formulation will also depend on the route of administration, and the seriousness of a Nectin-4-mediated disease, and should be decided according to the judgment of the practitioner and each patient's circumstances.

Effective doses may be extrapolated from dose-response curves derived from in vitro or animal model test systems.

For the antibodies provided herein, the dosage administered to a patient is typically 0.1 mg/kg to 100 mg/kg of the patient's body weight. In some embodiments, the dosage administered to the patient is about 1 mg/kg to about 75 mg/kg of the patient's body weight. In some embodiments, the dosage administered to a patient is between 1 mg/kg and 20 mg/kg of the patient's body weight, such as 1 mg/kg to 5 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies provided herein may be reduced by enhancing uptake and tissue penetration of the antibodies by modifications such as, for example, lipidation.

In one embodiment, approximately 100 mg/kg or less, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less of an anti-Nectin-4 ADC is administered 5 times, 4 times, 3 times, 2 times or 1 time to manage a Nectin-4-mediated disease. In some embodiments, an anti-Nectin-4 ADC provided herein is administered about 1-12 times, wherein the doses may be administered as necessary, e.g., weekly, biweekly, monthly, bimonthly, trimonthly, etc., as determined by a physician. In some embodiments, a lower dose (e.g., 1-15 mg/kg) can be administered more frequently (e.g., 3-6 times). In other embodiments, a higher dose (e.g., 25-100 mg/kg) can be administered less frequently (e.g., 1-3 times). However, as will be apparent to those in the art, other dosing amounts and schedules are easily determinable and within the scope provided herein.

In a specific embodiment, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, approximately 0.1 mg/kg or less of an anti-Nectin-4 ADC in a sustained release formulation is administered to a subject, such as a human, to prevent, manage, treat and/or ameliorate a Nectin-4-mediated disease. In another specific embodiment, an approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less bolus of an anti-Nectin-4 ADC not in a sustained release formulation is administered to a subject, such as a human, to prevent, manage, treat and/or ameliorate a Nectin-4-mediated disease, and after a certain period of time, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 5 mg/kg or less of an anti-Nectin-4 ADC provided herein in a sustained release is administered to said subject (e.g., intranasally or intramuscularly) two, three or four times (such as one time). In accordance with this embodiment, a certain period of time can be 1 to 5 days, a week, two weeks, or a month.

In some embodiments, a single dose of an anti-Nectin-4 ADC provided herein is administered to a patient to prevent, manage, treat and/or ameliorate a Nectin-4-mediated disease two, three, four, five, six, seven, eight, nine, ten, eleven, twelve times, thirteen, fourteen, fifteen, sixteen, seventeen, eighteen, nineteen, twenty, twenty-one, twenty-two, twenty-three, twenty-four, twenty five, or twenty six at bi-weekly (e.g., about 14 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In another embodiment, a single dose of an anti-Nectin-4 ADC provided herein is administered to patient to prevent, manage, treat and/or ameliorate a Nectin-4-mediated disease two, three, four, five, six, seven, eight, nine, ten, eleven, or twelve times at about monthly (e.g., about 30 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In one embodiment, a single dose of an anti-Nectin-4 ADC provided herein is administered to a patient to prevent, manage, treat and/or ameliorate a Nectin-4-mediated disease two, three, four, five, or six times at about bi-monthly (e.g., about 60 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each bi-monthly dose may or may not be identical).

In some embodiments, a single dose of an anti-Nectin-4 ADC provided herein is administered to a patient to prevent, manage, treat and/or ameliorate a Nectin-4-mediated disease two, three, or four times at about tri-monthly (e.g., about 120 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each tri-monthly dose may or may not be identical).

In certain embodiments, the route of administration for a dose of an anti-Nectin-4 ADC provided herein to a patient is intranasal, intramuscular, intravenous, or a combination thereof, but other routes described herein are also acceptable. Each dose may or may not be administered by an identical route of administration. In some embodiments, an anti-Nectin-4 ADC provided herein may be administered via multiple routes of administration simultaneously or subsequently to other doses of the same or a different anti-Nectin-4 ADC provided herein.

In certain embodiments, anti-Nectin-4 ADCs provided herein are administered prophylactically or therapeutically to a subject. Anti-Nectin-4 ADCs provided herein can be prophylactically or therapeutically administered to a subject so as to prevent, lessen or ameliorate a Nectin-4-mediated disease or symptom thereof.

27. GENE THERAPY

In a specific embodiment, nucleic acids comprising sequences encoding antibodies or functional derivatives thereof, are administered to a subject for use in a method provided herein, for example, to prevent, manage, treat and/or ameliorate a Nectin-4-mediated disease, disorder or condition, by way of gene therapy. Such therapy encompasses that performed by the administration to a subject of an expressed or expressible nucleic acid. In an embodiment, the nucleic acids produce their encoded antibody that can be conjugated to provide an anti-Nectin-4 ADC, and the antibody or anti-Nectin-4 ADC mediates a prophylactic or therapeutic effect.

Any of the methods for recombinant gene expression (or gene therapy) available in the art can be used. Exemplary methods are described below and are provided in the Examples section.

For general review of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215. Methods commonly known in the art of recombinant DNA technology which can be used are described in Ausubel et al. (eds.), Current Protocols in Molecular Biology, John Wiley & Sons, N Y (1993); and Kriegler, Gene Transfer and Expression, A Laboratory Manual, Stockton Press, N.Y. (1990).

In a specific embodiment, a composition comprises nucleic acids encoding an anti-Nectin-4 antibody provided herein, the nucleic acids being part of an expression vector that expresses the antibody or chimeric proteins or heavy or light chains or the therapeutic or drug moieties thereof in a suitable host. In particular, such nucleic acids have promoters, such as heterologous promoters, operably linked to the anti-Nectin-4 antibody coding region, the promoter being inducible or constitutive, and, optionally, tissue-specific. In another particular embodiment, nucleic acid molecules are used in which the anti-Nectin-4 antibody coding sequences and any other desired sequences are flanked by regions that promote homologous recombination at a desired site in the genome, thus providing for intrachromosomal expression of the anti-Nectin-4 ADC encoding nucleic acids (Koller and Smithies, 1989, Proc. Natl. Acad. Sci. USA 86:8932-8935; Zijlstra et al., 1989, Nature 342:435-438). In some embodiments, the expressed anti-Nectin-4 antibody molecule comprises a single chain antibody; alternatively, the nucleic acid sequences include sequences encoding both the heavy and light chains, or fragments thereof, in the anti-Nectin-4 antibody.

Delivery of the nucleic acids into a subject can be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where the sequences are expressed to produce the encoded product. This can be accomplished by any of numerous methods known in the art, e.g., by constructing them as part of an appropriate nucleic acid expression vector and administering the vector so that the sequences become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO 92/20316; WO93/14188, WO 93/20221). Alternatively, the nucleic acid can be introduced intracellularly and incorporated within host cell DNA for expression, by homologous recombination (Koller and Smithies, 1989, Proc. Natl. Acad. Sci. USA 86:8932-8935; and Zijlstra et al., 1989, Nature 342: 435-438).

In a specific embodiment, viral vectors that contains nucleic acid sequences encoding an anti-Nectin-4 antibody are used. For example, a retroviral vector can be used (see Miller et al., 1993, Meth. Enzymol. 217:581-599). These retroviral vectors contain the components necessary for the correct packaging of the viral genome and integration into the host cell DNA. The nucleic acid sequences encoding the anti-Nectin-4 antibody to be used in gene therapy can be cloned into one or more vectors, which facilitates delivery of the gene into a subject. More detail about retroviral vectors can be found in Boesen et al., 1994, Biotherapy 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Klein et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in the recombinant production of antibodies. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang et al., 1995, Gene Therapy 2:775-783. In a specific embodiment, adenovirus vectors are used.

Adeno-associated virus (AAV) can also be utilized (Walsh et al., 1993, Proc. Soc. Exp. Biol. Med. 204:289-300; and U.S. Pat. No. 5,436,146). In a specific embodiment, AAV vectors are used to express an anti-Nectin-4 ADC provided herein. In certain embodiments, the AAV comprises a nucleic acid encoding a VH domain. In other embodiments, the AAV comprises a nucleic acid encoding a VL domain. In certain embodiments, the AAV comprises a nucleic acid encoding a VH domain and a VL domain. In some embodiments of the methods provided herein, a subject is administered an AAV comprising a nucleic acid encoding a VH domain and an AAV comprising a nucleic acid encoding a VL domain. In other embodiments, a subject is administered an AAV comprising a nucleic acid encoding a VH domain and a VL domain. In certain embodiments, the VH and VL domains are over-expressed.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Clin. Pharma. Ther. 29:69-92 (1985)) and can be used in accordance with the methods provided herein, provided that the necessary developmental and physiological functions of the recipient cells are not disrupted. The technique should provide for the stable transfer of the nucleic acid to the cell, so that the nucleic acid is expressible by the cell, such as heritable and expressible by its cell progeny.

The resulting recombinant cells can be delivered to a subject by various methods known in the art. Recombinant blood cells (e.g., hematopoietic stem or progenitor cells) can be administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; lymphoid and myeloid cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a specific embodiment, the cell used for gene therapy is autologous to the subject.

In an embodiment in which recombinant cells are used in gene therapy, nucleic acid sequences encoding an anti-Nectin-4 antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the methods provided herein (see e.g., PCT Publication WO 94/08598; Stemple and Anderson, 1992, Cell 7 1:973-985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

28. POLYNUCLEOTIDES ENCODING AN ANTIBODY

Also provided are polynucleotides comprising a nucleotide sequence encoding an antibody provided herein that immunospecifically binds to a Nectin-4 epitope. Also provided herein are polynucleotides that hybridize under high stringency, intermediate or lower stringency hybridization conditions, e.g., as defined supra, to polynucleotides that encode a modified antibody provided herein.

The polynucleotides may be obtained, and the nucleotide sequence of the polynucleotides determined, by any method known in the art. Since the amino acid sequences of certain Nectin-4 antibodies provided herein are known, nucleotide sequences encoding these antibodies and modified versions of these antibodies can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, fragments, or variants thereof, annealing and ligating of those oligonucleotides, and then amplification of the ligated oligonucleotides by PCR.

Alternatively, a polynucleotide encoding an antibody provided herein may be generated from nucleic acid from a suitable source (e.g., M22-321b41.1 hybridoma as provided herein having an ATCC Accession No. PTA-124245, deposited on Jun. 13, 2017). If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library or a cDNA library generated from, or nucleic acid, such as poly A+RNA, isolated from, any tissue or cells expressing the antibody, such as hybridoma cells selected to express an antibody provided herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

In certain embodiments, nucleic acid molecules provided herein comprise or consist of a nucleic acid sequence as depicted in any one of SEQ ID NO:38 (encoding a VH) and/or SEQ ID NO:37 (encoding a VL), or any combination thereof (e.g., as a nucleotide sequence encoding an antibody provided herein, such as a full-length antibody, heavy and/or light chain of an antibody, or a single chain antibody provided herein).

In certain aspects, provided herein are polynucleotides comprising a nucleotide sequence encoding an antibody described herein or a fragment thereof (e.g., a variable light chain region and/or variable heavy chain region) that immunospecifically binds to a Nectin-4 antigen, and vectors, e.g., vectors comprising such polynucleotides for recombinant expression in host cells (e.g., E. coli and mammalian cells). In certain aspects, provided herein are cells (e.g., host cells). Also provided herein are methods of making the antibodies and antigen-binding fragments described herein.

In certain aspects, provided herein are polynucleotides comprising a nucleotide sequence encoding the light chain or heavy chain of an antibody described herein. In certain embodiments, provided herein are polynucleotides comprising a nucleotide sequence encoding the light chain and heavy chain of an antibody described herein. The polynucleotides can comprise nucleotide sequences encoding a light chain comprising the VL FRs and CDRs of antibodies described herein (see, e.g., Tables 1-2, respectively). The polynucleotides can comprise nucleotide sequences encoding a heavy chain comprising the VH FRs and CDRs of antibodies described herein (see, e.g., Tables 1-2, respectively). In specific embodiments, a polynucleotide described herein encodes a VL chain region comprising the amino acid sequence of SEQ ID NO:37. In specific embodiments, a polynucleotide described herein encodes a VH chain region comprising the amino acid sequence of any one of SEQ ID NO:38.

In particular embodiments, provided herein are polynucleotides comprising a nucleotide sequence encoding an anti-Nectin-4 antibody comprising three VL chain CDRs, e.g., containing VL CDR1, VL CDR2, and VL CDR3 of the antibody M22-321b41.1 (e.g., see Table 1). In specific embodiments, provided herein are polynucleotides comprising three VH chain CDRs, e.g., containing VH CDR1, VH CDR2, and VH CDR3 of the antibody M22-321b41.1 (e.g., see Table 1).

In particular embodiments, provided herein are polynucleotides comprising a nucleotide sequence encoding an anti-Nectin-4 antibody comprising a VL chain region, e.g., containing FR1-CDR1-FR2-CDR2-FR3-CDR3-FR4, comprising an amino acid sequences described herein (e.g., see Tables 1-2). In specific embodiments, provided herein are polynucleotides comprising a nucleotide sequence encoding an anti-Nectin-4 antibody comprising a VH chain region, e.g., containing FR1-CDR1-FR2-CDR2-FR3-CDR3-FR4, comprising an amino acid sequence described herein (e.g., see Tables 1-2).

In certain embodiments, a polynucleotide described herein comprises a nucleotide sequence encoding an antibody provided herein comprising a variable light (VL) chain region comprising an amino acid described herein (e.g., see Table 1), wherein the antibody immunospecifically binds to a Nectin-4 polypeptide.

In certain embodiments, a polynucleotide described herein comprises a nucleotide sequence encoding an antibody provided herein comprising a variable heavy (VH) chain region comprising an amino acid sequence described herein (e.g., see Table 1), wherein the antibody immunospecifically binds to a Nectin-4 polypeptide.

In certain aspects, a polynucleotide comprises a nucleotide sequence encoding an antibody described herein comprising a VL chain region comprising one or more VL FRs having the amino acid sequence described herein (e.g., see Table 2), wherein the antibody immunospecifically binds to a Nectin-4 polypeptide. In certain aspects, a polynucleotide comprises a nucleotide sequence encoding an antibody described herein comprising a VH chain region comprising one or more VH FRs having the amino acid sequence described herein (e.g., see Table 2), wherein the antibody immunospecifically binds to a Nectin-4 polypeptide, e.g., a human Nectin-4 polypeptide.

In specific embodiments, a polynucleotide provided herein comprises a nucleotide sequence encoding an antibody described herein comprising: framework regions (e.g., framework regions of the VL domain and VH domain) that are human framework regions, wherein the antibody immunospecifically binds a Nectin-4 polypeptide.

In a certain embodiment, a polynucleotide provided herein comprises a nucleotide sequence as described in Table 3, encoding a VH or a VL, respectively, of the antibody M22-321b41.1 described herein, which immunospecifically binds to a Nectin-4 polypeptide. Recombinant Production of an Antibody Recombinant expression of an antibody provided herein (e.g., a full-length antibody, heavy and/or light chain of an antibody, or a single chain antibody provided herein) that immunospecifically binds to a Nectin-4 antigen requires construction of an expression vector containing a polynucleotide that encodes the antibody. Once a polynucleotide encoding an antibody molecule, heavy or light chain of an antibody, or fragment thereof (such as, but not necessarily, containing the heavy and/or light chain variable domain) provided herein has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule provided herein, a heavy or light chain of an antibody, a heavy or light chain variable domain of an antibody or a fragment thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody provided herein. Thus, also provided herein are host cells containing a polynucleotide encoding an antibody provided herein or fragments thereof, or a heavy or light chain thereof, or fragment thereof, or a single chain antibody provided herein, operably linked to a heterologous promoter. In certain embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules provided herein (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule provided herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV, tobacco mosaic virus, TMV) or transformed with recombinant plasmid expression vectors (e.g., Ti plasmid) containing antibody coding sequences; or mammalian cell systems (e.g., COS, CHO, BHK, 293, NSO, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or, eukaryotic cells, especially for the expression of whole recombinant antibody molecule, can be used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In some embodiments, antibodies provided herein are produced in CHO cells. In a specific embodiment, the expression of nucleotide sequences encoding antibodies provided herein which immunospecifically bind to a Nectin-4 antigen is regulated by a constitutive promoter, inducible promoter or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the E. coli expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells. In some embodiments, fully human, monoclonal anti-Nectin-4 antibodies provided herein are produced in mammalian cells, such as CHO cells.

For long-term, high-yield production of recombinant proteins, stable expression can be utilized. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors provided herein, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains may comprise cDNA or genomic DNA.

Once an antibody molecule provided herein has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies provided herein can be fused to heterologous polypeptide sequences described herein or otherwise known in the art to facilitate purification.

29. DIAGNOSTIC ASSAYS AND METHODS OF DETECTION

In one aspect, anti-Nectin-4 antibodies and fragments thereof the present disclosure are useful for detecting the presence of Nectin-4 in a biological sample. Such anti-Nectin-4 antibodies may include those that bind to human Nectin-4 but do not induce Nectin-4 signaling activity. The term "detecting" or "detection," as used herein, encompasses quantitative or qualitative detection, and refers to using readouts or results of an assay to make a determination with regard to the presence/absence of Nectin-4 in the sample, the relative expression level Nectin-4 in the sample (e.g. relative to one or more reference expressions, relative to other samples, or relative to one or more expression scales), or the concentration of Nectin-4 in the sample. The detected readout from the assay can be numerical data, e.g. results of qPCR, results of immunoassays, or a measured protein concentration; the detected readout can be non-numerical data, e.g. cells or tissues staining with anti-Nectin-4 antibodies in microscopy images or staining of Nectin-4 in an imaging flow cytometry; or the detected readout can be any experimental data that can be used as a proxy for the Nectin-4 expression as is well known to a person skilled in the art, e.g. fluorescent intensity, luminescence intensity, colorimetric readings, and absorption/emission spectroscopy. The detected readout in the assays is referred to herein as the signal of the assay.

As provided herein, a biological sample are samples or materials that have a biological origin. Biological samples include bodily fluid, a cell or a tissue sample. In some embodiments, the cell can be a cultured cell line, engineered cells, in vitro or ex vivo culture of cells obtained from a subject, e.g. a human subject, or cells obtained from a subject. In other embodiments, the tissue samples can include bodily fluid or a tissue obtained from a subject, including a human subject. In some embodiments, the tissue samples include samples from a region of a subject suspected of having a disease. Thus tissue samples can be, but are not limited to, tissues, bodily fluid, tissue fractions, and/or cells isolated from an organism such as a mammal, in particular a human. In a particular embodiment, the tissue samples are prepared into sections that have been formalin fixed, paraffin embedded (FFPE). The cells, bodily fluid, and/or the tissue can be obtained from a subject, e.g. a human subject, by methods well know to a person skilled in the art, e.g. biopsy (including liquid biopsy), surgical procedures, cell smear, and phlebotomy.

In one aspect, the present disclosure provides a method of detecting the presence of Nectin-4 in a biological sample. In certain embodiments, the method comprises contacting the biological sample with an anti-Nectin-4 antibody under conditions permissive for binding of the anti-Nectin-4 antibody to Nectin-4, and detecting the binding between an anti-Nectin-4 antibody and Nectin-4.

As is well known to a person skilled in the art, the amount of an antibody bound to an antigen in a biological sample correlates with the amount of the antigen in the biological sample. Therefore the amount of binding of an anti-Nectin-4 antibody as provided herein to Nectin-4 in a biological sample can be used to measure the amount or the expression level of Nectin-4 in the biological sample. In some embodiments, the amount of Nectin-4 in the biological sample is detected in the linear detection range of the anti-Nectin-4 antibody. The "linear detection range" refers to the range of the amount or concentration of an antigen, within which the bound antibody linearly correlates with the amount or concentration of the antigen in the biological sample. Such linear range depends on factors such as the affinity between the antibody and the antigen, the concentration of the antibody used for the antibody-antigen binding, and the condition used for the antibody-antigen binding.

The concentration of the antibody used for antibody-antigen binding can be assessed in a titration experiments. In one embodiment of such titration experiments, the concentration of an antibody is serially diluted by a factor of twofold, threefold, fivefold, or tenfold, and the serially diluted antibodies were each bound to control samples with known amount of the corresponding antigen. In one embodiment, the desirable antibody concentration is that at which the amount of antibody binding differentiates the broadest linear detection range.

The expression of Nectin-4 in a biological sample refers to the amount of Nectin-4 in the biological sample at a given time. The expression of Nectin-4 as measured reflects accumulation of Nectin-4 in the biological sample over a period of time and can include degradation or modification products such as full length Nectin-4, fragments of Nectin-4, and naturally modified, e.g. glycosylated, Nectin-4. As proteins are translated from mRNAs, the levels of mRNA in the biological samples can be used as a proxy for the expression of Nectin-4 in the biological samples.

Provided herein are methods for assessing Nectin-4 expression in a tissue sample from a subject suspected of having cancer, including: (a) contacting said tissue sample with an antibody or antigen binding fragment thereof as provided herein; (b) detecting the binding of said antibody or antigen binding fragment thereof to said tissue sample; (c) determining the expression of Nectin-4 in the tissue sample, wherein the expression level of Nectin-4 in the tissue sample is compared with a reference expression level of Nectin-4.

Also provided herein are methods for assessing Nectin-4 expression in a tissue sample from a subject suspected of having cancer, including: (a) performing an IHC assay on the tissue sample with an antibody or antigen binding fragment thereof as provided herein; (b) determining the expression of Nectin-4 in the tissue sample, wherein the expression level of Nectin-4 in the tissue sample is compared with a reference expression level of Nectin-4.

Provided herein are also methods of assessing responsiveness of a cancer patient to an anti-cancer therapeutic agent, said method based on Nectin-4 expression in a tissue sample from said patient, including: (a) contacting said tissue sample with an antibody or antigen binding fragment thereof as provided herein; (b) detecting the binding of said antibody or antigen binding fragment thereof to said tissue sample; (c) determining the expression of Nectin-4 in the tissue sample, wherein the expression level of Nectin-4 in the tissue sample is compared with a reference expression level of Nectin-4; wherein an increased expression level of Nectin-4 compared to the reference is indicative of responsiveness to said anti-cancer therapy.

Provided herein are also methods for assessing responsiveness of a cancer patient to an anti-cancer therapeutic agent, said method based on Nectin-4 expression in a tissue sample from said patient, including: (a) performing an IHC assay on the tissue sample with an antibody or antigen binding fragment thereof as provided herein; (b) determining the expression of Nectin-4 in the tissue sample, wherein the expression level of Nectin-4 in the tissue sample is compared with a reference expression level of Nectin-4, wherein an increased expression level of Nectin-4 in the tissue sample compared to the reference is indicative of responsiveness to said anti-cancer therapy.

Provided herein are methods of treating cancer in a subject including (a) determining expression level of Nectin-4 in a tissue sample from the subject with an antibody or antigen binding fragment thereof as provided herein, wherein the expression level of Nectin-4 in the tissue sample is higher than a reference expression level of Nectin-4; (b) administering an anti-cancer therapeutic agent to the subject.

Provided herein are methods of treating cancer in a subject including (a) contacting a tissue sample from the subject with an antibody or antigen binding fragment thereof as provided herein; (b) determining expression level of Nectin-4 in the tissue sample from the subject with antibody or antigen binding fragment thereof as provided herein, wherein the expression level of Nectin-4 in the tissue sample is higher than a reference expression level of Nectin-4; (c) administering an anti-cancer therapeutic agent to the subject.

Provided herein are methods of treating cancer in a subject including (a) obtaining a tissue sample from the subject; (b) contacting the tissue sample from the subject with an antibody or antigen binding fragment thereof as provided herein; (c) determining expression level of Nectin-4 in a tissue sample from the subject with an antibody or antigen binding fragment thereof as provided herein, wherein the expression level of Nectin-4 in the tissue sample is higher than a reference expression level of Nectin-4; (d) administering an anti-cancer therapeutic agent to the subject.

The subject in any of the method provided herein can be a human subject and the subject can have any cancer for which the determination of Nectin-4 expression can be performed and/or for which Nectin-4 expression can provide diagnostic, prognostic, or predictive value. Exemplary cancers include acute lymphoblastic leukemia; acute lymphoblastic lymphoma; acute lymphocytic leukemia; acute myelogenous leukemia; acute myeloid leukemia (adult/childhood); adrenocortical carcinoma; AIDS-related cancers; AIDS-related lymphoma; anal cancer; appendix cancer; astrocytomas; atypical teratoid/rhabdoid tumor; basal-cell carcinoma; bile duct cancer, extrahepatic (cholangiocarcinoma); bladder cancer; bone osteosarcoma/malignant fibrous histiocytoma; brain cancer (adult/childhood); brain tumor, cerebellar astrocytoma (adult/childhood); brain tumor, cerebral astrocytoma/malignant glioma brain tumor; brain tumor, ependymoma; brain tumor, medulloblastoma; brain tumor, supratentorial primitive neuroectodermal tumors; brain tumor, visual pathway and hypothalamic glioma; brainstem glioma; breast cancer; bronchial adenomas/carcinoids; bronchial tumor; Burkitt lymphoma; cancer of childhood; carcinoid gastrointestinal tumor; carcinoid tumor; carcinoma of adult, unknown primary site; carcinoma of unknown primary; central nervous system embryonal tumor; central nervous system lymphoma, primary; cervical cancer; childhood adrenocortical carcinoma; childhood cancers; childhood cerebral astrocytoma; chordoma, childhood; chronic lymphocytic leukemia; chronic myelogenous leukemia; chronic myeloid leukemia; chronic myeloproliferative disorders; colon cancer; colorectal cancer; craniopharyngioma; cutaneous T-cell lymphoma; desmoplastic small round cell tumor; emphysema; endometrial cancer; ependymoblastoma; ependymoma; esophageal cancer; ewing's sarcoma in the Ewing family of tumors; extracranial germ cell tumor; extragonadal germ cell tumor; extrahepatic bile duct cancer; gallbladder cancer; gastric (stomach) cancer; gastric carcinoid; gastrointestinal carcinoid tumor; gastrointestinal stromal tumor; germ cell tumor: extracranial, extragonadal, or ovarian gestational trophoblastic tumor; gestational trophoblastic tumor, unknown primary site; glioma; glioma of the brain stem; glioma, childhood visual pathway and hypothalamic; hairy cell leukemia; head and neck cancer; heart cancer; hepatocellular (liver) cancer; hodgkin lymphoma; hypopharyngeal cancer; hypothalamic and visual pathway glioma; intraocular melanoma; islet cell carcinoma (endocrine pancreas); Kaposi Sarcoma; kidney cancer (renal cell cancer); langerhans cell histiocytosis; laryngeal cancer; lip and oral cavity cancer; liposarcoma; liver cancer (primary); lung cancer; lymphoma, primary central nervous system; macroglobulinemia, Waldenstrom; male breast cancer; malignant fibrous histiocytoma of bone/osteosarcoma; medulloblastoma; medulloepithelioma; melanoma; melanoma, intraocular (eye); merkel cell cancer; merkel cell skin carcinoma; mesothelioma; mesothelioma, adult malignant; metastatic squamous neck cancer with occult primary; mouth cancer; multiple endocrine neoplasia syndrome; multiple myeloma/plasma cell neoplasm; mycosis fungoides, myelodysplastic syndromes; myelodysplastic/myeloproliferative diseases; myelogenous leukemia, chronic; myeloid leukemia, adult acute; myeloid leukemia, childhood acute; myeloma, multiple (cancer of the bone-marrow); myeloproliferative disorders, chronic; nasal cavity and paranasal sinus cancer; nasopharyngeal carcinoma; neuroblastoma, non-small cell lung cancer; non-hodgkin lymophoma; oligodendroglioma; oral cancer; oral cavity cancer; oropharyngeal cancer; osteosarcoma/malignant fibrous histiocytoma of bone; ovarian cancer; ovarian epithelial cancer (surface epithelial-stromal tumor); ovarian germ cell tumor; ovarian low malignant potential tumor; pancreatic cancer; pancreatic cancer, islet cell; papillomatosis; paranasal sinus and nasal cavity cancer; parathyroid cancer; penile cancer; pharyngeal cancer; pheochromocytoma; pineal astrocytoma; pineal germinoma; pineal parenchymal tumors of intermediate differentiation; pineoblastoma and supratentorial primitive neuroectodermal tumors; pituary tumor; pituitary adenoma; plasma cell neoplasia/multiple myeloma; pleuropulmonary blastoma; primary central nervous system lymphoma; prostate cancer; rectal cancer; renal cell carcinoma (kidney cancer); renal pelvis and ureter, transitional cell cancer; respiratory tract carcinoma involving the NUT gene on chromosome 15;

retinoblastoma; rhabdomyosarcoma, childhood; salivary gland cancer; sarcoma, Ewing family of tumors; Sézary syndrome; skin cancer (melanoma); skin cancer (non-melanoma); small cell lung cancer; small intestine cancer soft tissue sarcoma; soft tissue sarcoma; spinal cord tumor; squamous cell carcinoma; squamous neck cancer with occult primary, metastatic; stomach (gastric) cancer; supratentorial primitive neuroectodermal tumor; T-cell lymphoma, cutaneous (Mycosis Fungoides and Sézary syndrome); testicular cancer; throat cancer; thymoma; thymoma and thymic carcinoma; thyroid cancer; thyroid cancer, childhood; transitional cell cancer of the renal pelvis and ureter; urethral cancer; uterine cancer, endometrial; urothelial cancer, bladder cancer, cancer of an ureter, cancer of an urethra, and cancer of an urachus, uterine sarcoma; vaginal cancer; vulvar cancer; Wilms Tumor; and other cancers of epithelial origin in which nectin-4 is expressed.

In some embodiments of the methods provided herein, a subject, e.g. a human subject is suspected of having cancer selected from a group consisting of endometrial cancer, urothelial cancer, bladder cancer, cancer of an ureter, cancer of an urethra, lung cancer, ovarian cancer, breast cancer, esophageal cancer, pancreatic cancer, head and neck cancer, prostate cancer, penile cancer, anal cancer, vulvar cancers, cancer of an urachus, and other cancers of epithelial origin in which nectin-4 is expressed.

As used herein, the term "responsiveness" refers to the probability of a cell or an individual or a patient or a subject responding or having a reaction to the treatment of an anti-cancer therapeutic agent. The responsiveness can include the probability of a wide range of reactions to the anti-cancer therapeutic agent, for example and without any limitation, decreased proliferation or growth of cancerous cells, increased cell death of cancerous cells, reduction in the number of cancerous cells or the size of the tumor, reduced rate of increase of the size of the tumor, retarded progression of the stages of the cancer, regression of the stages of cancer or the size of the tumor, reduction in the expression of cancer markers, reduced metastasis of cancer, and/or improved patient outcome such as the recovery of the patient's body-mass, the 6 month, 1-year, 2-year, 3-year, or 5-year patient survival rate, and/or the survival duration of the patients. In certain embodiments, the responsiveness can be scaled as insensitive (i.e., less likely to respond), sensitive (likely to respond) and/or uncertain. In certain embodiments, the cell or tissue or individual or patient or subject is more likely to respond to an anti-cancer therapeutic agent when the cell, tissue, patient, or subject shows a significant expression Nectin-4 in its tumor or cancerous cell. In certain embodiments, the responsiveness increases with the increased level of Nectin-4 in the tumor or cancerous cells/tissues. In certain embodiments, the responsiveness correlates with the level of Nectin-4 expression in the tumor or cancerous cells/tissues. In certain embodiments, the responsiveness is linearly proportional to the level of Nectin-4 expression in the tumor or cancerous cells/tissues. In other embodiments, the responsiveness of a cell, tissue, patient, or subject to an anti-cancer therapeutic agent can be 10%, 20%, 30%, 40%, 50%, 60%, 70%, 80%, 90%, 100%, 120%, 150%, 200%, 250%, 300%, 400%, 500%, 750%, 10 times, 15 times, 20 times, 30 times, 40 times, 50 times, 60 times, 70 times, 80 times, 90 times, 100 times, or more than the cells negative for Nectin-4 expression.

As used herein, "indicative of responsiveness" refers to a prediction that the responsiveness will be higher in one cell, tissue, human individual, or subject, over another cell, tissue, human individual, or subject. Such predictions are made based on certain criteria. In some embodiments, the prediction of the responsiveness is made based on the expression level of Nectin-4 in the cell, tissue, tumor, human individual, or subject. As described above, in certain embodiments, the cell or tissue or individual or patient or subject is predicted to be more likely to respond to an anti-cancer therapeutic agent when the cell, tissue, patient, or subject shows a significant expression Nectin-4 in its tumor or cancerous cell. In certain embodiments, the responsiveness is predicted to increase with the increased level of Nectin-4 in the tumor or cancerous cells/tissues. In certain embodiments, the responsiveness is predicted to correlate with the level of Nectin-4 expression in the tumor or cancerous cells/tissues. In certain embodiments, the responsiveness is predicted to be linearly proportional to the level of Nectin-4 expression in the tumor or cancerous cells/tissues. In other embodiments, the responsiveness of a cell, tissue, patient, or subject to an anti-cancer therapeutic agent is predicted to be 10%, 20%, 30%, 40%, 50%, 60%, 70%, 80%, 90%, 100%, 120%, 150%, 200%, 250%, 300%, 400%, 500%, 750%, 10 times, 15 times, 20 times, 30 times, 40 times, 50 times, 60 times, 70 times, 80 times, 90 times, 100 times, or more than the cells negative for Nectin-4 expression.

The anti-cancer therapeutic agent can be any anti-cancer therapeutic agent or any anti-cancer therapy for which Nectin-4 expression can provide diagnostic, prognostic, or predictive value. In certain embodiments, the therapeutic agent is one that targets biological processes, e.g. a signaling pathway, a metabolic pathway, or a protein synthesis/degradation pathway, in which Nectin-4 plays a role. In certain embodiments, the therapeutic agent is one that targets Nectin-4 activity, Nectin-4 signaling, or Nectin-4 mediated diseases. In a specific embodiments, the therapeutic agent is an anti-Nectin-4 antibody or an anti-Nectin-4 antibody drug conjugate.

For determining the expression of Nectin-4 in the tissue sample, the expression level of Nectin-4 in the tissue sample is compared or correlated with a reference expression level of Nectin-4. The "reference expression level" as used herein refers to an expression level in a reference sample that, when compared with the Nectin-4 expression level in the test sample, provides relative information about Nectin-4 expression in the test sample. The reference expression level can be a known expression level, e.g. expression in a reference sample where the amount, concentration, and/or mole quantity of Nectin-4 is known. For example, the reference expression level can be the Nectin-4 expression in a cell line where the cells have been transfected or otherwise engineered to express a known amount of Nectin-4. In some embodiments, reference expression level can be the Nectin-4 expression in a cell where the Nectin-4 expression has been quantitated by methods provided herein or known to a person skilled in the art, such as ELISA, SDS-PAGE, quantitative immunoprecipitation, and/or quantitative western blotting. In other embodiments, reference expression level involves more than one references, such as 2, 3, 4, 5, 6, 7, 8, 9, 10, 12, 14, 16, 18, 20, 25, 30, 35, 40, 45, 50, 75, 100, and more references. In one embodiment, the reference level has 4 references: one negative for Nectin-4 expression, one with weak Nectin-4 expression, one with moderate Nectin-4 expression, and one with high/strong Nectin-4 expression.

Alternatively, a reference expression level can be a level where the exact concentration or quantity of Nectin-4 is unknown but the status, activity, and/or function of the reference sample is known. In some embodiments, the reference expression levels can be those of a non-cancerous cell from the same patient that is suspected of having cancer. In such embodiments, by comparing Nectin-4 expression in the test sample with that in the reference sample, the Nectin-4 expression in the test sample relative to (e.g. higher than, lower than, or substantially the same as) the Nectin-4 expression of the non-cancerous cells can be determined. In other embodiments, the reference expression levels can be those of a cancerous cell, wherein by comparing Nectin-4 expression in the test sample with that in the reference sample, the Nectin-4 expression in the test sample relative to (e.g. higher than, lower than, or substantially the same as) the Nectin-4 expression of the cancerous cells can be determined. In other embodiments, the reference expression levels can be those of a cell from a second subject, wherein by comparing Nectin-4 expression in the test sample with that in the reference sample, the Nectin-4 expression in the test sample relative to (e.g. higher than, lower than, or substantially the same as) the Nectin-4 expression of the cells from a second subject can be determined. The second subject can be a normal human subject having no cancer, a human subject having the same kind of cancer as that the patient is suspected of having, or a human subject having a different kind of cancer from what the patient is suspected of having.

The reference sample and reference cells as described herein can be a cell line, in vitro or ex vivo culture of cells obtained from patient suspected of having cancer, cells obtained from patient suspected of having cancer, in vitro or ex vivo culture of cells obtained from a second subject, cells obtained from a second subject.

Therefore, in some embodiments of the methods provided herein, the reference expression level of Nectin-4 can be the Nectin-4 expression level in cancerous cells, non-cancerous cells of said subject, or non-cancerous cells from a second subject.

As described above, in some embodiments, the Nectin-4 expression in a sample can be determined by correlating or comparing the anti-Nectin-4 antibody binding to the sample with the anti-Nectin-4 antibody binding to the negative and positive references, wherein the levels of Nectin-4 expression in the references are known. The reference Nectin-4 expression can be a positive Nectin-4 control or a negative Nectin-4 control. As used herein, a "positive Nectin-4 control" or a "positive control" refers to a cell, a tissue, a tumor, a human, and/or a subject known to express significant amount of Nectin-4. A "negative Nectin-4 control" or "negative control" refers to cells and/or tissues known to express no Nectin-4 or low level of Nectin-4 such that the Nectin-4 in the cells or tissues are not biologically significant. Nectin-4 level is biologically insignificant when (1) a person skilled in the art would consider the level of Nectin-4 expression low in light of a protein product of a house keeping gene; (2) the presence or absence of the low amount of Nectin-4 does not make a biological difference to the cell or tissue; and (3) if these insignificant amount of Nectin-4 is removed or deleted from the cells or tissues, the cells or tissues will continue to function substantially the same way as before such removal or deletion. The known Nectin-4 expression can be determined independently by a qPCR assay. The known Nectin-4 expression can also be independently determined using any below described immunoassays with an anti-Nectin-4 antibody that have been determined to be Nectin-4 specific, (e.g. a Nectin-4 specific antibody identified in the specificity-screening methods described above). Suitable immunoassays include, by way of example and without any limitation, an IHC assay, an immunoblotting assay, a FACS assay, or an ELISA. In some embodiments, the Nectin-4 mRNA level may not be zero in the negative control due to the background noise of the assays or due to the biologically insignificant low level of remaining Nectin-4. Negative Nectin-4 control can be properly considered negative for Nectin-4, for example, when the Nectin-4 mRNA level in a qPCR assay is substantially similar to the level of mRNA detected with a set of non-specific primers, or when the Nectin-4 mRNA level is biologically insignificant in light of the Nectin-4 mRNA level in a positive Nectin-4 control. Similarly, the Nectin-4 detected by immunoassays using another Nectin-4 specific antibody in a negative control may not be zero due to background noise of the assays or due to the biologically insignificant low level of remaining Nectin-4. The background noise can be caused by non-specific interactions between the assay reagents other than the anti-Nectin-4 antibodies and the samples. The negative Nectin-4 control can be properly considered negative for Nectin-4, for example, when the Nectin-4 level in the negative control detected by the anti-Nectin-4 antibody is substantially similar to the detection level from an isotype control antibody in the same assay. In some assays, the background noise can account for a substantial percentage of the detected signal from the Nectin-4 expression.

Additionally, positive and negative controls have be identified and published in the literature by persons skilled in the art, including positive and/or negative tissues, cells (including, e.g. cell lines), and pathological samples. Such literature can be readily identified by searching databases such as Pubmed (e.g. using search terms such as Nectin-4, expression, positive, negative, and/or distribution) and analyzing the search hits.

Accordingly, the relative amount of the antibody or antigen-binding fragment thereof bound to a negative control cell with no Nectin-4 expression can be about 50%, 40%, 30%, 20%, 10%, 5%, 4%, 3%, 2%, 1%, 0.5%, 0.3%, 0.2%, 0.1%, 0.05%, 0.03%, 0.01%, 0.001% or less of the amount of the antibody or antigen-binding fragment thereof bound to the sample cell expressing Nectin-4.

Therefore, in some embodiments of the methods provided herein, the reference expression level of Nectin-4 is the Nectin-4 expression level in a negative control, wherein the Nectin-4 expression in the negative control is independently determined by a qPCR assay, an IHC assay with a second antibody, an immunoblotting assay with a second antibody, a FACS assay with a second antibody, or an ELISA with a second antibody.

In other embodiments of the methods provided herein, the reference expression level of Nectin-4 is the Nectin-4 expression level in a positive control cell expressing Nectin-4, wherein the Nectin-4 expression in the positive control is independently determined by a qPCR assay, an IHC assay with a second antibody, an immunoblotting assay with a second antibody, a FACS assay with a second antibody, or an ELISA with a second antibody.

The expression level of Nectin-4 in a sample can be different from that in a positive control. The relative amount of the antibody or antigen-binding fragment thereof bound to the tissue sample can be about 5%, 10%, 20%, 30%, 40%, 50%, 60%, 70%, 80%, 90%, 100%, 120%, 150%, 200%, 250%, 300%, 400%, 500%, 750%, 10 times, 15 times, 20 times, 30 times, 40 times, 50 times, 60 times, 70 times, 80 times, 90 times, 100 times, 200 times, 500 times, or more of the amount of the antibody or antigen-binding fragment thereof bound to the positive control cell expressing Nectin-4.

Numerous different PCR or qPCR protocols are known in the art and exemplified herein below and can be directly applied or adapted for determining the Nectin-4 mRNA level in the samples or controls, which can be used as a proxy for the expression levels of Nectin-4 protein in the samples or controls. Quantitative PCR (qPCR) (also referred as real-time PCR) is applied and adapted in some embodiments as it provides not only a quantitative measurement, but also reduced time and contamination. As used herein, "quantitative PCR (or "qPCR") refers to the direct monitoring of the progress of PCR amplification as it is occurring without the need for repeated sampling of the reaction products. In quantitative PCR, the reaction products can be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time. When qPCR is applied to determine mRNA expression level, an extra step of reverse-transcription of mRNA to DNA is performed before the qPCR analysis. Examples of PCR methods can be found in the literature (Wong et al., BioTechniques 39:75-85 (2005); D'haene et al., Methods 50:262-270 (2010)), which is incorporated by reference herein in its entirety. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In one specific embodiment, qPCR can be performed to determine or measure the Nectin-4 mRNA levels as follows. Briefly, mean Ct (cycle threshold) values (or referred to herein interchangeably as Cq (quantification cycle)) of replicate qPCR reactions for Nectin-4 and one or more housekeeping genes are determined. Mean Ct values for Nectin-4 can be then normalized to the Ct values of the housekeeping genes using the following exemplary formula: Nectin-4-$\Delta$Ct=(mean Ct of Nectin-4—mean Ct of housekeeping gene A). The relative Nectin-4-$\Delta$Ct can then be used to determine relative level of Nectin-4 mRNA, for example by using the formula of mRNA expression=$2^{-\Delta Ct}$. For a summary of Ct and Cq values, see MIQE guideline (Bustin et al., The MIQE Guidelines: Minimum Information for Publication of Quantitative Real-Time PCR Experiments, Clinical Chemistry 55:4 (2009)).

Other commonly used methods known in the art for the quantification of mRNA expression in a sample can also be used, including northern blotting and in situ hybridization (Parker & Barnes, Methods in Molecular Biology 106:247-283 (1999)); RNAse protection assays (Hod, Biotechniques 13:852-854 (1992)); microarrays (Hoheisel et al., Nature Reviews Genetics 7:200-210 (2006); Jaluria et al., Microbial Cell Factories 6:4 (2007)); and polymerase chain reaction (PCR) (Weis et al, Trends in Genetics 8:263-264 (1992)). Alternatively, levels of mRNA expression can be determined by sequencing techniques. Representative methods for sequencing-based gene expression analysis include Serial Analysis of Gene Expression (SAGE), and gene expression analysis by massively parallel signature sequencing (MPSS).

As described earlier, tissue samples can be, but are not limited to, tissues, bodily fluid, tissue fractions, and/or cells isolated from an organism such as a mammal, in particular a human. Therefore, tissue samples can be obtained from a variety of organs of a subject, including a human subject. In some embodiments, tissue samples are obtained from organs suspected of having a disease, dysfunction or disorder, such as a cancer. In other embodiments, tissue samples are obtained from normal organs from the patient who is being tested or from a second human subject.

In certain embodiments of the methods provided herein, the tissue includes a tissue from bladder, ureter, breast, lung, colon, rectum, ovary, Fallopian tube, esophagus, cervix, uterine endometrium, skin, larynx, bone marrow, salivary gland, kidney, prostate, brain, spinal cord, placenta, adrenal, pancreas, parathyroid, hypophysis, testis, thyroid, spleen, tonsil, thymus, heart, stomach, small intestine, liver, skeletal muscle, peripheral nerve, mesothelium, or eye.

Anti-Nectin-4 antibodies bound to the samples can be detected by a variety of immunoassays known in the art, including an IHC approach, an immunoblotting assay, a FACS assay, and an ELISA.

Nectin-4 can be detected by an anti-Nectin-4 antibody in a variety of IHC approaches. IHC staining of tissue sections has been shown to be a reliable method of assessing or detecting the presence of proteins in a sample. IHC techniques utilize an antibody to probe and visualize cellular antigens in situ, generally by chromogenic or fluorescent methods. Primary antibodies or antisera, such as polyclonal antisera and monoclonal antibodies that specifically target Nectin-4, can be used to detect expression in an IHC assay. In some embodiments, the tissue sample is contacted with a primary antibody for a specific target for a period of time sufficient for the antibody-target binding to occur. As discussed in detail earlier, the antibodies can be detected by direct labels on the antibodies themselves, for example, radioactive labels, fluorescent labels, hapten labels such as biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. IHC protocols and kits are well known in the art and are commercially available. Automated systems for slide preparation and IHC processing are available commercially. The Leica BOND Autostainer and Leica Bond Refine Detection system is an example of such an automated system.

In some embodiments, an IHC assay is performed with an unlabeled primary antibody in conjunction with a labeled secondary antibody in an indirect assay. The indirect assay utilizes two antibodies for the detection of target proteins such as Nectin-4 in a tissue sample. First, an unconjugated primary antibody was applied to the tissue (first layer), which reacts with the target antigen in the tissue sample. Next, an enzyme-labeled secondary antibody is applied, which specifically recognize the antibody isotype of the primary antibody (second layer). The secondary antibody reacts with the primary antibody, followed by substrate-chromogen application. The second-layer antibody can be labeled with an enzyme such as a peroxidase, which reacts with the chromogen 3, 3'-diaminobenzidine (DAB) to produce brown precipitate at the reaction site. This method is sensitive and versatile due to the potential signal amplification through a signal amplification system.

In certain embodiments to increase the sensitivity of the detection, a signal amplification system can be used. "A signal amplification system", as used herein, means a system of reagents and methods that can be used to increase the signal from detecting the bound primary or the secondary antibody. A signal amplification system increases the sensitivity of the target protein detection, increases the detected signal, and decreases the lower boundary of the detection limits. There are several types of signal amplification systems including a enzyme labeling system and macrolabeling system. These systems/approaches are not mutually exclusive and can be used in combination for additive effect.

Macrolabels or macrolabeling system are collections of labels numbering in the tens (e.g. phycobiliproteins) to millions (e.g. fluorescent microspheres) attached to or incorporated in a common scaffold. The scaffold can be coupled to a target-specific affinity reagent such as an antibody, and the incorporated labels are thereby collectively associated with the target upon binding. The labels in the macrolabels can be any of the labels described herein such as fluorophores, haptens, enzymes, and/or radioisotopes. In one embodiment of the signal amplification system, a labeled chain polymer-conjugated secondary antibody was used. The polymer technology utilized an HRP enzyme-labeled inert "spine" molecule of dextran to which 1, 2, 3, 4, 5, 6, 7, 8, 9 10, 15, 20, 25, 30, 50 or more molecules of secondary antibodies can be attached, making the system even more sensitive.

Signal amplification system based on an enzyme labeling system utilizes the catalytic activity of enzymes, such as horseradish peroxidase (HRP) or alkaline phosphatase to generate high-density labeling of a target protein or nucleic acid sequence in situ. In one embodiment, tyramide can be used to increase the signal of HRP. In such a system, HRP enzymatically converts the labeled tyramide derivative into highly reactive, short-lived tyramide radicals. The labeled active tyramide radicals then covalently couple to residues (principally the phenol moiety of protein tyrosine residues) in the vicinity of the HRP-antibody—target interaction site, resulting amplification of the number of labels at the site with minimal diffusion-related loss of signal localization. Consequently, the signal can be amplified 1, 2, 3, 4, 5, 6, 7, 8, 9 10, 15, 20, 25, 30, 50, 75, or 100 folds. As known to a person skilled in the art, the labels on the tyramide can be any labels described herein, including fluorophores, enzymes, haptens, radioisotopes, and/or photophores. Other enzyme-based reactions can be utilized to create signal amplification as well. For example, Enzyme-Labeled Fluorescence (ELF) signal amplification is available for alkaline phosphatase, wherein the alkaline phosphatase enzymatically cleaves a weakly blue-fluorescent substrate (ELF 97 phosphate) and converts it into a bright yellow-green-fluorescent precipitate that exhibits an unusually large Stokes shift and excellent photostability. Both tyramide-based signal amplification system and ELF signal amplification are available commercially, for example from ThermoFisher Scientific (Waltham, Mass. USA 02451).

Thus in some embodiments of the methods provided herein, the expression level of Nectin-4 is detected with a signal amplification system.

In some embodiments, the specimen is then counterstained to identify cellular and subcellular elements.

In some embodiments, the expression level of Nectin-4 can also be detected with antibodies described herein using an immunoblotting assay. In some embodiments of an immunoblotting assay proteins are often (but do not have to be) separated by electrophoresis and transferred onto membranes (usually nitrocellulose or PVDF membrane). Similar to the IHC assays, primary antibodies or antisera, such as polyclonal antisera and monoclonal antibodies that specifically target Nectin-4, can be used to detect protein expression. In some embodiments, the membrane is contacted with a primary antibody for a specific target for a period of time sufficient for the antibody-antigen binding to occur and the bound antibodies can be detected by direct labels on the primary antibodies themselves, e.g. with radioactive labels, fluorescent labels, hapten labels such as biotin, or enzymes such as horseradish peroxidase or alkaline phosphatase. In other embodiments, unlabeled primary antibody is used in an indirect assay as described above in conjunction with a labeled secondary antibody specific for the primary antibody. As described herein, the secondary antibodies can be labeled, for example, with enzymes or other detectable labels such as fluorescent labels, luminescent labels, colorimetric labels, or radioisotopes. Immunoblotting protocols and kits are well known in the art and are commercially available. Automated systems for immunoblotting, e.g. iBind Western Systems for Western blotting (ThermoFisher, Waltham, Mass. USA 02451), are available commercially. Immunoblotting includes, but is not limited to, Western blot, in-cell Western blot, and dot blot. Dot blot is a simplified procedure in which protein samples are not separated by electrophoresis but are spotted directly onto a membrane. In cell Western blot involves seeding cells in microtiter plates, fixing/permeabilizing the cells, and subsequent detection with a primary labeled primary antibody or unlabelled primary antibody followed by labeled secondary antibody as described herein.

In other embodiments, the expression levels of Nectin-4 can also be detected with the antibodies described herein in a flow cytometry assay, including a fluorescence-activated cell sorting (FACS) assay. Similar to the IHC or immunoblotting assays, primary antibodies or antisera, such as polyclonal antisera and monoclonal antibodies that specifically target Nectin-4, can be used to detect protein expression in a FACS assay. In some embodiments, cells are stained with primary antibodies against specific target protein for a period of time sufficient for the antibody-antigen binding to occur and the bound antibodies can be detected by direct labels on the primary antibodies, for example, fluorescent labels or hapten labels such as biotin on the primary antibodies. In other embodiments, unlabeled primary antibody is used in an indirect assay as described above in conjunction with a fluorescently labeled secondary antibody specific for the primary antibody. FACS provides a method for sorting or analyzing a mixture of fluorescently labeled biological cells, one cell at a time, based upon the specific light scattering and fluorescent characteristics of each cell. The flow cytometer thus detects and reports the intensity of the fluorichrome-tagged antibody, which indicates the expression level of the target protein. Therefore, the expression level of surface proteins (such as Nectin-4) can be detected using antibodies against the target protein. Non-fluorescent cytoplasmic proteins can also be observed by staining permeablized cells. Methods for performing FACS staining and analyses are well know to a person skilled in the art and are described by Teresa S. Hawley and Robert G. Hawley in Flow Cytometry Protocols, Humana Press, 2011 (ISBN 1617379506, 9781617379505).

In other embodiments, the expression levels of Nectin-4 can also be detected using immunoassays such as an Enzyme Immune Assay (EIA) or an ELISA. Both EIA and ELISA assays are known in the art, e.g. for assaying a wide variety of tissues and samples, including blood, plasma, serum or bone marrow. A wide range of ELISA assay formats are available, see, e.g., U.S. Pat. Nos. 4,016,043, 4,424,279, and 4,018,653, which are hereby incorporated by reference in their entireties. These include both single-site and two-site or "sandwich" assays of the non-competitive types, as well as in the traditional competitive binding assays. These assays also include direct binding of a labeled antibody to a target protein. Sandwich assays are commonly used assays. A number of variations of the sandwich assay technique exist. For example, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of target protein.

In some embodiments of the EIA or ELISA assays, an enzyme is conjugated to the second antibody. In other embodiments, fluorescently labeled secondary antibodies can be used in lieu of the enzyme-labeled secondary antibody to produce a detectable signal an ELISA assay format. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA and ELISA, the fluorescent labeled antibody is allowed to bind to the first antibody-target protein complex. After washing off the unbound reagent, the remaining tertiary complex is then exposed to the light of the appropriate wavelength, the fluorescence observed indicates the presence of the target protein of interest. Immunofluorescence and EIA techniques are both very well established in the art and are disclosed herein.

For the immunoassays described herein, any of a number of enzymes or non-enzyme labels can be utilized so long as the enzymatic activity or non-enzyme label, respectively, can be detected. The enzyme thereby produces a detectable signal, which can be utilized to detect a target protein. Particularly useful detectable signals are chromogenic or fluorogenic signals. Accordingly, particularly useful enzymes for use as a label include those for which a chromogenic or fluorogenic substrate is available. Such chromogenic or fluorogenic substrates can be converted by enzymatic reaction to a readily detectable chromogenic or fluorescent product, which can be readily detected and/or quantified using microscopy or spectroscopy. Such enzymes are well known to those skilled in the art, including but not limited to, horseradish peroxidase, alkaline phosphatase, β-galactosidase, glucose oxidase, and the like (see Hermanson, *Bioconjugate Techniques*, Academic Press, San Diego (1996)). Other enzymes that have well known chromogenic or fluorogenic substrates include various peptidases, where chromogenic or fluorogenic peptide substrates can be utilized to detect proteolytic cleavage reactions. The use of chromogenic and fluorogenic substrates is also well known in bacterial diagnostics, including but not limited to the use of α- and β-galactosidase, β-glucuronidase,6-phospho-β-D-galatoside 6-phosphogalactohydrolase, β-gluosidase, α-glucosidase, amylase, neuraminidase, esterases, lipases, and the like (Manafi et al., *Microbiol. Rev.* 55:335-348 (1991)), and such enzymes with known chromogenic or fluorogenic substrates can readily be adapted for use in methods of the present invention.

Various chromogenic or fluorogenic substrates to produce detectable signals are well known to those skilled in the art and are commercially available. Exemplary substrates that can be utilized to produce a detectable signal include, but are not limited to, 3,3'-diaminobenzidine (DAB), 3,3',5,5'-tetramethylbenzidine (TMB), Chloronaphthol (4-CN)(4-chloro-1-naphthol), 2,2'-azino-bis(3-ethylbenzothiazoline-6-sulphonic acid) (ABTS), o-phenylenediamine dihydrochloride (OPD), and 3-amino-9-ethylcarbazole (AEC) for horseradish peroxidase; 5-bromo-4-chloro-3-indolyl-1-phosphate (BCIP), nitroblue tetrazolium (NBT), Fast Red (Fast Red TR/AS-MX), and p-Nitrophenyl Phosphate (PNPP) for alkaline phosphatase; 1-Methyl-3-indolyl-β-D-galactopyranoside and 2-Methoxy-4-(2-nitrovinyl)phenyl β-D-galactopyranoside for β-galactosidase; 2-Methoxy-4-(2-nitrovinyl)phenyl β-D-glucopyranoside for β-glucosidase; and the like. Exemplary fluorogenic substrates include, but are not limited to, 4-(Trifluoromethyl) umbelliferyl phosphate for alkaline phosphatase; 4-Methylumbelliferyl phosphate bis (2-amino-2-methyl-1,3-propanediol), 4-Methylumbelliferyl phosphate bis (cyclohexylammonium) and 4-Methylumbelliferyl phosphate for phosphatases; QuantaBlu™ and QuantaRed™ for horseradish peroxidase; 4-Methylumbelliferyl β-D-galactopyranoside, Fluorescein di(β-D-galactopyranoside) and Naphthofluorescein di-(β-D-galactopyranoside) for β-galactosidase; 3-Acetylumbelliferyl β-D-glucopyranoside and 4-Methylumbelliferyl-β-D-glucopyranoside for β-glucosidase; and 4-Methylumbelliferyl-α-D-galactopyranoside for α-galactosidase. Exemplary enzymes and substrates for producing a detectable signal are also described, for example, in US publication 2012/0100540. Various detectable enzyme substrates, including chromogenic or fluorogenic substrates, are well known and commercially available (Pierce, Rockford Ill.; Santa Cruz Biotechnology, Dallas Tex.; Invitrogen, Carlsbad Calif.; 42 Life Science; Biocare). Generally, the substrates are converted to products that form precipitates that are deposited at the site of the target nucleic acid. Other exemplary substrates include, but are not limited to, HRP-Green (42 Life Science), Betazoid DAB, Cardassian DAB, Romulin AEC, Bajoran Purple, Vina Green, Deep Space Black™, Warp Red™, Vulcan Fast Red and Ferangi Blue from Biocare (Concord Calif.; biocare.net/products/detection/chromogens).

In some embodiments of the immunoassays, a detectable label can be directly coupled to either the primary antibody or the secondary antibody that detects the unlabeled primary antibody can have. Exemplary detectable labels are well known to those skilled in the art, including but not limited to chromogenic or fluorescent labels (see Hermanson, *Bioconjugate Techniques*, Academic Press, San Diego (1996)). Exemplary fluorophores useful as labels include, but are not limited to, rhodamine derivatives, for example, tetramethylrhodamine, rhodamine B, rhodamine 6G, sulforhodamine B, Texas Red (sulforhodamine 101), rhodamine 110, and derivatives thereof such as tetramethylrhodamine-5-(or 6), lissamine rhodamine B, and the like; 7-nitrobenz-2-oxa-1, 3-diazole (NBD); fluorescein and derivatives thereof; napthalenes such as dansyl (5-dimethylaminonapthalene-1-sulfonyl); coumarin derivatives such as 7-amino-4-methylcoumarin-3-acetic acid (AMCA), 7-diethylamino-3-[(4'-(iodoacetyl)amino)phenyl]-4-methylcoumarin (DCIA), Alexa fluor dyes (Molecular Probes), and the like; 4,4-difluoro-4-bora-3a,4a-diaza-s-indacene (BODIPY™) and derivatives thereof (Molecular Probes; Eugene Oreg.); pyrenes and sulfonated pyrenes such as Cascade Blue' and derivatives thereof, including 8-methoxypyrene-1,3,6-trisulfonic acid, and the like; pyridyloxazole derivatives and dapoxyl derivatives (Molecular Probes); Lucifer Yellow (3,6-disulfonate-4-amino-naphthalimide) and derivatives thereof; CyDye™ fluorescent dyes (Amersham/GE Healthcare Life Sciences; Piscataway N.J.), and the like. Exemplary chromophores include, but are not limited to, phenolphthalein, malachite green, nitroaromatics such as nitrophenyl, diazo dyes, dabsyl (4-dimethylaminoazobenzene-4'-sulfonyl), and the like.

Methods well known to a person skilled in the art such as microscopy or spectroscopy can be utilized to visualize chromogenic or fluorescent detectable signals associated with the bound primary or secondary antibodies.

"Determining the expression of Nectin-4" refers to putting the expression of Nectin-4 in the test biological sample in a referenced system (or a referenced scale) so that a person familiar with the referenced system can tell the relative expression of Nectin-4 in the test sample with respect to other samples that have been positioned in the referenced system. Consequently, such a determination involves comparing the expression of Nectin-4 in the test tissue sample with a reference expression level of Nectin-4.

In some embodiments, the referenced system can be a quantitative system where the actual molar concentration or mole quantity of Nectin-4 in the test sample is compared with the molar concentration or mole quantity of the reference expression levels. In some embodiments, other surrogate numerical measurements that are linearly proportional to the molar concentration or mole quantity can be used. Examples of these surrogate measurements include fluorescence intensity measurements of bound antibodies, luminescence intensity measurements of bound antibodies, radioactivity measurements of bound antibodies, and/or colorimetric or chromogenic measurements of bound antibodies.

In other embodiments, the referenced system can be a categorization system. A categorization system can have as few as 2 categories and as many as 3, 4, 5, 6, 7, 8, 9, 10, 12, 14, 16, 18, 20, 25, 30, 35, 40, 45, 50, 75, 100, or more categories. In one embodiment, the referenced system has a positive category for samples that are positive for Nectin-4 expression (positive) and a negative category for samples that are negative for Nectin-4 expression (negative). In such a categorization system, determining the expression of Nectin-4 in a test sample involves comparing the expression of Nectin-4 in the test sample with Nectin-4 expression of a positive reference sample and/or with a negative reference, and placing the test sample in the positive category if the test sample expresses Nectin-4 at a similar or higher level than the positive reference. In another embodiment, the categorization system has 3 categories, e.g. negative, medium, and high expression categories. In another embodiment, the categorization system has 4 categories, e.g. negative, low/weak, medium/moderate, and high/strong expression categories. In some aspects, determining the expression of Nectin-4 in a test sample involves comparing the expression of Nectin-4 in the test sample with one or more references of Nectin-4 expression of known categories and placing the test sample in a category according to its relative expression to the reference(s).

In some embodiments, the referenced system can be a scoring system. A scoring system can be similar to a categorization system except that the categories are replaced by a score. For example, a 2-category system of negative and positive Nectin-4 expression can be a scoring system of 0 and 1, where 0 means negative and 1 means positive. In another embodiment, a 3-category system can be a scoring system of 0, 1, and 2, wherein 0 is negative, 1 is low/weak expression, and 2 is medium/moderate and high/strong expression. In another embodiment, a 4-category system can be a scoring system of 0, 1, 2, and 3, where in 0 is negative, 1 is low/weak, 2 is medium/moderate, and 3 is high/strong expression. Similar to the categorization system, determining the expression of Nectin-4 in a test sample in the scoring system involves comparing the expression of Nectin-4 in the test sample with one or more references of Nectin-4 expression having a known score and assigning the test sample a score according to its relative expression to the references. The scoring system, however, can be scores of discontinuous and discrete numbers (e.g. a system of 0, 2, 4, 6, 8, and 10, or a system of 1, 4, 6, 11, 13, and 19), numbers with fractions (e.g. 1, 1.5, 2, 2.5, 3, 3.5 etc), negative numbers, numbers starting from any number (e.g. 1000, 2000, 3000, etc), and any set of numbers that can be used to track the relative protein expression in biological samples.

In some embodiments, the referenced system can be percentages of cells in conjunction with the categorization or scoring systems. The combination of percentage of cells with a categorization or scoring system provides finer gradation of the samples. In such a combined system, each cell from the biological sample is assigned or placed in the categorization or scoring system, and the approximate percentage of cells of the test sample in each category or score is determined. In one example, measurements of percentages of cells can be coupled with a 2-category system of positive and negative Nectin-4 expression, wherein the sample is not measured as a whole but break into the percentage of cells that are positive for Nectin-4 expression and percentage of cells that are negative for Nectin-4 expression. For example, in a 2-category system of positive and negative Nectin-4 expression, a test sample may be negative for Nectin-4 expression if placed in a 2 category system but have 10% cells positive for Nectin-4 expression and 90% of cells negative for Nectin-4 expression. In one embodiment, the referenced system includes percentages of cells in conjunction with a 2-category or 2-score system. In one embodiment, the referenced system includes percentages of cells in conjunction with a 3-category or 3-score system. In one embodiment, the referenced system includes percentages of cells in conjunction with a 4-category or 4-score system. In one embodiment, the referenced system includes percentages of cells in conjunction with a 5-category or 5-score system. In one embodiment, the referenced system includes percentages of cells in conjunction with a 6-category or 6-score system. In one embodiment, the referenced system includes percentages of cells in conjunction with a 7-category or 7-score system. In one embodiment, the referenced system includes percentages of cells in conjunction with an 8-category or 8-score system. In one embodiment, the referenced system includes percentages of cells in conjunction with a 9-category or 9-score system. In one embodiment, the referenced system includes percentages of cells in conjunction with a 10-category or 10-score system. In one embodiment, the referenced system includes percentages of cells in conjunction with any categorization or any scoring system. In one embodiment, the referenced system includes percentages of cells in conjunction with a 4-score system comprising 0 (negative for Nectin-4), 1 (low/weak Nectin-4 expression), 2 (medium/moderate Nectin-4 expression), and 3 (high/strong Nectin-4 expression).

In some aspects, the referenced system can be a ratio of the Nectin-4 expression to the expression of at least one reference protein. In some embodiments, the ratio could be a ratio of quantitative measurements of Nectin-4 expression and those of a reference protein, wherein the quantitative measurements include those described herein such as molar concentration, mole quantity, fluorescence intensity measurements of bound antibodies, luminescence intensity measurements of bound antibodies, radioactivity measurements of bound antibodies, and/or colorimetric or chromogenic measurements of bound antibodies. In other embodiments, the ratio could also be a ratio of scores assigned to Nectin-4 expression and the reference protein according to any scoring system provided herein. A reference protein could be a protein of ordinary cell function such as actin, GAPDH, GDI, or any protein expressed by a house-keeping gene. For example, if a test sample has a score of 3 for Nectin-4 expression and score of 1 for expression of actin, the ratio can be determined to be 3.

In other aspects, the reference system can utilize the results of a mathematical function using one or more of the categorization, score, ratio, percentage, and quantitative measurement as input. In some embodiments, the mathematical function uses compounding, addition, multiplication, or combination these operators to combine the various inputs to produce results that provide more detailed information about Nectin-4 expression in the sample and/or finer gradation on the Nectin-4 expression scale. In one embodiment, the mathematical function calculates an H score based on the combination of percentage and a 4-score system. For example, an H-score was calculated by summing the products of the percentage of cells (0-100) having each Nectin-4 expression score (0=negative, 1=low/weak, 2=moderate/medium, and 3=high/strong). For example: a specimen with 10% of cells scoring 3, 30% of cells scoring 2, 20% of cells scoring 1, and 40% of cells scoring 0 would have an H-score of $(3\times10)+(2\times30)+(1\times20)+(0\times40)=110$.

Therefore, as provided herein, the expression level of Nectin-4 can be determined using a categorization system, a scoring system, a ratio of Nectin-4 expression to the expression of at least one reference protein, percentage of cells in said categorization or scoring system, a quantitative measurement of Nectin-4 staining signal, or a result of a mathematical function using one or more of said categorization, score, ratio, percentage, and quantitative measurement as input.

Most formalin-fixed tissues require an antigen retrieval step before immunohistochemical staining. Methylene bridges formed during fixation cross-link proteins and mask the epitopes of the antigens. Antigen retrieval methods break these methylene bridges and expose the epitopes, allowing antibodies to bind. In some embodiments, antigens are retrieved by a heat induced epitope retrieval (HIER) method. In other embodiments, antigens are retrieved by an enzymatic retrieval (e.g. proteolytic digestion) method. For HIER, formalin-fixed, paraffin-embedded (FFPE) tissue sections can be heated at 50° C., 55° C., 60° C., 65° C., 70° C., 75° C., 80° C., 85° C., 90° C., 95° C., 100° C., 105° C., 110° C., 115° C., 120° C., 125° C., or 130° C. The FFPE tissue section can be heated at any of these temperatures for 5, 10, 15, 20, 25, 30, 35, 40, 45, 50, 55, 60, 65, 70, 75, 80, 85, 90, 95, 100, 105, 110, 115, 120, 150, 180, 240, 300, 360, 420, 480, 540, 600, 660, 720, 780, 840, 900, 960, 1020, 1080, 1140, 1200, 1260, 1320, 1380, and 1440 minutes. The HIER procedure at any of the aforementioned temperatures and for any of the aforementioned durations can be performed in a solution having a pH of 2, 2.5, 3, 3.5, 4, 4.5, 5, 5.2, 5.4, 5.6, 5.8, 6.0, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.2, 10.4, 10.6, 10.8, 11, 11.5, or 12. In some embodiments, the HIER can be performed at a temperature selected from a group consisting of 80° C., 85° C., 90° C., 95° C., 100° C., 105° C., 110° C., 115° C., for a duration selected from a group consisting of 5, 10, 15, 20, 25, 30, 35, 40, and at a pH selected from a group consisting of 8, 8.2, 8.4, 8.6, 8.8, 9, 9.2, 9.4, 9.6, 9.8, 10, 10.2, 10.4.

Thus, the methods provided herein further include a step of retrieving the epitope of Nectin-4 by heat-induced epitope retrieval (HIER)

Unlabeled antibodies, labeled antibodies, and derivatives and analogs thereof, which immunospecifically bind to a Nectin-4 antigen can be used for diagnostic purposes to detect, diagnose, or monitor a Nectin-4-mediated disease. Thus, provided herein are methods for the detection of a Nectin-4-mediated disease comprising: (a) assaying the expression of a Nectin-4 antigen in cells or a tissue sample of a subject using one or more antibodies provided herein that immunospecifically bind to the Nectin-4 antigen; and (b) comparing the level of the Nectin-4 antigen with a reference level, e.g., levels in normal tissue samples (e.g., tissue samples from a patient not having a Nectin-4-mediated disease, tissue samples from the same patient before disease onset, normal cells in a tissue samples from the same patient, or normal tissue samples from an normal organ from the same patient), whereby an increase in the assayed level of Nectin-4 antigen compared to the control level of the Nectin-4 antigen is indicative of a Nectin-4-mediated disease.

Also provided herein is a diagnostic assay for diagnosing a Nectin-4-mediated disease comprising: (a) assaying for the level of a Nectin-4 antigen in cells or a tissue sample of an individual using one or more antibodies provided herein that immunospecifically bind to a Nectin-4 antigen; and (b) comparing the level of the Nectin-4 antigen with a reference level, e.g., levels in normal tissue samples, whereby an increase in the assayed Nectin-4 antigen level compared to the reference level of the Nectin-4 antigen is indicative of a Nectin-4-mediated disease. In certain embodiments, provided herein is a method of treating a Nectin-4-mediated disease in a subject, comprising: (a) assaying for the level of a Nectin-4 antigen in cells or a tissue sample of the subject using one or more antibodies provided herein that immunospecifically bind to a Nectin-4 antigen; and (b) comparing the level of the Nectin-4 antigen with a reference level, e.g., levels in normal tissue samples, whereby an increase in the assayed Nectin-4 antigen level compared to the reference level of the Nectin-4 antigen is indicative of a Nectin-4-mediated disease. In some embodiments, the method further comprises (c) administering an effective amount of an antibody provided herein to the subject identified as having the Nectin-4-mediated disease. A more definitive diagnosis of a Nectin-4-mediated disease may allow health professionals to employ preventative measures or aggressive treatment earlier thereby preventing the development or further progression of the Nectin-4-mediated disease.

Antibodies provided herein can be used to assay Nectin-4 antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell Biol. 105:3087-3096). Other antibody-based methods useful for detecting protein gene expression include immunoassays, such as the ELISA and the radioimmunoassay (MA). Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

One aspect provided herein is the detection and diagnosis of a Nectin-4-mediated disease in a human. In one embodiment, diagnosis comprises: a) administering (for example, parenterally, subcutaneously, or intraperitoneally) to a subject an effective amount of a labeled antibody that immunospecifically binds to a Nectin-4 antigen; b) waiting for a time interval following the administering for permitting the labeled antibody to concentrate at sites in the subject where the Nectin-4 antigen is expressed (and for unbound labeled molecule to be cleared to background level); c) determining background level; and d) detecting the labeled antibody in the subject, such that detection of labeled antibody above the background level indicates that the subject has a Nectin-4-mediated disease. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody to concentrate at sites in the subject and for unbound labeled antibody to be cleared to background level is 6 to 48 hours or 6 to 24 hours or 6 to 12 hours. In another embodiment the time interval following administration is 5 to 20 days or 5 to 10 days.

In one embodiment, monitoring of a Nectin-4-mediated disease is carried out by repeating the method for diagnosing the a Nectin-4-mediated disease, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods provided herein include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

30. KITS

Also provided herein are kits comprising an antibody (e.g., an anti-Nectin-4 antibody) provided herein, or a composition (e.g., a pharmaceutical composition) thereof, packaged into suitable packaging material. A kit optionally includes a label or packaging insert including a description of the components or instructions for use in vitro, in vivo, or ex vivo, of the components therein.

The term "packaging material" refers to a physical structure housing the components of the kit. The packaging material can maintain the components sterilely, and can be made of material commonly used for such purposes (e.g., paper, corrugated fiber, glass, plastic, foil, ampoules, vials, tubes, etc.).

Kits provided herein can include labels or inserts. Labels or inserts include "printed matter," e.g., paper or cardboard, separate or affixed to a component, a kit or packing material (e.g., a box), or attached to, for example, an ampoule, tube, or vial containing a kit component. Labels or inserts can additionally include a computer readable medium, such as a disk (e.g., hard disk, card, or memory disk), optical disk such as CD- or DVD-ROM/RAM, DVD, MP3, magnetic tape, or an electrical storage media such as RAM and ROM or hybrids of these such as magnetic/optical storage media, FLASH media, or memory type cards. Labels or inserts can include information identifying manufacturer information, lot numbers, manufacturer location, and date.

Kits provided herein can additionally include other components. Each component of the kit can be enclosed within an individual container, and all of the various containers can be within a single package. Kits can also be designed for cold storage. A kit can further be designed to contain antibodies provided herein, or cells that contain nucleic acids encoding the antibodies provided herein. The cells in the kit can be maintained under appropriate storage conditions until ready to use. The additional components can include, by way of example, a positive or negative reference sample (e.g., tissue samples from a patient known to have a Nectin-4-mediated disease, tissue samples from a patient not having a Nectin-4-mediated disease, tissue samples from the same patient before disease onset, normal cells in a tissue samples from a subject with a Nectin-4 mediated disease, or normal tissue samples from an normal organ from the same patient), buffers, washing solutions, an antibody detection reagents, and/or a signal amplification reagents.

Also provided herein are panels of antibodies that immunospecifically bind to a Nectin-4 antigen. In specific embodiments, provided herein are panels of antibodies having different association rate constants different dissociation rate constants, different affinities for Nectin-4 antigen, and/or different specificities for a Nectin-4 antigen. In certain embodiments, provided herein are panels of about 10, preferably about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96 well or 384 well plates, such as for assays such as ELISAs.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a," "and," and "the" include plural referents unless the context clearly indicates otherwise. Thus, for example, reference to "a peptide sequence" includes a plurality of such sequences and so forth.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1,000, 1,000-2,500, 2,500-5,000, 5,000-25,000, 25,000-50,000 includes any numerical value or range within or encompassing such values, e.g., 25, 26, 27, 28, 29 . . . 250, 251, 252, 253, 254 . . . 500, 501, 502, 503, 504 . . . , etc.

As also used herein a series of ranges are disclosed throughout this document. The use of a series of ranges include combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

For the sake of conciseness, certain abbreviations are used herein. One example is the single letter abbreviation to represent amino acid residues. The amino acids and their corresponding three letter and single letter abbreviations are as follows:

| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |

-continued

| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

The examples in this section are offered by way of illustration, and not by way of limitation.

Example 1: Antigen Preparation

A human Nectin-4 fragment, e.g. a fragment including amino acid sequence 31-346 (SEQ ID NO:2) of human Nectin-4 (SEQ ID NO:1) was generated and used as the antigen for subsequent immunization campaigns.

6×HN-tagged Nectin 4 (aa 31-346) was produced using commercially available pET expression vectors. Expression was carried out in BL21 (DE3) E. coli according to manufacturer's instructions and purified using IMAC-based purification (immobilized metal affinity chromatography). Purified Nectin 4 (aa31-346) was used as immunogen.

A recombinant Nectin 4 (aa (1-348) for antibody screening was produced in 293FT cells using a modified pTag5/mychis expression vector according to manufacturer's instructions. Protein was purified using standard IMAC based purification.

Example 2: Generation of Antibodies

A. Antibody Generation and Production

The monoclonal antibody M22-321b41.1 was generated by immunizing Balb/C mice with the bacterially produced recombinant fragment (31-346; SEQ ID NO:2) of extracellular domain of human Nectin 4 protein using standard hybridoma techniques described originally in Kohler and Milstein, Eur. J. Immunol. 6, 511 (1976). The hybridoma M22-321b41 was subcloned as M22-321b41.1 which produces a mouse IgG2a kappa antibody that binds specifically to the recombinant extracellular domain of human Nectin-4 protein by ELISA. In addition, the protein A purified antibody M22-321b41.1 was shown to stain specifically the tissues tested that express Nectin 4 by IHC.

The M22-321b41.1 hybridoma cells were subsequently grown, expanded, and viably frozen for long term storage in liquid nitrogen.

B. Hybridoma Sequencing

The M22-321b41.1 hybridoma antibody heavy and light chain genes were sequenced using RT-PCR.

Example 3: Screening and Selection of Antibodies

A. Screening Assays (or Binding Assays)

Primary ELISA screen was performed with Nectin-4 extracellular domain fragment (amino acid residues 31-346) produced as described above.

Secondary ELISA screen was performed with Nectin-4 extracellular domain fragment (amino acid residues 31-346) produced in E. coli, Nectin-4 extracellular domain fragment (amino acid residues 1-346) produced in 293FT cells, Nectin-4-tag5, and two control proteins (one a produced with pET and one produced with tag5).

B. Selection of Antibodies

Antibodies were selected initially if they showed staining in recombinant 3T3-Nectin-4 cells and lacked staining in controls. Subsequently the initially selected antibodies were tested in a panel of positive and negative control tissues with known Nectin-4 mRNA expression as determined by qPCR scores. The antibodies were tested at various concentrations and with various antigen retrieval protocols. Antibodies were selected if they produced specific staining in Nectin-4-mRNA-positive tissues, lacked staining in Nectin-4-mRNA-negative tissues, and were better than control anti-Nectin-4 antibodies tested in terms of staining intensity, ratio of stained cells, and nonspecific background staining.

Example 4: Screening for Antibodies Specific for Nectin-4

The antibodies generated as described above were screened to select the antibodies specific for Nectin-4. The screening was performed, for example, using an IHC assay. Briefly, human xenograft cancer tissues from various origins, e.g. bladder, breast, ovary, pancreas, kidney, skin, lung, and colon, were first tested in qPCR to determine the level of Nectin-4 expression in these tissues.

Real-time quantitative PCR (qPCR) analysis was employed to determine relative Nectin-4 mRNA expression levels. qPCR assay was performed using Bio-Rad CFX384 Real-Time PCR Detection system with SsoFast EvaGreen Supermix (Bio-Rad) and 5 ng RNA equivalent of cDNA template. Nectin-4 mRNA expression levels were calculated as relative to the expression levels of GAPDH, a housekeeping gene, using a modified delta Cq method with the following formula: $10,000 * 2^{-(CqNectin-4-CqGAPDH)}$; Nectin-4 relative expression was described in relative to GAPDH units.

Primers employed in qPCR analysis of Nectin-4 include: 191P4D12.1 forward primer: 5'-GGCTGGAGTTCAAT-GAGGTTTATTT-3' (SEQ ID NO:41); and 191P4D12.2 reverse primer: 5'-TCCAGCAGATTTCA-GACTAAGAAGA-3' (SEQ ID NO:42). Primers employed in qPCR analysis of GAPDH include: GAPDH.1 forward primer: 5'-AGAACATCATCCCTGCCTCTACTG-3' (SEQ ID NO:43); and GAPDH.2 reverse primer: 5'-AAAT-GAGCTTGACAAAGTGGTCGT-3' (SEQ ID NO:44).

cDNA template for qPCR was synthesized using Bio-Rad iScript Advanced cDNA synthesis kit from RNA isolated from tissue or cell line samples using TRIzol RNA extraction method followed by RNA clean-up and DNase I digestion using Qiagen RNeasy Cleanup kit.

The exemplary human xenograft tissues were shown in Table 5. Anti-Nectin-4 antibodies generated above were then used in an IHC assay to stain the tissues with known levels of Nectin-4 expression. The IHC assays were performed similarly as described in details in Example 5 below. The IHC staining of Nectin-4 in the various tissues were correlated with the Nectin-4 mRNA levels in these tissues. An antibody was selected as a Nectin-4 specific antibody when that it produced IHC staining signal that correlated with the Nectin-4 mRNA levels, e.g. strong staining in tissues with high level of Nectin-4 mRNA, moderate IHC staining signal in tissues with intermediate levels of Nectin-4 mRNA, low IHC staining signal in tissues with low Nectin-4 mRNA, and no IHC staining signal in tissues expressing no Nectin-4 mRNA. In total, at least 283 antibody clones were screened, leading to the identification of Nectin-4 specific antibody of M22-321b41.1 and M22-244b3.1.1.1

Example 5: Functional Assays:
Immunohistochemistry Staining of Xenograft Tissues Antibodies generated, screened, expressed, and purified, for example, as described herein, were further evaluated for their ability to specifically stain human xenograft tissues expressing Nectin-4 in an IHC assay.

For example, two anti-Nectin-4 mouse monoclonal antibodies, M22-244b3.1.1.1 and M22-321b41.1 (IgG1 and IgG2a isotypes, respectively), were tested in an IHC assay. The M22-244b3.1.1.1 and M22-321b41.1 antibodies were provided at 1.54 mg/mL and 1.3 mg/mL in phosphate buffered saline, pH 7.4. As a negative control, a commercial mouse IgG2a isotype control from murine myeloma (clone: UPC10, Sigma-Aldrich, St. Louis, Mo.) raised to β-2,6-fructosan that does not bind to human Nectin-4 or other mammalian antigens was used.

IHC staining was performed according to the following exemplary protocols. Briefly, an indirect IHC technique was used to detect Nectin-4 in the IHC assay. The samples were fixed in 10% buffered neutral formalin, processed and embedded into paraffin wax, and prepared as 4 μm tissue sections. After deparaffinization and re-hydration, sections were treated for antigen retrieval. The antigen epitopes in Nectin-4 were retrieved, for example, by application of heat to the tissue sections in an aqueous medium, commonly referred to as a Heat-Induced Epitope Retrieval (HIER) procedure. For example, the antigen epitopes in Nectin-4 were retrieved by applying Epitope Retrieval 2 (ER2, an EDTA-based buffer at pH 8.9-9.1) on the Leica automated platform for 20 minutes at 100° C. The tissue sections after antigen retrieval were then incubated with mouse primary antibodies M22-321b41.1, M22-244b3.1.1.1, or IgG2a (antibody control). The tissue sections bound with primary antibodies were washed and detected with an enzyme-labeled, e.g. peroxidase-labeled, secondary antibody. The bound secondary antibody was color-developed, for example, using the Leica Bond Refine Polymer Detection system, which can use the reaction between peroxidase with the chromogen 3, 3'-diaminobenzidine (DAB) to produce brown precipitate at the reaction site. The stained tissue sections were then scanned, imaged, and evaluated with light microscopy, for example, using an Aperio ScanScope CS (Aperio, Vista, Calif.).

To assess the level of Nectin-4 expression in the tissue sections by the level of antibody staining, stained tissue sections were assessed, evaluated, categorized, and recorded into different categories or scores according to the intensity of the IHC staining and cancer cell positivity ratio. The categories includes strong ("3" or interchangeably with as "3+"), moderate ("2" or interchangeably with as "2+"), and weak ("1" or interchangeably with as "1+"). Lack of specific staining was recorded as negative ("0" or interchangeably with as "–").

Human xenograft cancer tissues from various origins, e.g. bladder, breast, ovary, pancreas, kidney, skin, lung, and colon, with known Nectin-4 mRNA expression levels were tested. The levels of Nectin-4 mRNA in these exemplary human xenograft tissues were first assessed using qPCR and shown in Table 5.

TABLE 5

Tissues for Antibody Titration Experiment

| Human Xenograft Tissues | Mouse ID | Origin of Xenograft Tissue | Nectin-4 mRNA (qPCR) |
|---|---|---|---|
| AG-B1 | 61668 | Bladder papillary urothelial carcinoma | 681 |
| AG-B11 | 68618 | Bladder invasive keratinizing squamous cell carcinoma | 391 |
| AG-Br29 | 71838 | Breast infiltrating ductal carcinoma | 76 |
| AG-OV35 | 67431 | Ovarian high-grade serous carcinoma | 45 |
| AG-Panc3 | 62103 | Pancreatic moderately differentiated invasive adenocarcinoma | 12 |
| AG-C6 | 61674 | Colon moderately differentiated adenocarcinoma | 6 |
| AG-K24 | 65766 | Renal cell carcinoma | 0.4 |
| AG-Mel10 | 70845 | Malignant melanoma | 0 |
| MDA-MB-231-MFP-XCL | 58624 | Breast adenocarcinoma | 0 |

To find the proper staining concentration for the antibodies, the antibodies M22-321b41.1 and M22-244b3.1.1.1 were first titrated at 2.5 µg/mL, 5.0 µg/mL, and 7.5 µg/mL using the exemplary xenograft tissues listed in Table 5 in an IHC staining assay as described above. The results were shown in Table 6.

TABLE 6

Summary of Results for the Titration of M22-321b41.1 and M22-244b3.1.1.1

| Human Xenograft Tissues | Mouse ID | Nectin-4 mRNA (qPCR) | M22-321b41.1 Conc. (µg/mL) | Score | M22-244b3.1.1.1 Conc. (µg/mL) | Score |
|---|---|---|---|---|---|---|
| AG-B1 | 61668 | 681 | 2.5 | 3+ | 2.5 | 3+ |
| AG-B11 | 68618 | 391 | 2.5 | 3+ | 2.5 | 2+ |
| AG-Br29 | 71838 | 76 | 2.5 | 2+ | 2.5 | 3+ |
| AG-OV35 | 67431 | 45 | 2.5 | 3+ | 2.5 | 2+ |
| AG-Panc3 | 62103 | 12 | 2.5 | 3+ | 2.5 | 3+ |
| AG-C6 | 61674 | 6 | 2.5 | 1+ | 2.5 | + |
| AG-K24 | 65766 | 0.4 | 2.5 | – | 2.5 | 2+ |
| MDA-MB-231-MFP-XCL | 58624 | 0 | 2.5 | – | 2.5 | 1+ |
| AG-Mel10 | 70845 | 0 | 2.5 | – | 2.5 | – |
| AG-B1 | 61668 | 681 | 5 | 3+ | 5 | 3+ |
| AG-B11 | 68618 | 391 | 5 | 3+ | 5 | 2+ |
| AG-Br29 | 71838 | 76 | 5 | 2+ | 5 | 3+ |
| AG-OV35 | 67431 | 45 | 5 | 3+ | 5 | 3+ |
| AG-Panc3 | 62103 | 12 | 5 | 3+ | 5 | 3+ |
| AG-C6 | 61674 | 6 | 5 | + | 5 | + |
| AG-K24 | 65766 | 0.4 | 5 | – | 5 | 3+ |
| MDA-MB-231-MFP-XCL | 58624 | 0 | 5 | + | 5 | 1+ |
| AG-Mel10 | 70845 | 0 | 5 | – | 5 | – |
| AG-B1 | 61668 | 681 | 7.5 | 3+ | 7.5 | 3+ |
| AG-B11 | 68618 | 391 | 7.5 | 3+ | 7.5 | 2+ |
| AG-Br29 | 71838 | 76 | 7.5 | 2+ | 7.5 | 3+ |
| AG-OV35 | 67431 | 45 | 7.5 | 3+ | 7.5 | 3+ |
| AG-Panc3 | 62103 | 12 | 7.5 | 3+ | 7.5 | 3+ |
| AG-C6 | 61674 | 6 | 7.5 | + | 7.5 | + |
| AG-K24 | 65766 | 0.4 | 7.5 | + | 7.5 | 3+ |
| MDA-MB-231-MFP-XCL | 58624 | 0 | 7.5 | + | 7.5 | 1+ |
| AG-Mel10 | 70845 | 0 | 7.5 | – | 7.5 | – |

Figure 1:
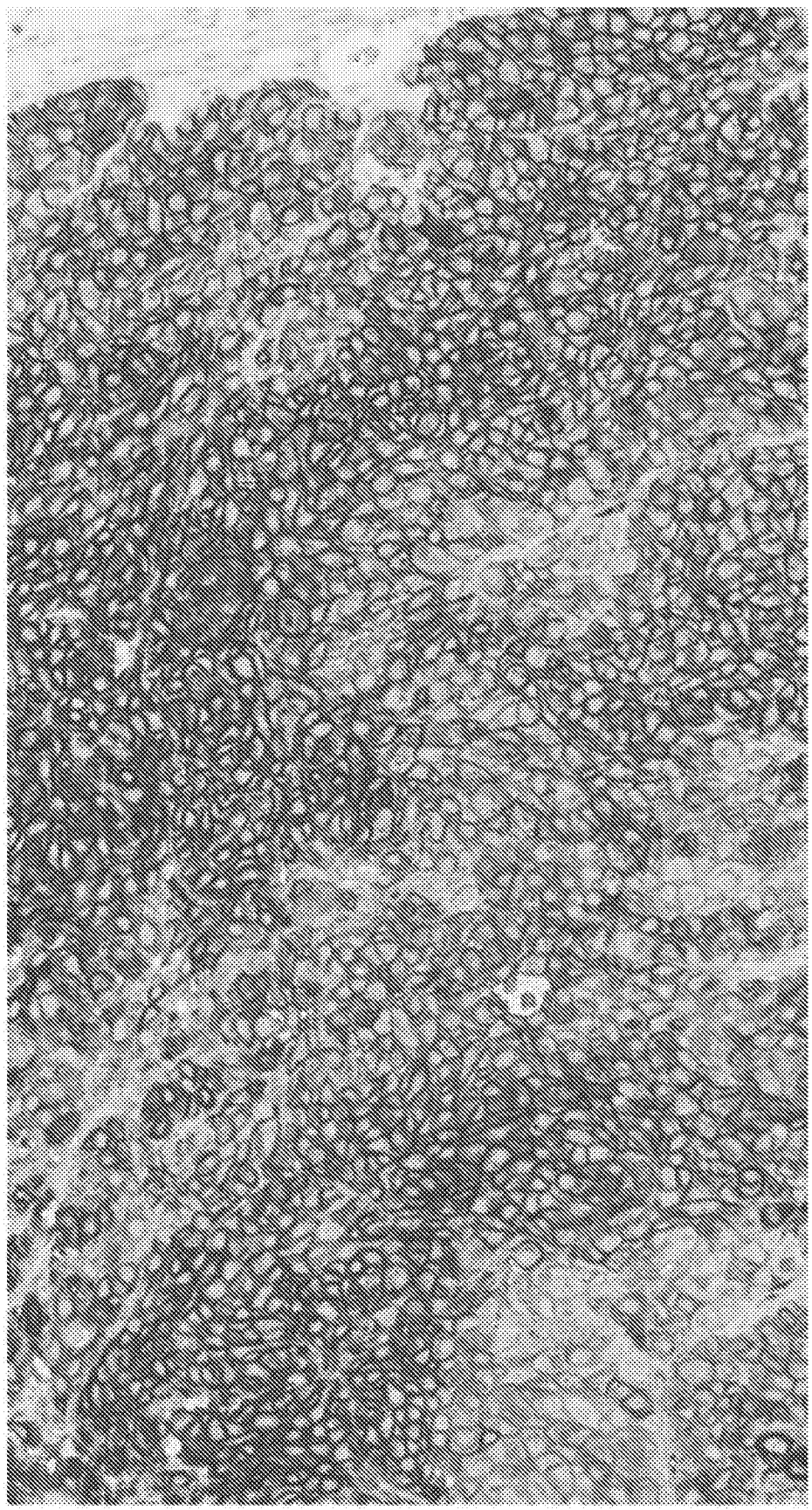
FIG. 1 depicts the result of an experiment showing all cancerous cells were positively stained in an IHC staining assay of Nectin-4 mRNA-positive AG-B1 xenograft with 2.5 µg/mL M22-321b41.1.
Figure 2:
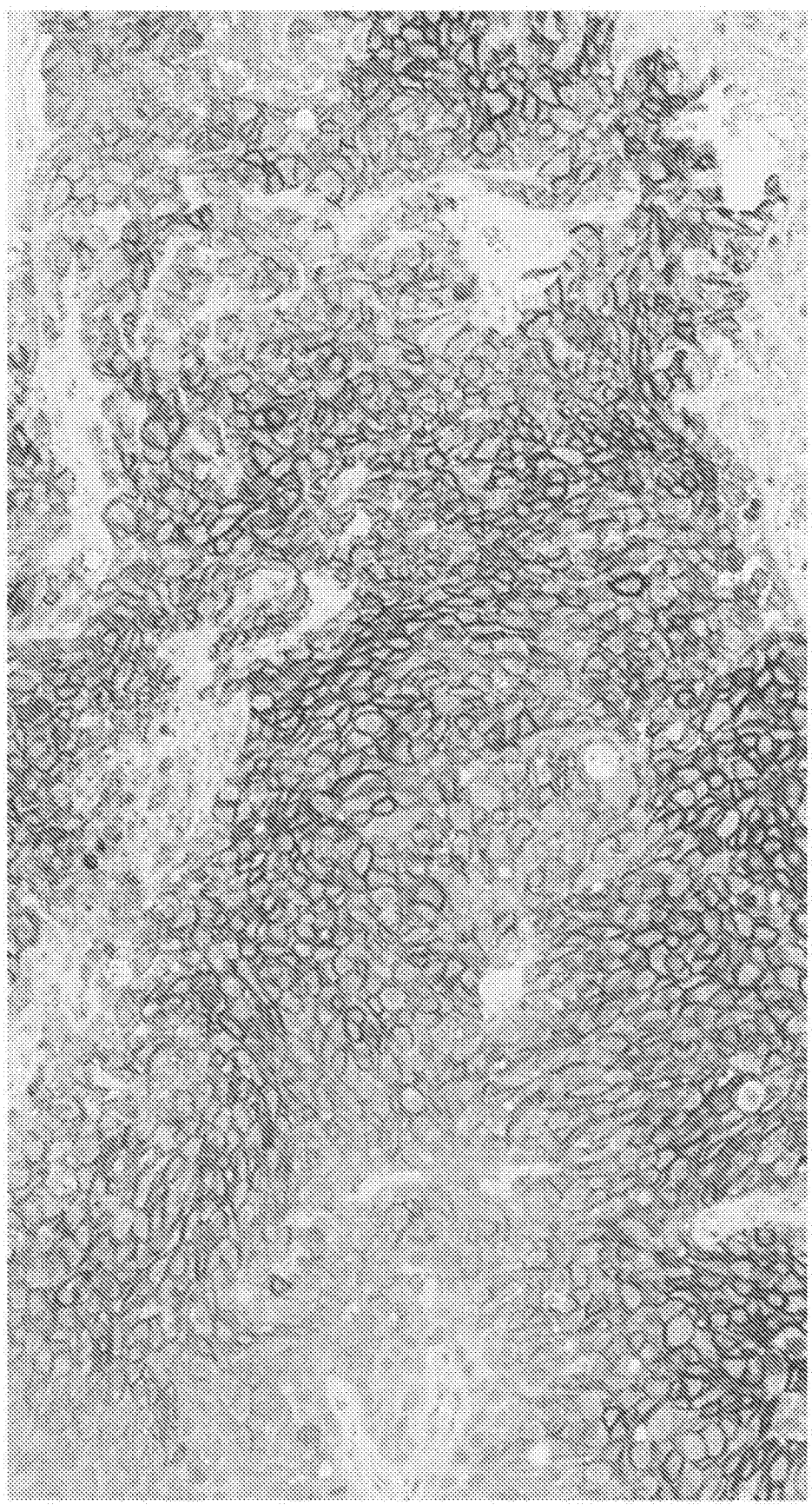
FIG. 2 depicts the result of an experiment showing all cancerous cells were positively stained in an IHC staining assay of Nectin-4 mRNA-positive AG-B1 xenograft with 2.5 µg/mL M22-244b3.1.1.1.

The optimal concentration for the anti-Nectin-4 antibody IHC staining was determined as the concentration at which the anti-Nectin-4 antibody IHC staining was observed in the Nectin-4 mRNA-expressing tissues but not in the Nectin-4-negative tissues. At 2.5 µg/mL, both M22-321b41.1 and M22-244b3.1.1.1 antibodies showed positive staining in the human xenograft tissues positive for Nectin-4 mRNA (FIG. 1 and FIG. 2) and showed the least background staining in the negative control tissues. Table 6 and the detailed staining results in Table 7 indicate that the concentration of 2.5 µg/mL was an exemplary optimal concentration for both antibodies.

TABLE 7

Detailed Staining Results for the Titration of M22-321b41.1 and M22-244b3.1.1.1

| Xenograft | Mouse Number | Nectin-4 mRNA (qPCR) | Primary Antibody | Conc (µm/mL) | Staining Result |
|---|---|---|---|---|---|
| AG-B1 | 61668 | 681 | M22-244b3.1.1.1 | 2.5 | 3+ |
| AG-B11 | 68618 | 391 | M22-244b3.1.1.1 | 2.5 | 2+ |
| AG-Br29 | 71838 | 76 | M22-244b3.1.1.1 | 2.5 | 3+ |
| AG-OV35 | 67431 | 45 | M22-244b3.1.1.1 | 2.5 | 2+ |
| AG-Panc3 | 62103 | 12 | M22-244b3.1.1.1 | 2.5 | 3+ |
| AG-C6 | 61674 | 6 | M22-244b3.1.1.1 | 2.5 | + |

TABLE 7-continued

Detailed Staining Results for the Titration of M22-321b41.1 and M22-244b3.1.1.1

| Xenograft | Mouse Number | Nectin-4 mRNA (qPCR) | Primary Antibody | Conc (μm/mL) | Staining Result |
|---|---|---|---|---|---|
| AG-K24 | 65766 | 0.4 | M22-244b3.1.1.1 | 2.5 | 2+ |
| AG-Mel10 | 70845 | 0 | M22-244b3.1.1.1 | 2.5 | − |
| MDA-MB-231-MFP-XCL | 58624 | 0 | M22-244b3.1.1.1 | 2.5 | + |
| AG-B1 | 61668 | 681 | M22-244b3.1.1.1 | 5.0 | 3+ |
| AG-B11 | 68618 | 391 | M22-244b3.1.1.1 | 5.0 | 2+ |
| AG-Br29 | 71838 | 76 | M22-244b3.1.1.1 | 5.0 | 3+ |
| AG-OV35 | 67431 | 45 | M22-244b3.1.1.1 | 5.0 | 3+ |
| AG-Panc3 | 62103 | 12 | M22-244b3.1.1.1 | 5.0 | 3+ |
| AG-C6 | 61674 | 6 | M22-244b3.1.1.1 | 5.0 | + |
| AG-K24 | 65766 | 0.4 | M22-244b3.1.1.1 | 5.0 | 3+ |
| AG-Mel10 | 70845 | 0 | M22-244b3.1.1.1 | 5.0 | − |
| MDA-MB-231-MFP-XCL | 58624 | 0 | M22-244b3.1.1.1 | 5.0 | + |
| AG-B1 | 61668 | 681 | M22-244b3.1.1.1 | 7.5 | 3+ |
| AG-B11 | 68618 | 391 | M22-244b3.1.1.1 | 7.5 | 2+ |
| AG-Br29 | 71838 | 76 | M22-244b3.1.1.1 | 7.5 | 3+ |
| AG-OV35 | 67431 | 45 | M22-244b3.1.1.1 | 7.5 | 3+ |
| AG-Panc3 | 62103 | 12 | M22-244b3.1.1.1 | 7.5 | 3+ |
| AG-C6 | 61674 | 6 | M22-244b3.1.1.1 | 7.5 | + |
| AG-K24 | 65766 | 0.4 | M22-244b3.1.1.1 | 7.5 | 3+ |
| AG-Mel10 | 70845 | 0 | M22-244b3.1.1.1 | 7.5 | − |
| MDA-MB-231-MFP-XCL | 58624 | 0 | M22-244b3.1.1.1 | 7.5 | + |
| AG-B1 | 61668 | 681 | M22-321b41.1 | 2.5 | 3+ |
| AG-B11 | 68618 | 391 | M22-321b41.1 | 2.5 | 3+ |
| AG-Br29 | 71838 | 76 | M22-321b41.1 | 2.5 | 2+ |
| AG-OV35 | 67431 | 45 | M22-321b41.1 | 2.5 | 3+ |
| AG-Panc3 | 62103 | 12 | M22-321b41.1 | 2.5 | 3+ |
| AG-C6 | 61674 | 6 | M22-321b41.1 | 2.5 | + |
| AG-K24 | 65766 | 0.4 | M22-321b41.1 | 2.5 | − |
| AG-Mel10 | 70845 | 0 | M22-321b41.1 | 2.5 | − |
| MDA-MB-231-MFP-XCL | 58624 | 0 | M22-321b41.1 | 2.5 | − |
| AG-B1 | 61668 | 681 | M22-321b41.1 | 5.0 | 3+ |
| AG-B11 | 68618 | 391 | M22-321b41.1 | 5.0 | 3+ |
| AG-Br29 | 71838 | 76 | M22-321b41.1 | 5.0 | 2+ |
| AG-OV35 | 67431 | 45 | M22-321b41.1 | 5.0 | 3+ |
| AG-Panc3 | 62103 | 12 | M22-321b41.1 | 5.0 | 3+ |
| AG-C6 | 61674 | 6 | M22-321b41.1 | 5.0 | + |
| AG-K24 | 65766 | 0.4 | M22-321b41.1 | 5.0 | − |
| AG-Mel10 | 70845 | 0 | M22-321b41.1 | 5.0 | − |
| MDA-MB-231-MFP-XCL | 58624 | 0 | M22-321b41.1 | 5.0 | + |
| AG-B1 | 61668 | 681 | M22-321b41.1 | 7.5 | 3+ |
| AG-B11 | 68618 | 391 | M22-321b41.1 | 7.5 | 3+ |
| AG-Br29 | 71838 | 76 | M22-321b41.1 | 7.5 | 2+ |
| AG-OV35 | 67431 | 45 | M22-321b41.1 | 7.5 | 3+ |
| AG-Panc3 | 62103 | 12 | M22-321b41.1 | 7.5 | 3+ |
| AG-C6 | 61674 | 6 | M22-321b41.1 | 7.5 | + |
| AG-K24 | 65766 | 0.4 | M22-321b41.1 | 7.5 | + |
| AG-Mel10 | 70845 | 0 | M22-321b41.1 | 7.5 | − |
| MDA-MB-231-MFP-XCL | 58624 | 0 | M22-321b41.1 | 7.5 | + |

Figure 3:
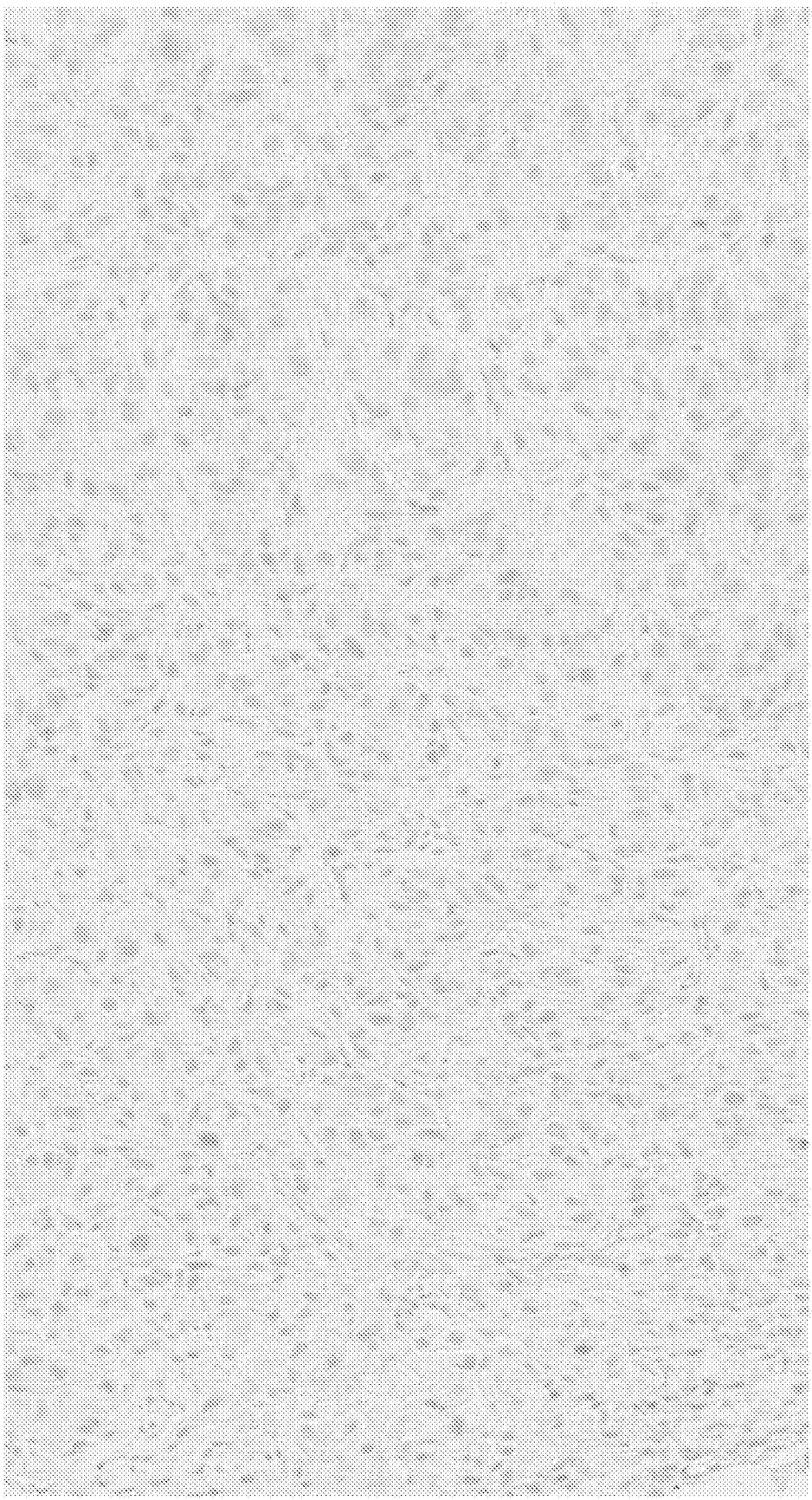
FIG. 3 depicts the result of an experiment showing all cells did not stain in an IHC staining assay of Nectin-4 mRNA-Negative AG-K24 xenograft with 2.5 µg/mL M22-321b41.1.
Figure 4:
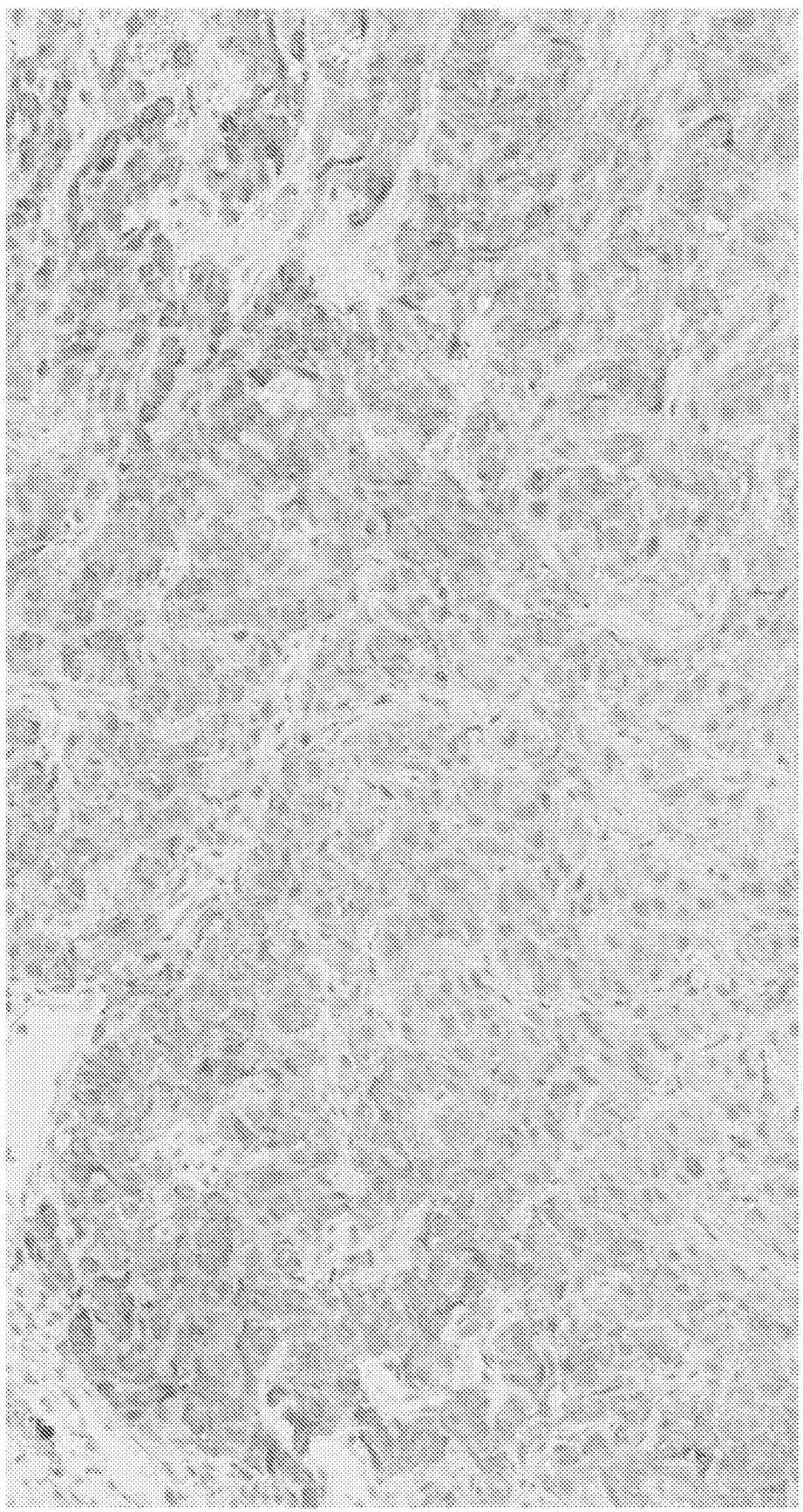
FIG. 4 depicts the result of an experiment showing many cells stained positively in an IHC staining assay of Nectin-4 mRNA-Negative AG-K24 xenograft with 2.5 µg/mL M22-244b3.1.1.1.
Figure 5:
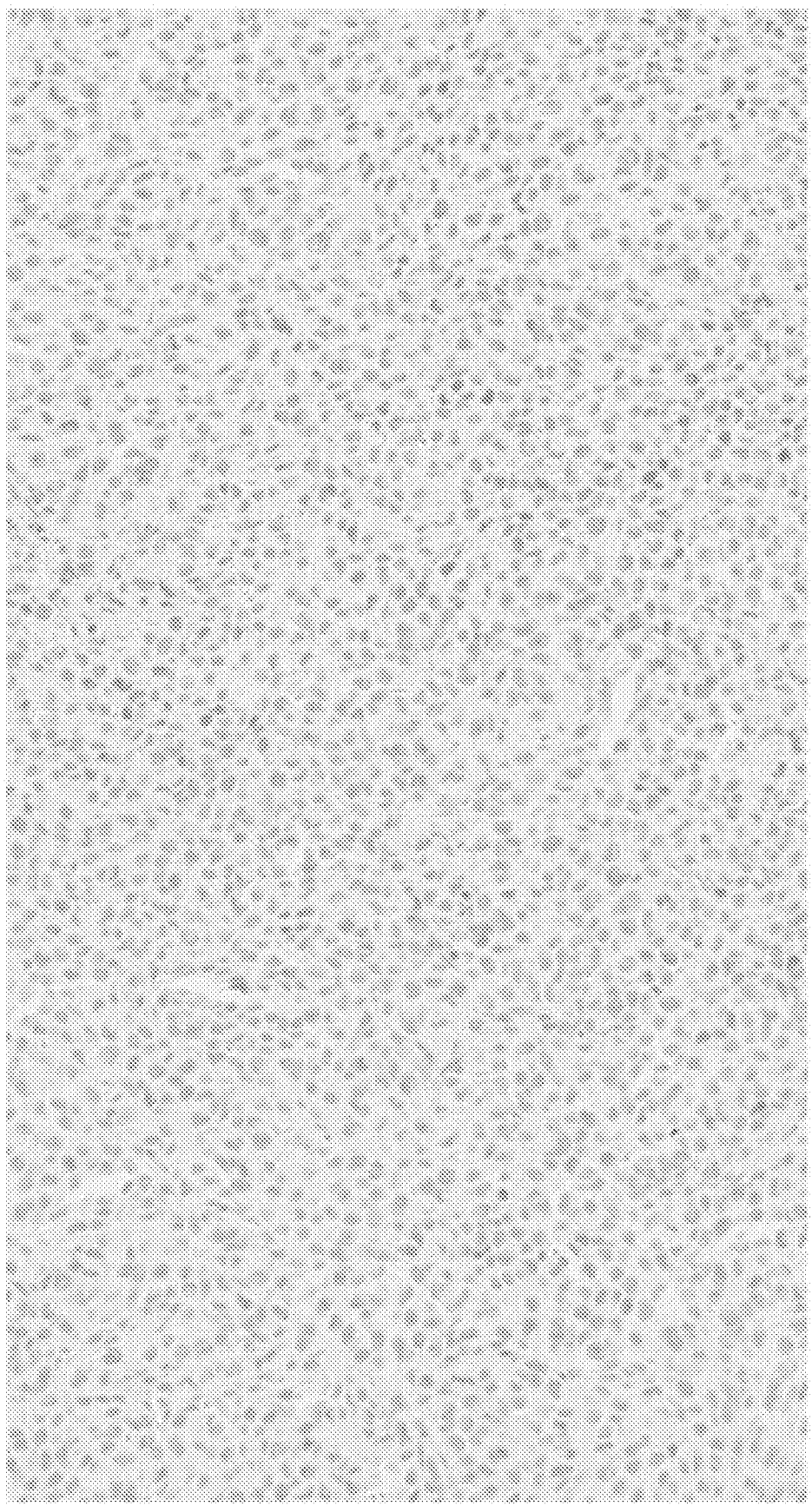
FIG. 5 depicts the result of an experiment showing all cells did not stain in an IHC staining assay of Nectin-4 mRNA-Negative MDA-MB-231-MFP-XCL xenograft with 2.5 µg/mL M22-321b41.1.
Figure 6:
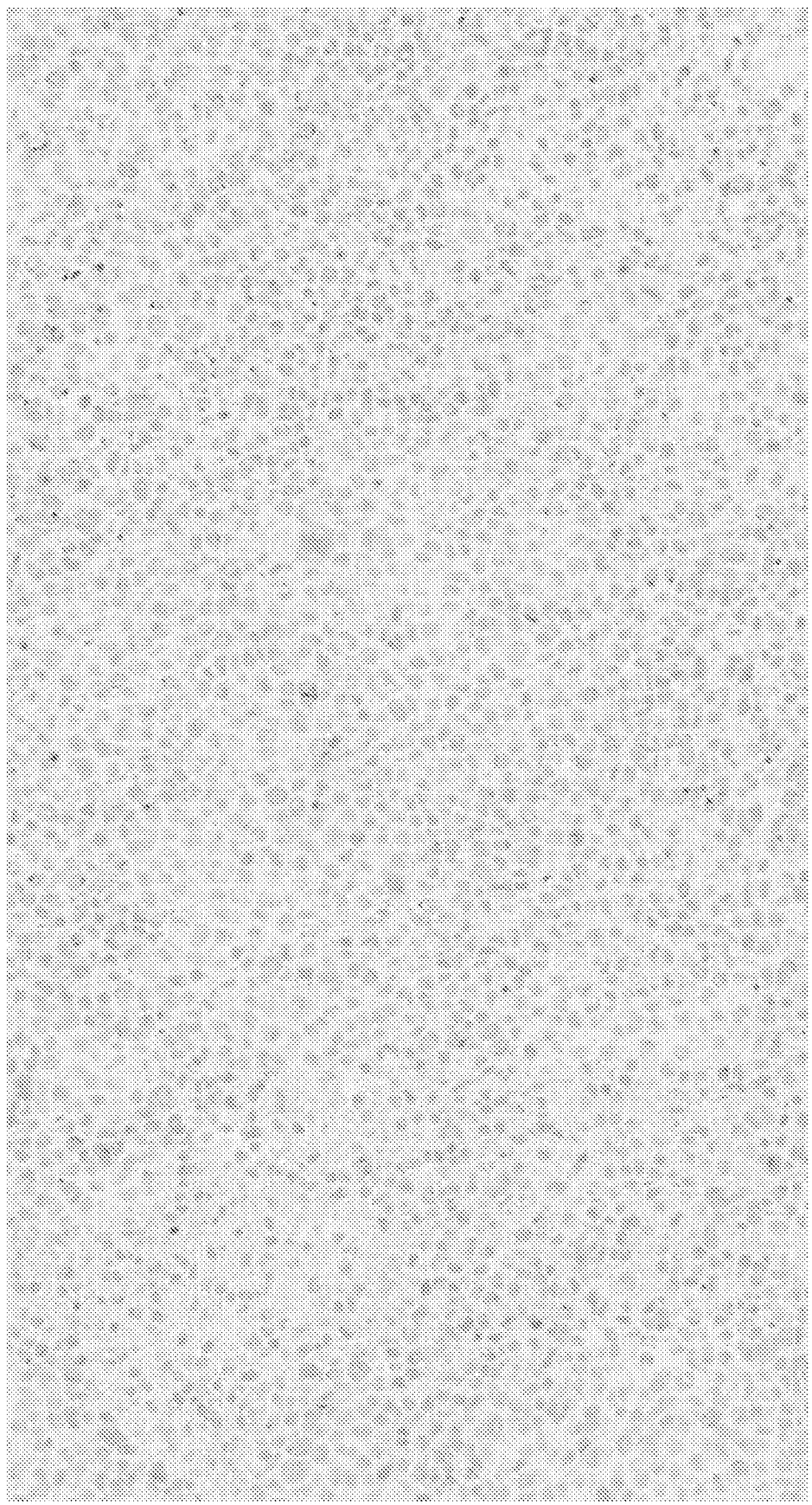
FIG. 6 depicts the result of an experiment showing many cells stained positively in an IHC staining assay of Nectin-4 mRNA-Negative MDA-MB-231-MFP-XCL xenograft with 2.5 µg/mL M22-244b3.1.1.1.
Figure 7:
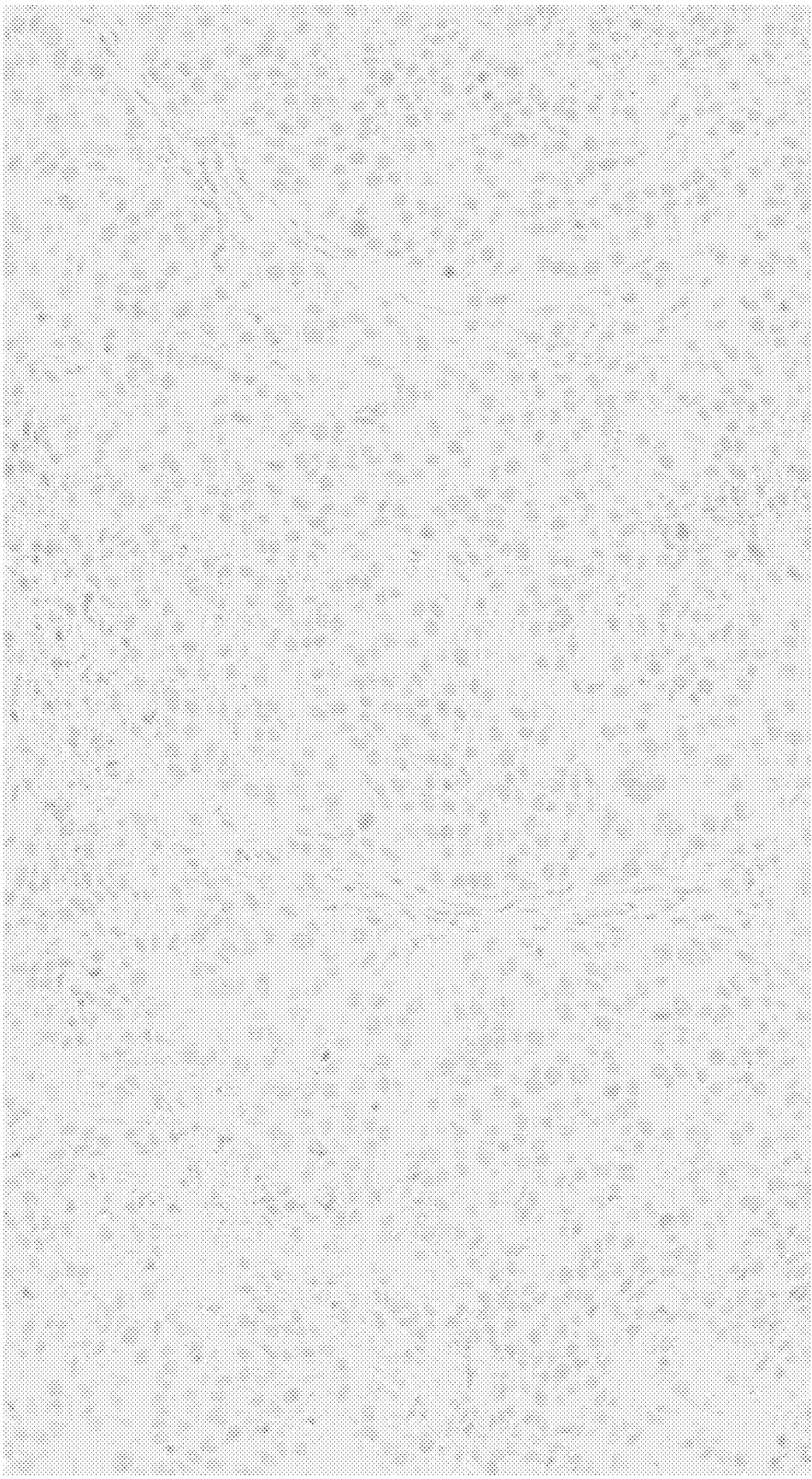
FIG. 7 depicts the result of an experiment showing all cells did not stain in an IHC staining assay of Nectin-4 mRNA-Positive AG-B1 xenograft with 2.5 µg/mL Negative Control IgG2a antibody

The M22-321b41.1 antibody at 2.5 μg/mL gave no staining in Nectin-4 mRNA-negative tissues AG-K24 and MDAMB-231-MFP-XCL (FIG. 3 and FIG. 5); whereas M22-244b3.1.1.1 had nonspecific staining in the Nectin-4 mRNA-negative xenograft cancer cells AG-K24 (FIG. 4) and MDAMB-231-MFP-XCL (FIG. 6). There was no staining seen in sections incubated with the mouse IgG2a negative control antibody (FIG. 7). Therefore, M22-321b41.1 specifically stained tissues that express Nectin-4 mRNA and produced no staining, or produced staining as low as an isotype IgG control did, for the tissues that do not express Nectin-4 mRNA.

Figure 8:
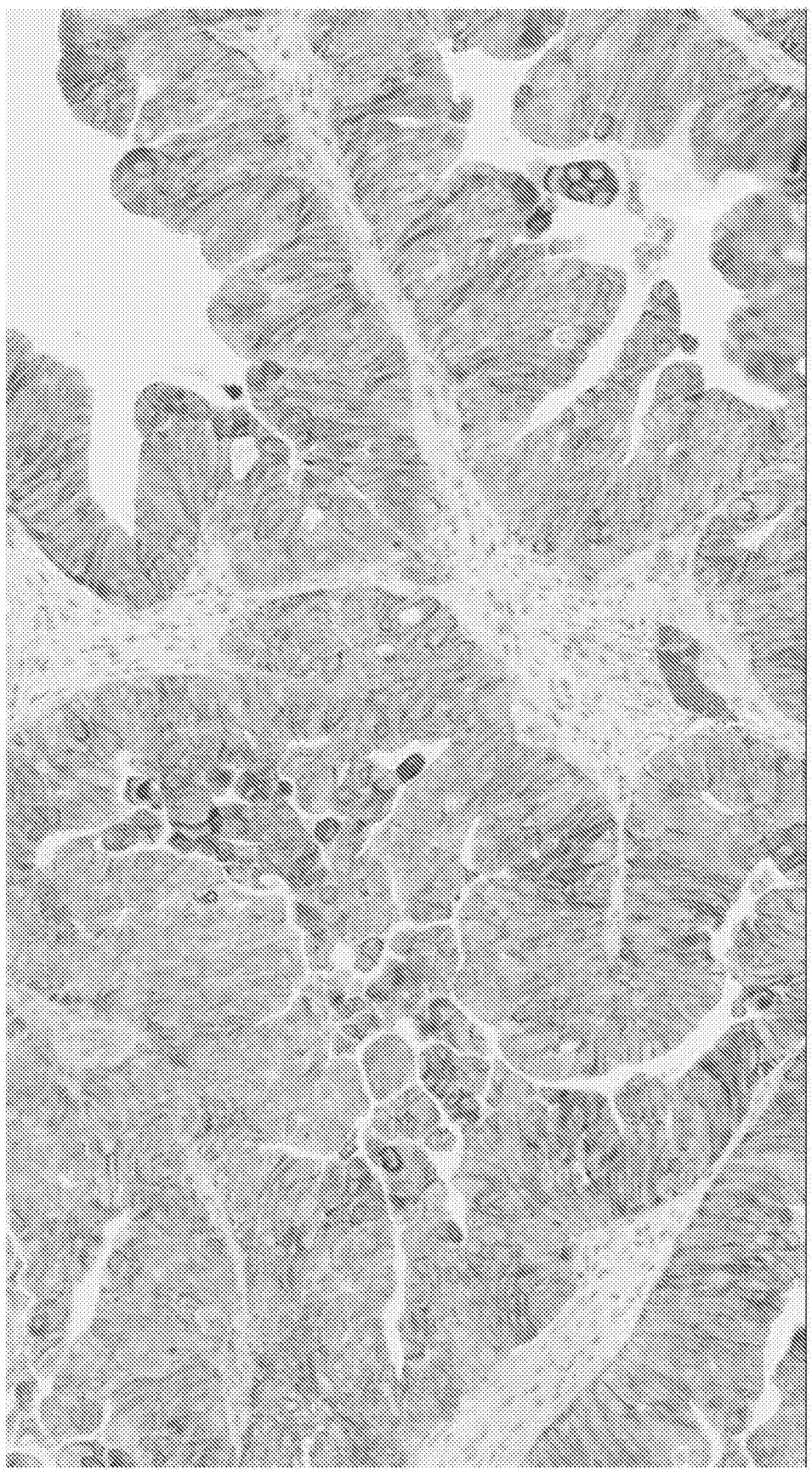
FIG. 8 depicts the result of an experiment showing all cancerous cells stained positively in an IHC staining assay of Nectin-4 mRNA-Positive AG-L16 xenograft with 2.5 µg/mL M22-321b41.1.
Figure 9:
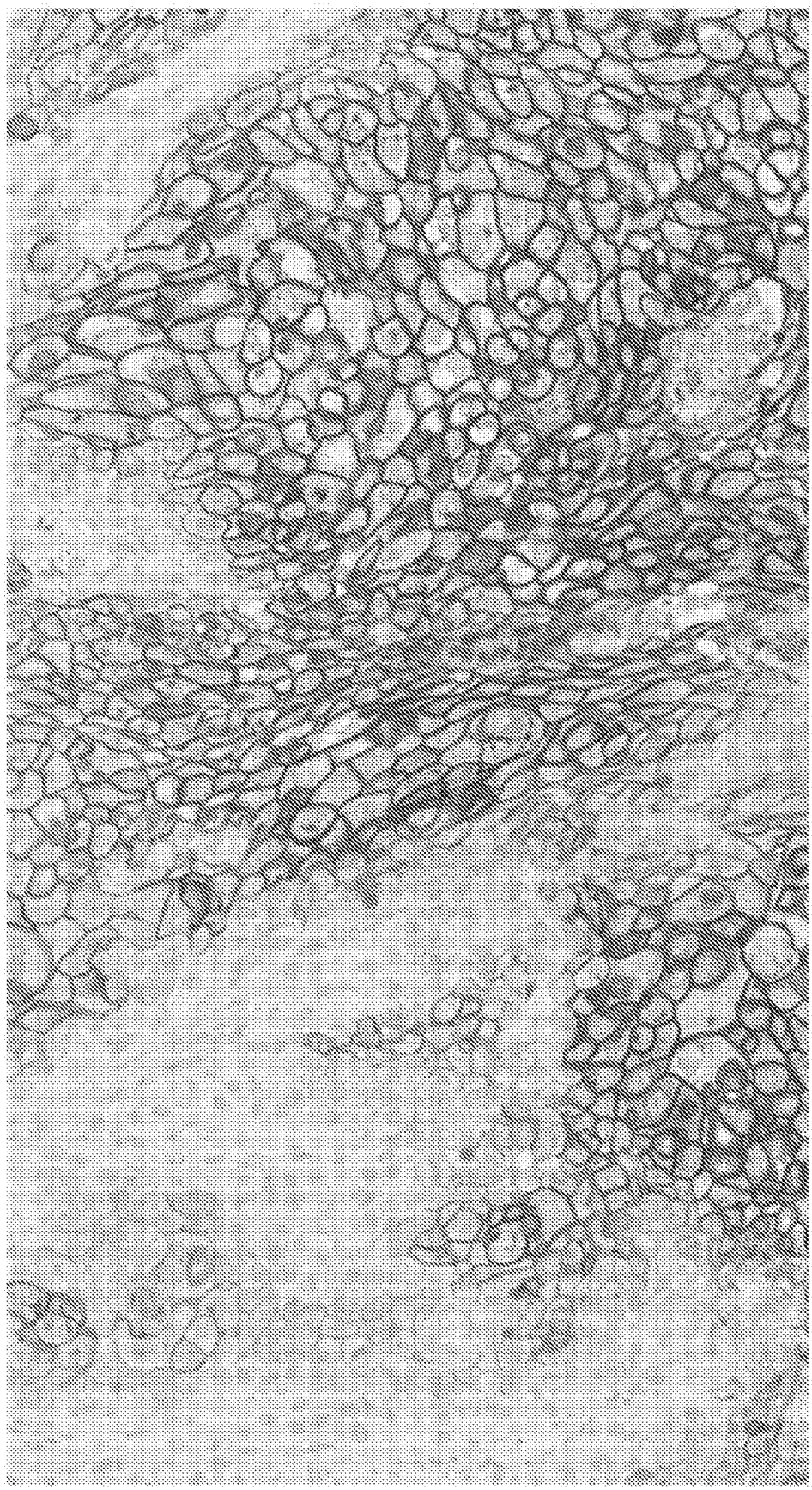
FIG. 9 depicts the result of an experiment showing the majority of cancerous cells stained positively in an IHC staining assay of Nectin-4 mRNA-Positive AG-B11 xenograft with 2.5 µg/mL M22-321b41.1.

The specificity of M22-321b41.1 was further tested in an expanded panel of positive and negative control tissues as shown in Table 8. Results showed that the antibody at 2.5 μg/mL was specific for Nectin-4 mRNA-expressing tissues and cells, including AG-B1, AG-UT5, AG-L16 (FIG. 8), AG-Br29, AG-B11 (FIG. 9), AG-OV35, AG-Panc3, AG-C16, AG-C6, Rat1(E)-Nectin-4 and T47D. Results also showed that the antibody was negative for tissues and cells that did not express Nectin-4 mRNA, including AG-K24 (FIG. 3), AG-Mel10, MDA-MB-231-MFPXCL (FIG. 5), AG-Mel5, AG-K31, CALU-1, MDA-MB-231, UG-K3, Rat1(E)-neo, Rat1(E)-Nectin-1, Rat1(E)-Nectin-2, Rat1(E)-Nectin-3, JMSU-1, Hep3B and ACHN. These findings demonstrated that M22-321b41.1 was specific for Nectin-4 in an IHC assay, because, for all tissues and cells tested here, M22-321b41.1 positively stained tissues and cells that expressed Nectin-4 mRNA and stained negatively with those that did not. (Table 8 and Table 9).

TABLE 8

Summary of the Nectin-4 Expression in an Expanded Panel of FFPE Samples using M22-321b41.1 at 2.5 µg/mL

| Sample | ID Number | Nectin-4 mRNA (qPCR) | Score (M22-321b41.1 staining) |
|---|---|---|---|
| Rat1(E) Neo | C974 | negative | — |
| Rat1(E) Nectin1 | C975 | negative | — |
| Rat1(E) Nectin2 | C976 | negative | — |
| Rat1(E) Nectin3 | C977 | negative | — |
| Rat1(E) Nectin4 | C978 | positive | 3 |
| T47D | C1035 | positive | 3 |
| MDA-MB-231 | C1033 | negative | — |
| JMSU-1 | C979 | negative | — |
| Hep3B | C951 | negative | — |
| ACHN | C955 | negative | — |
| AG-B1 | 61668 | 681 | 3 |
| AG-B11 | 68618 | 391 | 3 |
| AG-B10 | 68687 | 374 | 3 |
| AG-UT5 | 71078 | 188 | 2 |
| AG-L16 | 62092 | 105 | 3 |
| AG-Br29 | 71838 | 76 | 2 |
| AG-OV35 | 67431 | 45 | 3 |
| AG-Panc3 | 62103 | 12 | 3 |
| AG-C16 | 66746 | 7 | 1 |
| AG-C6 | 61674 | 6 | 1 |
| AG-K24 | 65766 | 0.4 | — |
| AG-Mel10 | 70845 | 0 | — |
| MDA-MB-231-MFP-XCL | 58624 | 0 | — |
| MDA-MB-231 | 58480 | 0 | — |
| AG-Mel5 | 57775 | 0 | — |
| AG-K31 | 600-B681 | 0 | — |

TABLE 9

M22-244b3.1.1.1 Staining Results from the Expanded Panel

| Xenograft | Mouse Number | Nectin-4 mRNA (qPCR) | Primary Antibody | Conc (µm/mL) | Staining Result |
|---|---|---|---|---|---|
| AG-B1 | 61668 | 681 | M22-321b41.1 | 2.5 | 3+ |
| AG-B11 | 68618 | 391 | M22-321b41.1 | 2.5 | 3+ |
| AG-Br29 | 71838 | 76 | M22-321b41.1 | 2.5 | 2+ |
| AG-OV35 | 67431 | 45 | M22-321b41.1 | 2.5 | 3+ |
| AG-Panc3 | 62103 | 12 | M22-321b41.1 | 2.5 | 3+ |
| AG-C6 | 61674 | 6 | M22-321b41.1 | 2.5 | + |
| AG-K24 | 65766 | 0.4 | M22-321b41.1 | 2.5 | – |
| AG-Mel10 | 70845 | 0 | M22-321b41.1 | 2.5 | – |
| MDA-MB-231-MFP-XCL | 58624 | 0 | M22-321b41.1 | 2.5 | – |
| AG-B1 | 61668 | 681 | M22-321b41.1 | 5.0 | 3+ |
| AG-B11 | 68618 | 391 | M22-321b41.1 | 5.0 | 3+ |
| AG-Br29 | 71838 | 76 | M22-321b41.1 | 5.0 | 2+ |
| AG-OV35 | 67431 | 45 | M22-321b41.1 | 5.0 | 3+ |
| AG-Panc3 | 62103 | 12 | M22-321b41.1 | 5.0 | 3+ |
| AG-C6 | 61674 | 6 | M22-321b41.1 | 5.0 | + |
| AG-K24 | 65766 | 0.4 | M22-321b41.1 | 5.0 | – |
| AG-Mel10 | 70845 | 0 | M22-321b41.1 | 5.0 | – |
| MDA-MB-231-MFP-XCL | 58624 | 0 | M22-321b41.1 | 5.0 | + |
| AG-B1 | 61668 | 681 | M22-321b41.1 | 7.5 | 3+ |
| AG-B11 | 68618 | 391 | M22-321b41.1 | 7.5 | 3+ |
| AG-Br29 | 71838 | 76 | M22-321b41.1 | 7.5 | 2+ |
| AG-OV35 | 67431 | 45 | M22-321b41.1 | 7.5 | 3+ |
| AG-Panc3 | 62103 | 12 | M22-321b41.1 | 7.5 | 3+ |
| AG-C6 | 61674 | 6 | M22-321b41.1 | 7.5 | + |
| AG-K24 | 65766 | 0.4 | M22-321b41.1 | 7.5 | + |
| AG-Mel10 | 70845 | 0 | M22-321b41.1 | 7.5 | – |
| MDA-MB-231-A/FP-XCL | 58624 | 0 | M22-321b41.1 | 7.5 | + |
| Rat1(E) Neo | C974 | negative | M22-321b41.1 | 2.5 | – |
| Rat1(E) Nectin1 | C975 | negative | M22-321b41.1 | 2.5 | – |
| Rat1(E) Nectin2 | C976 | negative | M22-321b41.1 | 2.5 | – |
| Rat1(E) Nectin3 | C977 | negative | M22-321b41.1 | 2.5 | – |
| Rat1(E) Nectin4 | C978 | negative | M22-321b41.1 | 2.5 | 3+ |
| T47D | C1035 | negative | M22-321b41.1 | 2.5 | 3+ |
| MDA-MB-231 | C1033 | negative | M22-321b41.1 | 2.5 | – |
| JMSU-1 | C979 | negative | M22-321b41.1 | 2.5 | – |
| Hep3B | C951 | negative | M22-321b41.1 | 2.5 | – |
| ACHN | C955 | negative | M22-321b41.1 | 2.5 | – |
| AG-B1 | 61668 | 681 | M22-321b41.1 | 2.5 | 3+ |
| AG-B11 | 68618 | 391 | M22-321b41.1 | 2.5 | 3+ |
| AG-B10 | 68687 | 374 | M22-321b41.1 | 2.5 | 3+ |
| AG-UT5 | 71078 | 188 | M22-321b41.1 | 2.5 | 2+ |
| AG-L16 | 62092 | 105 | M22-321b41.1 | 2.5 | 3+ |
| AG-Br29 | 71838 | 76 | M22-321b41.1 | 2.5 | 2+ |
| AG-OV35 | 67431 | 45 | M22-321b41.1 | 2.5 | 3+ |
| AG-Panc3 | 62103 | 12 | M22-321b41.1 | 2.5 | 3+ |
| AG-C16 | 66746 | 7 | M22-321b41.1 | 2.5 | + |
| AG-C6 | 61674 | 6 | M22-321b41.1 | 2.5 | + |
| AG-K24 | 65766 | 0.4 | M22-321b41.1 | 2.5 | – |
| AG-Mel10 | 70845 | 0 | M22-321b41.1 | 2.5 | – |
| MDA-MB-231-MFP-XCL | 58624 | 0 | M22-321b41.1 | 2.5 | – |
| MDA-MB-231 | 58480 | 0 | M22-321b41.1 | 2.5 | – |
| AG-Mel5 | 57775 | 0 | M22-321b41.1 | 2.5 | – |
| AG-K31 | 600-B681 | 0 | M22-321b41.1 | 2.5 | – |
| CALU-1 | 72902 | 0 | M22-321b41.1 | 2.5 | – |
| UG-K3 | 74323 | 0 | M22-321b41.1 | 2.5 | – |

The anti-Nectin-4 antibodies generated and screened as described above were further compared with other commercial anti-Nectin-4 antibodies in an IHC assay. For example, Nectin-4/PVRL4 antibody (referred to as "Novus PVRL4 antibody") from Novus Biologicals (catalog number NBP1-82829), a rabbit polyclonal anti-Nectin-4 antibody, was obtained and tested for its ability to specifically stain Nectin-4 in an IHC assay in various xenograft tissues in which the Nectin-4 mRNA levels have been determined by qPCR. In experiments where the Novus PVRL4 Antibody was titrated at 2 µg/ml, 1.5 µg/ml, 1 µg/ml, and 0.5 µg/ml, the Novus PVRL4 antibody produced specific Nectin-4 staining weaker than that produced by M22-244b3.1.1.1.1 antibody and produced non-specific staining at all concentrations in MDA-MB-231 xeno that expressed no Nectin-4 mRNA, as shown in Table 10. Thus the Novus PVRL4 antibody was non-specific for Nectin-4.

TABLE 10

Staining results of Novus PVRL4 antibody at different concentrations

| Tissue | Mouse# | RNA | IHC Results |
|---|---|---|---|
| MDA-MB-231-MFP-XCL | 58624 | 0 | scattered positive cells even at 0.5 ug/ml. |
| AG-B10 P8 | 64069 | 286 | patchy mod-strong at 2 µg/ml. Weaker at lower concentrations |
| AG-Mel10 P5 | 72088 | 0 | Tumor negative with weak cytoplasmic background at 1.5 ug/ml |
| AG-OV20 P7 | 72260 | 67 | weak cytoplasmic throughout with small foci of moderate positive cells |
| AG-C18 P9 | 67921 | 3 | patchy weak to negative at 2 µg/ml. |
| AG-C16 P4 | 68679 | 50 | weak-modest, patchy, apical at 2 µg/ml |

The Novus PVRL4 antibody was further tested in an IHC assay against a wider panel of tissues in which the Nectin-4 mRNA levels had been determined by qPCR. Background cytoplasmic staining was observed in majority of xenografts tested, regardless of the Nectin-4 mRNA levels, as shown in Table 11.

TABLE 11

Staining results of Novus PVRL4 antibody in a wider panel of xenograft tissues

| Tissue | Mouse# | RNA | Novus PVRL4 (NBP1-82829) 2 µg/ml |
|---|---|---|---|
| AG-B10 P8 | 64069 | 286 | Strong Patchy Membranous |
| AG-Mel10 P5 | 72088 | 0 | negative to weak background |
| AG-OV20 P7 | 72260 | 67 | dirty cytoplasmic |
| AG-Br8 P3 | 59161 | 41 | moderate-strong membrane on one half of tumor |
| AG-K24 P3 | 64812 | 1 | negative to weak background |
| MDA-MB-231-MFP-XCL | 58624 | 0 | weak-moderate background? |
| AG-K9 P17 | 52376 | 0.1 | weak positive background? |
| AG-OV23 P3 | 55635 | 2 | moderate patchy membrane/cytoplasm |
| AG-C18 P9 | 67921 | 3 | weak-moderate positive, patchy |
| AG-C16 P4 | 68679 | 50 | patchy moderate |
| AG-Br12 P2 | 62109 | 1024 | strong membrane throughout |

As the Novus PVRL4 antibody is an exhaustible rabbit polyclonal antibody with potential lot-to-lot variability, a different rabbit polyclonal anti-Nectin-4 antibody, PA5-30837 from ThermoFischer Scientific (as "Thermo PVRL4 antibody"), was obtained, tested, and compared in an IHC assay in three different xenograft tissues in which Nectin-4 mRNA levels had been determined by qPCR. The three xenograft tissues tested included AG-B1(+) PS26 with Nectin-4 mRNA level at 478, AG-OV35P3 with Nectin-4 mRNA level at 78, and AG-Mel5 P17 expressing no Nectin-4 mRNA. The Thermo PVRL4 antibody produced weak/moderate IHC staining in AG-B1 and negative IHC staining in AG-OV35.

Therefore, neither the Novus PVRL4 antibody nor the Thermo PVRL4 antibody was as specific to Nectin-4 in an IHC assay as the M22-244b3.1.1.1.1 or M22-321b41.1. antibodies generated and screened herein.

Two other commercial antibodies (a monoclonal mouse anti-Nectin-4 antibody MAB2659 and a goat polyclonal anti-Nectin-4 antibody AF2659), both from R&D Systems, were also obtained, and tested in an IHC assay in three different xenograft tissues in which Nectin-4 mRNA levels were determined by qPCR. The three xenograft tissues tested included AG-B1(+) PS26 with Nectin-4 mRNA level at 478, AG-OV35P3 with Nectin-4 mRNA level at 78, and AG-Mel5 P17 with no Nectin-4 mRNA. The MAB2659 antibody when used at 1 µg/ml or 5 µg/ml produced dirty punctate/cytoplasmic like staining at periphery of tumor in AG-B1 and AG-OV35. The goat polyclonal anti-Nectin-4 antibody AF2659 produced strong membranous staining with background stromal staining in AG-B1 and AG-OV35 at 5 µg/ml but weak staining at 1 µg/ml. Therefore the AF2659 antibody was further evaluated at 2.5 µm/ml in the other tissues. The AF2659 antibody, however, produced background staining in MDA-MB-231 xenografts that do not express Nectin-4 mRNA. Therefore, neither MAB2659 antibody nor AF2659 antibody was as specific as the M22-321b41.1 antibody generated and screened herein.

Example 6: Functional Assays: Immunohistochemistry Staining of Primary Tissues Antibodies, e.g. anti-Nectin-4 M22-321b41.1, generated, screened, expressed, and purified, for example, as described in Examples herein, were further evaluated for their ability to specifically stain primary human tissues expressing Nectin-4 in an IHC assay.

The IHC assay was performed, for example, using an indirect IHC technique. The indirect IHC method utilized two antibodies for the detection of tissue antigens. First, an unconjugated primary antibody was applied to the tissue (first layer), which reacted with the tissue antigen. Next, an enzyme-labeled secondary antibody was applied, which was directed against the IgG of the animal species in which the primary antibody has been raised (second layer). The secondary antibody reacted with the primary antibody, followed by substrate-chromogen application. The second-layer antibody was labeled with an enzyme peroxidase, which reacted with the chromogen 3, 3'-diaminobenzidine (DAB) to produce brown precipitate at the reaction site. This method is sensitive and versatile due to the potential signal amplification through several secondary antibody reactions with different antigenic sites on the primary antibody.

As an example to further increase the sensitivity of the test, a labeled chain polymer-conjugated secondary antibody was used. The polymer technology utilized an HRP enzyme-labeled inert "spine" molecule of dextran to which up to 10 molecules of secondary antibodies were attached, making the system even more sensitive.

The specimen was then counterstained to identify cellular and subcellular elements.

6.A. Staining Procedure

The IHC assay was performed according to the following exemplary protocol. Briefly, the tissue samples were fixed, processed and embedded into paraffin wax, and prepared as tissue sections. The slides were then incubated in an oven at 60±5° C. for 1-2 hours, removed from the oven, and allowed to cool to room temperature (RT) before proceeding. After routine deparaffinization and rehydration of the tissue samples, antigen retrieval was performed to reverse protein cross-linking that occurred following formalin fixation. Antigen retrieval was achieved through either proteolytic digestion of the tissues in protease solutions, or through application of heat to the tissue sections in an aqueous medium, commonly referred to as an HIER procedure. For this assay, Epitope Retrieval 2 (ER2, an EDTA-based buffer at pH 8.9-9.1) on the Leica automated platform for 20 minutes at 100° C. was used.

The staining was programmed to be run on the Bond instruments using Leica Bond Autostainers at RT unless specified otherwise. Briefly, the following steps were programmed onto the Leica Bond autostainers as the staining protocol: (1) an Epitope Retrieval 2 procedure (ER2): 20 minutes at 100° C. (Bond Epitope Retrieval Solution 2 (Leica), Part #AR9640); (2) 3×Bond Wash: 0 min (Bond Wash Solution (Leica), Part #AR9590); (3) Marker: 15 minutes (staining with monoclonal mouse anti-Nectin-4 antibody M22-321b41.1 or negative control mouse IgG2a (BD Biosciences) Part #550339, in Bond Primary Antibody Diluent (Leica), Part #AR9352); (4) 3×Bond Wash: 0 minutes (Bond Wash Solution (Leica), Part #AR9590); (5) Post Primary: 8 minutes (Rabbit anti mouse IgG2a); (6) 3×Bond Wash: 2 minutes (Bond Wash Solution (Leica), Part #AR9590); (7) Polymer: 8 minutes (Anti-rabbit Poly-HRP-IgG from Bond Polymer Refine Detection (Leica), Part #D59800); (8) 2×Bond Wash: 0 min, 2 min; (9) 1× DI water: 0 minutes; (10) Peroxide Block: 5 minutes (3-4% hydrogen peroxide) and 3×Bond Wash: 0 min; (11) 2×DI water: 0 minutes; (12) Mixed DAB refine: 0 minutes (66 mM 3,3-Diaminobenzidine Tetrahydrochloride and ≤0.1% Hydrogen Peroxide from Bond Polymer Refine Detection (Leica), Part #D59800); (13) Mixed DAB refine: 10 minutes (66 mM 3,3-Diaminobenzidine Tetrahydrochloride and ≤0.1% Hydrogen Peroxide from Bond Polymer Refine Detection (Leica), Part #D59800); (14) 3×DI water: 0 minutes; (15) Hematoxylin: 15 minutes (<0.1% Hematoxylin from Bond Polymer Refine Detection (Leica), Part #D59800); (16) 1×DI water: 0 minutes; (17) 1× Bond Wash: 0 minutes; (18) 1×DI water: 0 minutes. As indicated in the procedure, a negative reagent control mouse IgG2a from BD Biosciences was used for each specimen tested to evaluate the presence of non-specific (background) staining. The presence of background staining was also a criterion for acceptance/rejection of a particular assay run.

6.B Tissue Samples

Positive and negative control specimens were utilized to validate and control all steps of the IHC analysis. For this assay, mouse human tumor xenografts with variable levels of Nectin-4 expression were used as controls.

Example 5 were prepared and tested with their matched negative control tissue sections.

Anti-Nectin-4 antibody M22-321b41.1 and its corresponding negative control antibody were applied to the tissue sections in accordance with the appropriate IHC protocol for paraffin-embedded specimens, as stated in Examples 4 and 5. The results were evaluated and compared by the study pathologists using light microscopy. The study pathologists determined the optimal titer (the optimal antibody concentration) as the lowest titer (the lowest concentration of the antibody) that yielded the highest staining intensity without significant background staining. In this Example, as shown by Table 12, an antibody concentration of 2.5 µg/ml was selected and used in subsequent IHC assays.

TABLE 12

Determine the Optimal Antibody Concentration for Anti-Nectin-4 M22-321b41.1.

| Specimen # | Run ID | Antibody Concentration µg/ml | Background | % Positive | Target Staining Intensity | Stromal Staining | Sub | Morph- ology | Comments |
|---|---|---|---|---|---|---|---|---|---|
| X14-126 | 0VE7 | 3.75 | 0 | 0 | NA | 0 | NA | A | Small Fragment of positive tissue noted, likely a contaminant |
| X14-126 | 0VE8 | 2.5 | 0 | 0 | NA | 0 | NA | A | Same as above |
| X14-126 | 0VE9 | 1.25 | 0 | 0 | NA | 0 | NA | A | Same as above |
| X14-33 | 0VDZ | 3.75 | 0 | 25 | 1-3+ | 0 | M, C, Ap | A | |
| X14-33 | 0VE0 | 2.5 | 0 | 25 | 1-3+ | 0 | M, C, Ap | A | |
| X14-33 | 0VE1 | 1.25 | 0 | 25 | 1-3+ | 0 | M, C, Ap | A | |
| X14-139 | 0VDS | 3.75 | 0 | 90 | 1-3+ | 0 | M, C, Ap | A | |
| X14-139 | 0VDT | 2.5 | 0 | 90 | 1-3+ | 0 | M, C, Ap | A | |
| X14-139 | 0VDU | 1.25 | 0 | 80 | 1-3+ | 0 | M, C, Ap | A | |
| X14-43 | 0VDK | 3.75 | 0 | 100 | 3++ | 1-3+ | M, C | A | Scattered IG |
| X14-43 | 0VDL | 2.5 | 0 | 100 | 3++ | 1-2+ | M, C | A | |
| X14-43 | 0VDM | 1.25 | 0 | 100 | 3+ | 1-2+ | M, C | A | 2 + F |

Formalin-fixed, paraffin-embedded human tissue specimens were obtained as remnant material from surgery or autopsy from Institutional Review Board-approved sources, for example government repositories (e.g., Cooperative Human Tissue Network), academic collaborations (e.g., UCLA, UC Irvine), and commercial sources, including for example human normal urothelial and transitional cell carcinoma (BL802) and normal (FDA999) tissue microarray (TMA), Biomax USA. Tissue samples were tested for Nectin-4 expression using protocol described in Example 6.A. Four mouse human tumor xenografts which include one negative (X14-126), one weakly positive (X14-33), one moderately positive (X14-139) and one strongly positive (X14-43) for Nectin-4 expression, were also tested.

6.C Titration of Staining Concentration of Anti-Nectin-4 Antibodies

The optimal primary antibody titer was determined by performing titration analysis on the xenografts tissue sections, for example, using the protocol described in Examples 4 and 5. The titration analysis for paraffin-embedded specimens was performed in an effort to determine the optimal antibody concentration for the IHC assays. In order to perform titration analysis, 2-fold serial dilutions bracketing the optimal concentration (2.5 µg/ml) as determined in 6.D. Assessment of the Nectin-4 IHC Staining Assessment of IHC staining was performed by board-certified pathologists. Staining intensity was assessed and reported as 0 (negative), 1+ (weak), 2+ (moderate), and 3+ (strong). The approximate percentage of cells staining at each intensity level or positively stained cells overall was assessed and reported from 0 to 100%.

For comparison of staining among tissues, the various parameters of Nectin-4 staining assessment were either directly compared or the results of Nectin-4 staining were further processed, for example, calculated as an H-score that considers both staining intensity and the percentage of cells stained at a specific range of intensities. For example, an H-score was calculated by summing the products of the percentage of cells stained at a given staining intensity (0-100) and the staining intensity (0-3). For example: a specimen with 10% of cells staining 3+, 30% of cells staining 2+, 20% of cells staining 1+, and 40% of cells unstained would have an H-score of (3×10)+(2×30)+(1×20)+(0×40)=110.

The Coefficient of Variation (CV) was used to assess the intra-run variation or precision in the H-score. The intra-run precision of the assay's performance was determined from five separate runs, utilizing three positive xenograft specimens. Qualitatively, intra-run precision is considered acceptable by a generally consistent staining pattern of each tissue tested in three separate runs. The CV was calculated as follows:

CV=Standard Deviation/Mean×100

For example, CV less than or equal to 35% was considered acceptable.

As shown in Table 13 for the intra-run precision assessment, the patterns (combinations of 3+, 2+, 1+) of staining intensity were consistent for each tissue over the five replicates. Furthermore, the CVs for all tissues were less than 35%, which is within the exemplary acceptable range. Therefore, M22-321b41.1 provided precision for detecting Nectin-4 in the Nectin-4 IHC assay.

The between-run reproducibility of the assay's performance was determined from five separate runs, utilizing the same xenograft specimens as for the precision assay. Qualitatively, between-run precision was considered acceptable by a generally consistent staining pattern of each tissue tested in five separate runs. As shown in Table 14 for the between-run reproducibility, the patterns (combinations of 3+, 2+, 1+) of staining intensity were consistent for each tissue over the three replicates. Furthermore, the CVs for all tissues were less than 35%, which was within the exemplary acceptable range. Therefore, M22-321b41.1 provided reproducibility for detecting Nectin-4 in the Nectin-4 IHC assay.

TABLE 13

Intra-run Precision of Anti-Nectin-4 M22-321b41.1 in IHC Assays

| GENERAL SPECIMEN INFORMATION | | | | | TEST ARTICLE STAINING OF DISTINCTIVE CELLS | | | | | | | | | |
|---|---|---|---|---|---|---|---|---|---|---|---|---|---|---|
| Quest Accession # | Slide ID | Staining Date/ Instrument | Tissue (Diagnosis) | Isotype Control | % and Subcellular Localization of Cells Staining at Each Intensity | | | | | | | H- score | % Nectin-4 | OTHER Comment |
| | | | | | 3+ % | 3 + sub Tissue | 2+ % | 2 + sub | 1+ % | 1 + sub | 0% | | | |
| X14-43 | 0VH4 | 30 Jun. 2014 Bond III | Xenografts | 0 | 95 | M, C | 5 | M, C | 0 | NA | 0 | 295 | 100 | Necrotic tissue excluded |
| X14-43 | 0VH5 | 30 Jun. 2014 Bond III | Xenografts | 0 | 95 | M, C | 5 | M, C | 0 | NA | 0 | 295 | 100 | |
| X14-43 | 0VH6 | 30 Jun. 2014 Bond III | Xenografts | 0 | 98 | M, C | 2 | M, C | 0 | NA | 0 | 298 | 100 | |
| X14-43 | 0VH7 | 30 Jun. 2014 Bond III | Xenografts | 0 | 98 | M, C | 2 | M, C | 0 | NA | 0 | 298 | 100 | |
| X14-43 | 0VH8 | 30 Jun. 2014 Bond III | Xenografts | 0 | 98 | M, C | 2 | M, C | 0 | NA | 0 | 298 | 100 | |
| | | | Mean | | | | | | | | | 296.8 | 100.0 | |
| | | | STDEV | | | | | | | | | 1.6 | 0.0 | |
| | | | CV | | | | | | | | | 0.6 | 0.0 | |
| X14-139 | 0VHB | 30 Jun. 2014 Bond III | Xenografts | 0 | 40 | M, C | 45 | M, C | 10 | M, C | 5 | 220 | 95 | |
| X14-139 | 0VHC | 30 Jun. 2014 Bond III | Xenografts | 0 | 40 | M, C | 40 | M, C | 15 | M, C | 5 | 215 | 95 | |
| X14-139 | 0VHD | 30 Jun. 2014 Bond III | Xenografts | 0 | 40 | M, C | 35 | M, C | 20 | M, C | 5 | 210 | 95 | |
| X14-139 | 0VHE | 30 Jun. 2014 Bond III | Xenografts | 0 | 45 | M, C | 40 | M, C | 10 | M, C | 5 | 225 | 95 | |
| X14-139 | 0VHF | 30 Jun. 2014 Bond III | Xenografts | 0 | 45 | M, C | 40 | M, C | 10 | M, C | 5 | 225 | 95 | |
| | | | Mean | | | | | | | | | 219.0 | 95.0 | |
| | | | STDEV | | | | | | | | | 6.5 | 0.0 | |
| | | | CV | | | | | | | | | 3.0 | 0.0 | |
| X14-33 | 0VHI | 30 Jun. 2014 Bond III | Xenografts | 0 | 10 | M, C | 15 | M, C | 5 | M, C | 70 | 65 | 30 | |
| X14-33 | 0VHJ | 30 Jun. 2014 Bond III | Xenografts | 0 | 10 | M, C | 10 | M, C | 10 | M, C | 70 | 60 | 30 | |
| X14-33 | 0VHK | 30 Jun. 2014 Bond III | Xenografts | 0 | 10 | M, C | 10 | M, C | 5 | M, C | 75 | 55 | 25 | |
| X14-33 | 0VHL | 30 Jun. 2014 Bond III | Xenografts | 0 | 8 | M, C | 12 | M, C | 5 | M, C | 75 | 53 | 25 | |
| X14-33 | 0VHM | 30 Jun. 2014 Bond III | Xenografts | 0 | 5 | M, C | 15 | M, C | 5 | M, C | 75 | 50 | 25 | |
| | | | Mean | | | | | | | | | 56.6 | 27.0 | |
| | | | STDEV | | | | | | | | | 5.9 | 2.7 | |
| | | | CV | | | | | | | | | 10.5 | 10.1 | |

GENERAL COMMENT/NOTE:
± = Equivocal Results
NA = Not Applicable
NS = Not Seen
c/w = Consistent With
Ca = Carcinoma

TABLE 14

Between-run Reproducibility of Anti-Nectin-4 M22-321b41.1 in IHC Assays

| GENERAL SPECIMEN INFORMATION | | | | | TEST ARTICLE STAINING OF DISTINCTIVE CELLS | | | | | | | | |
|---|---|---|---|---|---|---|---|---|---|---|---|---|---|
| | | | | | Isotype Control TISSUE | % and Subcellular Localization of Cells Staining at Each Intensity | | | | | | % Nectin-4 | |
| Quest Accession # | Reproducibility # | Run Date and Platform | Slide ID | Tissue (Diagnosis) | | 3+ % | 3 + sub | 2+ % | 2 + sub | 1+ % | 1 + sub | 0% | H-score | | Comment |
| X14-43 | #1 | 26 Jun. 2014 Bond III | 0VDL | Xenografts | 0 | 100 | M, C | 0 | NA | 0 | NA | 0 | 300 | 100 | |
| X14-43 | #2 | 30 Jun. 2014 Bond III | 0VH4 | Xenografts | 0 | 95 | M, C | 5 | M, C | 0 | NA | 0 | 295 | 100 | |
| X14-43 | #3 | 30 Jun. 2014 Bond Max | 0VHQ | Xenografts | 0 | 95 | M, C | 5 | M, C | 0 | NA | 0 | 295 | 100 | |
| X14-43 | #4 | 1 Jul. 2014 Bond Max | 0VJS | Xenografts | 0 | 100 | M, C | 0 | NA | 0 | NA | 0 | 300 | 100 | |
| X14-43 | #5 | 1 Jul. 2014 Bond III | 0VJQ | Xenografts | 0 | 98 | M, C | 2 | M, C | 0 | NA | 0 | 298 | 100 | |
| | | | | Mean | | | | | | | | | 297.6 | 100.0 | |
| | | | | STDEV | | | | | | | | | 2.5 | 0.0 | |
| | | | | CV | | | | | | | | | 0.8 | 0.0 | |
| X14-139 | #1 | 26 Jun. 2014 Bond III | 0VDT | Xenografts | 0 | 40 | M, C | 40 | M, C | 15 | M, C | 5 | 215 | 95 | Apical staining noted |
| X14-139 | #2 | 30 Jun. 2014 Bond III | 0VHB | Xenografts | 0 | 40 | M, C | 45 | M, C | 10 | M, C | 5 | 220 | 95 | |
| X14-139 | #3 | 30 Jun. 2014 Bond Max | 0VHT | Xenografts | 0 | 45 | M, C | 40 | M, C | 10 | M, C | 5 | 225 | 95 | |
| X14-139 | #4 | 1 Jul. 2014 Bond Max | 0VJX | Xenografts | 0 | 45 | M, C | 45 | M, C | 10 | M, C | 0 | 235 | 100 | |
| X14-139 | #5 | 1 Jul. 2014 Bond III | 0VJV | Xenografts | 0 | 45 | M, C | 40 | M, C | 15 | M, C | 0 | 230 | 100 | |
| | | | | Mean | | | | | | | | | 225.0 | 97.0 | |
| | | | | STDEV | | | | | | | | | 7.9 | 2.7 | |
| | | | | CV | | | | | | | | | 3.5 | 2.8 | |
| X14-33 | #1 | 26 Jun. 2014 Bond III | 0VED | Xenografts | 0 | 8 | M, C | 12 | M, C | 10 | C | 70 | 58 | 30 | Apical staining noted |
| X14-33 | #2 | 30 Jun. 2014 Bond III | 0VHI | Xenografts | 0 | 10 | M, C | 15 | M, C | 5 | M, C | 70 | 65 | 30 | |
| X14-33 | #3 | 30 Jun. 2014 Bond Max | 0VHW | Xenografts | 0 | 8 | M, C | 12 | M, C | 5 | M, C | 75 | 53 | 25 | |
| X14-33 | #4 | 1 Jul. 2014 Bond Max | 0VK3 | Xenografts | 0 | 8 | M, C | 10 | M, C | 7 | C | 75 | 51 | 25 | |
| X14-33 | #5 | 1 Jul. 2014 Bond III | 0VK0 | Xenografts | 0 | 8 | M, C | 12 | M, C | 5 | C | 75 | 53 | 25 | |
| | | | | Mean | | | | | | | | | 56.0 | 27.0 | |
| | | | | STDEV | | | | | | | | | 5.7 | 2.7 | |
| | | | | CV | | | | | | | | | 10.1 | 10.1 | |

GENERAL COMMENT/NOTE:
± = Equivocal Results
NA = Not Applicable
NS = Not Seen
c/w = Consistent With
Ap = Apical Staining
B = Basal Layer Staining
C = Cytoplasmic Staining
F = Focally Positive
H = Heterogeneous Staining
I = Inflammatory Cells
Ca = Carcinoma
M = Membrane Staining
SCC* = Squamous Cell Ca
L1 = Link 1
L2 = Link 2
N = Nuclear Staining The parameters and results provided by 6.A to 6.D is summarized in the following table 15:

TABLE 15

Exemplary Parameters, Results, and Their Ranges.

| Performance Specifications | Methods and Results |
|---|---|
| Assay Precisions: Exemplary intra-run CVs | 0.6%, 0.3%, 10.5% |
| Assay Reproducibility: Exemplary between-run CVs | 0.8%, 3.5%, 10.1% |
| Staining in Tissues | 0 = no, 1 = weak, 2 = moderate, and 3 = strong staining |
| Parameters, results, and their ranges | H-score (0-300); 0-3+, % cells stained |

6.E Sensitivity and Specificity of the Nectin-4 IHC Staining.

A Nectin-4 IHC assay was considered sensitive, for example, if it positively stained the tissues that expressed the Nectin-4 antigen. A Nectin-4 IHC assay was considered specific, for example, if differential staining was observed across various tissue types and the Nectin-4 IHC staining correlated with the known expression of the Nectin-4 antigen in the stained tissues. As the assessments of specificity and sensitivity were not mutually exclusive, an assay often provided information on both sensitivity and specificity.

The sensitivity and specificity of Nectin-4 IHC assay with M22-321b41.1 was determined with a TMA of 60 unique cores of bladder carcinomas and 20 normal urothelial tissues, 4 mouse human tumor xenografts, and 13 human whole tissue sections (WTS) of various carcinomas including bladder, lung, and breast. The summary of the sensitivity and specificity of the M22-321b41.1 antibody with respect to Nectin-4 staining in IHC assays were listed in Table 16 and Table 17 below. In these and some other exemplary assays, the tissue samples were divided by their H-score results into one of four categories: high (201-300), moderate (101-200), low (1-100), negative (0).

TABLE 16

Summary of Tissue Staining Sensitivity
Sensitivity Tissue Staining Summary

| H-Score Tier | Location | Neoplastic Tissues* Whole Tissue Carcinomas |
|---|---|---|
| High (201-300) | M, C | Bladder: 6/8, Breast: 1/4, Lung: 2/4, Xenografts: 2/4 |
| Moderate (101-200) | M, C | Bladder: 1/8, Breast: 2/4, Colon: 2/3, Ovary: 1/1, |
| Low (1-100) | NA | Bladder: 1/8, Lung: 1/4, Colon: 1/3. Xenografts: 1/4; Breast: 1/4 |
| Negative (<=0) | NA | Lung: 1/4, Colon: 1/3, Xenografts: 1/4 |

TABLE 17

Summary of Tissue Staining Specificity
Specificity Tissue Staining Summary

| H-Score Tier | Location | Normal Tissues* |
|---|---|---|
| High (201-300) | M, C | Esophagus: 1/3, Uterine Cervix: 1/3, Skin: 2/3 |
| Moderate (101-200) | M, C | Breast 1/3, Uterine cervix 1/3, Larynx 1/3 |

TABLE 17-continued

Summary of Tissue Staining Specificity
Specificity Tissue Staining Summary

| H-Score Tier | Location | Normal Tissues* |
|---|---|---|
| Low (1-100) | M, C | Uterine cervix 1/3, Breast 2/3, Bone Marrow 1/3, Lung 1/3, Salivary gland 3/3, Kidney 1/3, Prostate 2/3, Endometrium 2/3, Larynx 1/3 |
| Negative | NA | Bone Marrow 2/3, Lung 2/3, Esophagus 1/3, Kidney 2/3, Prostate 1/3, Endometrium 1/3, Skin 1/3, Larynx 1/3 The following were negative in all replicates: Cerebrum (N), Cerebellum (N), Adrenal (N), Ovary, Pancreas, Parathyroid, Hypophysis, Testis, Thyroid, Spleen, Tonsil, Thymus, Cardiac Muscle, Stomach, Small Intestine, Colon, Liver, Skeletal Muscle, Peripheral Nerve, Mesothelium, and Eye |

In some exemplary assays for assessing the specificity and sensitivity of M22-321b41.1, the H-scores for the 13 WTS carcinomas, from staining with either X antibody, which is known to be Nectin-4 specific, or the anti-Nectin-4 antibody M22-321b41.1 at 2.5 µg/ml respectively, were compared. The comparison, shown in Table 18 below, indicated that the IHC staining by M22-321b41.1 was consistent with known Nectin-4 expression as shown by X antibody staining in vast majority of cases.

TABLE 18

Correlation Between M22-321b41.1 IHC Staining and X Antibody IHC Staining
Correlation Between M22-321b41.1 and X Antibody

| | M22-321b41.1 | | X Antibody |
|---|---|---|---|
| No. of Samples | Accession # | H-score 2.5 µg/mL | H-score 2.5 µg/mL |
| 1 | H882 | 300 | 280 |
| 2 | H704 | 290 | 275 |
| 3 | H716 | 230 | 200 |
| 4 | H785 | 257 | 275 |
| 5 | H878 | 180 | 100 |
| 6 | H695 | 170 | 180 |
| 7 | H734 | 140 | 135 |
| 8 | H700 | 40 | 38 |
| 9 | H737 | 45 | 120 |
| 10 | H788 | 56 | 55 |
| 11 | H838 | 90 | 125 |
| 12 | H739 | 0 | 0 |
| 13 | H774 | 0 | 0 |
| 14 | X14-43 | High | 300 |
| 15 | X14-139 | High | 215 |
| 16 | X14-33 | Low | 58 |
| 17 | X14-126 | Negative | 0 |

The results from Table 18 above were re-classified into positive and negative Nectin-4 staining to determine the correlation of staining positivity between X antibody and the anti-Nectin-4 antibody M22-321b41.1. A tissue was considered positive if it showed an H-score ≥150. The overall findings in Table 19 below showed a percentage of concordance of 89% between X antibody and the anti-Nectin-4 antibody M22-321b41.1 for the positively stained tissues, a concordance rate of 100% for the negatively stained tissues, and an overall concordance rate of 94%. Thus, there is a high degree of correlation between Nectin-4 IHC staining with M22-321b41.1 and the expression of Nectin-4 in the tissue. Therefore, the Nectin-4 IHC assay with M22-321b41.1 is both sensitive and specific.

TABLE 19

Nectin-4 X Antibody Vs. M22-321b41.1
When the threshold is an H-score ≥150

| | | M22-321b41.1 | | |
|---|---|---|---|---|
| | | Pos | Neg | Total |
| X Antibody | Pos | 8 | 0 | 8 |
| | Neg | 1 | 8 | 9 |
| | Total | 9 | 8 | 17 |

Figure 10:
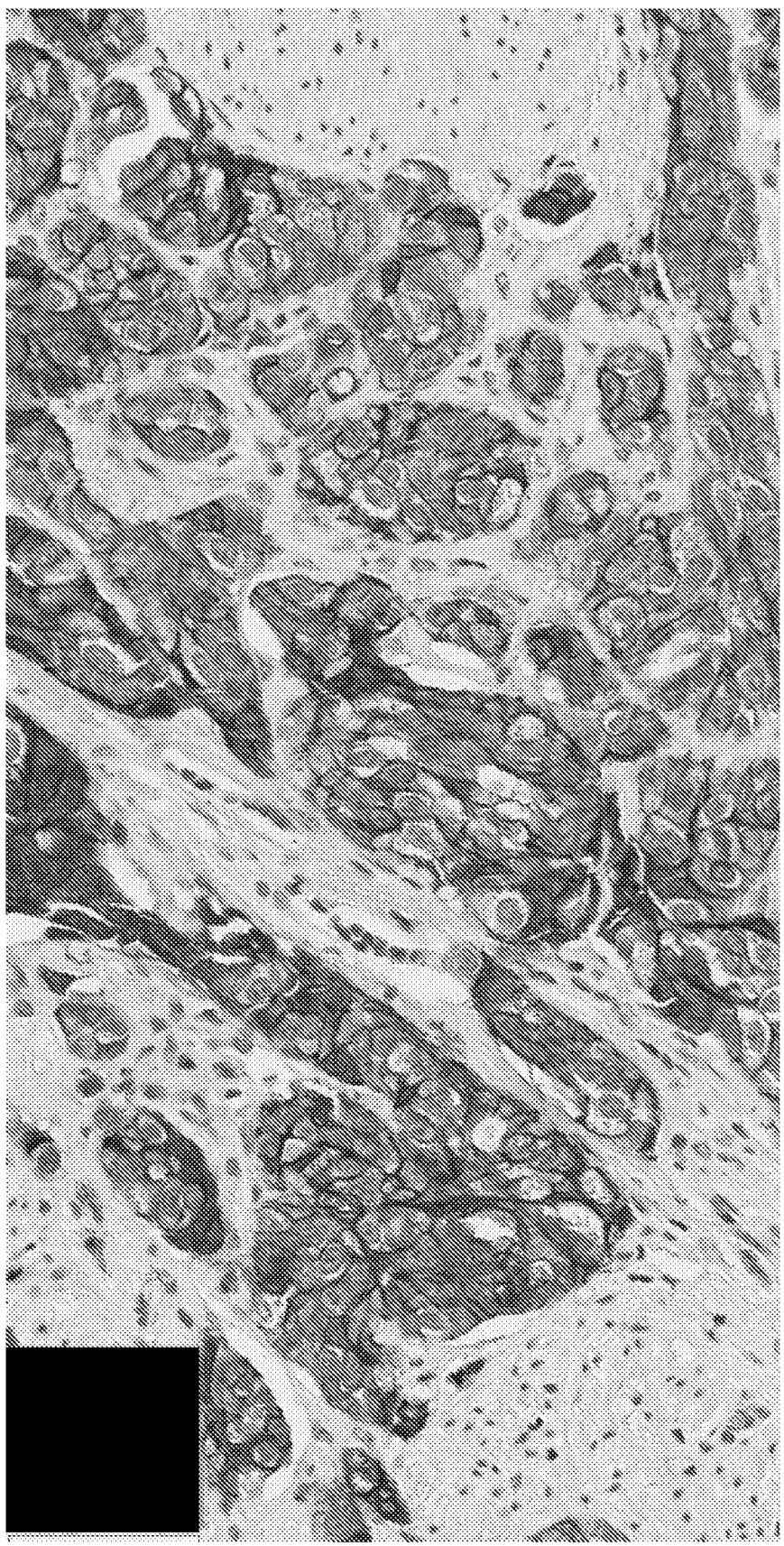
FIG. 10 depicts the result of an experiment showing strong Nectin-4 staining in an IHC staining assay of urothelial carcinoma with M22-321b41.1.
Figure 11:
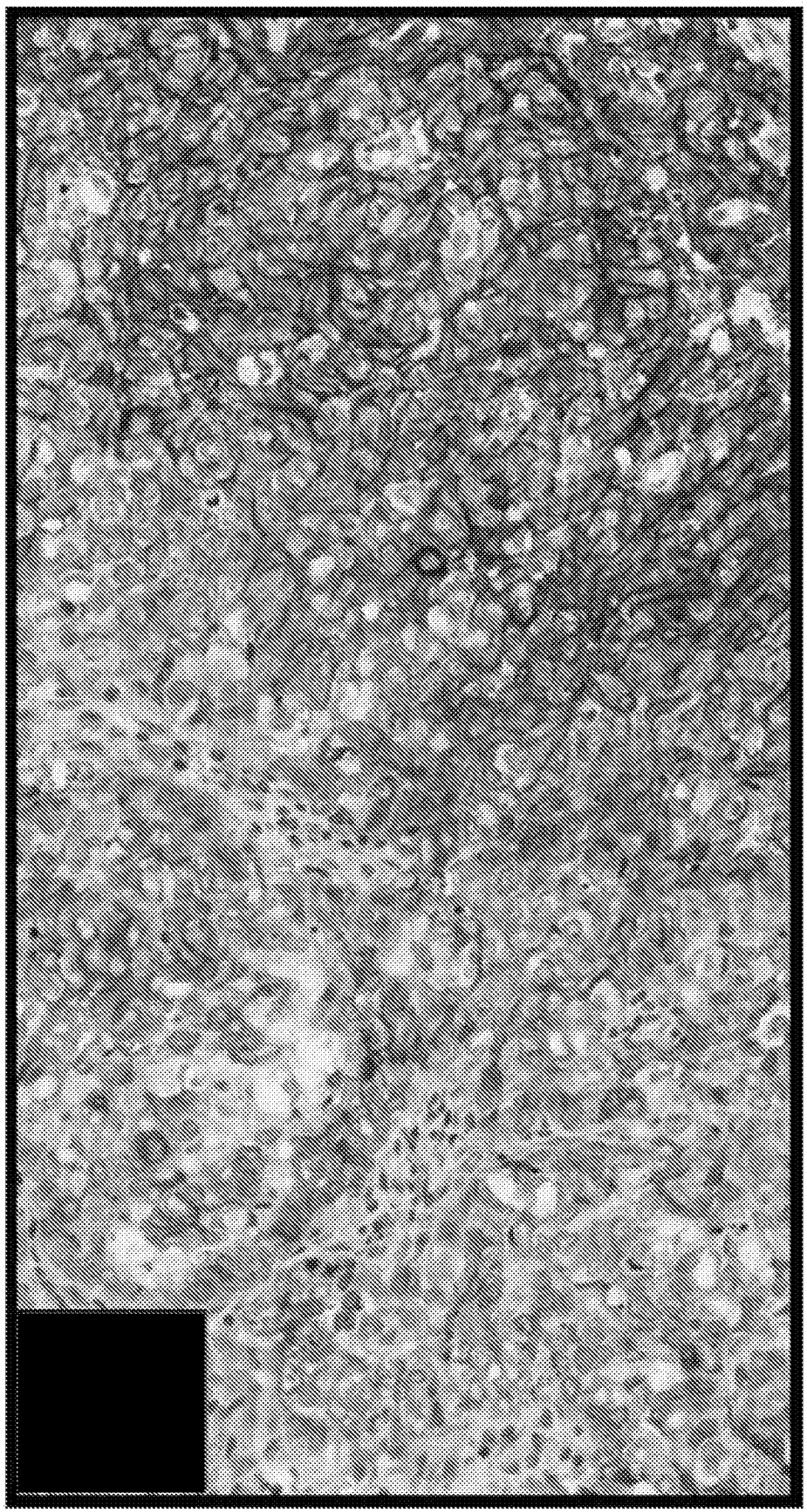
FIG. 11 depicts the result of an experiment showing heterogeneity of Nectin-4 staining in an IHC staining assay of breast carcinoma with M22-321b41.1.

The specificity and sensitivity of M22-321b41.1 were further determined using a larger set of tissue samples including a TMA of 60 unique cores of bladder carcinomas and 20 normal urothelial tissues, 4 mouse human tumor xenografts, and 13 human whole tissue sections (WTS) of various carcinomas including bladder, lung, and breast. A total of 94 cases were evaluable with an overall detection of the Nectin-4 in 95% of cases (82% in WTS and 98% in the TMA) by the IHC assays with the X antibody. Representative IHC staining of Carcinomas with M22-321b41.1 was shown in FIGS. 10 and 11. The sub-cellular localization was mostly membranous and cytoplasmic, with some apical staining which was considered membraneous. The results in Table 20 further demonstrated the sensitivity and specificity of the Nectin-4 IHC assays with M22-321b41.1, because the percentage of positive staining in tumor specimens with M22-321b41.1 was consistent with the known expression of Nectin-4 in carcinomas as provided by the IHC assays with the X antibody. Therefore, the Nectin-4 IHC assay with M22-321b41.1 was both sensitive and specific.

TABLE 20

Sensitivity of Anti-Nectin-4 Antibody M22-321b41.1 in IHC Staining of Different Tissues.

Part I.

| | GENERAL SPECIMEN INFORMATION | | | Iso-type Control | TEST ARTICLE STAINING OF DISTINCTIVE CELLS | | | | | | | | | TEST ARTICLE STAINING OF OTHER CELL TYPES | | | | | |
|---|---|---|---|---|---|---|---|---|---|---|---|---|---|---|---|---|---|---|---|
| | | | | | % and Subcellular Localization of Cells | | | | | | | | | | | | | | |
| | | | | | Staining at Each Intensity | | | | | | | | | | | | | | |
| Line # | Accession # | Run Date/ Tissue Type | Run ID | | 3+% | 3+ sub | 2+% | 2+ sub | 1+% | 1+ sub | 0% | H-score | Nectin-4 % | Nor-mal | Endo-thelium | Smooth Muscle | Fibro-blast | Stroma | Inflam. Cells | OTHER Comment |
| | | | | | Controls | | | | | | | | | | | | | | | |
| 1 | X14-126 | Jul. 7 2014 Xenografts | 0VRV | 0 | 0 | NA | 0 | NA | 0 | NA | 100 | 0 | 0 | NA | 0 | NS | 0 | 0 | NS | |
| 2 | X14-139 | Jul. 7 2014 Xenografts | 0VRY | 0 | 30 | M, C | 45 | M, C | 20 | M, C | 5 | 200 | 95 | NA | 0 | NS | 0 | 0 | NS | |
| | | | | | Tissue | | | | | | | | | | | | | | | |
| 1 | PTBL01172A | Jun. 23 2014 Bladder Ca | 0V6J | 0 | 40 | M, C | 45 | M, C | 10 | M, C | 5 | 220 | 95 | NS | 0 | 0 | 0 | 0 | 2 + F | |
| 2 | PTBL00626B | Jun. 23 2014 Bladder Ca | 0V6M | 0 | 50 | M, C | 15 | M, C | 15 | M, C | 20 | 195 | 80 | NS | 0 | 2+ | 0 | 0 | 2+ | |
| 3 | PTBL00696A | Jun. 23 2014 Bladder Ca | 0V6Q | 0 | 30 | M, C | 55 | M, C | 10 | M, C | 5 | 210 | 95 | NS | 0 | 1+ | 0 | 0-1+ | 2+ | |
| 4 | PTBL01177A | Jun. 23 2014 Bladder Ca | 0V6T | 0 | 50 | M, C | 45 | M, C | 5 | C | 0 | 245 | 100 | NS | 0 | 0 | 0 | 0 | 3+ | |
| 5 | PTBL01228A | Jun. 23 2014 Bladder Ca | 0V6W | 0 | 80 | M, C | 10 | M, C | 0 | NA | 10 | 260 | 90 | 3+ | 0 | 3+ | 0 | 1+ | 3+ | |
| 6 | PTBL01247A | Jun. 23 2014 Bladder Ca | 0V6Z | 0 | 90 | M, C | 10 | M, C | 0 | NA | 0 | 290 | 100 | 3+ | 0 | 1+ | 0 | 1+ | 3+ | |
| 7 | PTLQ01824 | Jun. 23 2014 Lung SCC* | 0V72 | 0 | 70 | M, C | 20 | M, C | 10 | C | 0 | 260 | 100 | 2+ | 0 | 0 | 1+ | 2+ | 2+ | |
| 8 | H882 | Jul. 7 2014 Urinary BL. | 0VS1 | 0 | 80 | M, C | 20 | M, C | 0 | NA | 0 | 280 | 100 | 2+ | 0 | 2+ | 0 | 0 | 2 + F | |
| 9 | H704 | Jul. 7 2014 Breast (IDC) | 0VS4 | 0 | 80 | M, C | 15 | M, C | 5 | C | 0 | 275 | 100 | 3+ | 0 | NS | 0 | 1-2+ | 3+ | |
| 10 | H716 | Jul. 7 2014 Breast (IDC) | 0VS7 | 0 | 50 | M, C | 20 | M, C | 10 | C | 20 | 200 | 80 | 2+ | 0 | NS | 0 | 0 | 2+ | |
| 11 | H785 | Jul. 7 2014 Lung (SCC) | 0VSA | 0 | 80 | M, C | 15 | M, C | 5 | C | 0 | 275 | 100 | 2+ | 0 | NS | 0 | 1-2+ | 2+ | |
| 12 | H878 | Jul. 7 2014 Urinary BL. | 0VSD | 0 | 20 | M, C | 15 | M, C | 10 | C | 55 | 100 | 45 | NS | 0 | 0 | 0 | 0 | 2+ | |
| 13 | H695 | Jul. 7 2014 Breast (IDC) | 0VSG | 0 | 25 | M, C | 40 | M, C | 25 | C | 10 | 180 | 90 | 2+ | 0 | NS | 0 | 0 | 2 + F | |
| 14 | H734 | Jul. 7 2014 Colon | 0VSJ | 0 | 5 | M, C | 45 | M, C | 30 | C | 20 | 135 | 80 | 2+ | 0 | 0 | 0 | 0 | 0 | |

TABLE 20-continued

Sensitivity of Anti-Nectin-4 Antibody M22-321b41.1 in IHC Staining of Different Tissues.

| | | | | | | | | | | | | | | | | | | |
|---|---|---|---|---|---|---|---|---|---|---|---|---|---|---|---|---|---|---|
| 15 | H700 | Jul. 7 2014 Breast (IDC) | 0 | 10 | M, C | 3 | M, C | 2 | C | 85 | 38 | 15 | NS | 0 | 0 | 0 | 0 | |
| 16 | H737 | Jul. 7 2014 Colon | 0 | 10 | M | 40 | M, C | 10 | C | 40 | 120 | 60 | 0 | 0 | 0 | 0 | 2 + F | M = mostly apical |
| 17 | H788 | Jul. 7 2014 Lung | 0 | 5 | C | 15 | C | 10 | C | 70 | 55 | 30 | 3+ | 0 | 0 | 0 | 3+ | |
| 18 | H838 | Jul. 7 2014 Ovary | 0 | 10 | M, C | 35 | M, C | 25 | M, C | 30 | 125 | 70 | NS | 0 | NS | 0 | 3+ | |
| 19 | H739 | Jul. 7 2014 Colon | 0 | 0 | NA | 0 | NA | 0 | NA | 100 | 0 | 0 | NS | 0 | 0 | 0 | 0 | |
| 20 | H774 | Jul. 7 2014 Lung | 0 | 0 | NA | 0 | NA | 0 | NA | 100 | 0 | 0 | 3+ | 0 | NS | 0 | 0 | |
| 21 | X14-43 | Jun. 26 2014 Xenografts | 0 | 100 | M, C | 0 | NA | 0 | NA | 0 | 300 | 100 | NS | 0 | NS | 0 | NS | |
| 22 | X14-139 | Jun. 26 2014 Xenografts | 0 | 40 | M, C | 40 | M, C | 15 | M, C | 5 | 215 | 95 | NS | 0 | NS | 0 | NS | |
| 23 | X14-33 | Jun. 26 2014 Xenografts | 0 | 8 | M, C | 12 | M, C | 10 | C | 70 | 58 | 30 | NS | 0 | NS | 0 | NS | |
| 24 | X14-126 | Jun. 26 2014 Xenografts | 0 | 0 | NA | 0 | NA | 0 | NA | 100 | 0 | 0 | NS | 0 | NS | 0 | NS | |

GENERAL COMMENT/NOTE:
NA = Not Applicable
NS = Not Seen
I.I. = Invasive/Intraductal
Ca = Carcinoma tissue
LCC = Large Cell Carcinoma
NC = Negative Control
F = Focal
N = Nuclear
NAT = Cancer adjacent normal
PSC Ca = Papillary serous cystadenocarcinoma
A = Apical
C = Cytoplasmic Staining
IC = Inflammatory cells
N = Normal
PC = Plasma cells
TCC = Transitional cell carcinoma
SCC* = Squamous Cell Ca
IDC = Infiltrating Ductal Carcinoma TABLE 20-continued Sensitivity of Anti-Nectin-4 Antibody M22-321b41.1 in IHC Staining of Different Tissues.

Part II.

| Accession # | Run ID | TMA Location | Bladder Diagnosis Grade | Isotype Control | 3+% | 3+ sub | 2+% | 2+ sub | 1+% | 1+ sub TISSUE | 0% | H-score | % Nectin-4 | Normal | Endo-thelium | Smooth Muscle | Fibroblast | Stroma | Inflam Cells | Comment |
|---|---|---|---|---|---|---|---|---|---|---|---|---|---|---|---|---|---|---|---|---|
| BL802 | 0VK8 | A1 | TCC G1 | 0 | 85 | M, C | 15 | M, C | 0 | NA | 0 | 285 | 100 | NS | 0 | 0 | 0 | 0 | NS | |
| BL802 | 0VK8 | A2 | TCC G1-G2 | 0 | 25 | M, C | 50 | M, C | 15 | M, C | 10 | 190 | 90 | NS | 0 | 0 | 0 | 0 | 3+ | |
| BL802 | 0VK8 | A3 | TCC G1 | 0 | 0 | NA | 5 | M, C | 10 | M, C | 85 | 20 | 15 | NS | 0 | 0 | 0 | 0 | 2+ | |
| BL802 | 0VK8 | A4 | TCC G1-G2 | 0 | 15 | M, C | 40 | M, C | 35 | M, C | 10 | 160 | 90 | NS | 0 | NS | 0 | 1+ | 2+ | |
| BL802 | 0VK8 | A5 | TCC G2 | 0 | 65 | M, C | 20 | M, C | 10 | M, C | 5 | 245 | 95 | NS | 0 | 0 | 0 | 0 | NS | |
| BL802 | 0VK8 | A6 | TCC G2-G3 | 0 | 25 | M, C | 55 | M, C | 15 | M, C | 5 | 200 | 95 | NS | 0 | 0 | 0 | 1+ | 3+ | |
| BL802 | 0VK8 | A7 | TCC G2 | 0 | 25 | M, C | 35 | M, C | 25 | M, C | 15 | 170 | 85 | NS | 0 | NS | 0 | 0 | 3+ | |
| BL802 | 0VK8 | A8 | TCC G2 | 0 | 30 | M, C | 45 | M, C | 15 | M, C | 10 | 195 | 90 | NS | 0 | NS | 0 | 0 | 3+ | |
| BL802 | 0VK8 | A9 | TCC G1 | 0 | 0 | NA | 5 | M, C | 15 | M, C | 80 | 25 | 20 | NS | 0 | NS | 0 | 0 | NS | |
| BL802 | 0VK8 | A10 | TCC G2 | 0 | 80 | M, C | 10 | M, C | 10 | M, C | 0 | 270 | 100 | NS | 0 | NS | 0 | 0 | 3+ | |
| BL802 | 0VK8 | B1 | TCC G2 | 0 | 95 | M, C | 5 | M, C | 0 | NA | 0 | 295 | 100 | NS | 0 | NS | 0 | 0 | 3+ | |
| BL802 | 0VK8 | B2 | TCC G2 | 0 | 5 | M, C | 45 | M, C | 30 | M, C | 20 | 135 | 80 | NS | 0 | NS | 0 | 0 | 0 | |
| BL802 | 0VK8 | B3 | TCC G2 | 0 | 60 | M, C | 20 | M, C | 10 | M, C | 10 | 230 | 90 | NS | 0 | NS | 0 | 3 + F | 3+ | |
| BL802 | 0VK8 | B4 | TCC G2 | 0 | 30 | M, C | 45 | M, C | 15 | M, C | 10 | 195 | 90 | NS | 0 | NS | 0 | 2+ | 3+ | |
| BL802 | 0VK8 | B5 | TCC G3 | 0 | 70 | M, C | 15 | M, C | 5 | M, C | 10 | 245 | 90 | NS | 0 | NS | 0 | 2 + F | 3+ | |
| BL802 | 0VK8 | B6 | TCC G2 | 0 | 20 | M, C | 50 | M, C | 20 | M, C | 10 | 180 | 90 | NS | 0 | NS | 0 | 2+ | 2+ | |
| BL802 | 0VK8 | B7 | TCC G3 | 0 | 30 | M, C | 10 | M, C | 45 | M, C | 15 | 155 | 85 | NS | 0 | 0 | 0 | 2+ | 3+ | |
| BL802 | 0VK8 | B8 | TCC G3 | 0 | 80 | M, C | 20 | M, C | 0 | NA | 0 | 280 | 100 | NS | 0 | NS | 0 | 0 | NS | Partial core |
| BL802 | 0VK8 | B9 | TCC G1 | 0 | 20 | M, C | 40 | M, C | 20 | M, C | 20 | 160 | 80 | NS | 0 | 0 | 0 | 0 | NS | |
| BL802 | 0VK8 | B10 | TCC G1 | 0 | 20 | M, C | 30 | M, C | 20 | M, C | 30 | 140 | 70 | NS | 0 | NS | 0 | 0 | 2+ | |
| BL802 | 0VK8 | C1 | TCC G1 | 0 | 90 | M, C | 10 | NA | 0 | NA | 0 | 290 | 100 | NS | 0 | NS | 0 | 2+ | 3+ | |
| BL802 | 0VK8 | C2 | TCC G2 | 0 | 15 | M, C | 65 | M, C | 15 | M, C | 5 | 190 | 95 | NS | 0 | NS | 0 | 0 | 2+ | |
| BL802 | 0VK8 | C3 | TCC G3 | 0 | 60 | M, C | 20 | M, C | 10 | M, C | 10 | 230 | 90 | NS | 0 | NS | 0 | 2 + F | 3+ | |
| BL802 | 0VK8 | C4 | TCC (sparse) G1 | 0 | 40 | C | 10 | C | 0 | NA | 50 | 140 | 50 | NS | 0 | NS | 0 | 3+ | 3+ | |
| BL802 | 0VK8 | C5 | TCC G2-G3 | 0 | 30 | M, C | 20 | M, C | 20 | M, C | 30 | 150 | 70 | NS | 0 | 0 | 0 | 2+ | 3+ | |
| BL802 | 0VK8 | C6 | TCC G3 | 0 | 0 | M, C | 40 | M, C | 40 | M, C | 20 | 120 | 80 | NS | 0 | NS | 0 | 0 | 3+ | |
| BL802 | 0VK8 | C7 | TCC G2 | 0 | 80 | M, C | 20 | M, C | 0 | NA | 0 | 280 | 100 | NS | 0 | NS | 0 | 2 + F | 0 | |
| BL802 | 0VK8 | C8 | TCC G3 | 0 | 2 | M, C | 2 | M, C | 0 | NA | 96 | 10 | 4 | NS | 0 | 0 | 0 | 0 | 3+ | |
| BL802 | 0VK8 | C9 | TCC G3 | 0 | 65 | M, C | 20 | M, C | 15 | C | 0 | 250 | 100 | NS | 0 | 0 | 0 | 1 + F | 3+ | |
| BL802 | 0VK8 | C10 | TCC G3 | 0 | 5 | M, C | 60 | M, C | 10 | M, C | 25 | 145 | 75 | 2+ | 0 | 0 | 0 | 0 | 0 | |
| BL802 | 0VK8 | D1 | TCC G2 | 0 | 25 | M, C | 55 | M, C | 20 | C | 0 | 205 | 100 | NS | 0 | NS | 0 | 2+ | 3+ | |
| BL802 | 0VK8 | D2 | TCC G2 | 0 | 50 | M, C | 10 | M, C | 10 | C | 30 | 180 | 70 | NS | 0 | 0 | 0 | 0 | 2+ | |

TABLE 20-continued

Sensitivity of Anti-Nectin-4 Antibody M22-321b41.1 in IHC Staining of Different Tissues.

| | | | | | | | | | | | | | | | | | |
|---|---|---|---|---|---|---|---|---|---|---|---|---|---|---|---|---|---|
| BL802 | OVK8 | D3 | TCC G3 | 0 | 35 | M, C | 15 | C | 5 | 210 | 95 | NS | 0 | 0 | 0 | 2+ | |
| BL802 | OVK8 | D4 | TCC G2 | 0 | 30 | M, C | 10 | C | 0 | 220 | 100 | NS | 0 | 2+ | 0 | 2+ | |
| BL802 | OVK8 | D5 | TCC G3 | 0 | 40 | C | 5 | C | 5 | 225 | 95 | 2+ | 0 | 0 | 0 | 2+ + F | Rare cells M+ |
| BL802 | OVK8 | D6 | TCC G3 | 0 | 80 | M, C | 5 | C | 5 | 265 | 95 | 2+ | 0 | 2+ | 0 | 2+ | |
| BL802 | OVK8 | D7 | TCC G1-G2 | 0 | 55 | C | 3 | C | 2 | 248 | 98 | NS | 0 | 2+ | 0 | 2+ | |
| BL802 | OVK8 | D8 | TCC G2 | 0 | 25 | M, C | 15 | M, C | 15 | 180 | 85 | 2+ | 0 | 0 | 0 | 3+ | |
| BL802 | OVK8 | D9 | TCC G2 | 0 | 0 | NA | 30 | C | 50 | 70 | 50 | NS | 0 | 0 | 0 | 0 | Stroma adipose tissue. |
| BL802 | OVK8 | D10 | TCC G3 | 0 | 40 | M, C | 20 | M, C | 0 | 220 | 100 | NS | 0 | 2+ | 0 | 2+ | |
| BL802 | OVK8 | E1 | TCC G2 | 0 | 90 | M, C | 0 | NA | 0 | 290 | 100 | NS | 0 | 2+ | 0 | 3+ | |
| BL802 | OVK8 | E2 | TCC G2 | 0 | 70 | C | 10 | C | 5 | 250 | 95 | NS | 0 | 2+ | 0 | 3+ | |
| BL802 | OVK8 | E3 | TCC G2 | 0 | 25 | M, C | 20 | M, C | 5 | 195 | 95 | 1+ | 0 | 1+ | 0 | 2+ | |
| BL802 | OVK8 | E4 | TCC G2 | 0 | 100 | C | 0 | NA | 5 | 300 | 100 | 3+ | 0 | 3+ | 0 | 3+ | |
| BL802 | OVK8 | E5 | TCC G2 | 0 | 70 | M, C | 10 | M, C | 0 | 235 | 85 | NS | 0 | 2+ | 0 | 3+ | |
| BL802 | OVK8 | E6 | TCC G2 | 0 | 80 | M, C | 20 | M, C | 15 | 280 | 100 | NS | 0 | 2+ + F | 0 | 2+ | |
| BL802 | OVK8 | E7 | TCC G3 | 0 | 65 | M, C | 0 | | 0 | 240 | 90 | 0 | 0 | 0 | 0 | 0 | |
| BL802 | OVK8 | E8 | TCC G2 | 0 | 30 | M, C | 5 | M, C | 10 | 205 | 95 | NS | 0 | 0 | 0 | 0 | |
| BL802 | OVK8 | E9 | TCC G2 | 0 | 75 | M, C | 15 | C | 5 | 270 | 100 | NS | 0 | 0 | 0 | 0 | |
| BL802 | OVK8 | E10 | TCC G2 | 0 | 2 | C | 5 | C | 50 | 72 | 50 | NS | 0 | 0 | 0 | 0 | |
| BL802 | OVK8 | F1 | TCC G2 | 0 | 100 | C | 30 | M, C | 0 | 300 | 100 | NS | 0 | 2+ | 0 | 3+ | |
| BL802 | OVK8 | F2 | TCC G2-G3 | 0 | 80 | M, C | 0 | NA | 0 | 280 | 100 | NS | 0 | 3+ | 0 | 3+ | |
| BL802 | OVK8 | F3 | TCC G3 | 0 | 10 | C | 85 | C | 2 | 203 | 98 | NS | 0 | 0 | 0 | 2+ | |
| BL802 | OVK8 | F4 | TCC G3 | 0 | 50 | C | 30 | C | 2 | 228 | 98 | NS | 0 | 1+ | 0 | 2+ | |
| BL802 | OVK8 | F5 | TCC G3 | 0 | 40 | M, C | 40 | C | 0 | 220 | 100 | NS | 0 | 1+ | 0 | 2+ | |
| BL802 | OVK8 | F6 | TCC* | 0 | 20 | C | 10 | C | 60 | 90 | 40 | NS | 0 | 0 | 0 | 0 | |
| BL802 | OVK8 | F7 | TCC G3 | 0 | 0 | NA | 0 | NA | 100 | 0 | 0 | NS | 0 | 0 | 0 | 0 | |
| BL802 | OVK8 | F8 | AdenoCa G2 | 0 | 0 | NA | 3 | M, C | 97 | 6 | 3 | NS | 0 | 0 | 0 | 0 | |
| BL802 | OVK8 | F9 | AdenoCa (SM & BU) | 0 | 0 | NA | 5 | M, C | 90 | 15 | 10 | NS | 0 | 0 | 0 | 0 | |
| BL802 | OVK8 | F10 | TCC G2 | 0 | 95 | C | 5 | C | 0 | 295 | 100 | 3+ | 0 | 1+ | 0 | 2+ | |
| BL802 | OVK8 | G1 | NAT | 0 | 0 | NA | 10 | C | 60 | 50 | 40 | NA | 0 | 0 | 0 | 0 | |
| BL802 | OVK8 | G2 | NAT | 0 | 40 | M, C | 30 | C | 20 | 190 | 80 | NA | 0 | 0 | 0 | 0 | |
| BL802 | OVK8 | G3 | NAT | 0 | 0 | NA | 0 | M, C | 100 | 0 | 0 | NA | 0 | 0 | 0 | 0 | |
| BL802 | OVK8 | G4 | NAT (SM & BV) | 0 | 15 | C | 45 | C | 10 | 150 | 90 | NA | 0 | 0 | 0 | 0 | |
| BL802 | OVK8 | G5 | NAT (chronic inflammation of mucosa) | 0 | 80 | M, C | 20 | NA | 0 | 280 | 100 | NA | 0 | 0 | 0 | 0 | |
| BL802 | OVK8 | G6 | NAT (chronic inflammation of mucosa) | 0 | 25 | M, C | 15 | C | 20 | 145 | 80 | NA | 0 | 0 | 0 | 0 | |
| BL802 | OVK8 | G7 | NAT | 0 | 30 | M, C | 10 | M, C | 0 | 220 | 100 | NA | 0 | 0 | 0 | 0 | |
| BL802 | OVK8 | G8 | NAT | 0 | 20 | M, C | 30 | M, C | 30 | 130 | 70 | NA | 0 | 0 | 0 | 0 | |
| BL802 | OVK8 | G9 | NAT | 0 | 60 | M, C | 15 | C | 5 | 235 | 95 | NA | 0 | 0 | 0 | 0 | |

TABLE 20-continued

Sensitivity of Anti-Nectin-4 Antibody M22-321b41.1 in IHC Staining of Different Tissues.

| | | | | | | | | | | | | | | | | | | |
|---|---|---|---|---|---|---|---|---|---|---|---|---|---|---|---|---|---|---|
| BL802 | 0VK8 | G10 | NAT (fibrous tissue and blood vessel) | 0 | NA | NA | NA | NA | NA | NA | NA | NA | NA | NA | NA | NA | NA | No urothelium present |
| BL802 | 0VK8 | H1 | NAT (Sparse) Normal | 0 | NA | 15 | M, C | 15 | C | 70 | 45 | 30 | NA | 0 | NA | 0 | 0 | Calcification noted |
| BL802 | 0VK8 | H2 | NAT (SM & BV) Normal | 0 | NA | NA | NA | NA | NA | NA | NA | NA | NA | NA | NA | NA | NA | Disrupted tissue |
| BL802 | 0VK8 | H3 | NAT (Sparse) Normal | 0 | NA | 70 | M, C | 30 | C | 0 | 170 | 100 | NA | 0 | NA | 0 | 0 | |
| BL802 | 0VK8 | H4 | NAT (SM & BV) Normal | 0 | NA | NA | NA | NA | NA | NA | NA | NA | NA | NA | NA | NA | NA | Disrupted tissue |
| BL802 | 0VK8 | H5 | NAT (SM & BV) Normal | 0 | NA | 80 | M, C | 15 | M, C | 5 | 175 | 95 | NA | 0 | NA | 0 | 0 | |
| BL802 | 0VK8 | H6 | NAT (Sparse) Normal | 0 | NA | 0 | NA | 10 | C | 90 | 10 | 10 | NA | 0 | NA | 0 | 0 | Scant urothelium |
| BL802 | 0VK8 | H7 | NAT Normal | 0 | NA | 25 | M, C | 15 | C | 60 | 65 | 40 | NA | 0 | NA | 0 | 0 | |
| BL802 | 0VK8 | H8 | NAT Normal | 0 | M, C | 20 | M, C | 0 | NA | 10 | 250 | 90 | NA | 0 | NA | 0 | 0 | Basal layer Negative |
| BL802 | 0VK8 | H9 | NAT Normal | 0 | NA | 0 | NA | 40 | C | 60 | 40 | 40 | NA | 0 | NA | 0 | 0 | |
| BL802 | 0VK8 | H10 | NAT Normal | 0 | NA | 0 | NA | 30 | M, C | 70 | 30 | 30 | NA | 0 | NA | 0 | 0 | Scant urothelium present |

GENERAL COMMENT/NOTE:
G = Grad
NA = Not Applicable
NS = Not Seen
Ca = Carcinoma
*= Chronic inflammation of fibrous tissue and blood vessel
Occ = Occasional
Sc = Scattered
BLA = Bladder
N = Normal
C = Cytoplasmic Staining
M = Membrane Staining
BV = Blood Vessel
F = Focally Positive
TCC = Transitional Cell Carcinoma
SM = Smooth Muscle
NAT = Normal Adjacent to Tumor The specificity and sensitivity of M22-321b41.1 were further determined from all 33 normal human specimens contained in triplicates in the FDA999d. As shown in Table 21, The IHC staining with the anti-Nectin-4 antibody M22-321b41.1 was consistent with the expression of Nectin-4 in normal cells reported in the literature (Rabet et al., 2016.) except that normal breast showed partial and weak to moderate immunoreactivity. Red blood cells stained for Nectin-4 at a moderated to strong intensity. Squamous epithelium stained strongly while the basal layer was negative.

TABLE 21

Specificity of Anti-Nectin-4 Antibody M22-321b41.1 in IHC Staining of Different Tissues.

| | GENERAL SPECIMEN INFORMATION | | | | TEST ARTICLE STAINING OF DISTINCTIVE CELLS | | | | | | | TEST ARTICLE STAINING OF OTHER CELL TYPES | | | | |
|---|---|---|---|---|---|---|---|---|---|---|---|---|---|---|---|---|
| Accession # | Run ID | TMA Location | Cell Line/Tissue | Isotype Location | 3+ % 3 + sub | 2+ % 2 + sub | 1+ % 1 + sub TISSUE | 0% | H-Score | % Nectin 4 | Endo-thelium | Smooth Muscle | Fibro-blast | Stroma | Inflam. Cells | Comments |
| FDA999d | 0VK5 A1 | Cerebrum (N) | 0 | 0 NA | 0 NA | 0 NA | 100 | 0 | 0 | 0 | NA | NS | 0 | NS | |
| FDA999d | 0VK5 A2 | Cerebrum (N) | 0 | 0 NA | 0 NA | 0 NA | 100 | 0 | 0 | 0 | NA | NS | 0 | NS | |
| FDA999d | 0VK5 A3 | Cerebrum (N) | 0 | 0 NA | 0 NA | 0 NA | 100 | 0 | 0 | 0 | NA | NS | 0 | NS | |
| FDA999d | 0VK5 A4 | Cerebrum (N) | 0 | 0 NA | 0 NA | 0 NA | 100 | 0 | 0 | 0 | NA | NS | 0 | NS | |
| FDA999d | 0VK5 A5 | Cerebrum (N) | 0 | 0 NA | 0 NA | 0 NA | 100 | 0 | 0 | 0 | NA | NS | 0 | NS | |
| FDA999d | 0VK5 A6 | Cerebrum (N) | 0 | 0 NA | 0 NA | 0 NA | 100 | 0 | 0 | 0 | NA | NS | 0 | NS | |
| FDA999d | 0VK5 A7 | Cerebellum (N) | 0 | 0 NA | 0 NA | 0 NA | 100 | 0 | 0 | 0 | NA | NS | 0 | NS | |
| FDA999d | 0VK5 A8 | Cerebellum (N) | 0 | 0 NA | 0 NA | 0 NA | 100 | 0 | 0 | 0 | NA | NS | 0 | NS | |
| FDA999d | 0VK5 A9 | Cerebellum (N) | 0 | 0 NA | 0 NA | 0 NA | 100 | 0 | 0 | 0 | NA | NS | 0 | NS | |
| FDA999d | 0VK5 B1 | Adrenal (N) | 0 | 0 NA | 0 NA | 0 NA | 100 | 0 | 0 | 0 | NA | 0 | 0 | NS | |
| FDA999d | 0VK5 B2 | Adrenal (N) | 0 | 0 NA | 0 NA | 0 NA | 100 | 0 | 0 | 0 | NA | 0 | 0 | NS | Endogenous pigment present |
| FDA999d | 0VK5 B3 | Adrenal (N) | 0 | 0 NA | 0 NA | 0 NA | 100 | 0 | 0 | 0 | NA | 0 | 0 | NS | |
| FDA999d | 0VK5 B4 | Ovary (N) | 0 | 0 NA | 0 NA | 0 NA | 100 | 0 | 0 | 0 | NA | 0 | 0 | NS | |
| FDA999d | 0VK5 B5 | Ovary (N) | 0 | 0 NA | 0 NA | 0 NA | 100 | 0 | 0 | 0 | NA | 0 | 0 | NS | |
| FDA999d | 0VK5 B6 | Ovary (N) | 0 | 0 NA | 0 NA | 0 NA | 100 | 0 | 0 | 0 | NA | 0 | 0 | NS | |
| FDA999d | 0VK5 B7 | Pancreas (N) | 0 | 0 NA | 0 NA | 0 NA | 100 | 0 | 0 | 0 | NA | 0 | 0 | NS | |
| FDA999d | 0VK5 B8 | Pancreas (N) | 0 | 0 NA | 0 NA | 0 NA | 100 | 0 | 0 | 0 | NA | 0 | 0 | NS | Staining artifact occ cells 2+ |
| FDA999d | 0VK5 B9 | Pancreas (N) | 0 | 0 NA | 0 NA | 0 NA | 100 | 0 | 0 | 0 | NA | 0 | 0 | NS | |
| FDA999d | 0VK5 C1 | Parathyroid (NAT) | 0 | 0 NA | 0 NA | 0 NA | 100 | 0 | 0 | 0 | NA | 0 | 0 | NS | |
| FDA999d | 0VK5 C2 | Parathyroid (NAT) | 0 | 0 NA | 0 NA | 0 NA | 100 | 0 | 0 | 0 | NA | 0 | 0 | NS | |
| FDA999d | 0VK5 C3 | Parathyroid (NAT) | 0 | 0 NA | 0 NA | 0 NA | 100 | 0 | 0 | 0 | NA | 0 | 0 | NS | |
| FDA999d | 0VK5 C4 | Hypophysis (N) | 0 | 0 NA | 0 NA | 0 NA | 100 | 0 | 0 | 0 | NA | 0 | 0 | NS | |
| FDA999d | 0VK5 C5 | Hypophysis (NAT) | 0 | 0 NA | 0 NA | 0 NA | 100 | 0 | 0 | 0 | NA | 0 | 0 | NS | |
| FDA999d | 0VK5 C6 | Hypophysis (N) | 0 | 0 NA | 0 NA | 0 NA | 100 | 0 | 0 | 0 | NA | 0 | 0 | NS | |
| FDA999d | 0VK5 C7 | Testis (N) | 0 | 0 NA | 0 NA | 0 NA | 100 | 0 | 0 | 0 | NA | 0 | 0 | NS | RBC's 2+ |
| FDA999d | 0VK5 C8 | Testis (N) | 0 | 0 NA | 0 NA | 0 NA | 100 | 0 | 0 | 0 | NA | 0 | 0 | NS | |
| FDA999d | 0VK5 C9 | Testis (N) | 0 | 0 NA | 0 NA | 0 NA | 100 | 0 | 0 | 0 | NA | 0 | 0 | NS | OCC interotical cells 2+ |
| FDA999d | 0VK5 D1 | Thyroid (N) | 0 | 0 NA | 0 NA | 0 NA | 100 | 0 | 0 | 0 | NA | 0 | 0 | NS | |
| FDA999d | 0VK5 D2 | Thyroid (N) | 0 | 0 NA | 0 NA | 0 NA | 100 | 0 | 0 | 0 | NA | 0 | 0 | NS | |
| FDA999d | 0VK5 D3 | Thyroid (N) | 0 | 0 NA | 0 NA | 0 NA | 100 | 0 | 0 | 0 | NA | 0 | 0 | NS | Stroma 2+F colloid 2+ |
| FDA999d | 0VK5 D4 | Breast (NAT) | 0 | 0 NA | 20 M,C | 30 C | 50 | 70 | 50 | 0 | NA | 0 | 0-1+ | 0 | |
| FDA999d | 0VK5 D5 | Breast (NAT) | 0 | 0 NA | 15 C | 25 C | 60 | 55 | 40 | 0 | NA | 0 | 0 | 0 | |
| FDA999d | 0VK5 D6 | Breast (NAT) | 0 | 10 M | 25 M,C | 25 M,C | 40 | 105 | 60 | 0 | NA | 0 | 0 | 0 | |
| FDA999d | 0VK5 D7 | Spleen (N) | 0 | 0 NA | 0 NA | 0 NA | 100 | 0 | 0 | 0 | NS | 0 | 0 | 0 | |
| FDA999d | 0VK5 D8 | Spleen (N) | 0 | 0 NA | 0 NA | 0 NA | 100 | 0 | 0 | 0 | NS | 0 | 1-2+ | 0 | |
| FDA999d | 0VK5 D9 | Spleen (N) | 0 | 0 NA | 0 NA | 0 NA | 100 | 0 | 0 | 0 | NS | 0 | 1-2+ | 0 | |
| FDA999d | 0VK5 E1 | Tonsil (N) | 0 | 0 NA | 0 NA | 0 NA | 100 | 0 | 0 | 0 | NA | 0 | 0 | 0 | RBC's 2+ |
| FDA999d | 0VK5 E2 | Tonsil (N) | 0 | 0 NA | 0 NA | 0 NA | 100 | 0 | 0 | 0 | NS | 0 | 0-1 + F | 0 | |
| FDA999d | 0VK5 E3 | Tonsil (N) | 0 | 0 NA | 0 NA | 0 NA | 100 | 0 | 0 | 0 | NS | 0 | 0 | 0 | |
| FDA999d | 0VK5 E4 | Thymus (N) | 0 | 0 NA | 0 NA | 0 NA | 100 | 0 | 0 | 0 | NS | 0 | 0 | 0 | |
| FDA999d | 0VK5 E5 | Thymus (N) | 0 | 0 NA | 0 NA | 0 NA | 100 | 0 | 0 | 0 | NS | 0 | 0 | 0 | |

TABLE 21-continued

Specificity of Anti-Nectin-4 Antibody M22-321b41.1 in IHC Staining of Different Tissues.

| | GENERAL SPECIMEN INFORMATION | | | Isotype | TEST ARTICLE STAINING OF DISTINCTIVE CELLS | | | | | | | | TEST ARTICLE STAINING OF OTHER CELL TYPES | | | | | |
|---|---|---|---|---|---|---|---|---|---|---|---|---|---|---|---|---|---|---|
| Accession # | Run ID | TMA Location | Cell Line/Tissue | Location | 3+ % | 3+ sub | 2+ % | 2+ sub | 1+ % | 1+ sub TISSUE | 0% | H-Score | % Nectin 4 | Endo-thelium | Smooth Muscle | Fibro-blast | Stroma | Inflam. Cells | Comments |
| FDA999d | 0VK5 | E6 | Thymus (N) | 0 | 0 | NA | 0 | NA | 0 | NA | 100 | 0 | 0 | 0 | NS | 0 | 0 | 0 | |
| FDA999d | 0VK5 | E7 | Bone Marrow (N) | 0 | 0 | NA | 0 | NA | 0 | NA | 100 | 0 | 0 | 0 | NS | 0 | 0 | 0 | |
| FDA999d | 0VK5 | E8 | Bone Marrow (N) | 0 | 0 | NA | 0 | NA | 0 | NA | 100 | 0 | 0 | 0 | NS | 0 | 0 | 0 | |
| FDA999d | 0VK5 | E9 | Bone Marrow (N) | 0 | 25 | C | 5 | C | 0 | NA | 70 | 85 | 30 | 0 | 0 | 0 | 0 | 0 | |
| FDA999d | 0VK5 | F1 | Lung (N) | 0 | 0 | NA | 10 | M, C | 20 | M, C | 70 | 40 | 30 | 0 | 0 | 0 | 0 | 0 | Bronchial epithelium scored |
| FDA999d | 0VK5 | F2 | Lung (N) | 0 | 0 | NA | 0 | NA | 0 | NA | 100 | 0 | 0 | 0 | 0 | 0 | 0 | 0 | |
| FDA999d | 0VK5 | F3 | Lung (N) | 0 | 0 | NA | 0 | NA | 0 | NA | 100 | 0 | 0 | 0 | 0 | 0 | 0 | 0 | |
| FDA999d | 0VK5 | F4 | Cardiac Muscle (N) | 0 | 0 | NA | 0 | NA | 0 | NA | 100 | 0 | 0 | 0 | NS | NS | 0 | NS | Basal layer Neg. RBC's = 3+ |
| FDA999d | 0VK5 | F5 | Cardiac Muscle (N) | 0 | 0 | NA | 0 | NA | 0 | NA | 100 | 0 | 0 | 0 | NS | NS | 0 | NS | |
| FDA999d | 0VK5 | F6 | Cardiac Muscle (N) | 0 | 0 | NA | 0 | NA | 0 | NA | 100 | 0 | 0 | 0 | NS | NS | 0 | NS | |
| FDA999d | 0VK5 | F7 | Esophagus (N) | 0 | 70 | M, C | 10 | M, C | 0 | NA | 20 | 230 | 80 | 0 | 2+ | 0 | 0 | 2+ | |
| FDA999d | 0VK5 | F8 | Esophagus (N) | 0 | 0 | NA | 0 | NA | 0 | NA | 100 | 0 | 0 | 0 | 0 | 0 | 0 | 0 | Basal layer Neg |
| FDA999d | 0VK5 | F9 | Esophagus (N) | 0 | 30 | M, C | 30 | M, C | 10 | M, C | 30 | 160 | 70 | 0 | 3+ | 0 | 0 | 3+ | |
| FDA999d | 0VK5 | G1 | Stomach (N) | 0 | 0 | NA | 0 | NA | 0 | NA | 100 | 0 | 0 | 0 | 0 | 0 | 0 | 0 | |
| FDA999d | 0VK5 | G2 | Stomach (N) | 0 | 0 | NA | 0 | NA | 0 | NA | 100 | 0 | 0 | 0 | 0 | 0 | 0 | 0 | |
| FDA999d | 0VK5 | G3 | Stomach (N) | 0 | 0 | NA | 0 | NA | 0 | NA | 100 | 0 | 0 | 0 | 0 | 0 | 0 | 0 | |
| FDA999d | 0VK5 | G4 | Sm. Intestine (N) | 0 | 0 | NA | 0 | NA | 0 | NA | 100 | 0 | 0 | 0 | 0 | 0 | 0 | 0 | |
| FDA999d | 0VK5 | G5 | Sm. Intestine (N) | 0 | NA | NA | NA | NA | NA | NA | NA | NA | NA | NA | NA | NA | NA | NA | No epithelium seen |
| FDA999d | 0VK5 | G6 | Sm. Intestine (N) | 0 | 0 | NA | 0 | NA | 0 | NA | 100 | 0 | 0 | 0 | 0 | 0 | 0 | 0 | |
| FDA999d | 0VK5 | G7 | Colon (NAT) | 0 | 0 | NA | 0 | NA | 0 | NA | 100 | 0 | 0 | 0 | 0 | 0 | 0 | 2+ | |
| FDA999d | 0VK5 | G8 | Colon (NAT) | 0 | 0 | NA | 15 | C | 10 | C | 75 | 40 | 25 | 0 | 0 | 0 | 0 | 0 | |
| FDA999d | 0VK5 | G9 | Colon (NAT) | 0 | 0 | NA | 0 | NA | 10 | C | 90 | 10 | 10 | 0 | 0 | 0 | 0 | 0 | Mostly ductal cells staining |
| FDA999d | 0VK5 | H1 | Liver (N) | 0 | 10 | C | 10 | C | 0 | NA | 80 | 50 | 20 | 0 | 0 | 0 | 0 | 2+ | Serous cells + ductal cells staining |
| FDA999d | 0VK5 | H2 | Liver (N) | 0 | 0 | NA | 0 | NA | 0 | NA | 100 | 0 | 0 | 0 | 0 | 0 | 0 | 0 | |
| FDA999d | 0VK5 | H3 | Liver (N) | 0 | 0 | NA | 0 | NA | 0 | NA | 100 | 0 | 0 | 0 | 0 | 0 | 0 | 0 | |
| FDA999d | 0VK5 | H4 | Salivary gland (N) | 0 | 0 | NA | 5 | C | 0 | NA | 95 | 10 | 5 | 0 | NS | NS | NS | NS | Proximal tubuls staining |
| FDA999d | 0VK5 | H5 | Salivary gland (N) | 0 | 0 | NA | 0 | NA | 0 | NA | 100 | 0 | 0 | 0 | NS | NS | NS | 0 | |
| FDA999d | 0VK5 | H6 | Salivary gland (N) | 0 | 0 | NA | 0 | NA | 0 | NA | 100 | 0 | 0 | 0 | NS | NS | NS | 0 | |
| FDA999d | 0VK5 | H7 | Kidney (N) | 0 | 0 | NA | 10 | C | 30 | C | 60 | 50 | 40 | 0 | 3+ | 0 | 0 | 0 | |
| FDA999d | 0VK5 | H8 | Kidney (N) | 0 | 0 | NA | 10 | C | 20 | C | 70 | 40 | 30 | 0 | 2+ | 0 | 0 | 0 | |
| FDA999d | 0VK5 | H9 | Kidney (N) | 0 | 0 | NA | 20 | M | 20 | M | 60 | 100 | 40 | 0 | 3+ | 0 | 0 | 0 | |
| FDA999d | 0VK5 | I1 | Prostate (N) | 0 | 0 | NA | 0 | NA | 0 | NA | 100 | 0 | 0 | 0 | 0 | 0 | 0 | 0 | |
| FDA999d | 0VK5 | I2 | Prostate (N) | 0 | 20 | M, C | 20 | M | 0 | NA | 60 | 60 | 40 | 0 | 0 | 0 | 0 | NS | |
| FDA999d | 0VK5 | I3 | Prostate (N) | 0 | 0 | NA | 0 | NA | 0 | NA | 100 | 0 | 0 | 0 | 0 | 0 | 0 | NS | |
| FDA999d | 0VK5 | I4 | Endometrium (N) | 0 | 0 | NA | 20 | M | 20 | M | 60 | 60 | 40 | 0 | 0 | 0 | 0 | NS | Mostly apical staining |
| FDA999d | 0VK5 | I5 | Endometrium (N) | 0 | 0 | NA | 0 | NA | 10 | M | 70 | 50 | 30 | 0 | 0 | 0 | 0 | 0 | |
| FDA999d | 0VK5 | I6 | Endometrium (N) | 0 | 70 | M, C | 20 | M, C | 0 | NA | 10 | 250 | 90 | 0 | 0 | 0 | 0 | 0 | Cytoplasmic basal 3+ |
| FDA999d | 0VK5 | I7 | Uterine cervix (NAT) | 0 | 45 | M, C | 5 | M, C | 5 | C | 45 | 150 | 55 | 0 | 0 | 0 | 0 | 0 | Ectocervic basal not staining |
| FDA999d | 0VK5 | I8 | Uterine cervix (NAT) | 0 | 0 | NA | 0 | NA | 0 | NA | 100 | 0 | 0 | 0 | 0 | 0 | 0 | 0 | |
| FDA999d | 0VK5 | I9 | Uterine cervix (NAT) | 0 | 0 | NA | 0 | NA | 0 | NA | 100 | 0 | 0 | 0 | 0 | 0 | 0 | 0 | |
| FDA999d | 0VK5 | J1 | Skeletal Muscle (N) | 0 | 0 | NA | 0 | NA | 0 | NA | 100 | 0 | 0 | 0 | 0 | 0 | 0 | NS | |

TABLE 21-continued

Specificity of Anti-Nectin-4 Antibody M22-321b41.1 in IHC Staining of Different Tissues.

| GENERAL SPECIMEN INFORMATION | | | | TEST ARTICLE STAINING OF DISTINCTIVE CELLS | | | | | | | | TEST ARTICLE STAINING OF OTHER CELL TYPES | | | | |
|---|---|---|---|---|---|---|---|---|---|---|---|---|---|---|---|---|
| Accession # | Run ID | TMA Location | Cell Line/Tissue | Isotype Location | 3+ % 3+ sub | 2+ % 2+ sub | 1+ % 1+ sub TISSUE | 0% | H-Score | % Nectin 4 | Endo-thelium | Smooth Muscle | Fibro-blast | Stroma | Inflam. Cells | Comments |
| FDA999d | 0VK5 | J2 | Skeletal Muscle (N) | 0 | 0 NA | 0 NA | 0 NA | 100 | 0 | 0 | 0 | 0 | 0 | 0 | NS | |
| FDA999d | 0VK5 | J3 | Skeletal Muscle (N) | 0 | 0 NA | 0 NA | 0 NA | 100 | 0 | 0 | 0 | 0 | 0 | 0 | NS | |
| FDA999d | 0VK5 | J4 | Skin (N) | 0 | 0 NA | 0 NA | 0 NA | 100 | 0 | 0 | 0 | 0 | 0 | 0 | 0 | Pigmented skin |
| FDA999d | 0VK5 | J5 | Skin (N) | 0 | 80 M, C | 10 M, C | 0 NA | 10 | 260 | 90 | 0 | 0 | 0 | 0 | 0 | Basal layer Negative |
| FDA999d | 0VK5 | J6 | Skin (N) | 0 | 70 M, C | 20 M, C | 0 NA | 10 | 250 | 90 | 0 | 0 | 0 | 0 | 3+ | |
| FDA999d | 0VK5 | J7 | Peripheral Nerve (N) | 0 | 0 NA | 0 NA | 0 NA | 100 | 0 | 0 | 0 | 0 | 0 | 0 | NS | |
| FDA999d | 0VK5 | J8 | Peripheral Nerve (N) | 0 | 0 NA | 0 NA | 0 NA | 100 | 0 | 0 | 0 | 0 | 0 | 0 | NS | |
| FDA999d | 0VK5 | J9 | Peripheral Nerve (N) | 0 | 0 NA | 0 iNA | 0 NA | 100 | 0 | 0 | 0 | 0 | 0 | 0 | NS | Occ IC = 2+ |
| FDA999d | 0VK5 | K1 | Mesothelium (N) | 0 | 0 NA | 0 NA | 0 NA | 100 | 0 | 0 | 0 | NS | 0 | 0 | 0 | |
| FDA999d | 0VK5 | K2 | Mesothelium (N) | 0 | 0 NA | 0 NA | 0 NA | 100 | 0 | 0 | 0 | NS | 0 | 0 | 0 | |
| FDA999d | 0VK5 | K3 | Mesothelium (N) | 0 | 0 NA | 0 NA | 0 NA | 100 | 0 | 0 | 0 | NS | 0 | 0 | 0 | |
| FDA999d | 0VK5 | K4 | Eye (NAT) | 0 | 0 NA | 0 NA | 0 NA | 100 | 0 | 0 | 0 | NS | 0 | 0 | 0 | |
| FDA999d | 0VK5 | K5 | Eye (NAT) | 0 | 0 NA | 0 NA | 0 NA | 100 | 0 | 0 | 0 | NS | 0 | 0 | 0 | |
| FDA999d | 0VK5 | K6 | Eye (NAT) | 0 | 0 NA | 0 NA | 0 NA | 100 | 0 | 0 | 0 | NS | 0 | 0 | 0 | |
| FDA999d | 0VK5 | K7 | Larynx (NAT) | 0 | 0 NA | 5 M, C | 5 M, C | 90 | 15 | 10 | 0 | 0 | 0 | 0 | 0 | |
| FDA999d | 0VK5 | K8 | Larynx (NAT) | 0 | 25 M, C | 15 M, C | 0 NA | 60 | 105 | 40 | 0 | 0 | 0 | 0-1+ | 0 | Basal layer Neg. |
| FDA999d | 0VK5 | K9 | Larynx (NAT) | 0 | 0 NA | 0 NA | 0 NA | 100 | 0 | 0 | 0 | 0 | 0 | 0 | 0 | Scant epithelium fragment present |

GENERAL COMMENT/NOTE:
NA = Not Applicable
NS = Not Seen
NAT = Cancer adjacent normal tissue
Occ = Occasional
Sc = Scattered
IC = Inflammatoly Cells
N = Normal
C = Cytoplasmic Staining
M = Membrane Staining
F = Focal Positive Therefore, the IHC assay for Nectin-4 expression based on M22-321b41.1 is sensitive and specific for Nectin-4 expression. The IHC assay with M22-321b41.1 showed excellent precision and reproducibility.

Example 7: Functional Assays: Immunoblotting

Figure 12A:
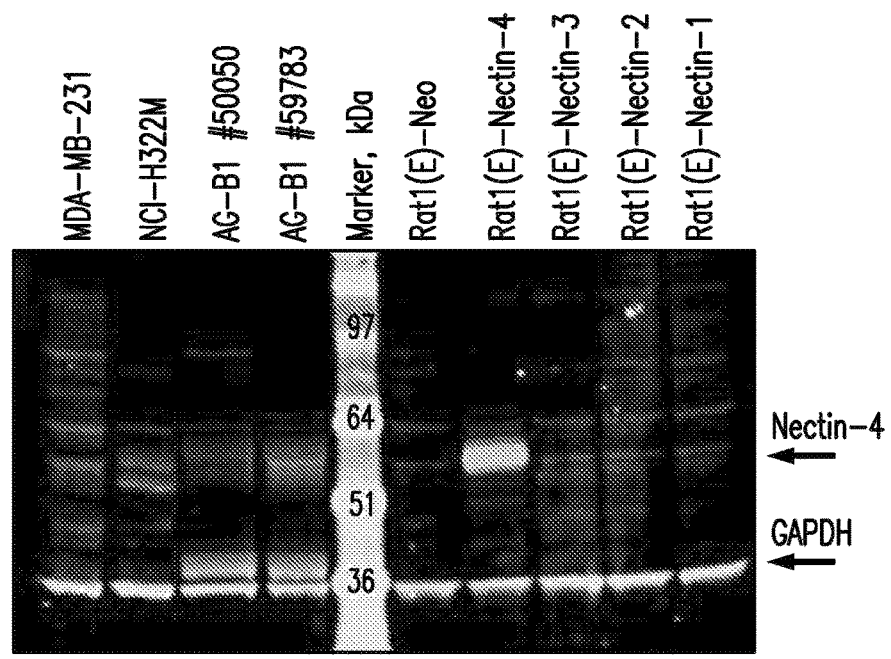
FIG. 12A depicts the results of a Western blotting experiment showing specific detection of Nectin-4 band in only those cells and xenografts that express Nectin-4
Figure 12B:
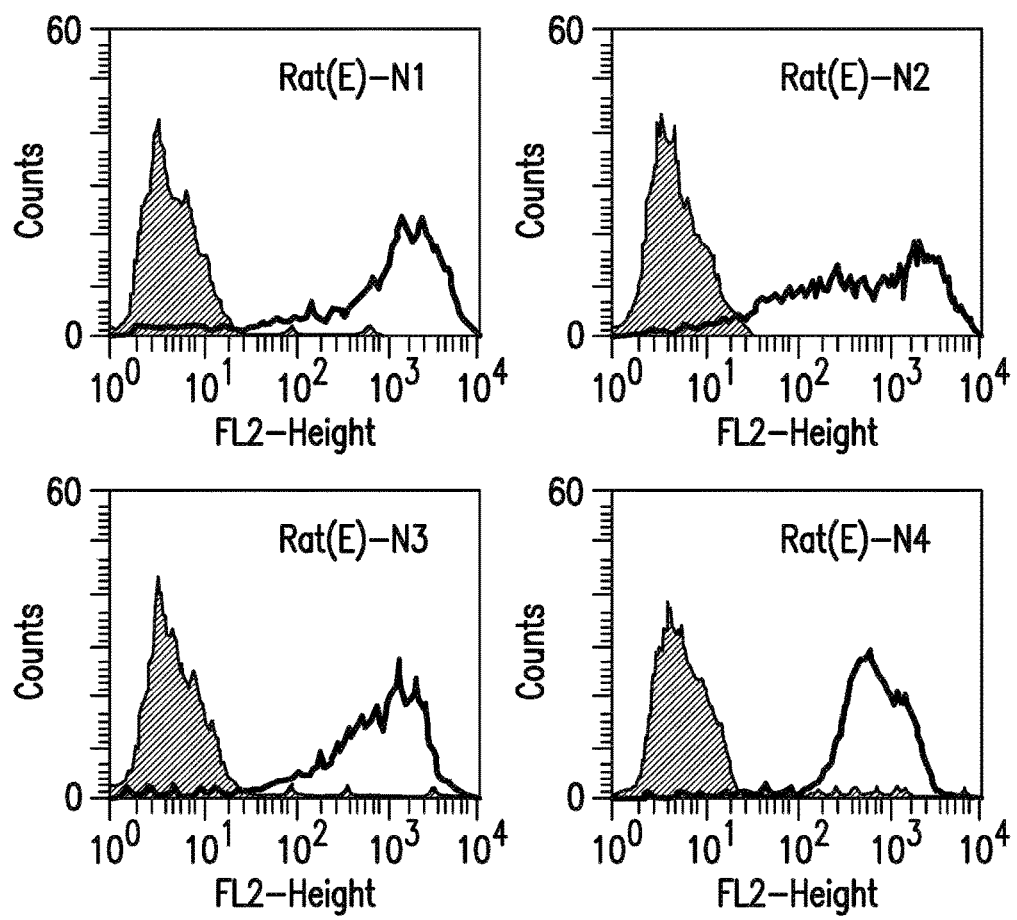
FIG. 12B depicts the results of a control FACS experiment showing that the Rat1(E)-Nectin-4 cells that blotted positively with M22-321b41.1 in FIG. 12A expressed high levels of Nectin-4; and the other Rat1(E) cells that blotted negatively with M22-321b41.1 in FIG. 12A expressed high levels of Nectin-1, Nectin-2, and Nectin-3, indicating that M22-321b41.1 is specific for Nectin-4.

The functional property and the specificity of mAb M22-321b41.1 was further evaluated in immunoblotting, for example in Western blotting. Briefly, protein lysates prepared from various Nectin-4 mRNA-positive and Nectin-4 mRNA-negative samples were subjected to SDS-PAGE, transferred onto a nitrocellulose membrane, and probed with M22-321b41.1. Anti-human GAPDH antibody was used as a loading control to confirm that appropriate and equal amounts of total cell lysate were resolved in each gel lane in the SDS-PAGE. As shown in FIG. 12A, M22-321b1.1 recognized and blotted a specific band of ~58-60 kDa, consistent with predicted human Nectin-4 molecular weight, in lysates of Nectin-4-mRNA-positive NCI H322M, AG-B1, and Rat1(E) cells engineered to overexpress Nectin-4. Smaller sized Nectin-4 cleavage products were observed in the AG-B1 xenograft samples as well as in the NCIH322M cell line, consistent with reported shedding of Nectin-4. (Buchanan et al., 2017.) No bands were detected in Nectin-4 mRNA-negative MDA-MB-231 and Rat1(E)-Neo cells. M22-321b41.1 also did not detect any of the Nectin-1, Nectin-2, and Nectin-3 over-expressed by engineered Rat1 (E) cells in Western blotting, even though all the Nectin family members (Nectin 1-4) were highly expressed in the engineered Rat1(E) cells as shown by FACS in FIG. 12B. Therefore, M22-321b41.1 specifically detected Nectin-4 in an immunoblotting assay.

Example 8: Epitope Mapping

To further map the epitope on Nectin-4 recognized by M22-321b41.1 antibody, various fragments of Nectin-4 were cloned, transfected into cells, and expressed in cells. The cells expressing various Nectin-4 fragments were cultured and lysed in RIPA buffer. Total protein concentrations of the RIPA lysates were quantitated using BSA standard and a total of 20 µg of reduced (50 mM TCEP) lystates were subjected to SDS-PAGE on a 4-12% BT 15-lane gel in 1×MES running buffer, transferred with I-Blot onto nitrocellulose membrane, blocked with LI-COR blocking buffer, probed with 2 µg/ml M22-321b41.1 antibody in 1:1 LI-COR blocking buffer. A 1:10000 dilution of α-GAPDH antibody (Chicken pAb, Millipore) was used detect GAPDH as a loading control. Antibodies bound to the protein bands were then detected with either 1:5000 dilution of Goat-anti-Mouse antibody conjugated with IRDye 680 (Odyssey) or 1:5000 Donkey anti-α-Chicken conjugated with IRDye 800 (Odyssey) and visualized in Odyssey system. M22-321b41.1 antibody recognized Nectin-4 fragment V (amino acid residues 1-150) (FIG. 13). Therefore, M22-321b41.1 antibody recognized an epitope located in amino acid residues 1-150 (SEQ ID NO:45) of human Nectin-4. Furthermore, because M22-321b41.1 antibody was generated against a Nectin-4 fragment of amino acid residues 31-346 (SEQ ID NO:2) of human Nectin-4 as shown in Examples 1, 2 and 3, M22-321b41.1 antibody can recognize an epitope located in amino acid residues 31-150 (SEQ ID NO:46) of human Nectin-4 (the overlapping region of fragment 1-150 and fragment 31-346).

Example 9: Diagnostic and Prognostic Use of the Nectin-4 IHC Assays

Nectin-4 expression was first examined in normal tissue samples using IHC staining with M22-321b41.1 antibody. Variable, but mostly weak or moderate, Nectin-4 expression was detected in skin (epidermis, sweat glands and hair follicles), transitional epithelium of bladder, salivary gland (ducts), esophagus, breast, and stomach. To correlate Nectin-4 expression with various cancers, Nectin-4 expression was then examined in various tumor specimens using IHC staining with M22-321b41.1 antibody. Nectin-4 was highly expressed in bladder cancer and was more moderate expression in breast, pancreatic, lung and ovarian cancer tissue microarrays (TMA). Examination of the correlation between Nectin-4 expression and bladder cancers using the same IHC assay revealed that 83% (434 out of 524) of bladder cancers on TMA were positive and 60% were strongly or moderately stained by M22-321b41.1 IHC staining.

The effectiveness of the Nectin-4 expression in a patient tissue as determined by M22-321b41.1 IHC staining in predicting whether a patient will be responsive to an anti-cancer therapy (e.g. an anti-cancer therapy using anti-Nectin-4 conjugated to cytotoxic or cytostatic agents), was then evaluated, for example, by testing the response to a cancer therapy in patients who meet the following criteria: (1) having istologically confirmed metastatic malignant solid tumors (excluding sarcomas) that are resistant or have recurred; (2) having a tumor positive for Nectin-4 expression and having a Nectin-4 IHC H-score equal to or more than 150; (3) having failed at least one prior chemotherapy regimen for metastatic disease (urothelial and bladder cancer subjects are not required to have failed prior chemotherapy regimen if considered unfit for cisplatin-based chemotherapy) (Galsky et. al., Journal of Clinical Oncology, vol. 29, no. 17, 2432-2438 (2011)); (4) having documented disease progression if most recent systemic treatment was an investigational immunotherapy drug; (5) having Eastern Cooperative Oncology Group (ECOG) performance status of 0 or 1; (7) having measurable disease according to RECIST (version 1.1) (Eisenhauer, et. al. European Journal of Cancer; 45(2): 228-247 (2009)). A total of 184 clinical trial specimens were examined for their Nectin-4 expression using an IHC assay with M22-321b41.1 antibody; of the 184 specimens examined, 180 (98%) of clinical trial specimens had an H-score more than 0; and 171 (93%) had moderate to high Nectin-4 expression (H-Scores ≥150). Overall, 44 clinical subjects matched the inclusion criteria. The site of the tumor and/or metastasis in these 44 patients were listed in Table 22.

TABLE 22

Site Of Primary Tumor And Metastases

|  | N (%) |
| --- | --- |
| Site of Primary Tumor | |
| Bladder | 28 (63.6) |
| Renal Pelvis | 10 (22.7) |
| Ureter | 3 (6.8) |
| Bladder, other histology | 2 (4.5) |
| Other | 1 (2.3) |
| Site of Metastases | |
| Visceral | 25 (56.8) |
| Liver | 10 (22.7) |
| Lung | 20 (45.5) |

These 44 patients who had moderate to high Nectin-4 expression (H-Scores ≥150) were administered with an anti-cancer therapeutic agent comprising a fully human anti-Nectin-4 antibody (IgG1κ) conjugated to microtubule-disrupting agent monomethylauristatin-E. All subjects received a single 30 min IV infusion of the anti-Nectin-4 ADC once weekly for 3 weeks of every 4 week cycle (e.g., on days 1, 8, and 15), until disease progression, intolerability to treatment, investigator decision or consent withdrawal. Doses administered included 0.5 mg/kg, 0.75 mg/kg, 1 mg/kg, and 1.25 mg/kg. The disease response in the patients was assessed by investigator per RECIST version 1.1 once every 8 weeks (±7 days) (RECIST as described in Eisenhauer, et. al. European Journal of Cancer; 45(2): 228-247 (2009)). A total of 36 subjects produced results that could be evaluated.

The anti-Nectin-4 ADC produced anti-tumor activity in the treated patients who all have tumors expressing Nectin-4. Ten out of the 36 patients had partial responses, a 27.8% response rate (with both partial or complete response counted as a response). The anti-Nectin-4 ADC also produced anti-tumor activity in 4 out of 10 subjects with liver metastases (40% response rate) and in 3 out of 12 patients previously treated with checkpoint inhibitors (25% response rate).

Therefore, anti-Nectin-4 ADC produced anti-tumor activity in the patients who have tumors expressing Nectin-4.

Example 10: Diagnostic and Prognostic Use of the Nectin-4 IHC Assays—A Different Cohort The effectiveness of the Nectin-4 expression in a patient tissue as determined by M22-321b41.1 IHC staining in predicting whether a patient will be responsive to an anti-cancer therapy (e.g. an anti-cancer therapy using anti-Nectin-4 conjugated to cytotoxic or cytostatic agents), was then evaluated, for example, by testing the response to a cancer therapy in a different cohort of patients who meet the following criteria: (1) having histologically confirmed metastatic malignant solid tumors, including urothelial cancer; (2) having a tumor positive for Nectin-4 expression and having a Nectin-4 IHC H-score equal to or more than 150; (3) having failed one or more than one prior chemotherapy for metastatic disease and/or urothelial cancer subjects who were unfit for cisplatin-based chemotherapy (Galsky et al., Journal of Clinical Oncology, vol. 29, no. 17, 2432-2438 (2011)); (4) having documented disease progression for subjects treated with an immune checkpoint inhibitor (CPI) immediately prior to study; (5) having Eastern Cooperative Oncology Group (ECOG) performance status of 0 or 1; (7) having measurable disease according to RECIST (version 1.1) (Eisenhauer, et al. European Journal of Cancer; 45(2): 228-247 (2009)). A total of 295 clinical trial specimens were examined for their Nectin-4 expression using an IHC assay with M22-321b41.1 antibody; of the 295 specimens examined, 278 (94%) of clinical trial specimens had an H-score equal to or greater than 1; and 245 (83%) had moderate to high Nectin-4 expression (H-Scores ≥150). Overall, 58 clinical subjects matched the inclusion criteria. The site of the tumor and/or metastasis in these 58 patients were listed in Table 23.

TABLE 23

| Site Of Primary Tumor And Metastases | |
|---|---|
| | N (%) |
| Site of Primary Tumor | |
| Bladder | 39 (67.2) |
| Renal Pelvis | 14 (24.1) |
| Ureter | 4 (6.9) |
| Other, Right Kidney | 1 (1.7) |
| Site of Metastases | |
| Visceral | 34 (58.6) |
| Liver | 16 (27.6) |
| Lung | 26 (44.8) |

These 58 patients who have moderate to high Nectin-4 expression (H-Scores ≥150) were administered with an anti-cancer therapeutic agent comprising a fully human anti-Nectin-4 antibody (IgG1κ) conjugated to microtubule-disrupting agent monomethylauristatin-E. All subjects received a single 30 min IV infusion of the anti-Nectin-4 ADC once weekly for 3 weeks of every 4 week cycle (e.g., on days 1, 8, and 15), until disease progression, intolerability to treatment, investigator decision or consent withdrawal. Doses administered include 0.5 mg/kg, 0.75 mg/kg, 1 mg/kg, and 1.25 mg/kg. The disease response in the patients was assessed by investigator per RECIST version 1.1 once every 8 weeks (±7 days) (RECIST as described in Eisenhauer, et. al. European Journal of Cancer; 45(2): 228-247 (2009)). A total of 49 subjects produced results that can be evaluated.

The anti-Nectin-4 ADC produced anti-tumor activity in the treated patients who all have tumors expressing Nectin-4. One patient had a complete response and 17 patients had had partial responses, resulding in a total 36.7% response rate (with both partial and complete response counted as a response). In the 1.25 mg/kg group, the anti-Nectin-4 ADC produced response in 10 out of 17 patients treated, a response rate of 58.8%. The anti-Nectin-4 ADC also produced anti-tumor activity in 5 out of 12 subjects with liver metastases (41.7% response rate), in 6 out of 16 patients previously treated with checkpoint inhibitors (37.5% response rate), and in 8 out of 20 patients previously treated with taxanes (40% response rate).

Therefore, anti-Nectin-4 ADC produced anti-tumor activity in the patients who have tumors expressing Nectin-4.

Example 11: Therapeutic Use of the Anti-Nectin-4 ADC

The efficacy of anti-Nectin-4 ADC provided herein in treating patients with various cancers is evaluated, for example, by comparing the outcome of patients treated with anti-Nectin-4 ADC comprising a human or humanized M22-321b41.1 antibody and control patients treated with antibody istotype as placebo. Briefly, patients are randomized and assigned to the control group or the treatment group. Patients in the treatment group are injected with anti-Nectin-4 ADC at a range of doses, which are determined according to the range of mg (of antibodies) per kg (of bodyweight) doses optimized in animal models and or those in Example 9 and 10. Injection occurs once or multiple times over a period of time. The outcome in the treated patients are analyzed and compared between the treatment group and the placebo group periodically.

The outcome improves in patients treated with anti-Nectin-4 ADC when compared with those treated with placebo. When compared with the placebo treatment, The anti-Nectin-4 ADC treatment leads to higher survival rate at 6 month, 1 year, 2 year, 3 year or 5 year, increase survival duration, reduced level of cancer markers, reduced mean or median tumor size, and/or slower progression of the cancer.

Example 12: Additional Diagonostic and Prognostic Use of Nectin-4 IHC Assays

The effectiveness of the Nectin-4 expression in a patient tissue as determined by M22-321b41.1 IHC staining in predicting whether a patient will be responsive to an anti-cancer therapy (e.g. an anti-cancer therapy using anti-Nectin-4 conjugated to cytotoxic or cytostatic agents), is evaluated, for example, by correlating the response of patients to a cancer therapy with the Nectin-4 expression in the patient cancer tissues determined from IHC staining with the Nectin-4 specific antibody. Briefly, all patients are treated with the same cancer treatment regimen and levels of Nectin-4 expression in the patients' tissues having cancer are determined in IHC assays using M22-321b41.1 antibody as described herein. The patients are stratified into two, three, four, or more groups according to the Nectin-4 expression in their cancer tissues. For example, with four group stratification, patients are separated into a first group with high Nectin-4 expression in their cancer tissues, a second group with moderate expression, a third group with low expression, and a fourth group with no expression. The response to the cancer treatment regimen, as reflected by patient outcome such as the patients' bodymass, the size of the tumor in the patients, the 6 month, 1-year, 2-year, 3-year, or 5-year patient survival rate, or the survival duration of the patients in each stratified group are summarized and correlated with the Nectin-4 expression of the patients in each group. The correlation is performed using the mean or median values of each group or performed for the individual patient in each group.

Nectin-4 expression in the patient cancer tissues is indicative of how the patient will respond to a cancer treatment regimen, e.g. a cancer therapy using anti-Nectin-4 conjugated to cytotoxic or cytostatic agents (referred to as anti-Nectin-4 ADC). The patients with higher Nectin-4 expression in their cancer tissues respond better to the cancer treatment regimen, have higher survival rate at 6 month, 1 year, 2 year, 3 year or 5 year, and/or live longer on than the patients with lower Nectin-4 expression in their cancer tissues. The higher the Nectin-4 expression in the patient's cancer tissues, the more effective the cancer therapy, e.g. anti-Nectin-4 ADC treatment, is for the patient.

What is claimed is:

1. An antibody or antigen-binding fragment thereof that binds to an epitope of human Nectin-4 comprising a light chain variable region (VL) comprising a VL CDR1 having the amino acid sequence selected from the group consisting of SEQ ID NO:7 and 8, a VL CDR2 having the amino acid sequence selected from the group consisting of SEQ ID NO:9, 10, and 11, and a VL CDR3 having the amino acid sequence selected from the group consisting of SEQ ID NO:12, and 13;

and a light chain variable region (VH) comprising a VH CDR1 having the amino acid sequence selected from the group consisting of SEQ ID NO:14, 15, 16, and 17, a VH CDR2 having the amino acid sequence selected from the group consisting of SEQ ID NO:18, 19, 20, and 21, and a VH CDR3 having the amino acid sequence selected from the group consisting of SEQ ID NO:22, 23, and 24.

2. The antibody or antigen-binding fragment thereof of claim 1, wherein the VL CDR1, VL CDR2, and VL CDR3 comprise the amino acid sequences of SEQ ID NOS: 7, 10, and 12, respectively, and the VH CDR1, VH CDR2, and VH CDR3 comprise the amino acid sequences of SEQ ID NOS: 15, 19, and 23, respectively, wherein said VL and VH CDR sequences are determined according to Kabat CDR definition.

3. The antibody or antigen-binding fragment thereof of claim 1, wherein the antibody or antigen-binding fragment thereof comprises a VL comprising the amino acid sequence of SEQ ID NO: 3 and a VH comprising the amino acid sequence of SEQ ID NO: 4.

4. The antibody or antigen-binding fragment thereof of claim 1, wherein the antibody or antigen-binding fragment thereof comprises a mouse IgG2 Fc, human IgG1 Fc region, or a mutant thereof.

5. The antibody or antigen-binding fragment thereof of claim 1, wherein the antibody or antigen-binding fragment thereof comprises: a light chain constant region comprising the amino acid sequence of SEQ ID NO: 33 and a heavy chain Fc region comprising the amino acid sequence of SEQ ID NO: 35.

6. The antibody or antigen-binding fragment thereof of claim 1, wherein the antibody or antigen-binding fragment thereof comprises: a light chain comprising the amino acid sequence of SEQ ID NO: 5 and a heavy chain comprising the amino acid sequence of SEQ ID NO: 6.

7. The antibody or antigen-binding fragment thereof of claim 1, wherein the antibody is a monoclonal antibody, a humanized antibody, a chimeric antibody, or a deimmunized humanized antibody or the antibody or antigen-binding fragment thereof is a Fab, a Fab', a F(ab')$_2$, a Fv, a scFv, a dsFv, a diabody, a triabody, or a tetrabody formed from antibody fragments.

8. The antibody or antigen-binding fragment thereof of claim 3, wherein the glutamine at the first residue of SEQ ID NO: 4 is substituted with a pyroglutamate.

9. A polynucleotide comprising nucleotide sequences encoding the VH and the VL of the antibody or antigen-binding fragment thereof of claim 1 or nucleotide sequences encoding the heavy chain and the light chain of the antibody or antigen-binding fragment thereof of claim 1.

10. A vector comprising the polynucleotide of claim 9.

11. A cell comprising a polynucleotide encoding the VH and a polynucleotide encoding the VL, or comprising a polynucleotide encoding both the VH and VL of the antibody or antigen-binding fragment of claim 1; or comprising a polynucleotide encoding the heavy chain and a polynucleotide encoding the light chain or comprising a polynucleotide encoding both the heavy chain and the light chain of the antibody or antigen-binding fragment thereof of claim 1.

12. A method of making an antibody or antigen-binding fragment thereof which specifically binds to an epitope of human Nectin-4, comprising culturing the cell of claim 11 to express the antibody or antigen-binding fragment thereof.

13. A kit comprising the antibody or antigen-binding fragment thereof of claim 1.

14. A method for assessing Nectin-4 expression in a tissue sample from a subject suspected of having cancer, comprising:
  (a) contacting said tissue sample with the antibody or antigen binding fragment thereof of claim 1;
  (b) detecting the binding of said antibody or antigen binding fragment thereof to said tissue sample;
  (c) measuring the expression of Nectin-4 in the tissue sample, wherein the expression level of Nectin-4 in the tissue sample is compared with a reference expression level of Nectin-4.

15. A method for assessing Nectin-4 expression in a tissue sample from a subject suspected of having cancer, comprising:
  (a) performing an immunohistochemistry assay on the tissue sample with the antibody or antigen binding fragment thereof of claim 1;
  (b) measuring the expression of Nectin-4 in the tissue sample.

16. A method for assessing responsiveness of a cancer patient to an anti-cancer therapeutic agent, said method based on Nectin-4 expression in a tissue sample from said patient, comprising:
  (a) contacting said tissue sample with the antibody or antigen binding fragment thereof of claim 1;
  (b) detecting the binding of said antibody or antigen binding fragment thereof to said tissue sample;
  (c) measuring the expression level of Nectin-4 in the tissue sample, wherein the expression level of Nectin-4 in the tissue sample is compared with a reference expression level of Nectin-4;
  wherein an increased expression level of Nectin-4 compared to the reference is indicative of responsiveness to said anti-cancer therapy.

17. A method for assessing responsiveness of a cancer patient to an anti-cancer therapeutic agent, said method based on Nectin-4 expression in a tissue sample from said patient, comprising:
  (a) performing an immunohistochemistry assay on the tissue sample with the antibody or antigen binding fragment thereof of claim 1;
  (b) measuring the expression level of Nectin-4 in the tissue sample, wherein the expression level of Nectin-4 in the tissue sample is compared with a reference expression level of Nectin-4,
  wherein an increased expression level of Nectin-4 in the tissue sample compared to the reference is indicative of responsiveness to said anti-cancer therapy.

\* \* \* \* \*

UNITED STATES PATENT AND TRADEMARK OFFICE
CERTIFICATE OF CORRECTION

| | | |
|---|---|---|
| PATENT NO. | : 11,292,837 B2 | |
| APPLICATION NO. | : 16/619439 | |
| DATED | : April 5, 2022 | |
| INVENTOR(S) | : Karen Jane Meyrick Morrison et al. | |

It is certified that error appears in the above-identified patent and that said Letters Patent is hereby corrected as shown below:

In the Claims

Claim 1:

Column 223, Line 66, "SEQ ID NO:" should read -- SEQ ID NOS: --.

Column 224, Line 61, "NO:" should read -- NOS: --.

Column 224, Line 63, "NO:" should read -- NOS: --.

Column 224, Line 64, "light" should read -- heavy --.

Column 224, Line 66, "SEQ ID NO:" should read -- SEQ ID NOS: --.

Column 225, Line 1, "SEQ ID NO:" should read -- SEQ ID NOS: --.

Column 225, Line 4, "NO:" should read -- NOS: --.

Signed and Sealed this
Nineteenth Day of March, 2024

*Katherine Kelly Vidal*

Katherine Kelly Vidal
*Director of the United States Patent and Trademark Office*